(12) United States Patent
Thorson

(10) Patent No.: US 6,733,998 B1
(45) Date of Patent: May 11, 2004

(54) MICROMONOSPORA ECHINOSPORA GENES CODING FOR BIOSYNTHESIS OF CALICHEAMICIN AND SELF-RESISTANCE THERETO

(75) Inventor: Jon S. Thorson, New York City, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/724,797

(22) Filed: Nov. 28, 2000

Related U.S. Application Data

(63) Continuation-in-part of application No. 09/457,045, filed on Dec. 7, 1999, now abandoned
(60) Provisional application No. 60/111,325, filed on Dec. 7, 1998.

(51) Int. Cl.⁷ .......................... C12P 21/02; C07H 21/02; C07H 21/04; C12N 15/63
(52) U.S. Cl. .................... 435/71.1; 536/23.1; 536/23.2; 435/320.1; 424/93.21
(58) Field of Search .............................. 536/23.1, 23.2; 435/320.1, 71.1; 424/93.21

(56) References Cited

U.S. PATENT DOCUMENTS

| | | | |
|---|---|---|---|
| 5,264,586 A | 11/1993 | Nicolaou et al. | |
| 5,384,412 A | 1/1995 | Nicolaou et al. | |
| 5,436,361 A | 7/1995 | Jones et al. | |
| 5,512,444 A | * 4/1996 | Patard et al. | 435/6 |
| 5,550,246 A | 8/1996 | Nicolaou et al. | |
| 5,739,116 A | 4/1998 | Hamann et al. | |
| 5,763,165 A | * 6/1998 | Boon-Falleur et al. | 435/6 |
| 5,767,285 A | 6/1998 | Hamann et al. | |
| 5,773,001 A | 6/1998 | Hamann et al. | |
| 5,877,296 A | 3/1999 | Hamann et al. | |
| 5,985,571 A | * 11/1999 | Van Buren et al. | 435/6 |

FOREIGN PATENT DOCUMENTS

| | | | |
|---|---|---|---|
| WO | WO 91/16334 | * | 10/1991 |
| WO | WO 95/23874 | * | 9/1995 |
| WO | WO 98/08323 | * | 2/1998 |
| WO | WO 00 37608 | | 6/2000 |

OTHER PUBLICATIONS

F. Kunst et al, The completer genome sequence of the Gram–positive bacterium *Bacillus subtilis*, Nature Vol 390, Nov. 20, 1997.*
Temple F. Smith et al, The challenges of genome sequence annotation or The devil is in the details, Nature Biotechnology vol. 15 Nov. 1997.*
Steven E. Brenner, Errors in genome annotation, Vol 15, No. 4, Apr. 1999.*
Peer Bork, Genetwork, Oct. 1996 vol. 12, No. 10.*
Tobias Doerks et al, Genetwork, Protein annotation: detective work for function prediction, Jun. 1998, vol. 14, No. 6.*

Jeffrey Skolnick et al, From genes to protein structure and function: novel applications of computational approaches in the genomic era, 18 (1): 34–39 2000.*
Thorson et al., "Enediyne biosynthesis and self–reliance: A progress report", *Bioorganic Chemistry*, vol. 27, No. 2 (1999), pp. 172–188.
Thorson et al, "Understanding and exploiting nature's chemical arsenal : the past, present and future of calicheamicin research", *Current Pharmaceutical Design*, vol. 6, (Dec. 2000), pp. 1841–1879.
Altschul, S.F., et al., "Issues in Searching Molecular Sequence Databases", Nature Genetics, vol. 6, pp. 119–129 (1994).
Baum, E.Z., et al., "Transcription from the P1 Promoters of *Micromonospora echinospora* in the Absence of Native Upstream DNA Sequences", J. Bacteriol., vol. 171,No. 12, pp. 6503–6510 (1989).
Baum, EX., et al., "Temporally Regulated Tandem Promoters in *Micromonospora echinospora*", J. Bacteriol., vol. 170, No. 1, pp. 71–77 (1988).
Borisova, Svetlana A., et al., "Biosynthesis of Desosamine: Construction of a New Macrolide Carrying a Genetically Designed Sugar Moiety", Org. Lett., vol. 1, pp. 133–136 (1999).
Cane, D.E., et al., "Macrolide Biosynthesis. 7. Incorporation of Polyketide Chain Elongation Intermediates into Methymycin", J. Am. Chem. Soc., vol. 115, pp. 522–526 (1993).
Fujii, I., et al., "Anthracycline Biosynthesis in *Streptomyces galilaeus*", Chem. Rev., vol. 97, Nos. 7–8, pp. 2511–2523 (1977).
Hallis, T.M., et al., "Learning Nature's Strategies for Making Deoxy Sugars: Pathways, Mechanisms, and Cominatorial Applications", Acc. Chem. Res., pp. 579–588, in press (1999).
He, X., et al., "Probing the Coenzyme and Substrate Binding Events of $CDP_{-D}$–Glucose 4,6–Dehydratase: Mechanistic Implications", Biochem., 35, 4721–4731 (1996).
Hinman, L.M., et al., "Preparation of Conjugates to Monoclonal Antibodies", Enegiyne Antibiotics as Antitumor Agents, pp. 87–105 (1995).

(List continued on next page.)

Primary Examiner—James Ketter
Assistant Examiner—Daniel M. Sullivan
(74) Attorney, Agent, or Firm—Kenyon & Kenyon

(57) ABSTRACT

An isolated gene cluster of *Micromonospora echinospora* which codes for calicheamicin biosynthesis. The biosynthetic gene cluster contains genes encoding proteins and enzymes used in the biosynthetic production of calicheamicin, including the aryltetrasaccharide and aglycone. The gene cluster also includes the gene coding for the protein conferring calicheamicin resistance. The invention also provides isolated genes of the biosynthetic cluster and their corresponding proteins. In addition, the invention relates to DNA hybridizing with the calicheamicin gene cluster and the isolated genes of that cluster. Expression vectors containing genes of the biosynthetic gene and their functional variants are also provided. The invention also relates to host cells conjugated with DNA isolated from the *Micromonospora echinospora* spp. calichensis genome.

15 Claims, 22 Drawing Sheets

OTHER PUBLICATIONS

Figure 4A:
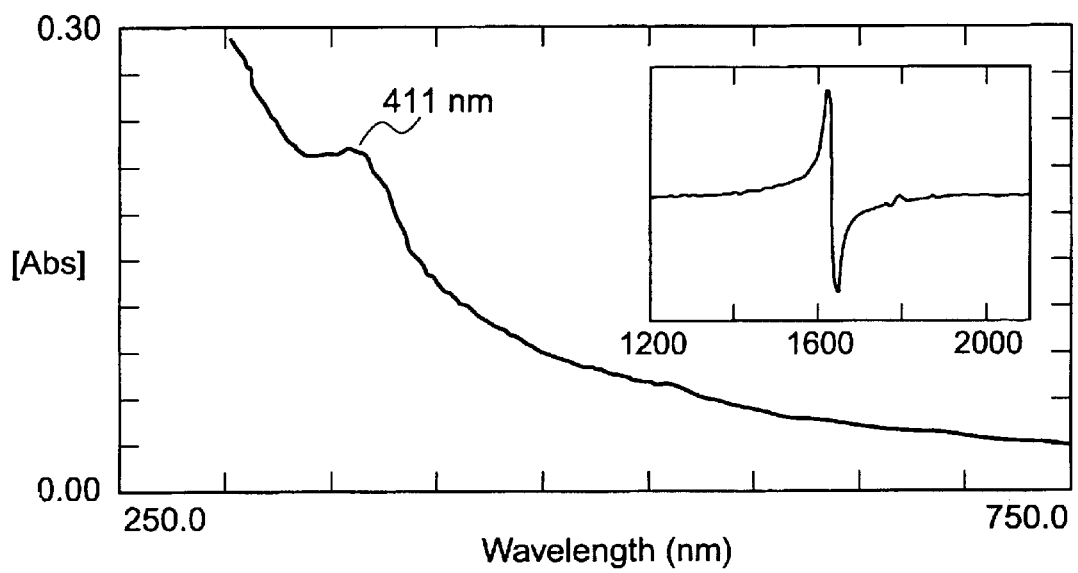
Figure 4B:
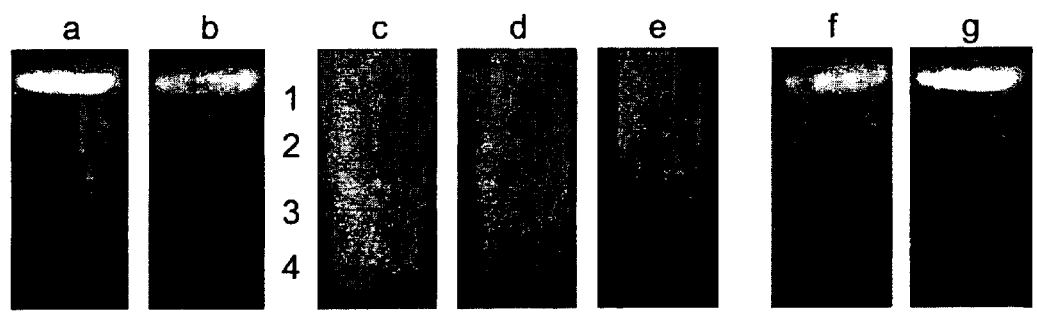

Hinman, L.M., et al., "Preparation and Characterization of Monoclonal Antibody Conjugates of the Calicheamicins: A Novel and Potent Family of Antitumor Antibiotics", Cancer Res., vol. 53, No. 14, 3336–3342 (1993).

Hopwood, D.A., "Genetic Contributions to Understanding Polyketide Synthases", Chem. Rev., vol. 97, Nos. 7–8, pp. 2465–2497, pp. 2465–2497 (1997).

Hopwood, D.A., et al., "Molecular Genetics of Polyketides and Its Comparison to Fatty Acid Biosynthesis", Ann. Rev. Genet., vol. 24, pp. 37–66, (1990).

Hutchinson, C.R., et al., "Biosynthetic Studies of Daunorubicin and Tetracenomycin C", Chem. Rev., vol. 97, pp. 2525–2535 (1977).

Kakavas, S.J., et al., "Identification and Characterization of the Niddamycin Polyketide Synthase Genes from *Streptomyces caelesstis*", J. Bacteriol., vol. 179, No. 23, pp. 7515–7522 (1997).

Karlin, S., et al., "Applications and Statistics for Multiple High–Scoring Segments in Molecular Sequences", Nat'l Acad. Sciences, U.S.A., 90, pp. 3873–5877 (1993).

Lin, L.S., et al., "Micromonospora RNA Polymerase Activity Changes During Stationary Phase", J. Gen. Microbiol., vol., Part 9, 138, pp. 1881–1885 (1992).

Lin, L.S., et al., "Mutations in the P1 Promoter Region of *Micromonspora echinospora*", J. Bacteriol., vol. 174, No. 10, pp. 3111–3117 (1992).

Liu, H–w., et al., "Pathways and Mechanisms in the Biogenesis of Novel Deoxysugars by Bacteria", Ann. Rev. Microbiol., vol. 48, pp. 223–256 (1994).

Lode, H.N., et al., "Targeted Therapy with a Novel enediyene Antibiotic Calicheamicin θth $^i{}_1$, Effectively Supresses Growth and Dissemination of Liver Metastases in a syngeneic Model of Murine Neuroblastoma", Cancer Res., vol. 58, No. 14, pp. 2925–2928 (1988).

Marsden, A.F.A., et al., "Engineering Broader Specificity Into an Antibiotic–Producing Polyketide Synthase", Science, vol. 279, pp. 199–201 (1998).

McGahren, W.J., et al., "Disulfide Calicheamicins and the Chemistry of the Allylic Trisulfide Group", Enediyne Antibiotics as Antitumor Agents, pp. 75–86 (1995).

Rothstein, D.M., "Genetic Analysis of Calicheamicin Biosynthesis", Enediyne Antibodiotics As Antitumor Agents, p. 2 (1995).

Siegel, M.M., et al., "Calicheamicin Derivatives Conjugated to Monoclonal Antibodies: Determination of Loading Values and Distributions by Infrared and UV Matrix–Assisted Laser Desorption/Ionization Mass Spectrometry and Electrospray Ionization Mass Spectrometry", Anal. Chem., vol. 69, No. 14, pp. 2716–2726 (1997).

Sievers, E.L., et al., "Selective Ablation of Acute Myeloid Leukemia Using Antibody–targeted Chemotherapy: A Phase I Study of an Anti–CD33 Calicheamicin Immunoconjugate", Blood, vol. 93, No. 11, pp. 3678–3684 (1999).

Staunton, J., et al., "Biosynthesis of Erythromycin and Rapamycin", Chem. Rev.., vol. 97, Nos. 7–8, pp. 2611–2629 (1977).

Strohl, W.R., et al., "Anthracyclines", Biotechnology of Antibiotics, $2^{nd}$ Ed., pp. 577–657.

Thompson, M.W., et al., "Purification and Characterization of TDP–D–Glucose 4,6–Dehydratase From Anthracycline–Producing Streptomycetes", J. Gen. Microbiol., vol. 138, pp. 779–786 (1992).

Wang, L. et al., "Organization of *Escherichia coli* 0157 O Antigen Gene Cluster and Identification of Its Specific Genes", Infect. Immunol., vol. 66, No. 8, pp. 3545–3551 (1998).

Wrasidle, W., et al., In Vivo Efficacy of Novel Synthetic Enediynes 1, Acta Oncologica, vol. 34, No. 2, pp. 157–164 (1995).

Zein, N., et al., "Calicheamicin $\gamma_1{}^1$: An Antitumor Antibiotic That Cleaves Double–Stranded DNA Site Specifically", Science, vol. 240, pp. 1198–1201 (1998).

Zhao, L., et al., "Mechanistic Studies of Desosamine Biosynthesis: C–4 Deoxygenation Procedes C–3 Transamination", J. Am. Chem. Soc., vol. 120, No. 46, pp. 12159–12160, (1998).

* cited by examiner

Summary of cosmid clones isolated from *M. echinospora* genomic library.

| clone[a] | type I PKS genes[b] | type II PKS genes[b] | deoxy sugar genes[b] | resistance ($\mu g\ mL^{-1}$)[c] |
|---|---|---|---|---|
| 3a | N.D.[d] | N.D.[d] | N.D.[d] | 0.5 |
| 4a | N.D.[d] | N.D.[d] | N.D.[d] | 0.5 |
| 4b | + | + | + | 0.5 |
| 10a | + | + | + | 0.5 |
| 13a | + | + | + | 0.5 |
| 16a | N.D.[d] | N.D.[d] | N.D.[d] | 0.5 |
| 56 | + | + | + | 0.1 |
| 58 | − | − | + | <0.01 |
| 60 | + | + | + | 0.05 |
| 66 | − | − | + | 0.04 |
| puc18/pBluescript[e] | − | − | − | <0.01 |

FIG. 1

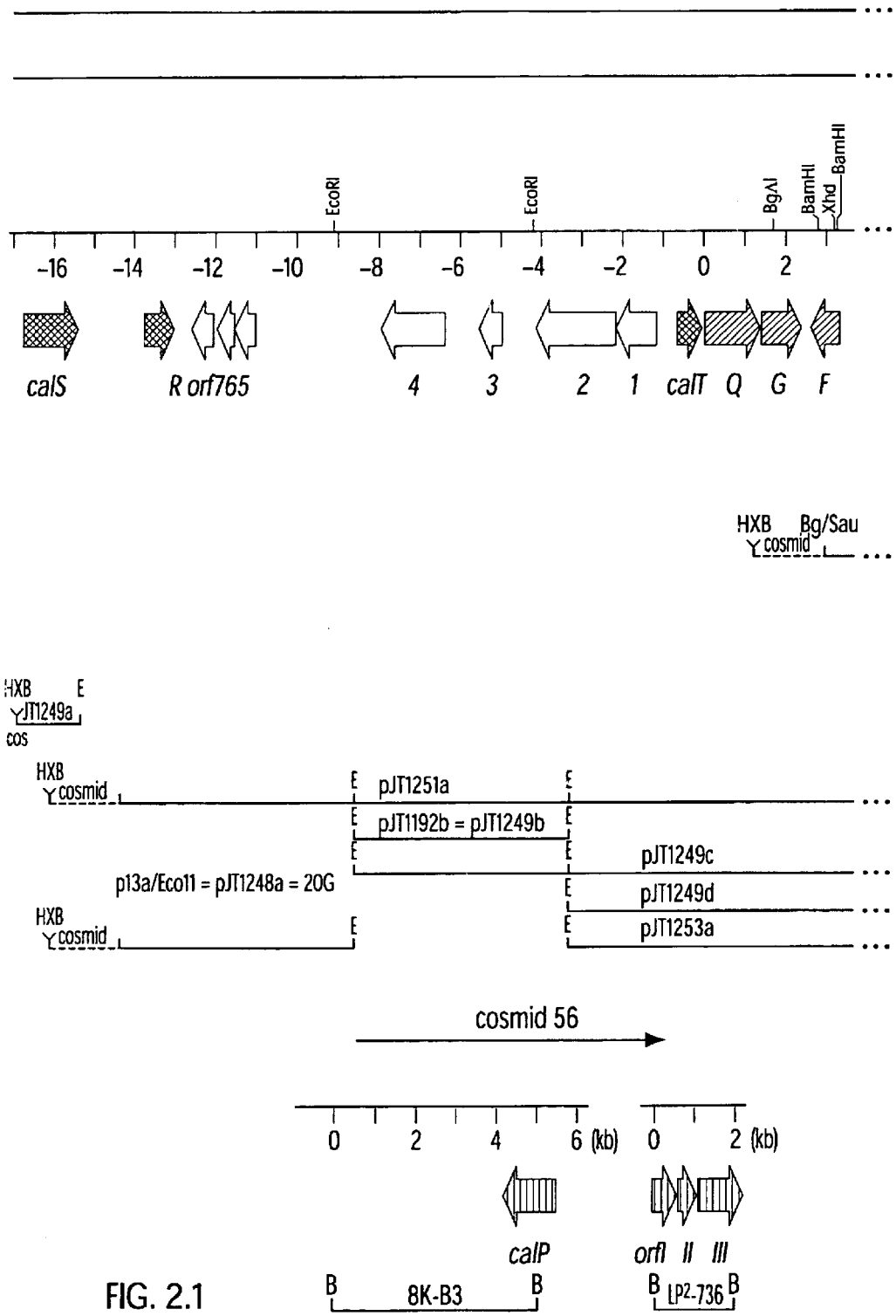
FIG. 2.1

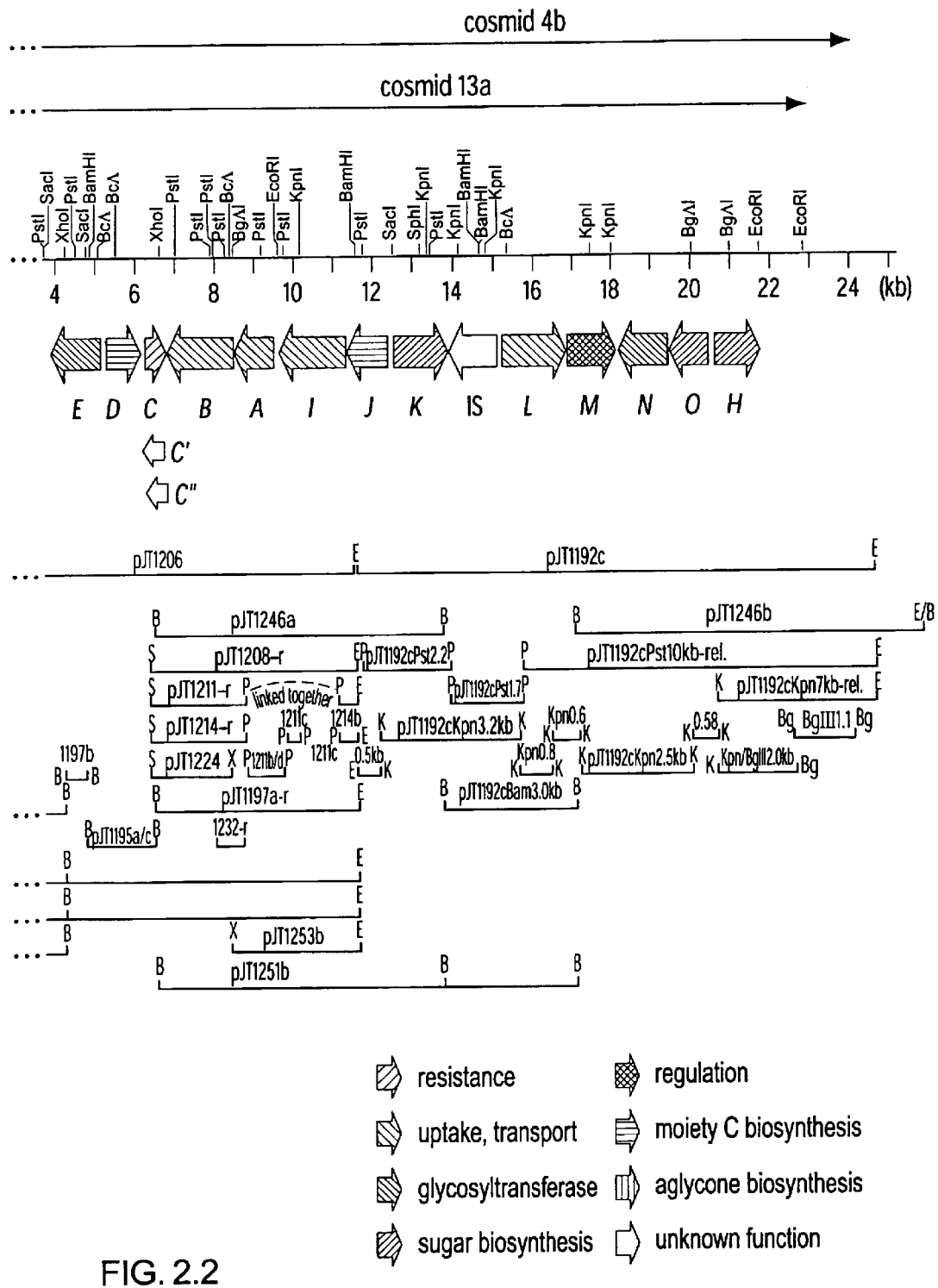
FIG. 2.2

| putative polypeptide | number of amino acids | proposed function or sequence similarity detected | probability | start/stop codons | best match |
|---|---|---|---|---|---|
| CalA | 328 | membrane transporter (ATP-binding) | 5.4x10⁻¹²⁴ | ATG/TGA | DrrA⁹⁷ |
| CalB | 561 | membrane transporter | 5.5x10⁻⁷⁰ | ATG/TGA | DrrB⁹⁷ |
| CalC | 181 | calicheamicin resistance protein | confirmed | ATG/TGA | |
| CalD | 263 | O-methyltransferase | 1.1x10⁻⁹⁹ | ATG/TGA | AveBVII⁹⁸ |
| CalE | 420 | glycosyltransferase | 4.7x10⁻³⁰ | GTG/TAG | EryCII⁹⁹ |
| CalF | 245 | N,N-dimethyltransferase | 1.5x10⁻⁷⁸ | ATG/TGA | DesVI¹⁰⁰ |
| CalG | 990 | TDP-D-glucose 4,6-dehydratase | confirmed | GTG/TAG | |
| CalH | 338 | Perosamine synthetase | confirmed | GTG/TGA | |
| CalI | 568 | Dipeptide transporter | 1.7x10⁻²⁴ | GTG/TGA | DciAE |
| CalJ | 332 | O-methyltransferase | 1.0x10⁻³⁷ | ATG/TGA | DmpM |
| CalK | 440 | L-cysteine/cystine C-S-lyase | 1.6x10⁻²⁸ | GTG/TGA | C-DES |
| CalL | 562 | Oligopeptide transporter protein | 9.5x10⁻¹⁴ | ATG/TGA | OppA |
| CalM | 416 | Regulatory protein | | GTG/TGA | |
| CalN | 398 | Glycosyltransferase | 3.4x10⁻⁷⁹ | ATG/TGA | OleI |
| CalO | 331 | Hexopyranosyl-2,3-reductase | 4.9x10⁻¹³⁹ | ATG/TGA | EryBII |
| CalP | (179) | Desaturase | 5.7x10⁻⁷ | /TGA | CrtI |
| CalQ | 453 | UDP-D-glucose 6-dehydrogenase | confirmed | GTG/TGA | |
| CalR | 282 | Transcriptional regulator | 6.7x10⁻¹¹ | ATG/TGA | SC5C7.03 |
| CalS | 1113 | P₄₅₀ oxidase | 2.9x10⁻⁶⁶ | GTG/TGA | BioI |
| CalT | 432 | oxygenase/halogenase | 2.0x10⁻⁶² | GTG/TAA | PCZA361.20 |
| CalU | 377 | glycosyltransferase | 2.0x10⁻⁵³ | ATG/TGA | SnogE/D |
| CalV | 125 | β-keto-acyl synthase III | 2.0x10⁻⁶⁵ | ATG/TGA | SC4A9 |
| CalW | (449) | cytochrome P450 | 1.0x10⁻⁹¹ | GTG/TGA | CYP105B1 |
| CalX | (197) | TDP-4-keto-6-deoxy-L-hexose 2,3-dehydratase | 1.0x10⁻²² | /TGA | MtmV |
| 6MSAS | (198) | orsellenic acid synthase | 6.5x10⁻⁷⁶ | ATG/ | AviM |
| ActI | (207) | polyketide cyclase | 3.0x10⁻⁶⁶ | /TGA | CurF |
| ActII | 136 | polyketide cyclase | 5.0x10⁻⁵³ | ATG/TGA | SchB |
| ActIII | (308) | polyketide synthase | 8.6x10⁻¹⁴⁸ | GTG/ | PmsI |
| orf1 | 322 | unknown | | ATG/TGA | |
| orf2 | 654 | unknown | | ATG/TGA | |
| orf3 | 373 | integrase | 3.0x10⁻¹³ | ATG/TGA | YId |
| orf4 | 521 | chromosome partitioning protein | 3.3x10⁻¹⁰ | GTG/TAA | ParA |
| orf5 | 175 | unknown | | ATG/TGA | |
| orf6 | 139 | unknown | | ATG/TGA | |
| orf7 | 187 | unknown | | GTG/TGA | |
| orf8 | 266 | regulatory protein | 3.0x10⁻⁶⁶ | ATG/TGA | KorSA |
| OrfI | 127 | hydroxylase | 1.5x10⁻⁷ | ATG/TGA | SC4C6.24c |
| OrfII | 248 | unknown | | GTG/TGA | |
| OrfIII | 298 | hydroxylase | 3.3x10⁻⁹⁰ | GTG/TGA | SCA32 |
| OrfIV | 363 | unknown | 5.3x10⁻⁴³ | GTG/TGA | SC9C7.25 |
| OrfV | 288 | aminotransferase | 2.9x10⁻³⁷ | GTG/TGA | SCF55 |
| OrfVI | 1012 | glu-ammonia-ligase adenylyltransferase | exact | GTG/TGA | SCA32 |
| OrfVII | 236 | Methyltransferase | 8.0x10⁻⁶³ | GTG/TAG | SCF43A.25c |
| OrfVIII | 441 | Integral membrane protein | 8.9x10⁻⁹ | GTG/TGA | SCA32 |
| OrfIX | 478 | Integral membrane protein | 1.1x10⁻²¹ | ATG/TGA | MLB268 |
| OrfX | 504 | Membrane protein | 5.5x10⁻²⁰ | GTG/TGA | B1496.F1.14 |
| OrfXI | 251 | Immunity resistance protein | 1.1x10⁻⁹ | ATG/TGA | TFXG |
| IS-element | 1209 bp | insertional element | 5.7x10⁻¹⁶⁸ | | IS1136¹¹¹ |

FIG. 3

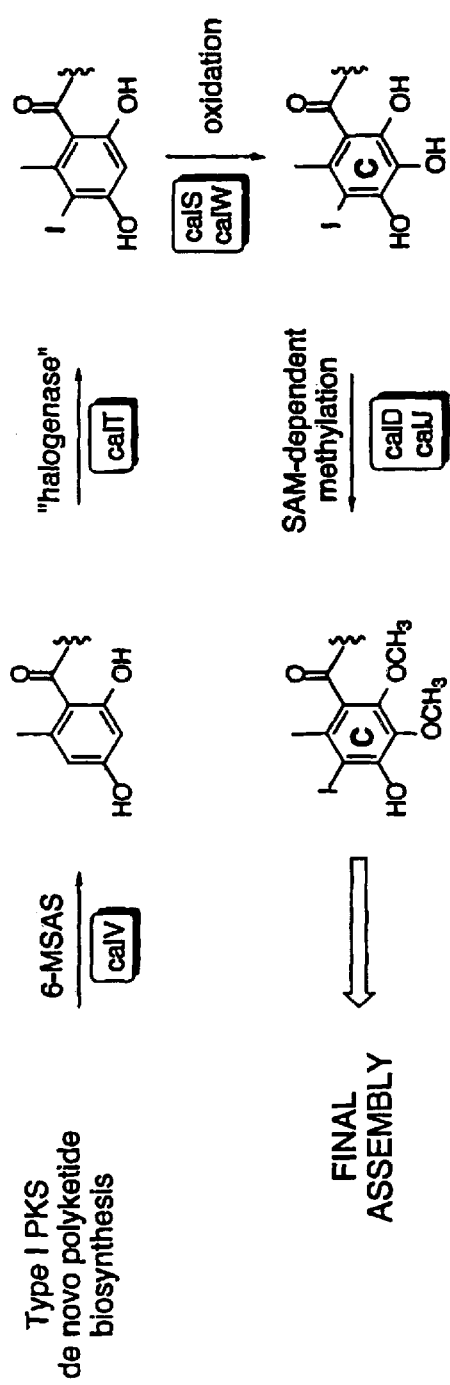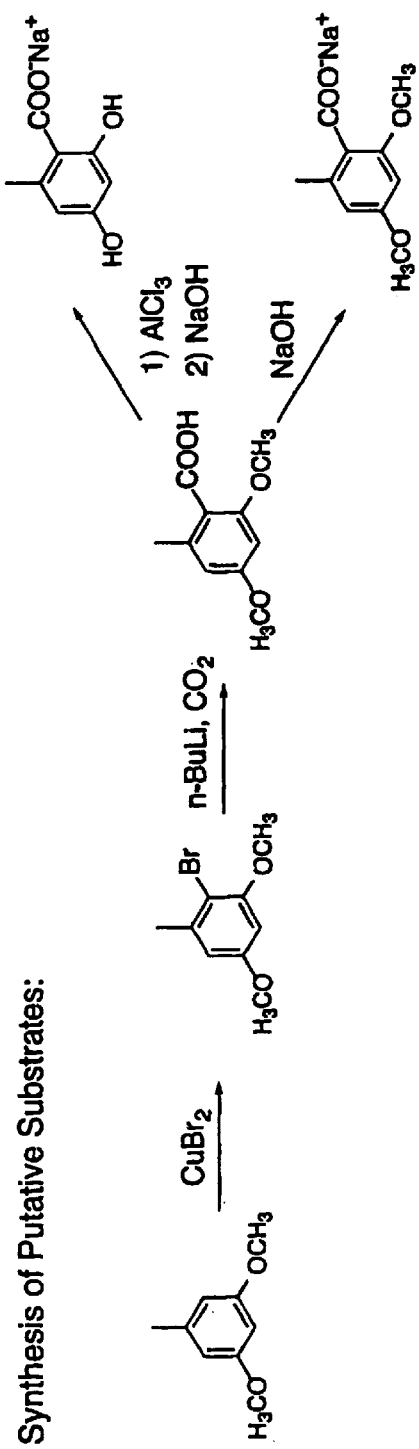
FIG. 11

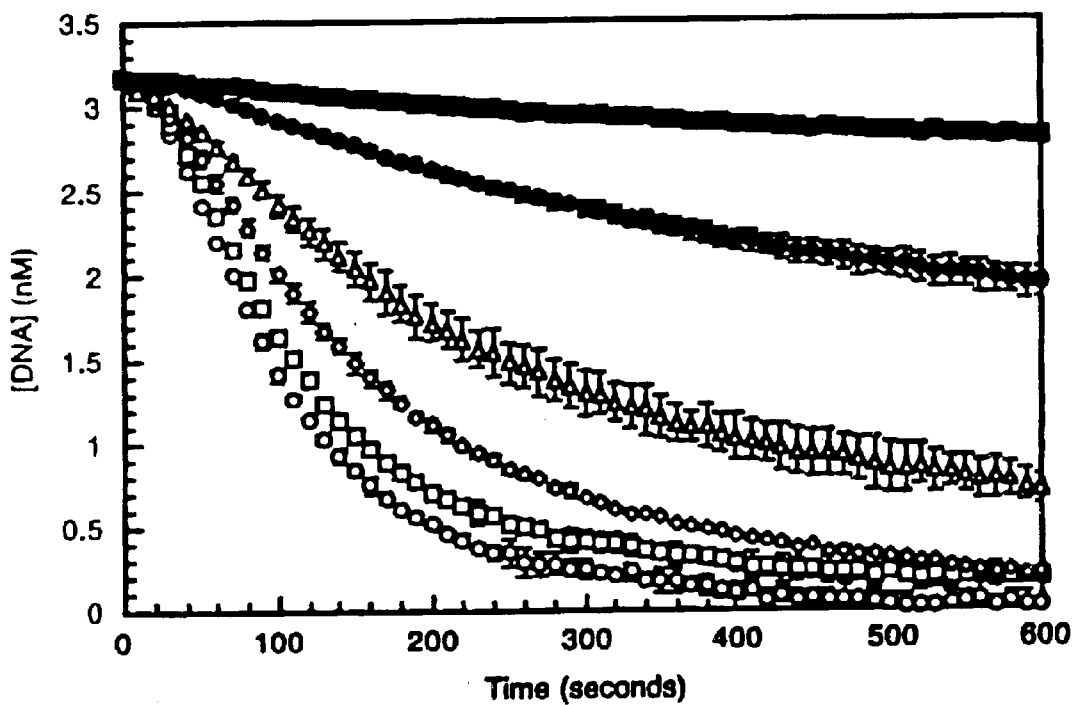
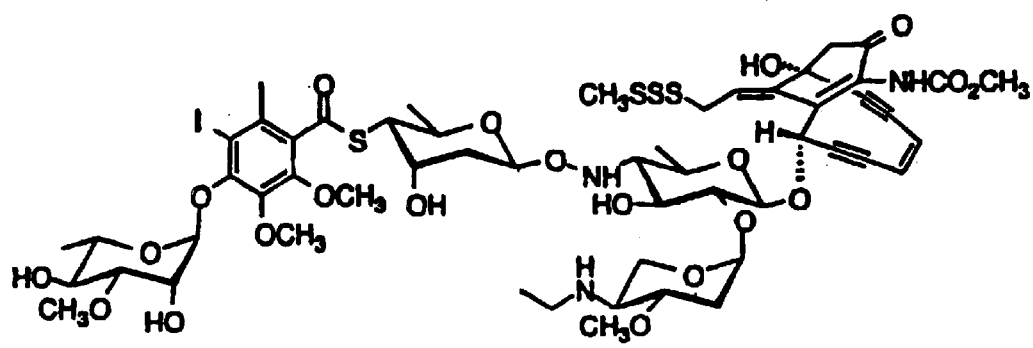
FIG. 15a

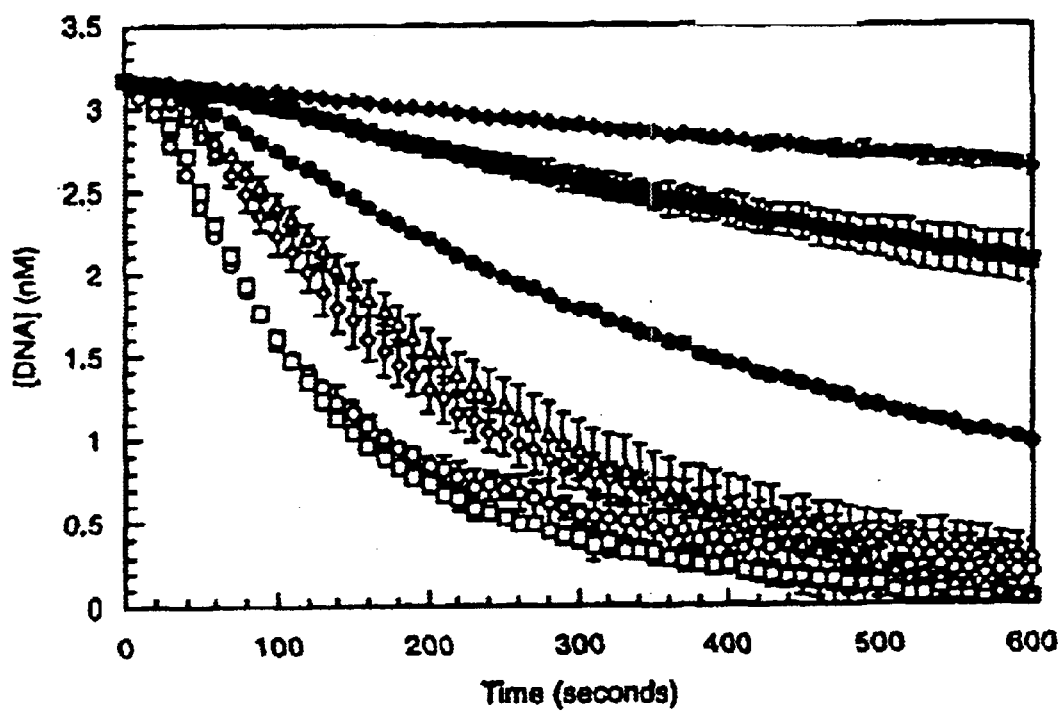
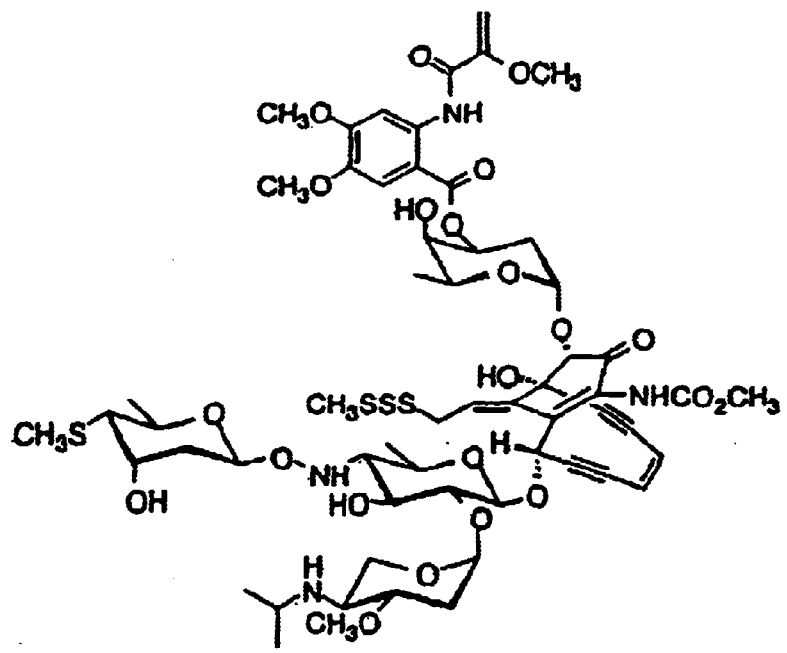
FIG. 15b

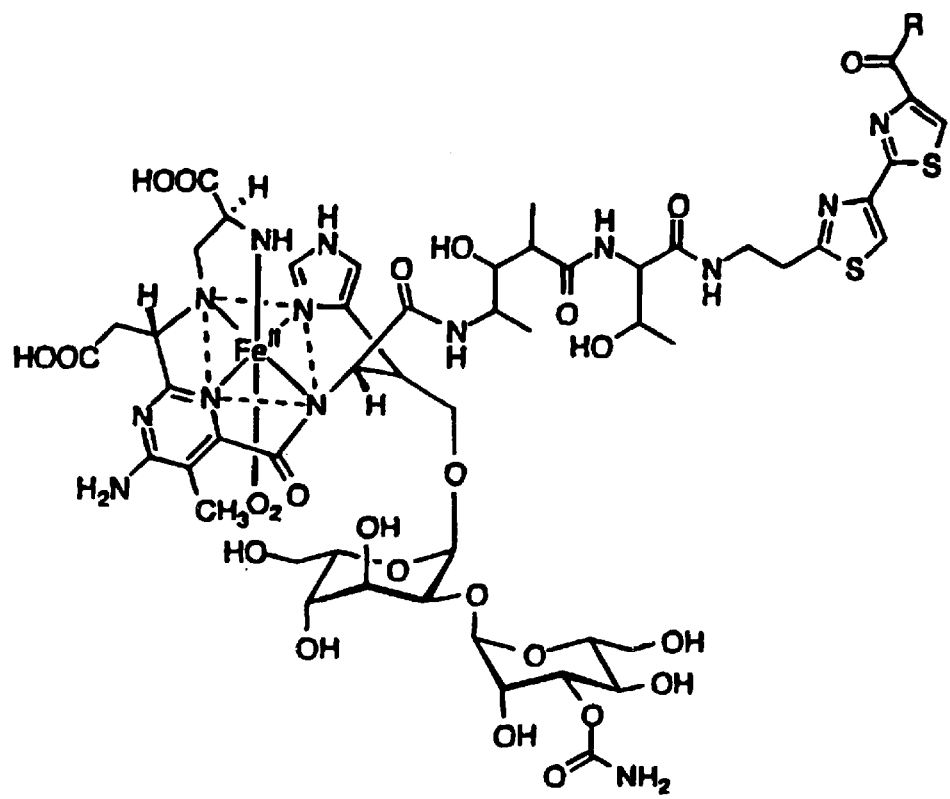
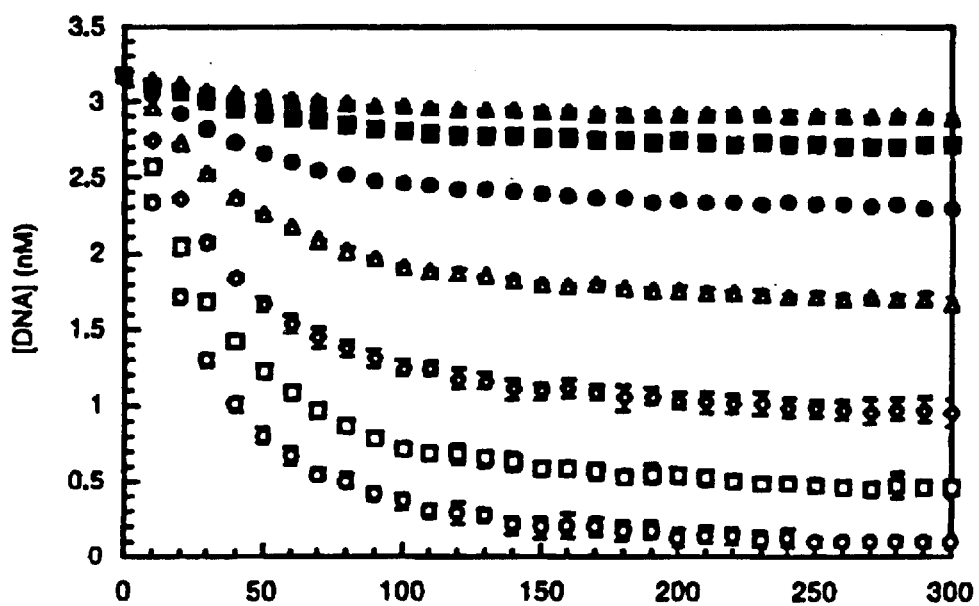
FIG. 16a

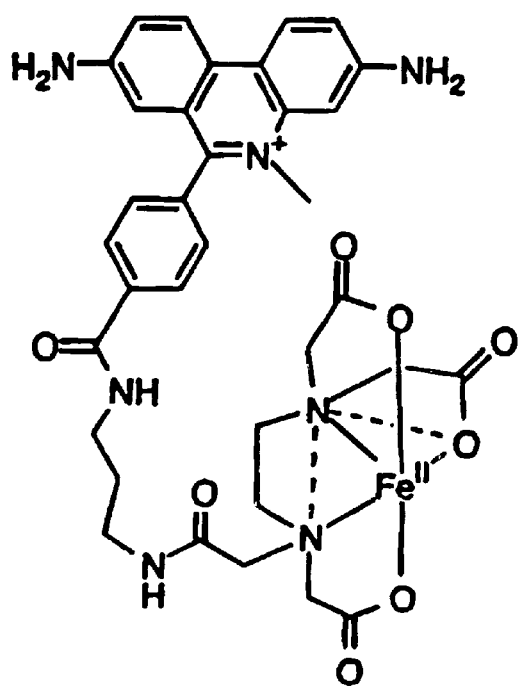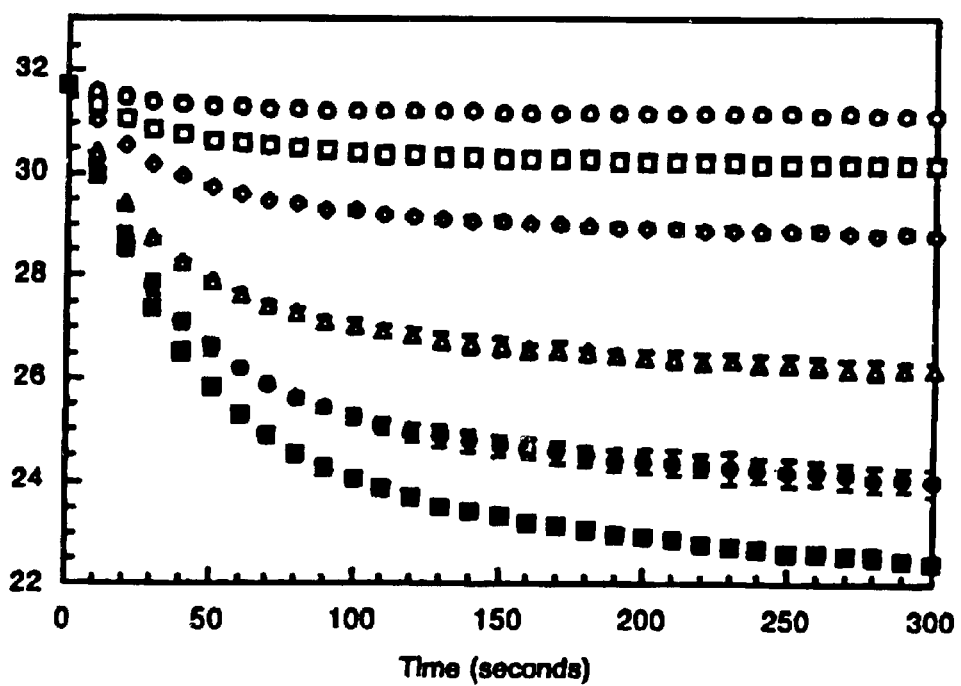
FIG.16c

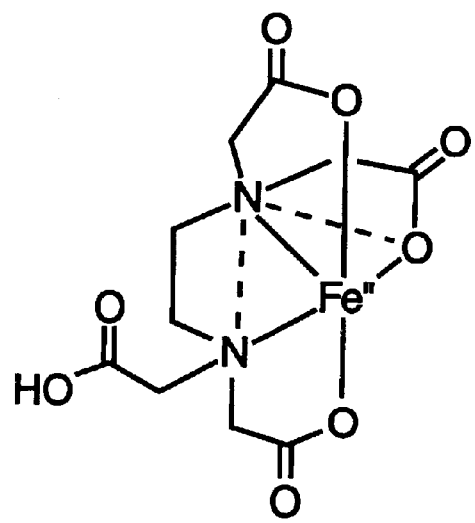
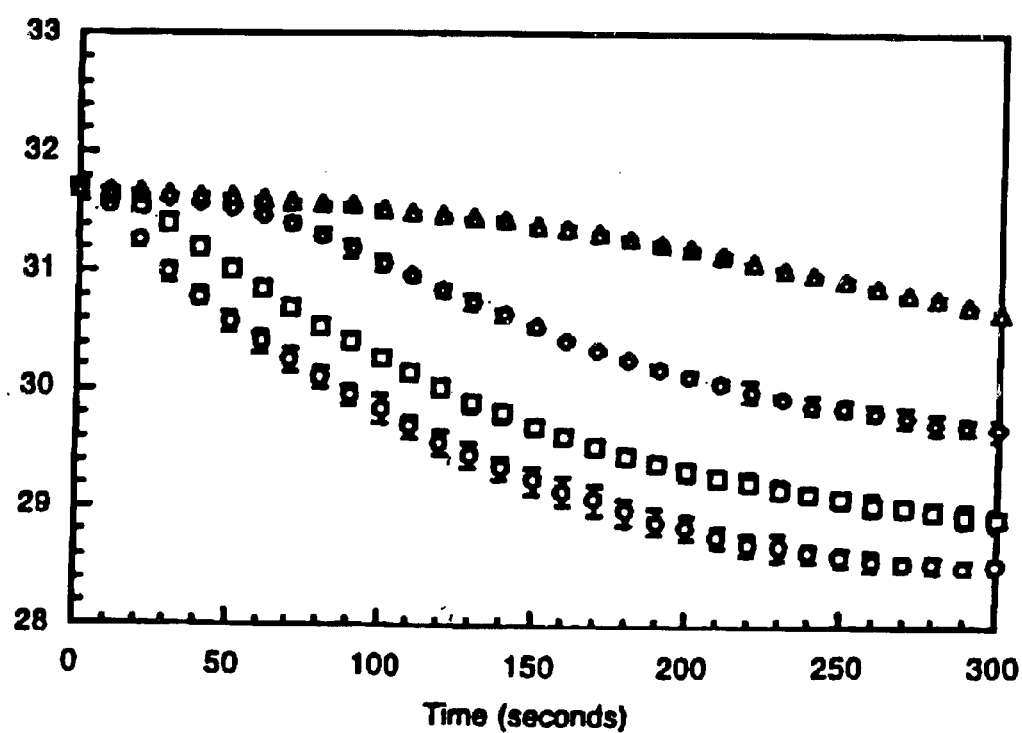
FIG. 16d

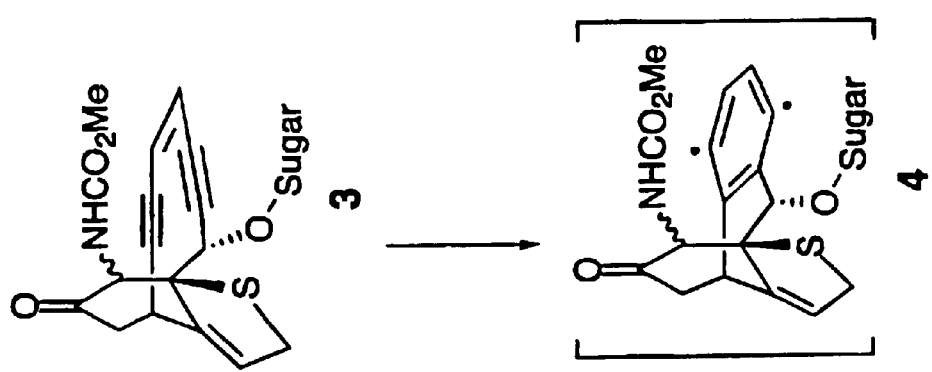
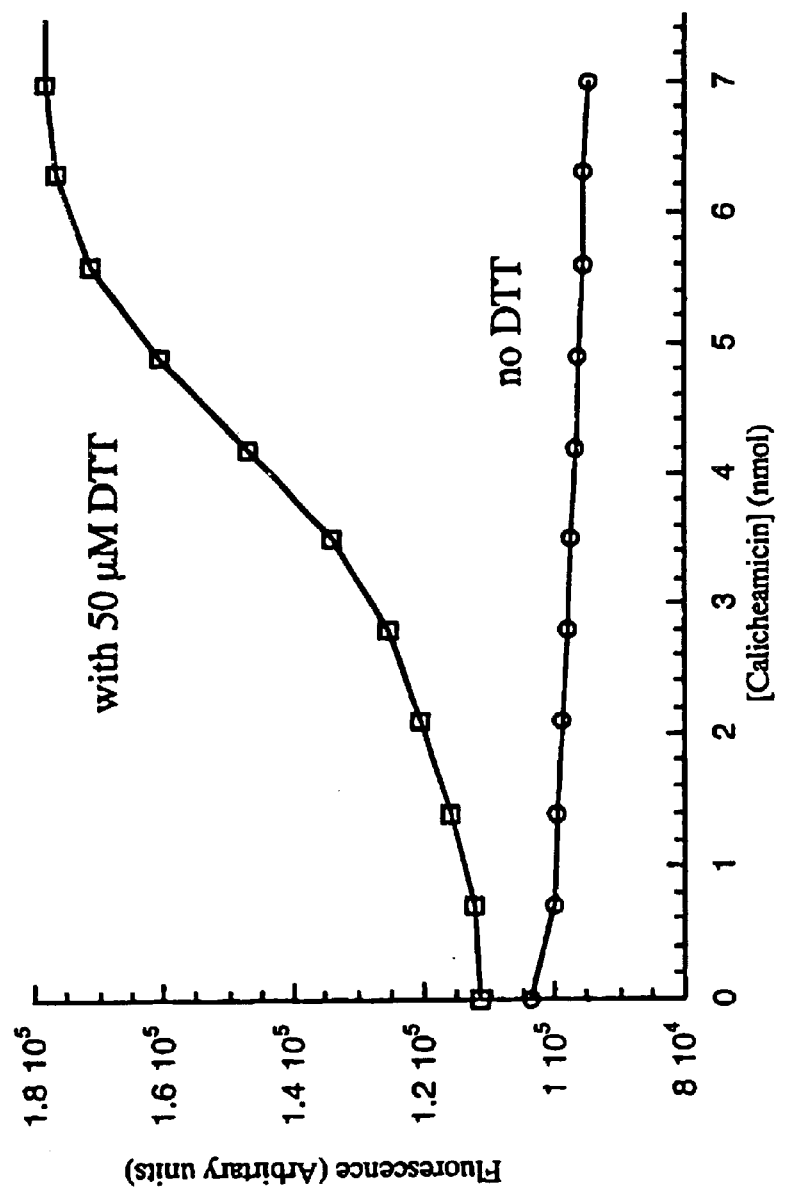
FIG. 18

MICROMONOSPORA ECHINOSPORA GENES CODING FOR BIOSYNTHESIS OF CALICHEAMICIN AND SELF-RESISTANCE THERETO

This application is a continuation-in-part of the non-provisional application Ser. No. 09/457,045, filed Dec. 7, 1999 now abandoned and claims benefit thereof, which application is incorporated herein by reference in its entirety. This application also claims benefit from provisional application Ser. No. 60/111,325 filed on Dec. 7, 1998, which application is incorporated herein by reference in its entirety.

FIELD OF THE INVENTION

The present invention relates to a biosynthetic gene cluster of *Micromonospora echinospora* spp. calichensis. In particular, the calicheamicin biosynthetic gene cluster contains genes coding for proteins and enzymes used in the biosynthetic pathway and construction of calicheamicin's aryltetrasaccharide and aglycone, and the gene conferring calicheamicin resistance. The present invention also relates to isolated genes of the biosynthetic cluster and their corresponding proteins. In addition, the invention relates to DNA hybridizing with the calicheamicin gene cluster and the isolated genes of that cluster. The invention also relates to expression vectors containing the biosynthetic gene cluster, the individual genes, or functional variants thereof.

BACKGROUND OF THE INVENTION

The enediyne antibiotics, which were discovered in the 1980's, have long been appreciated for their novel molecular architecture, their remarkable biological activity, and their fascinating mode of action. Enediyne antibiotics were originally derived by fermentation of microorganisms, including Micromonospora, Actinomadura, and Streptomyces. Rothstein, D. M., *Enediyne Antibiotics as Antitumor Agents*, p. 2 (1995). As a class, the enediyne antibiotics have been referred to as the most potent and highly active antitumor reagents yet discovered. Rothstein, D. M., *Enediyne Antibiotics as Antitumor Agents*, preface (1995).

To date, at least twelve members of this family of antibiotics have been discovered, all of which fall roughly into two categories. The members of the first category of enediynes are classified as chromoprotein enediynes because they possess a novel 9-membered ring chromophore core structure, which also requires a specific associated protein for chromophore stabilization. The members of the second category of enediyne are classified as non-chromoprotein enediynes. These enediynes contain a 10-membered ring, which requires no additional stabilization factors. This enediyne ring structure is often referred to as the "warhead." The warhead induces DNA damage, which is frequently a double-stranded cleavage and appears to be irreparable. This type of DNA damage is usually nonrepairable for the cell and is most often lethal. Because of these remarkable chemical and biological properties, there has been an intense effort by both the pharmaceutical industry and academia to study these substances with the goal of developing new and clinically useful therapeutic anti-tumor agents.

The 9-membered ring chromoprotein enediyne subfamily is comprised of: neocarzinostatin from *Streptomyces carzinostaticus*, (Myers, A. G., et al., *J. Am. Chem. Soc.*, 110, 7212–7214 (1988)); kedarcidin from Actinomycete L585-6, (Leet, J. E., et al., *J. Am. Chem. Soc.*, 114, 7946–7948 (1992)), N1999A2 from *Streptomyces globisporus*, (Yoshida, K., et al. *Tetrahedron Lett.*, 34, 2637–2640 (1993)), maduropeptin from *Actinomadura madurea*, (Schroeder, D. R., et al., *J. Am. Chem. Soc.*, 116, 9351–9352 (1994)); N1999A2 from Streptomyces sp. AJ9493, (Schroeder, D. R., et al., *J. Am. Chem. Soc.*, 116, 9351–9352 (1994)); actinoxanthin from Actinomyces globisporus, (Khokhlov, A. S., et al., *J. Antibiot., XXII*, 541–544 (1969)); largomycin from *Streptomyces pluricolorescens*, (Yamaguchi, T., et al., *J. Antibiot., XXIII*, 369–372 (1970)); auromomycin from *Streptomyces macromomyceticus*, (Yamashita, T., et al., *J. Antibiot., XXXII*, 330–339 (1979)), and sporamycin from *Streptosporangium pseudovulgare*, (Komiyama, K, et al., *J. Antibiot.*, XXX, 202–208 (1977)), all of which are believed to possess a novel bicylo[7.3.0.]dodecadiynene chromophore core structure essential for biological activity. In addition, with the exception of N1999A2, a required apoprotein acts as a stabilizer and specific carrier for the unstable chromophore, and for its transport and interaction with target DNA.

The non-chromophore enediyne subfamily is comprised of calicheamicin from *Micromonospora echinospora* spp. calichensis; namenamicin from *Polysyncraton lithostrotum*; esperamicin from *Actinomadura verrucosospora*; and dynemicin from *Micromonospora chersina*.

Enediyne antibiotics have potential as anticancer agents because of their ability to cleave DNA; however, many of these compounds are too toxic to be used currently in clinical studies. Today, only calicheamicin is known to be currently used in clinical trials; and it has provided promising results as an anticancer agent. For example, MyloTarg™, a calicheamicin-antibody conjugate also known as CMA-676 was approved by the FDA in January of 2000 to treat acute myelogenous leukemia. The enediynes also potentially have utility as anti-infective agents, provided that toxicity can be managed.

Calicheamicin has two distinct structural regions: the aryltetrasaccharide and the aglycone (also known as the warhead). The aryltetrasaccharide displays a highly unusual series of glycosidic, thioester, and hydroxylamine linkages and serves to deliver the drug primarily to specific tracts (5'-TCCT-3' and 5'-TTTT-3') within the minor groove of DNA when those sequences are available. However, specificity is also context-dependent. The aglycone of calicheamicin consists of a highly functionalized bicyclo[7.3.1] tridecadiynene core structure with an allylic trisulfide serving as the triggering mechanism. McGahren, W. J.,et al., *Enediyne Antibiotics as Antitumor Agents*, pp. 75–86 (1995). Once the aryltetrasaccharide is firmly docked, aromatization of the bicyclo[7.3.1]tridecadiynene core structure, via a 1,4-dehydrobenzene-diradical, results in the site specific oxidative double strand scission of the targeted DNA. Zein, N., et al., *Science*, 240, 1198–1201 (1988). The aglycone undergoes a reaction that yields carbon-centered diradicals, which are responsible for DNA cleavage.

This activity of calicheamicin has sparked considerable interest in the pharmaceutical industry culminating in the recent FDA approval of the calicheamicin-antibody conjugate MyloTarg™ (CMA-676) to treat acute myelogenous leukemia (AML). Additionally, similar strategies have been used in phase I trials to treat breast cancer. A massive program to examine calicheamicin conjugated to alternative delivery systems has also recently been undertaken. Hamann, P. R., et al., 87th *Annual Meeting of the American Association of Cancer Research*, Washington, D.C., pp. 471 (1996); Hinman, L. M., et al., *Cancer Res.*, 53, 3336 (1993); Hinman, L. M., et al., *Enediyne Antibiotics as Antitumor Agents*, pp. 87–105 (1995); Sievers, E. L., et al., *Blood*, 93, 3678–3684 (1999); Siegel, M. M., et al., *Anal. Chem.*, 69, 2716–2726 (1997); Ellestad, G. personal communication.

The biological activity and molecular architecture of calicheamicin has also prompted a search for potentially useful analogs. Of the numerous laboratories producing synthetic analogs, one group has produced a novel calicheamicin $\gamma^1_1$ shown to effectively suppress growth and dissemination of liver metastases in a syngeneic model of murine neuroblastoma. Lode, H. N., et al., *Cancer Res.*, 58, 2925–2928 (1998); Wrasidlo, W., et al., *Acta Oncologica*, 34, 157–164 (1995). In addition to synthesizing calicheamicin analogs, random mutagenesis of *M. echinospora* and screening for mutant strains with improved biosynthetic potential has also been pursued. Rothstein, D. M., *Enediyne Antibiotics as Antitumor Agents*, pp. 107–126 (1995).

The first total synthesis of calicheamicin was reported by Nicolaou and coworkers in 1992. Synthesizing this complex antibiotic, though, presents many disadvantages. For example, Nacelle's procedure only provides approximately a 0.007% yield and requires 47 steps. Halcomb, R. L., Enediyne Antibiotics as Antitumor Agents, pp. 383–439 (1995). Thus, the total synthesis of calicheamicin remains secondary to the isolation of calicheamicin from large fermentations of *M. echinospora*. Therefore, methods to produce mass amounts of calicheamicin and potentially useful variants are still needed. Fantini, A., et al., Enediyne Antibiotics as Antitumor Agents, pp. 29–48 (1995). Transferring calicheamicin DNA into producing strains of bacteria, such as Streptomyces, Micromonospora, other actinomyces species, or *E. coli*, as non-limiting examples, would address this need. However, prior to the discoveries of the present inventors, no cloned *M. echinospora* genes were available, and only a set of limited studies upon putative *M. echinospora* promoters were available. Lin, L. S., et al., *J. Gen. Microbiol.*, 138, 1881–1885 (1992); Lin, L. S., et al., *J. Bacteriol.*, 174, 3111–3117 (1992); Baum, E. Z., et al., *J. Bacteriol.*, 171, 6503–6510 (1989); Baum. E. Z., et al., *J. Bacteriol.*, 170, 71–77 (1988).

Calicheamicin's molecular architecture in conjunction with its useful biological activity and potential therapeutic value brand calicheamicin a target for the study of natural product biosynthesis. While the radical-based mechanism of oxidative DNA cleavage by calicheamicin (i.e. aromatization of the bicyclo[7.3.1]tridecadiynene core structure, via a 1,4-dehydrobenzene-diradical, resulting in the site specific oxidative double strand DNA cleavage) is well understood, it was unknown, prior to this invention, how Micromonospora constructs calicheamicin. As a result, before the present invention, there was a need to discover and understand calicheamicin biosynthesis. Prior to this discovery of the present inventors, knowledge of genes coding for non-chromoprotein enediyne biosynthesis was completely lacking.

The toxicity of the enediyne compounds, including calicheamicin, centers on the problem of directing the compound to cleave only the DNA of interest, such as tumor cell DNA, and not the DNA of the host. Due to calicheamicin's powerful ability to cleave DNA, scientists have investigated the mechanism by which calicheamicin-producing organism protects itself against the DNA-cleaving activity of the molecule (Rothstein, D. M., *Enediyne Antibiotics as Antitumor Agents*, p. 77 (1995)). Prior to this invention, knowledge of genes coding for non-chromoprotein enediyne self resistance was completely lacking.

SUMMARY OF THE INVENTION

The present invention relates to the first identification, isolation, and cloning of a nonchromoprotein enediyne biosynthetic gene cluster and mapping and nucleotide sequence analysis of the genes within the cluster. The invention provides the entire calicheamicin-biosynthetic cluster and biochemical studies of aryltetrasaccharide biosynthesis. Furthermore, the calicheamicin self-resistance gene and protein have been isolated, as have the genes and resulting enzymes for steps within the calicheainicin cascade. The invention also provides for construction of enediyne overproducing strains, for rational biosynthetic modification of bioactive secondary metabolites, for new drug leads, and for an enediyne combinatorial biosynthesis program.

The present invention provides an isolated nucleic acid molecule from a nonchromoprotein enediyne biosynthetic gene cluster from *Micromonospora echinospora* comprising said nucleic acid molecule, a portion or portions of said nucleic acid molecule wherein said portion or portions encode a protein, a portion or portions of said nucleic acid molecule wherein said portion or portions encode a biologically active fragment of a protein. The isolated nucleic acid molecule may be single- or double-stranded. As used herein, a nucleic acid molecule, polypeptide, or protein described as being "from" e.g., an organism or gene cluster, may have been isolated from such organism or gene cluster; alternatively, it may be a molecule which has been produced using synthetic, chemical, recombinant, or other such methods and comprise an amino acid or nucleotide sequence which may be isolated from such organism or gene cluster.

The present invention provides forty-eight genes, twenty-seven of which encode structural genes with the remainder encoding a variety of functions. The present invention is drawn to the following genes or nucleic acids: calC (SEQ ID No. 1), calH (SEQ ID No. 3), calG (SEQ ID No. 5), calA (SEQ ID No. 7), calB (SEQ ID No. 9), calD (SEQ ID No. 11, calF (SEQ ID No. 13), calI (SEQ ID No. 15), calJ (SEQ ID No. 17), calK (SEQ ID No. 19), calL (SEQ ID No. 21), calM (SEQ ID No. 23), calN (SEQ ID No. 25), calO (SEQ ID No. 27), calP (SEQ ID No. 29), calQ (SEQ ID No. 31), calR (SEQ ID No. 33), calS (SEQ ID No. 35), calT (SEQ ID No. 37), calU (SEQ ID No. 39), calV (SEQ ID No. 41), calW (SEQ ID No. 43), calX (SEQ ID No. 45), 6MSAS (SEQ ID No. 47), ActI (SEQ ID No. 49), ActII (SEQ ID No. 51), ActIII (SEQ ID No. 53), orf1 (SEQ ID No. 55), orf2 (SEQ ID No. 57), orf3 (SEQ ID No. 59), orf4 (SEQ ID No. 61), orf5 (SEQ ID No. 63), orf6 (SEQ ID No. 65), orf7 (SEQ ID No. 67), orf8 (SEQ ID No. 69), orfI (SEQ ID No. 71), orfII (SEQ ID No. 73), orfIII (SEQ ID No. 75), orfIV (SEQ ID No. 77), orfV (SEQ ID No. 79):, orfVI (SEQ ID No. 81), orfVII (SEQ ID No. 83), orfVIII (SEQ ID No. 85), orfIX (SEQ ID No. 87), orfX (SEQ ID No. 89), orfXI (SEQ ID No. 91), IS-element (DNA) (SEQ ID No. 93), calE (SEQ ID No. 94). The invention is also drawn to the following proteins or putative proteins: CalC (SEQ ID No. 2), CalH (SEQ ID No. 4), CalG (SEQ ID No. 6), CalA (SEQ ID No. 8), CalB (SEQ ID No. 10), CalD (SEQ ID No. 12), CalF (SEQ ID No. 14), CalI (SEQ ID No. 16), CalJ (SEQ ID No. 18), CalK (SEQ ID No. 20), CalL (SEQ ID No. 22), CalM (SEQ ID No. 24), CalN (SEQ ID No. 26), CalO (SEQ ID No. 28), CalP (SEQ ID No. 30), CalQ (SEQ ID No. 32), CalR (SEQ ID No. 34), CalS (SEQ ID No. 36), CalT (SEQ ID No. 38), CalU (SEQ ID No. 40), CalV (SEQ ID No. 42), CalW (SEQ ID No. 44), CalX (SEQ ID No. 46), 6MSAS (SEQ ID No. 48), ActI (SEQ ID No. 50), ActII (SEQ ID No. 52), ActIII (SEQ ID No. 54), Orf1 (SEQ ID No. 56), Orf2 (SEQ ID No. 58), Orf3 (SEQ ID No. 60):, Orf4 SEQ ID No. 62), Orf5 (SEQ ID No. 64), Orf6 (SEQ ID No. 66), Orf7 (SEQ ID No. 68), Orf8 (SEQ ID No. 70), OrfI (SEQ ID No. 72), OrfII (SEQ ID No.

74), OrfIII (SEQ ID No. 76), OrfIV (SEQ ID No. 78), OrfV (SEQ ID No. 80), OrfVI (SEQ ID No. 82), OrfVII (SEQ ID No. 84), OrfIII (SEQ ID No. 86), OrfIX (SEQ ID No. 88), OrfX (SEQ ID No. 90), OrfXI (SEQ ID No. 92), CalE (SEQ ID No. 95).

In one aspect, the present invention is directed to an isolated nucleotide molecule, wherein the nucleotide molecule hybridizes with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94, or a functional derivative of the isolated nucleotide molecule which hybridizes with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In one embodiment of the invention, the isolated nucleotide molecule has the nucleotide sequence of at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94, i.e., 100% complementarity (sequence identity) with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In another embodiment of the invention, the isolated nucleotide molecule has at least 90% complementarity (sequence identity) with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In yet another embodiment of the invention, the isolated nucleotide molecule has at least 80% complementarity (sequence identity) with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In yet another embodiment of the invention, the isolated nucleotide molecule has at least 70% complementarity (sequence identity) with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In yet another embodiment of the invention, the isolated nucleotide molecule has at least 60% complementarity (sequence identity) with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94. In still yet another embodiment of the invention, the isolated nucleotide molecule is substantially complementary to at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 94.

In another embodiment of the invention, there is provided an isolated protein encoded by a DNA molecule as described herein above, or a functional derivative thereof. A preferred protein has the amino acid sequence of at least one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, or 95 or a functional variant or derivative of one or more of those polypeptides.

In another embodiment, the present invention provides an isolated nucleic acid molecule from *Micromonospora echinospora* comprising a nonchromoprotein enediyne biosynthetic gene cluster, a portion or portions of said gene cluster wherein said portion or portions encode a protein, a portion or portions of said gene cluster wherein said portion or portions encode a biologically active fragment of a protein, a single-stranded nucleic acid molecule derived from said gene cluster, or a single-stranded nucleic acid molecule derived from a portion or portions of said gene cluster.

In particular, the present invention provides an isolated nucleic acid molecule from *Micromonospora echinospora* spp. calichensis that is involved in the biosynthesis of calicheamicin. In another embodiment, the present invention also relates to nucleic acids capable of hybridizing with one or more isolated nucleic acids from a nonchromoprotein enediyne biosynthetic gene cluster from *Micromonospora echinospora* spp. calichensis. In a further embodiment, the invention provides an expression vector comprising an isolated nucleic acid molecule from a nonchromoprotein enediyne biosynthetic gene cluster from *Micromonospora echinospora*. In yet a further embodiment the invention provides a cosmid comprising an isolated nucleic acid molecule from a nonchromoprotein enediyne biosynthetic gene cluster from *Micromonospora echinospora*.

In preferred embodiments, the invention provides the isolated nucleic acid molecules of SEQ ID Nos. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 and 94.

In an additional embodiment, the present invention provides a host cell transformed with an isolated nucleic acid molecule from a nonchromoprotein enediyne biosynthetic gene cluster from *Micromonospora echinospora*. Host cells can optionally be of bacterial, yeast, fungal, insect, plant or mammalian origin and can be transformed according to standard methods. In a preferred embodiment, the host cell is the bacterium *E. coli*, Streptomyces spp., or Micromonospora spp. In a more preferred embodiment, the host cell is the bacterium from the genus Streptomyces or from the genus Micromonospora.

In a further embodiment, the invention is directed to a host cell transformed with an expression vector comprising at least one of the nucleotide sequences of SEQ ID Nos. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, or 94 or a portion of portions thereof or an allele or alleles thereof. In preferred embodiments, the host cells produce a biologically functional protein or portion of a protein, which protein or portion thereof is encoded by the expression vector.

In a specific embodiment, the invention is directed to a host cell transformed with an expression vector comprising calC, or a portion(s) or allele(s) thereof, operably linked to regulatory sequences that enable expression of CalC. In another specific embodiment, the invention provides a host cell transformed with an expression vector comprising calH, or a portion(s) or allele(s) thereof, operably linked to regulatory sequences that enable expression of CalH. In a yet further specific embodiment, the invention provides a host cell transformed with an expression vector comprising calQ, or a portion(s) or allele(s) thereof, operably linked to regulatory sequences that enable expression of CalQ. Likewise, the invention provides a host cell transformed with an expression vector comprising calG, or a portion(s) or allele (s) thereof, operably linked to regulatory sequences that enable expression of CalG.

In a yet further embodiment, the invention is directed to a host cell transformed with an expression vector encoding at least one polypeptide comprising the amino acid sequence of SEQ ID Nos. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, or 95 or a functional variant of one or more of those polypeptides. In preferred embodiments, the host cells produce a biologically functional protein or portion of a protein, which protein or portion thereof is encoded by the expression vector.

In a specific embodiment, the invention is directed to a host cell transformed with an expression vector encoding CalC, or a functional derivative thereof, operably linked to regulatory sequences that enable expression the encoded polypeptide. In another specific embodiment, the invention provides a host cell transformed with an expression vector encoding CalH, or a functional derivative thereof, operably linked to regulatory sequences that enable expression of the encoded polypeptide. In a yet another specific embodiment, the invention provides a host cell transformed with an expression vector encoding CalQ, or a functional derivative thereof, operably linked to regulatory sequences that enable expression of the encoded polypeptide. Likewise, the invention provides a host cell transformed with an expression vector encoding the CalG, or a functional derivative thereof, operably linked to regulatory sequences that enable expression of the encoded polypeptide.

The invention further provides a method of expressing a protein by culturing a host cell transformed with an expression vector of the present invention, and incubating the host cell for a time and under conditions allowing for protein expression.

In yet another embodiment the invention provides a method of purifying calicheamicin using affinity chromatography. A sample containing calicheamicin is contacted with an affinity matrix having the protein CalC bound thereto, for a time and under conditions allowing calicheamicin to bind to the matrix, eluting calicheamicin from the matrix, and recovering calicheamicin.

In a further embodiment the present invention provides polypeptides comprising the amino acid sequences of SEQ ID Nos. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95.

In yet a further embodiment the invention provides the production of the following two new macrolides:

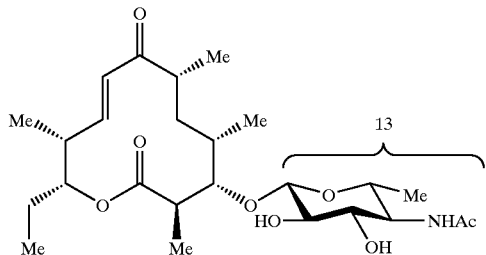

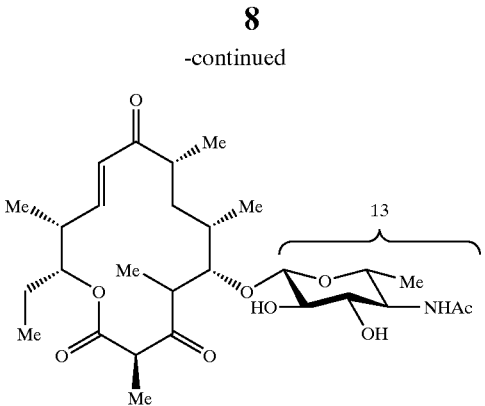

The invention further provides a method of conferring calicheamicin resistance to a subject comprising obtaining cells from the subject, transforming the cells with the calicheamicin self-resistance gene, and returning the cells to the subject. Alternatively, the calicheamicin self-resistance gene can be targeted and delivered to the desired host cells through known gene therapy delivery systems.

The invention further provides a method of producing calicheamicin analogs by altering calicheamicin or its bioactive metabolites through the modulation of the expression of calD, E, F, G, H, J, K, N, O, P, Q, S, T U, V, W, X, 6MSAS, actI-III, orfI, orfIII, orfV, and orfVII. Such modulation can be achieved through selective "knock out", as well as heterologous expression of these genes and their products. Various combinations of these either mutated or wild type gene products may be used in either in vitro or in vivo calicheamicin analog production.

The invention further provides a method for increasing the production of calicheamicin through the introduction of multiple copies of positive regulators and transporters and or by eliminating or reducing the expression of negative regulators (e.g., CalA, B, I, L, Orf8). Additionally, upregulation of calicheamicin resistance genes calC, calN and orfXI can be used to decrease the toxicity of calicheamicin to healthy tissues and cells during therapy.

In a yet further embodiment, the invention provides for a method of transposon mediated mutagenesis or moving chromosomal DNA fragments in vivo through expression of the orf3 integrase and the IS insertional element.

The advantages of the present invention are numerous. Isolation of and the ability to clone calicheamicin DNA opens the door for genetic analysis of calicheamicin biosynthesis, as such analysis requires the ability to obtain large quantities of DNA which codes for calicheamicin biosynthesis. Using the teachings of the present invention, one can study calicheamicin biosynthesis via mutagenesis of *M. echinospora*. For example, one can isolate and characterize mutants blocked in calicheamicin biosynthesis and then analyze their defective or partial calicheamicin products. Additionally, particular a enzyme or enzymes can be overexpressed or underexpressed after subcloning its gene into a host such as *E. coli*, and the results of such overexpression or underexpression can be studied to reveal the enzyme's function. Furthermore, the cloning of biosynthetic genes can ultimately result in increased yields of the gene product by cloning and expressing the biosynthetic gene encoding the rate-limiting enzyme back into the producing organism.

Further, it may also be possible to generate novel products by cloning biosynthetic genes into strains that make related compounds. Such genes could endow the host organism with the ability to carry out new reactions on the enediyne nucleus, and thus produce novel drugs. The present invention thus also provides means for biosynthetic modification of bioactive secondary metabolites through enediyne combinatorial biosynthesis. As most pharmaceutical drug leads are inspired by naturally occurring compounds, and given the challenge posed in synthesizing these metabolites, genetic manipulation of the sugar appendage on the metabolites offers avenues for creating potential new drugs. Thus the emerging field of combinatorial biosynthesis has become a rich new source for modified non-natural sugar scaffolds. Marsden, A., et al., Science 1998, 279, 199–201. Problems inherent with the genetic manipulation of the sugar appendage relate to the fact that naturally occurring bioactive secondary metabolites possess unusual carbohydrate ligands, which serve as molecular recognition elements critical for biological activity. Macrolide Antibiotics, Chemistry, Biology and Practice, 1984. Without these essential sugar attachments, the biological activities of most clinically important secondary metabolites are either completely abolished or dramatically decreased. Currently, techniques for the genetic manipulation of the sugar appendage for a given metabolite rely mainly on the alteration and/or deletion of a small subset of genes required to construct and attach each desired sugar moiety. Thus there is a need to develop alternate strategies to construct and attach non-naturally occurring sugars. The present invention addresses this need. The present invention utilizes the fact that glycosyltransferases, which are responsible for the final glycosylation of certain secondary metabolites, show a high degree of promiscuity toward the nucleotide sugar donor. Zhao, L., et al., J. Am. Chem. Soc. 1988, 120, 12159–12160. This unselectivity of the glycosyltransferases has the potential for allowing modification of the crucial glycosylation pattern of natural, or non-natural, secondary metabolite scaffolds in a combinatorial fashion. The present invention discloses a method using the recruitment and collaborative action of sugar genes from a variety of biosynthetic pathways to construct composite gene clusters, which make and attach non-natural sugars.

Insight into how Micromonospora self resistance gene and gene products act to control the toxic effects of calicheanicin offers new avenues of clinical research. For example, knowledge of the mechanisms underlying calicheamicin resistance, as provided by the present disclosure, can provide the means necessary to use higher doses of calicheamicin while simultaneously inhibiting the toxic effects of the drug on non-cancer cells. Additionally, understanding the mechanism behind calicheamicin's self-resistance may aid in the understanding of self-resistance in other enediyne antibiotics, thereby potentially making useful those enediynes once thought to be too toxic to be viably used as therapeutic agents. The calicheamicin self-resistance mechanisms elucidated utilizing the present invention provide gene therapy approaches, for example, via introduction of enediynes resistance genes into bone marrow cells, thereby increasing resistance and allowing tolerance to chemotherapeutic doses of calicheamicin. Banerjee, D., et al., *Stem Cells*, 12, 378–385 (1994). Thus, understanding calicheamicin self-resistance will significantly aid continuing clinical studies involving calicheamicin and the enediynes. The present invention addresses this need as it provides for the isolation and characterization of a resistance gene and its associated protein for any nonchromoprotein enediynes.

BRIEF DESCRIPTION OF THE FIGURES

FIG. 1 depicts the summary of the cosmid clones isolated from *M. echinospora* genomic library. This figure illustrates the results of the screening of the genomic library for clones carrying the calicheamicin biosynthetic cluster.

FIG. 2 shows a restriction map of a portion of cosmid clones 4b, 13a, and 56 and the corresponding location of cal genes from *M. echinospora*.

FIG. 3 is a table of the open reading frames ("orfs") in the calicheamicin biosynthetic cluster. This table lists the polypeptides that the genes encode for as well as their proposed or actual determined function in the biosynthetic pathway. [a]Assignments based upon BLAST search at the amino acid level unless otherwise noted. [b]Highest probability score obtained. [c]Assignment based on biochemical studies. [d]Only a portion of the orf has been elucidated.

FIG. 4 is a graph of the UV-visible absorption spectra of purified mbp-CalC. The purified mpb-CalC was analyzed in the following solution: 52 $\mu$M mpb-CalC; 10 mM Tris.-HCl, pH 7.5). The inset shows the results of low temperature (4.3 K) the X-band EPR analysis of CalC. 250 $\mu$M mpb-CalC containing 0.5 mol Fe per mol CalC was analyzed in 10 mM Tris.-HCl, pH 7.5. The spectrometer settings were as follows: field set=2050 G; scan range=4,000G; time constant=82 s; modulation amplitude=16 G; microwave power=31 $\mu$W; frequency=9.71 Ghz; gain=1000; determined spin quantitation=90±10$\mu$M Fe.

FIG. 4(*b*) provides the results of the mbp-CalC in vitro assay.

FIG. 5 depicts the postulated routes for the biosynthesis of required nucleotide sugars. The enzymes are depicted as follows: $E_{deox}$=deoxygenase; $E_{am}$=aminotransferase; $E_{ep}$=epimerase; $E_{met}$=methyltransferase; $E_{od}$=4,6-dehydratase; $E_{ox}$=oxidase; $E_{p}$=nucleotidyltransferase; $E_{red}$=reductase; $E_{sh}$=sulfhydrytransferase.

FIG. 6 illustrates a schematic representation of the in vivo production of pikromycin/methymycin-calicheamicin hybrid metabolites.

FIG. 7 depicts the *Streptomyces venezuela* methymycin/pikromycin gene cluster. Eight open reading frames (desI–desVIII) in this cluster have been assigned as genes involved in desosamine biosynthesis. This figure also depicts the hybrid pathway toward new methymycin/pikromycin derivatives (11 and 12) produced after heterologous expression of the calH gene of calicheamicin in a *S. venezuela* mutant.

FIG. 8 illustrates calicheamicin's (6) four unique sugars which are crucial to tight DNA binding. Sugar (9) is derived from 4-amino-4,6-dideoxyglucose (8) and is part of the restricted N—O connection between sugars A and B. Compound 8 is derived from the corresponding 4-ketosugar (7) via a transamination reaction. The gene calH encodes the desired C-4 aminotransferase allowing conversion of compound (7) to compound (8).

FIG. 9 is a map illustrating the relative loci of the 48 identified genes spanning approximately 65 KB of continuous sequence. Eight of the genes identified show no homologs in the public databases.

FIG. 10 depicts additional postulated routes for the biosynthesis of required nucleotide sugars. The enzymes are depicted as follows: $E_{deox}$=deoxygenase; $E_{am}$=aminotransferase; $E_{ep}$=epimerase; $E_{met}$=methyltransferase; $E_{od}$=4,6-dehydratase; $E_{ox}$=oxidase; $E_{p}$=nucleotidyltransferase; $E_{red}$=reductase; $E_{sh}$=sulfhydrytransferase.

FIG. 11 is a schematic showing the iodination of orsellenic acid mediated by CalV and CalT, as well as the subsequent steps of oxidation, mediated by CalS and CalW and methylation, mediated by CalD and CalJ. Additionally, the figure shows the synthesis of putative substrates for the reaction.

Figure 12:
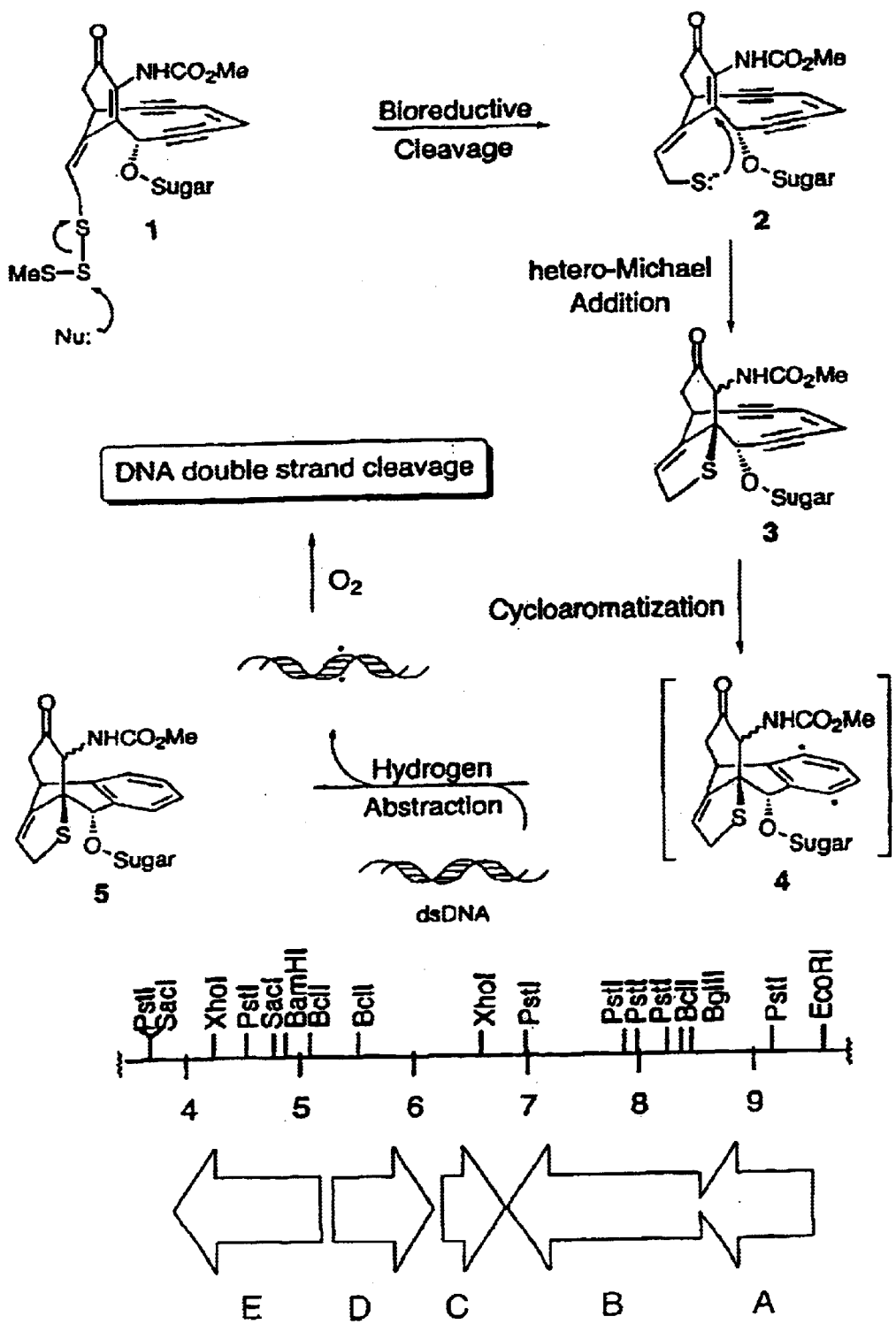

FIG. 12 describes the mechanism of calicheamicin resistance in Micromonospora. calC confers calicheamicin resistance to bacteria.

Figure 13:
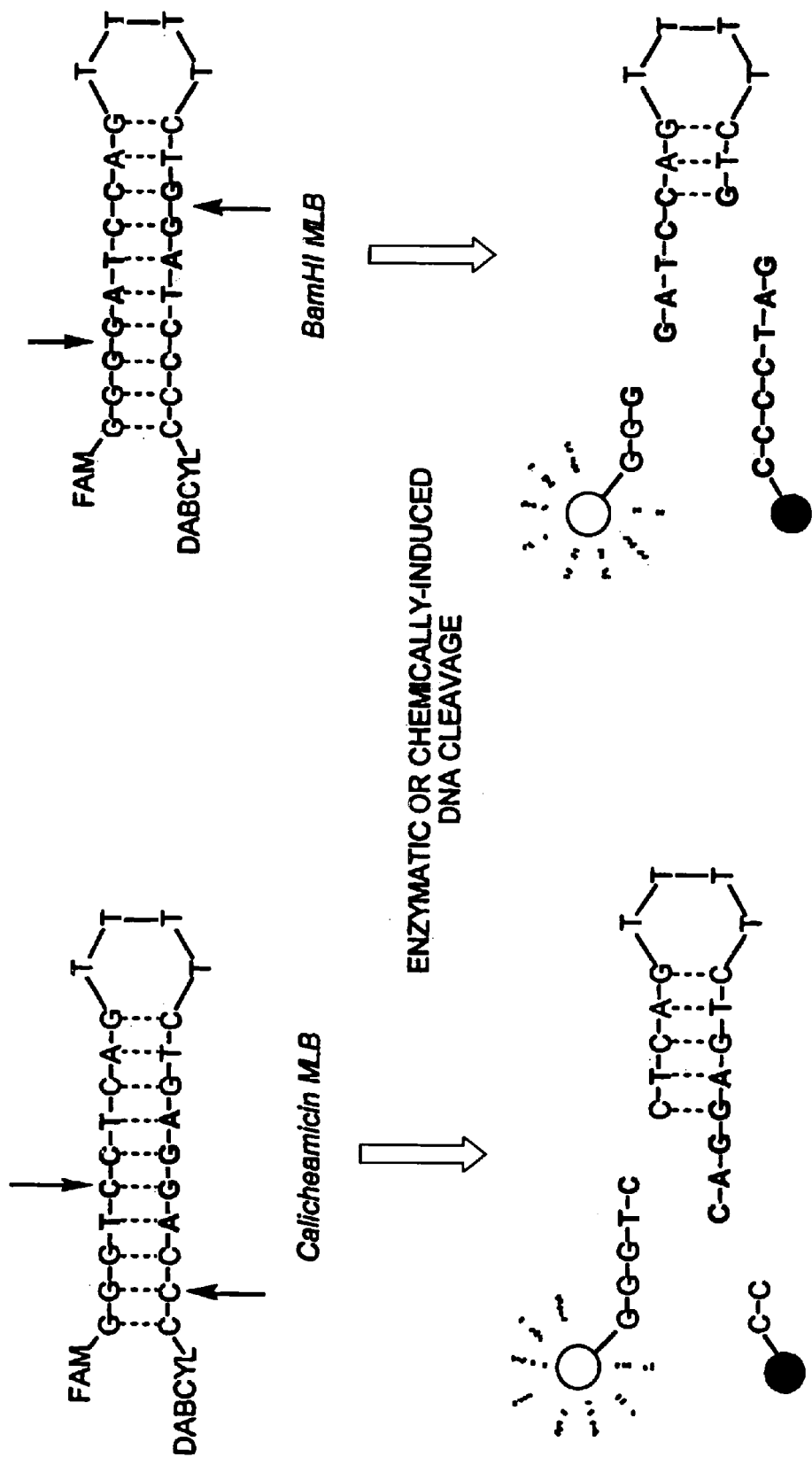

FIG. 13 A schematic diagram of the first continuous assay for enediyne-induced DNA cleavage, the Molecular Break Lights. The solid lines represent covalent bonds, dashed lines represent hydrogen bonding, letters represent arbitrary bases, the gray shaded ball represents the fluorophore (FAM: fluorescein), the black ball represents the corresponding quencher (DABCYL:4-(4-'demethylaminophenylazo)-benzoic acid) and the dashed wedges represent fluorescence. Generally, molecular beacons operate by a separation of the fluorophore-quencher pair resulting in a corresponding fluorescent signal. Molecular break lights, as illustrated in the figure, operate through cleavage of the stem by an enzymatic or non-enzymatic nuclease activity resulting in the separation of the fluorophore-quencher pair and corresponding fluorescent signal. In this study, Molecular break lights contain either a preferred calicheamicin recognition site (bold-faced, TCCT) or the BamHI recognition site (bold-faced, GGATCC). The predicted cleavage sites are illustrated by arrows.

Figure 14A:
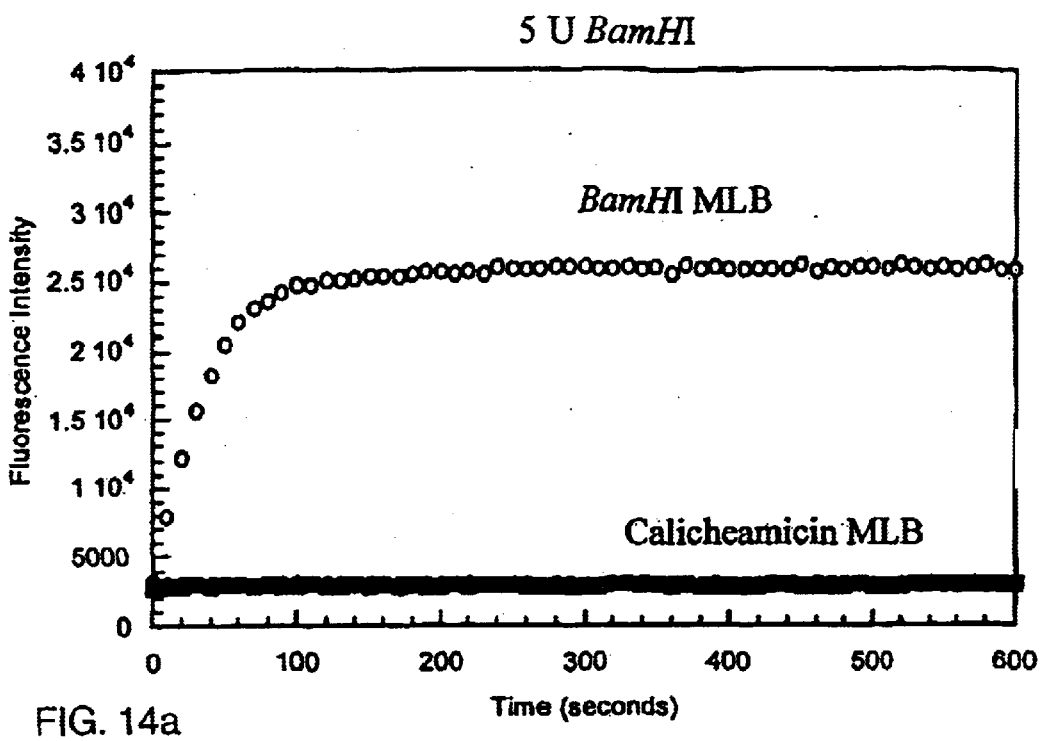

FIG. 14 shows the demonstration of molecular break light specificity and general proof of principle. The observed change in fluorescence intensity over time of an assay containing 3.2 nM break light at 37° C. (a) Break light calicheamicin MLB (break light A) with 100 U BamHI (□), BamHI MLB (break light B) with 100 U BamHI (○) and BamHI MLB without enzyme (♦) (10 mM Tris.HCl, 50 mM NaCl, 10 mM MgCl$_2$, 1 mM DTT, pH 7.9; $\lambda_{Ex}$=485 nm, $\lambda_{Em}$=517 nM). (b) calicheamicin MLB (break light A) with and 10 U DNaseI (□), BamHI MLB (break light B) with 10 U DNaseI (○) and calicheamicin MLB (break light A) without enzyme (•) (40 mM Tris.HCl, 10 mM MgSO$_4$, 1 mM CaCl$_2$, pH 8.0; $\lambda_{Ex}$=485 nm, $\lambda_{Em}$=517 nM). This is the most sensitive assay for BamHI and DNaseI DNA cleavage activity to date.

FIG. 15 shows the cleavage of calicheamicin MLB (break light A) by calicheamicin and esperamicin. The observed DNA cleavage over time of an assay containing 3.2 calicheamicin MLB at 37° C. (40 mM Tris.HCl, pH 7.5; $\lambda_{Ex}$=485 nm, $\lambda_{Em}$=517 nM), DTT (50 μM) and varied enediyne. (a) Calicheamicin concentrations: 31.7 nM (○), 15.9 nM (□), 3.2 nM (◇), 1.6 nM (Δ), 0.78 nM (•) and 0.31 nM (■). (b) Esperamicin concentrations: 31.7 nM (○), 15.9 nM (□), 3.2 nM (◇), 1.6 nM (Δ), 0.78 nM (•), 0.31 nM (■) and 0.15 nM (♦). These results represent the first continuous and most sensitive assay for enediyne-induced DNA cleavage.

FIG. 16(a) The observed DNA cleavage over time of an assay containing a constant 3.2 nM break light A at 37° C. (50 mM sodium phosphate, 2.5 mM ascorbate, pH 7.5; $\lambda_{Ex}$=485 nm, $\lambda_{Em}$=517 nM) and varied bleomycin. Bleomycin concentrations: 200 nM (○), 100 nM ( ), 50 nM (◇), 25 nM (Δ), 12.5 nM (●), 5 nM (■) and 2.5 nM (▲). (c) The observed DNA cleavage over time of an assay containing a constant 32 nM break light A at 37° C. (40 mM Tris.HCl, 2.5 mM ascorbate, pH 7.5; $\lambda_{Ex}$=485 nm, $\lambda_{Em}$=517 nM) and varied MPE. Fe(II) concentrations: 50 nM (○), 125 nM (□), 250 nM (◇), 500 nM (Δ), 1 μM (●) and 2 μM (■). (d) The observed DNA cleavage over time of an assay containing a constant 32 nM break light A at 37° C. (40 mM Tris.HCl, 2.5 mM ascorbate, pH 7.5; $\lambda_{Ex}$=485 nm, $\lambda_{Em}$=517 nM) and varied Fe$^{+2}$-EDTA. Fe(II) concentrations: 12.5 μM (○), 6.3 M (□), 3.1 μM (◇), and 1.3 μM (Δ).

Figure 17:
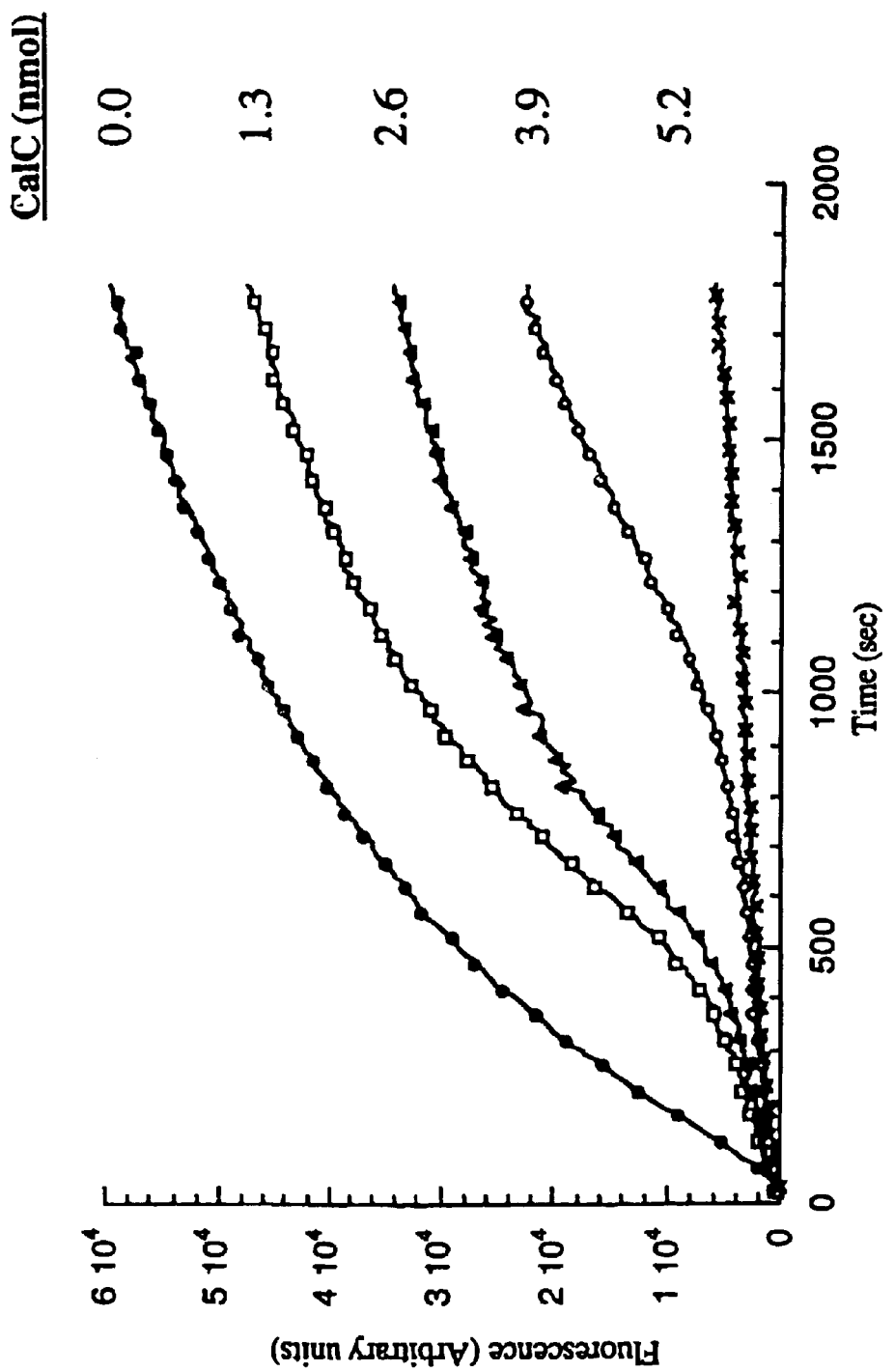

FIG. 17 shows the direct in vitro inhibition of calicheamicin-mediated DNA cleavage using the break light assay. 3.6 pM break light A is coincubated with 3.5 nM calicheamicin with increasing amounts of CalC. Complete inhibition of calicheamicin is achieved with roughly 2-fold excess of CalC. CalC has no effect on esperamicin-induced cleavage of DNA.

FIG. 18 shows the interaction between CalC and "activated" calicheamicin as measured by an increase in tryptophan fluorescence of CalC. CalC has 5 tryptophan and no cysteine residues and is unaffected by the reductive activator dithiothreitol (DTT). As the concentration of calicheamicin (3) increases in the absence of DTT there is little change in the CalC Trp fluorescence intensity. The addition of DTT to "activate" calicheamicin (4) results in increased binding to CalC as shown by the increase in CalC Trp fluorescence intensity.

DETAILED DESCRIPTION OF THE INVENTION

The present invention is directed to the isolation and characterization of the calicheamicin biosynthetic cluster. This cluster encodes the genes that encode the proteins and enzymes that are involved in deoxysugar synthesis (the aryltetrasaccharide), polyketide biosynthesis (the aglycone and aromatic residue of the aryltetrasaccharide) of calicheamicin synthesis, regulation, transport, cluster mobility and calicheamicin resistance. Forty-eight putative genes have been identified, twenty-seven of which encode putative structural proteins with the remainder encoding a variety of functions. Specifically, there are 15 genes that encode for the aryltetrasaccharide moiety (20,928 bp; D, E, F, G, H, J, K, N, O, Q, S, T, U, X, W, 6MSAS), 12 putative genes which encode for the aglycone (13,284 bp; P, S, V, W, ActI, ActII, ActIII, OrfI, OrfII, OrfV, OrfVI, OrfVII), 13 putative genes involved in membrane transport, regulation, DNA movement and/or resistance (19,704 bp; A, B, C, I, L, M, R, orf4, orf8, OrfVIII, OrfIX, OrfX, OrfXI, IS-element), and the remaining 8 genes of unknown function (7383 bp; orf1, orf2, orf3, orf5, orf6, orf7, OrfII, OrfIV).

The calicheamicin biosynthetic gene cluster comprises the following genes: calA, calB, calC, calD, calE, calF, calG, calH, calI, calJ, calK, calL, calM, calN, calO, calP, calQ, calR, calS, calT, calU, calV, calW, calX, 6MSAS, ActI, ActII, ActIII, orf1, orf2, orf3, orf4, orf5, orf6, orf7, orf8, orfI, orfII, orfIII, orfIV orfV, orfVI, orfVII, orfVIII, orfIX, orfX, orfXI and an IS-element gene. It should be noted that orf1–8 may contain DNA derived in whole or in part from recombinant vectors LP46 and/or LP54. The above listed genes encode the following polypeptides: CalA (328 amino acids), CalB (561 amino acids), CalC (181 amino acids), CalD (263 amino acids), CalE (420 amino acids), CalF (245 amino acids), CalG (990 amino acids), CalH (338 amino acids), CalI (568 amino acids), CalJ (332 amino acids), CalK (440 amino acids), CalL (562 amino acids), CalM (416 amino acids), CalN (398 amino acids), CalO (331 amino acids), CalP (approximately 179 amino acids), CalQ (453 amino acids), CalR (265 amino acids), CalS (1113 amino acids), CalT (280 amino acids), CalU (377 amino acids), CalV (125 amino acids), CalW (449 amino acids), CalX (197 amino acids), 6MSAS (198 amino acids), ActI (207 amino acids), ActII (136 amino acids), ActIII (308 amino acids), Orf1 (322 amino acids), Orf2 (654 amino acids), Orf3 (209 amino acids), Orf4 (521 amino acids), Orf5 (175 amino acids), Orf6 (139 amino acids), Orf7 (187 amino acids), Orf8 (266 amino acids), OrfI (127 amino acids), OrfII (248 amino acids) OrfIII (298 amino acids), OrfIV (363 amino acids) OrfV (288 amino acids), OrfVI (1012 amino acids), OrfVII (236 amino acids), OrfVIII (441 amino acids), OrfIX (504 amino acids), OrX (504 amino acids), OrfXI (251 amino acids) and IS-element (402 amino acids).

In elucidating the calicheamicin biosynthetic gene cluster, the inventors began with a genomic library containing the genome of Micromonospora echinospora spp. calichensis. The cosmid library was generated by isolating chromosomal DNA of Micromonospora echinospora spp. calichensis, fragmenting that chromosomal DNA, inserting the DNA into a cosmid vector and generating a cosmid library according to methods well known in the art. This procedure can be performed using any species of Micromonospora, Streptomyces, or other suitable bacteria.

Based upon prior enediyne metabolic labeling studies it was postulated that the calicheamicin aglycone would be polyketide derived. Polyketide metabolites encompass a vast variety of structural diversities yet share a common mechanism of biosynthesis. Hutchinson, C. R., et al., Chem. Rev., 97, 2525–2535 (1997); Strohl, W. R., et al, Biotechnology of Antibiolics pp. 577–657; Fujii, I., et al., Chem. Rev., 97, 2511–2523 (1997); Hopwood, D. A., et al., Chem. Rev., 97, 2465–2497 (1997); Hopwood, D. A., et al., Ann. Rev. Genet., 24, 37–66 (1990); Staunton, J., et al., Chemical Reviews, 97, 2611–2629 (1997). Most important, polyketide synthase ("PKS") genes display a high degree of sequence homology (from pathway to pathway and organism to organism) and are often clustered with genes encoding self resistance and deoxysugar ligand biosynthesis. Hopwood, D. A., et al., Chem. Rev., 97, 2465–2497 (1997); Hopwood, D. A., et al., Ann. Rev. Genet., 24, 37–66 (1990); Staunton, J., et al., Chem. Rev., 97, 2611–2629 (1997).

Degenerate primers based upon conserved regions within PKS genes were used in Southern hybridizations to identify clones from the M. echinospora genomic library that carried putative PKS genes. The Southern hybridizations were performed by methods known in the art. Southern hybridization of the genomic M. echinospora cosmid library with a DNA probe designed to target type I PKS genes (KS$^1$), (Kakavas, S. J., et al., J. Bacteriol., 179, 7515–7522 (1997)), unveiled five positive clones, which were designated clones 4b, 10a, 13a, 56, and 60. See FIG. 1. The same five clones were also identified upon rescreening the genomic library with type II DNA probe (acti). See FIG. 1. Although this preliminary analysis clearly demonstrated the presence of Micromonospora PKS gene homologues, a secondary screen was performed, as PKS hybridization analyses are often plagued by false hybridization to gene clusters that encode spore pigment biosynthesis.

The second screening was based on the assumption that calicheamicin's biosynthetic cluster would also contain genes coding for deoxysugar ligand synthesis. Further, it was postulated that all hexopyranosyl ligands of calicheamicin diverged from the common intermediate 4-keto-6-deoxy TDP-D-glucose (30), FIG. 5, as macromolecule-sugar synthesis in many organisms began with a similar common intermediate. Thus, it was believed that the cluster coding for calicheamicin biosynthesis, in addition to carrying a PKS-encoding region, would carry both a common glucose-1-phosphate nucleotidyltransferase and a NDP-α-D-glucose 4,6-dehydratase gene, encoding the putative enzymes $E_{pl}$, and $E_{od}$, respectively. See FIG. 5. These enzymes are necessary to convert a sugar (12)(FIG. 5) to the hypothesized common intermediate, 4-keto-6-deoxy TDP-D-glucose (30). Analogs to 4,6-dehydratases have been previously characterized from E. coli, Salmonella, and Streptomyces. Additionally, a nucleotide transferase from Salmonella has been characterized as an α-D-glucose-1-phosphate thymidylyltransferase. The secondary screen was performed using a probe based upon the postulation that the M. echinospora's calicheamicin synthesis would begin from a similar precursor found in E. coli, Streptomyces and Salmonella, and that this precursor required a dehydratase to convert it into the common intermediate, 4-keto-6-deoxy TDP-D-glucose (30). In particular, a DNA probe (designated $E_{od}^{-1}$) was designed from the conserved NAD$^+$-binding site of bacterial NDP-α-D-glucose 4,6-dehydratases. He, X., et al., Biochem., 35, 4721–4731 (1996). Southern hybridization of the genomic M. echinospora cosmid library with the $E_{od}^{-1}$ probe revealed cross-hybridization with clones 4b, 10a, 13a, 56, and 60. Two additional clones, designated 58 and 66, were also identified in this screen. See FIG. 1. This secondary hybridization indicated the clustering of genes encoding both polyketide and deoxysugar biosynthesis.

For final corroboration, since secondary metabolite biosynthesis is typically clustered with resistance genes in actinomycetes, all hybridization-positive clones were tested for their ability to grow in the presence of varying concentrations of calicheamicin. In this final screen, six of the seven hybridizing clones displayed differing levels of resistance to calicheamicin (4b≈10a≈13a≧56≧66>60)(See FIG. 1) while clone 58 lacked the ability to grow in the presence of calicheamicin. In addition, these resistance screens revealed that clones 4b, 10a, 13a conferred much higher levels of resistance to calicheamicin than the other clones. Upon rescreening the genomic library for calicheamicin-resistant clones, three additional clones (3a, 4a, and 16a) were found to confer similar levels of resistance. Cumulatively, the results demonstrated that clones 4b, 10a, 13a, 56, and 60 carried PKS I and II homologues and deoxy sugar biosynthetic genes, as well as encoded the gene responsible for conferring calicheamicin-self resistance.

The clones positive for PKS I and II and deoxy sugar biosynthesis homology and calicheamicin resistance were used to map the biosynthetic cluster. Southern hybridization established similarity between clones 3a, 4a, 4b, 10a, 13a, 16a and 56. In addition, nucleotide sequence overlaps were found between clones 4b, 13a, and 56. See FIG. 1. Restriction mapping and Southern hybridization of these clones indicated that the positive cosmid clones corresponded to a continuous region of the M. echinospora chromosome spanning >100 kb. The present invention thus provides for cosmids having a nucleic acid molecule from Micromonospora echinospora coding for a nonchromoprotein enediyne biosynthetic cluster.

After isolating the biosynthetic gene cluster and elucidating the sequence, open reading frames ("orfs") were assigned. Tentative gene assignments were derived from amino acid sequence similarity of translated orfs to gene products of known function via direct BLAST (Basic Local Alignment Search Tool) database searches on the amino acid level. Karlin, et al., Proceed Natl. Acad. Sci., USA., 87, 2264–2268 (1990); Karlin, et al., Proceed Natl. Acad. Sci., USA., 90, 5873–5877 (1993); Altchul, Nature Genet., 6, 119–129 (1994). The gene cluster organization is provided in FIG. 1.

Based on BLAST analysis tentative gene assignments were made. Specifically, there are 15 genes that encode for the aryltetrasaccharide moiety (20,928 bp; D, E, F, G, H, J, K, N, O, Q, S, T U, X, W, 6MSAS), 12 putative genes which encode for the aglycone (13,284 bp; P, S, V, W, ActI, ActII, ActIII, OrfI, OrfIII, OrfV, OrJVI, OrfVII), 13 putative genes involved in membrane transport, regulation, DNA movement and/or resistance (19,704 bp; A, B, C, I, L, M, R, orf4, orf8, OrfVIII, OrfIX, OrfX, OrfXI, IS-element), and the remaining 8 genes of unknown function (7383 bp; orf1, orf2, orf3, orf5, orf6, orf7, OrfII, OrfIV).

One aspect of the invention relates to transformation of a host cell with *M. echinospora* DNA. This method provides a reproducible transformation efficiency of ~$10^3$ kanamycin resistant transform ants/g DNA using a pKC1139-based vector. The invention further provides that the host cell can be but is not limited to bacteria, yeast, fungus, insect, plant or mammalian. Transformations of bacteria, yeast, fungus, insect, plant or mammalian cells are performed by methods known in the art.

Figure 5:
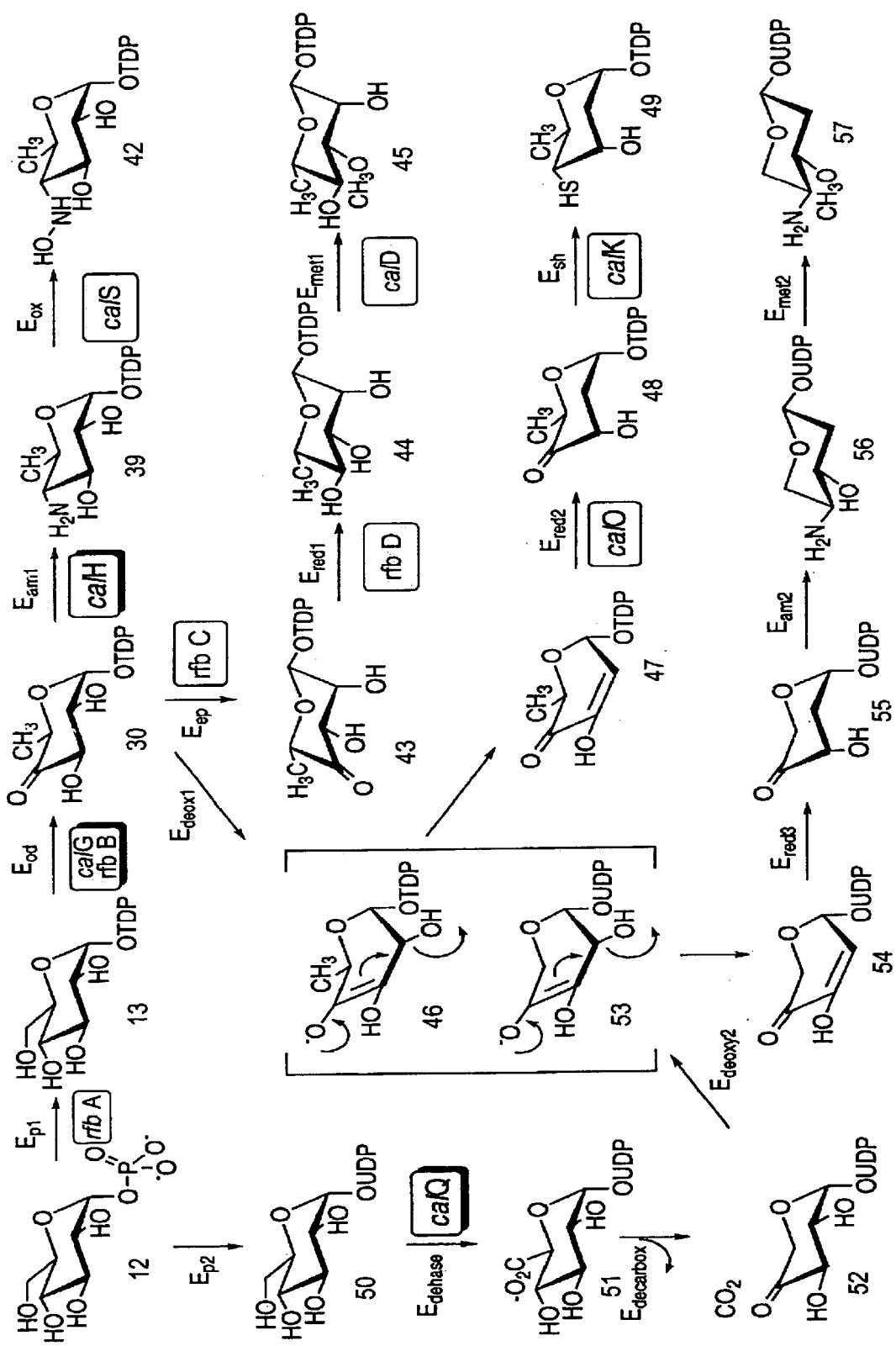
Figure 6:
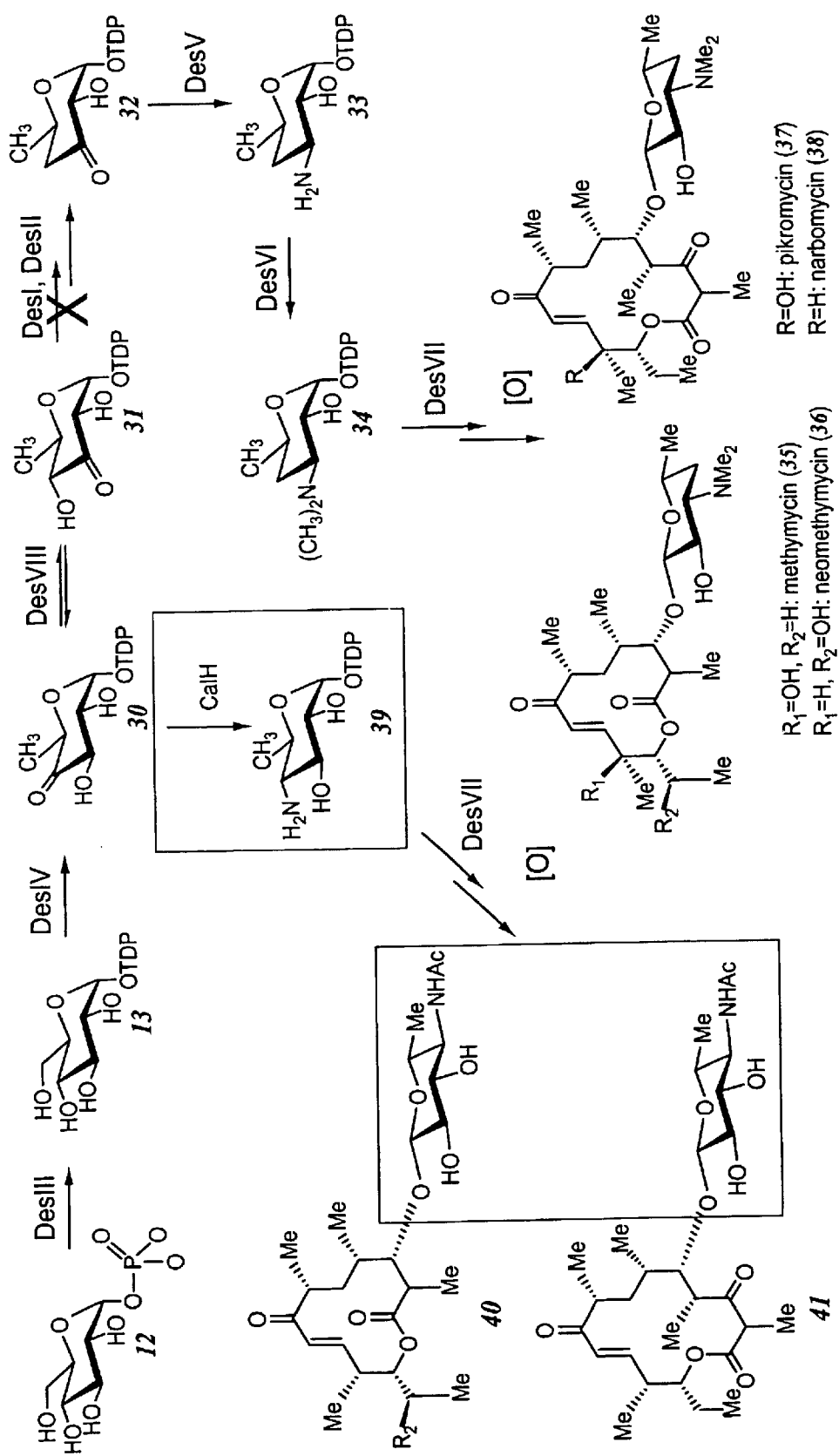

The present invention also provides the isolation and characterization of genes encoding polypeptides involved in calicheamicin resistance such as orfXI and calC. One aspect of the invention relates to an isolated DNA strand having the gene calC and having the DNA sequence SEQ. ID No.: 1. The present invention also relates to an isolated protein CalC, having the amino acid sequence, SEQ ID. NO. 2. The invention further provides for calC gene fragments coding for a bioactive CalC polypeptide. The polypeptide, CalC, confers calicheamicin resistance and has 181 amino acids. The invention also provides for CalC fragments conferring calicheamicin resistance.

The calC locus was isolated by identifying calicheamicin genomic cosmid clones that were able to grow on Luria Bertani ("LB") agar plates containing ampicillin and calicheamicin. The DNA of the positive clones (clones that grew on the plates containing calicheamicin) was isolated and subsequent restriction mapping localized the desired phenotype (calicheamicin resistance). The DNA was then sequenced and the open reading frames analyzed to ascertain the orf coding for the desired phenotype. In vitro studies were also performed and confirmed the ability of CalC to inhibit DNA cleavage.

DNA containing calC was cloned into an inducible vector, using known methods, resulting in overexpression of calC. The polypeptide product (CalC) was then isolated and purified to homogeneity. Analysis of the purified CalC revealed that it is a non-heme iron metalloprotein that functions via inhibition of calicheamicin-induced DNA cleavage in vitro. Another aspect of the invention is an expression vector containing calC or a fragment of calC coding for a bioactive molecule. There is also provided a transformed host cell, preferably bacteria, more preferably *E. coli*, containing calC or a fragment of calC coding for a bioactive molecule. Such transgenic expression of calC results in an $10^5$-fold increase in calicheamicin resistance in *E. coli*, a 100-fold increase in resistance in *S. lividans*, and a 50-fold increase in resistance in yeast.

The present invention provides for the transformation of human cells with the calC gene. The transgenic expression of calC in the HT1080 (human) cell line increased its resistance to calicheamicin 10-fold. This technique allows bone marrow cells, for example, to be removed from a patient being treated with calicheamicin, and for these cells to be transformed with calC, and for the transformed cells to be returned to the patient. This allows the patient to tolerate treatment with calicheamicin or allows the patient to receive higher doses of calicheamicin as the returned human-calC-transformed cells have calicheamicin resistance. The transformation is performed by methods known in the art. The embodiment of the invention would be applicable to many diseases being treated with calicheamicin.

The invention further provides for a method of assaying the calicheamicin-induced DNA cleavage and its CalC-mediated inhibition using the molecular break light assay. Two molecular break lights (MLBs) for the experiments are described in example 7. Break light A is comprised of a 10-base pair stem which contained the known calicheamicin recognition sequence 5'-TCCT-3', while break light B carries the BamHI endonuclease recognition sequence 5'-GGATCC-3'. The 5'-fluorophore of both probes was fluorescein (FAM, $absorbance_{max}$=485 nm, $emission_{max}$=517 nm) while the corresponding 3'-quencher was 4-(4'-dimethylaminophenylazo)benzoic acid (DABCYL). Generally, MLBs operate by a separation of the fluorophore-quencher pair resulting a corresponding fluorescent signal. The molecular break lights, as illustrated in FIG. 13, operate through cleavage of the stem by specific enzymatic or non-enzymatic nuclease activity resulting in the separation of the fluorophore-quencher pair and corresponding fluorescent signal (see FIG. 14). CalC in a two-fold molar excess of calicheamicin, completely abolishes calicheamicin mediated DNA cleavage as monitored by the break light assay (see FIG. 15).

CalC acts as a "cleavage sink". In essence the protein is cleaved as an alternative to the desired DNA target. Thus, the invention provides the first such demonstrated mechanism for resistance to a cleavage agent and explains why CalC is able to function in all organisms tested so far (i.e. *E. coli, S. lividans*, yeast, and humans).

The invention further provides for the use of the break light assay to determine calicheamicin titers during production of thereof. Furthermore, the molecular break light assay may be used to determine the DNA cleavage activity of calicheamicin analogs generated using the techniques of this invention.

Another aspect of the invention relates to an isolated DNA strand containing the calH gene having the DNA sequence SEQ ID. No: 3. The invention also relates to the polypeptide CalH, having amino acid sequence SEQ ID. No. 4. The invention further provides for calH gene fragments coding for a bioactive CalH. CalH is involved in the formation of the aryltetrasaccharide 4,6-dideoxy-4-hydroxylamino-D-glucose moiety. CalH catalyzes the conversion of intermediate (30) to intermediate (39) (FIG. 5). CalH is a TDP-6-deoxy-D-glycerol-L-threo-4-hexulose 4-transaminase, which catalyzes a pyridoxal phosphate ("PLP")-dependent transamination from glutamate to provide 4-amino-6-deoxy TDP-D glucose (intermediate 39)(FIG. 5). The invention also provides for CalH fragments that retain bioactivity. There is also provided an expression vector containing the calH gene or fragments of the calH gene that encode for a bioactive polypeptide. CalH were overexpressed as a $(histidine)_{10}$-fusion protein and subsequently purified by nickel affinity chromatography.

According to BLAST analysis, CalH closely resembles perosanine synthase, an enzyme which converts compound 30 to compound 39 (See FIG. 5) en route to the biosynthesis of TDP-perosamine (TDP-4,6-dideoxy-4-amino-D-mannose) in *E. coli*. Wang, L., et al., *Infect. Immunol.*, 66, 3545–3551 (1998). Thus CalH is believed to be a 4-ketohexose aminotransferase. To confirm the tentative BLAST assigned function, a combinatorial biosynthesis was performed. Specifically the calH gene from calicheamicin was incorporated into a mutant strain of *Streptomyces venezuela*. The 4-dehydrase gene (des1) in the methymycin/ pikromycin pathway was deleted in this mutant strain. A promoter sequence from the *S. venezuela* methymycin/pikromycin cluster was incorporated in the expression vector to drive the expression of foreign genes (the calH of calicheamicin) in *S. venezuela*. In wild type *S. venezuela* methymycin/pikromycin pathway is known to produce methymycin, neomethymycin, pikromycin, and narbomycin. See FIG. 6. Deletion of the des1 gene in the mutant strain led to the accumulation of the CalH substrate, TDP-4-keto-6-deoxyglucose (compound 30, FIG. 6). The constructed expression vector with the *S. venezuela* promoter expressed the calH gene to make the CalH protein. CalH acted on the substrate, 30, to produce compound 39 (FIG. 6). Compound 39 in turn, with the action of *S. venezuela*'s DesVII (a glycosyltransferase) produced two methymycin/pikromycin-calicheamicin hybrid compounds. See FIG. 6, compounds 40 and 41. These hybrid compounds carry the 4-aminohexose ligand of calicheamicin. This work provides indisputable support for the calH gene assignment as encoding the TDP-6-deoxy-D-glycero-L-threo-4-hexulose 4-arninotransferase of the calicheamicin pathway. The CalH acted on the TDP-4-keto-deoxyglucose substrate (compound 30) to produce compound 39. (FIG. 5).

Moreover, CalH is able to directly mediate the synthesis of the product TDP-4,6-dideoxy-alpha-D-glucose as demonstrated by HPLC isolation of the product and confirmation by high-resolution mass spectrometry. In addition this compound was found to co-elute with chemically synthesized TDP-4-amino-4,6-dideoxy-alpha-D-glucose.

In addition, these results reinforce the indiscriminate nature of the corresponding glycosyltransferase (DesVII) as they reveal that the glycosyltransferase (DesVII) of the *S. venezuela* pathway can recognize alternative sugar substrates whose structures are considerably different from the original amino sugar substrate, TDP-D-desosamine. The results also clearly demonstrate the ability to engineer secondary metabolite glycosylation through a rational selection of gene combinations. The successful expression of the CalH protein in *S. venezuela* by the newly constructed expression vector highlights the potential of using this system to express other foreign genes in this strain.

Figure 7:
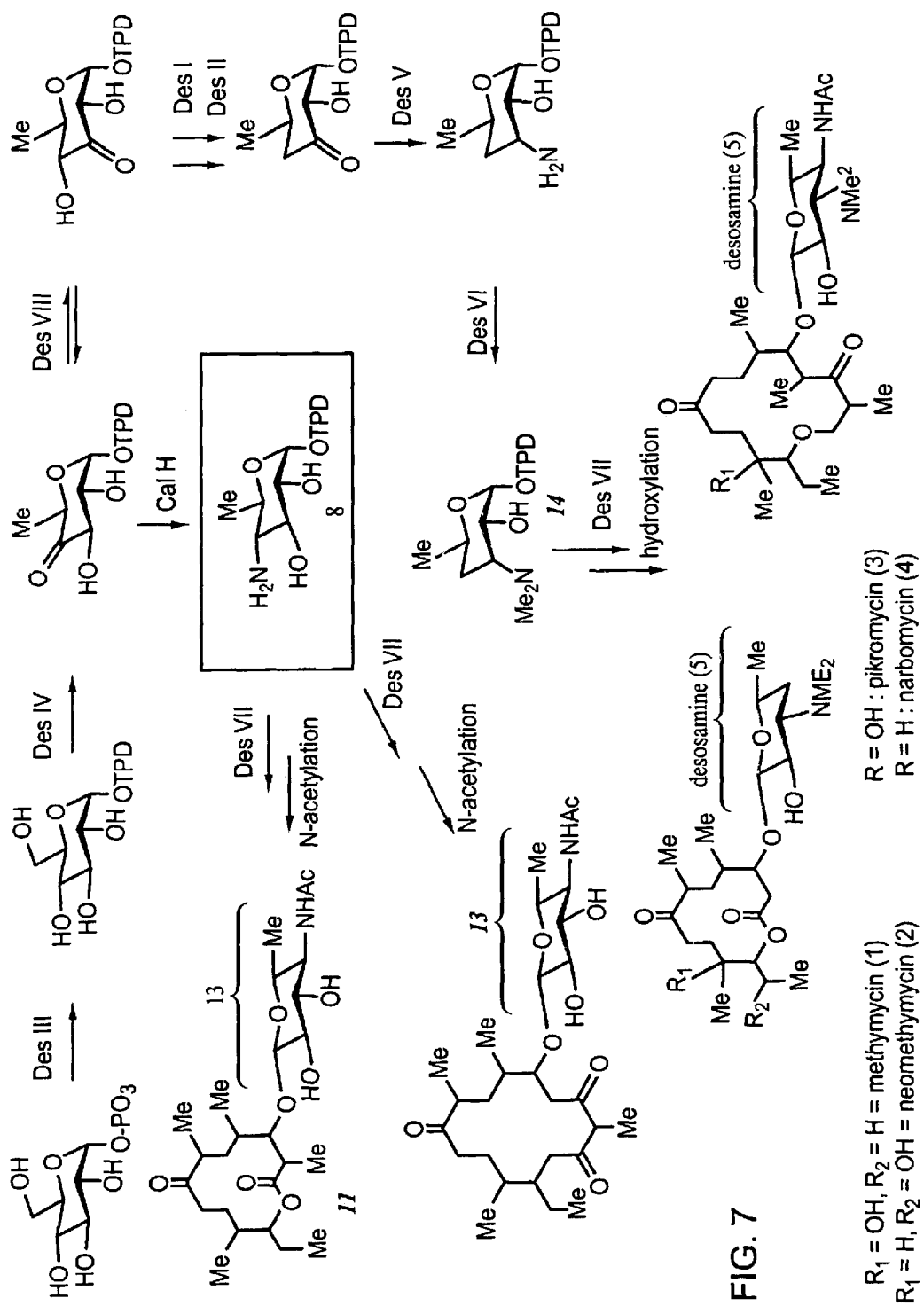
Figure 8:
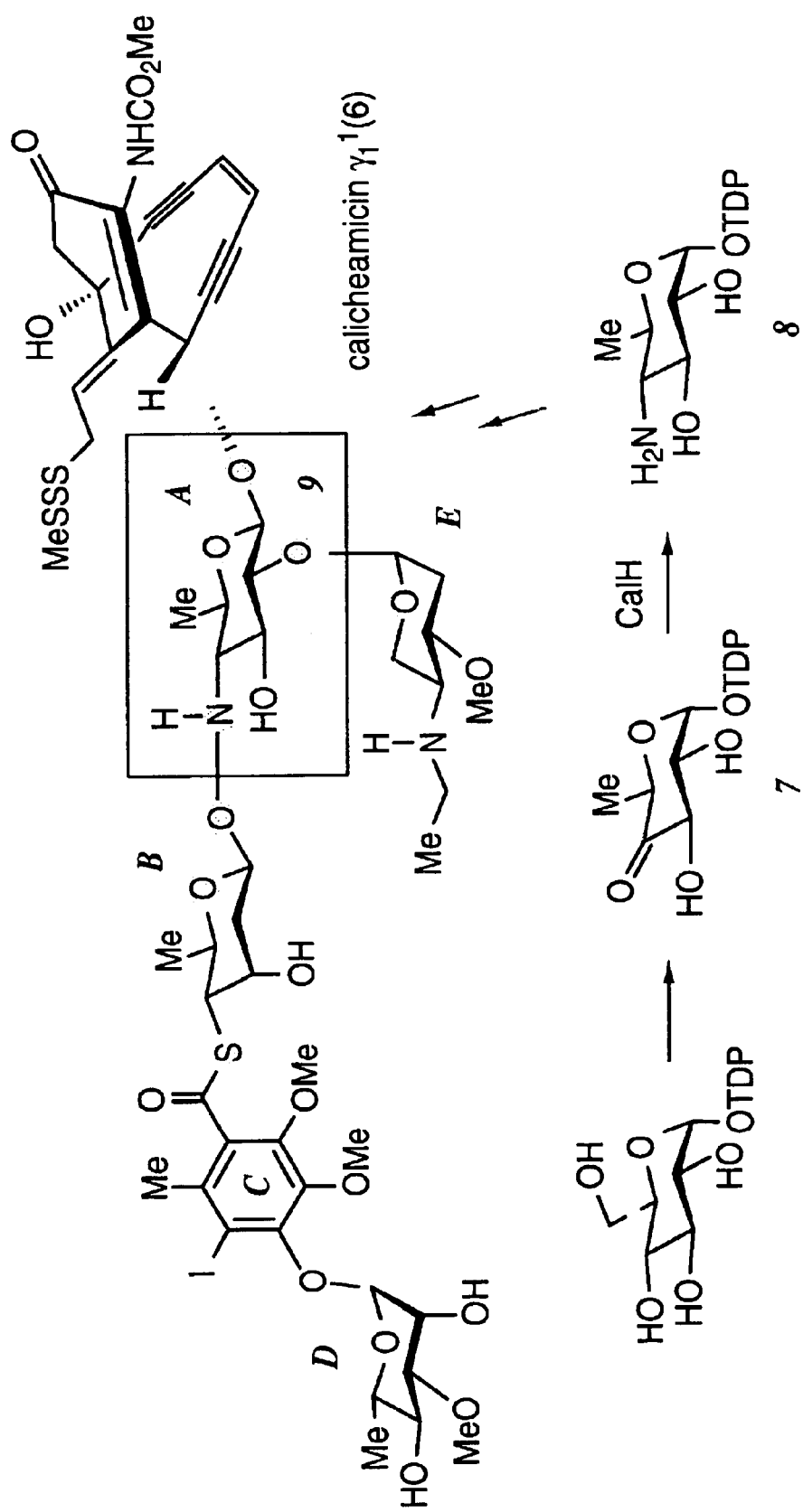
Figure 9:
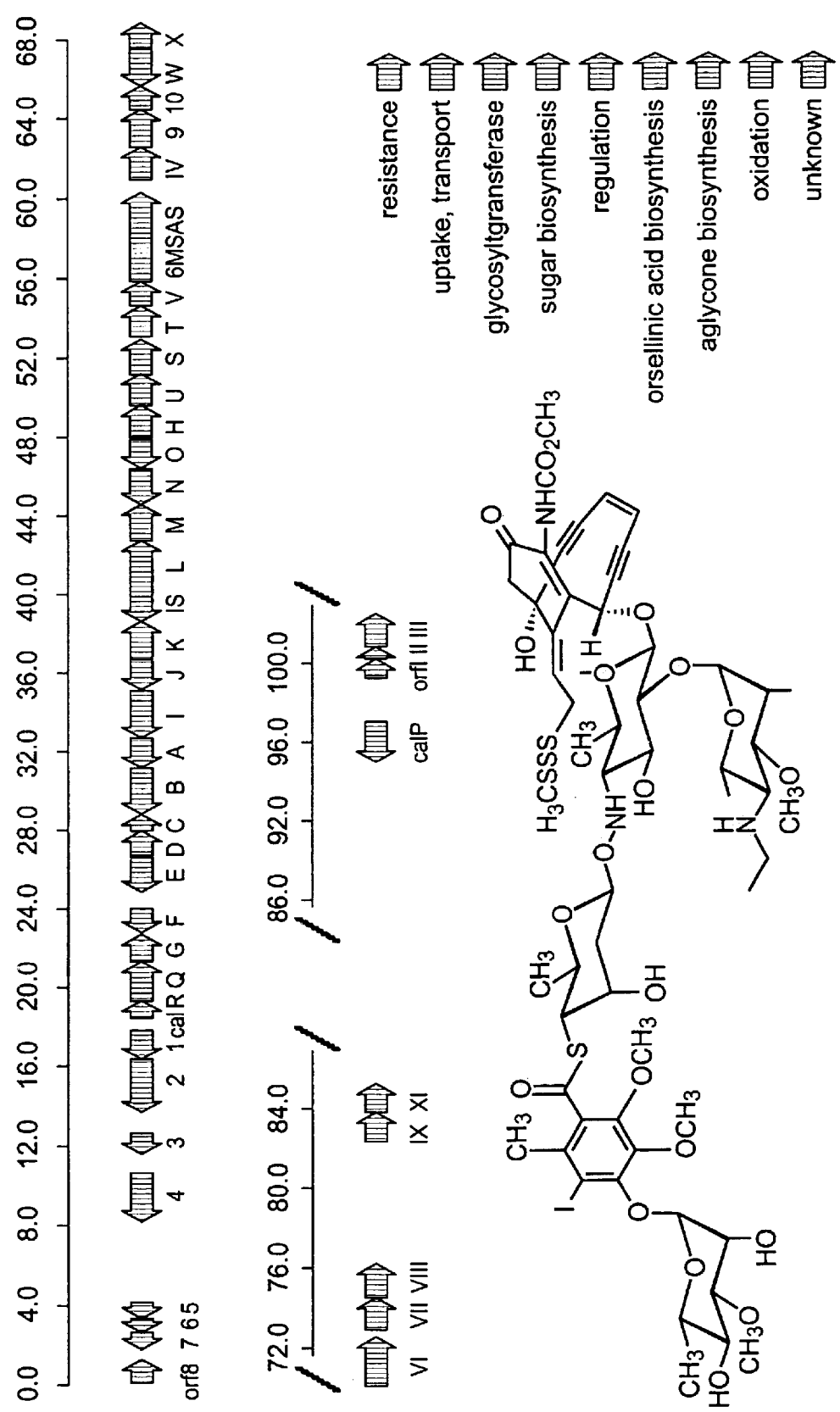
Figure 10:
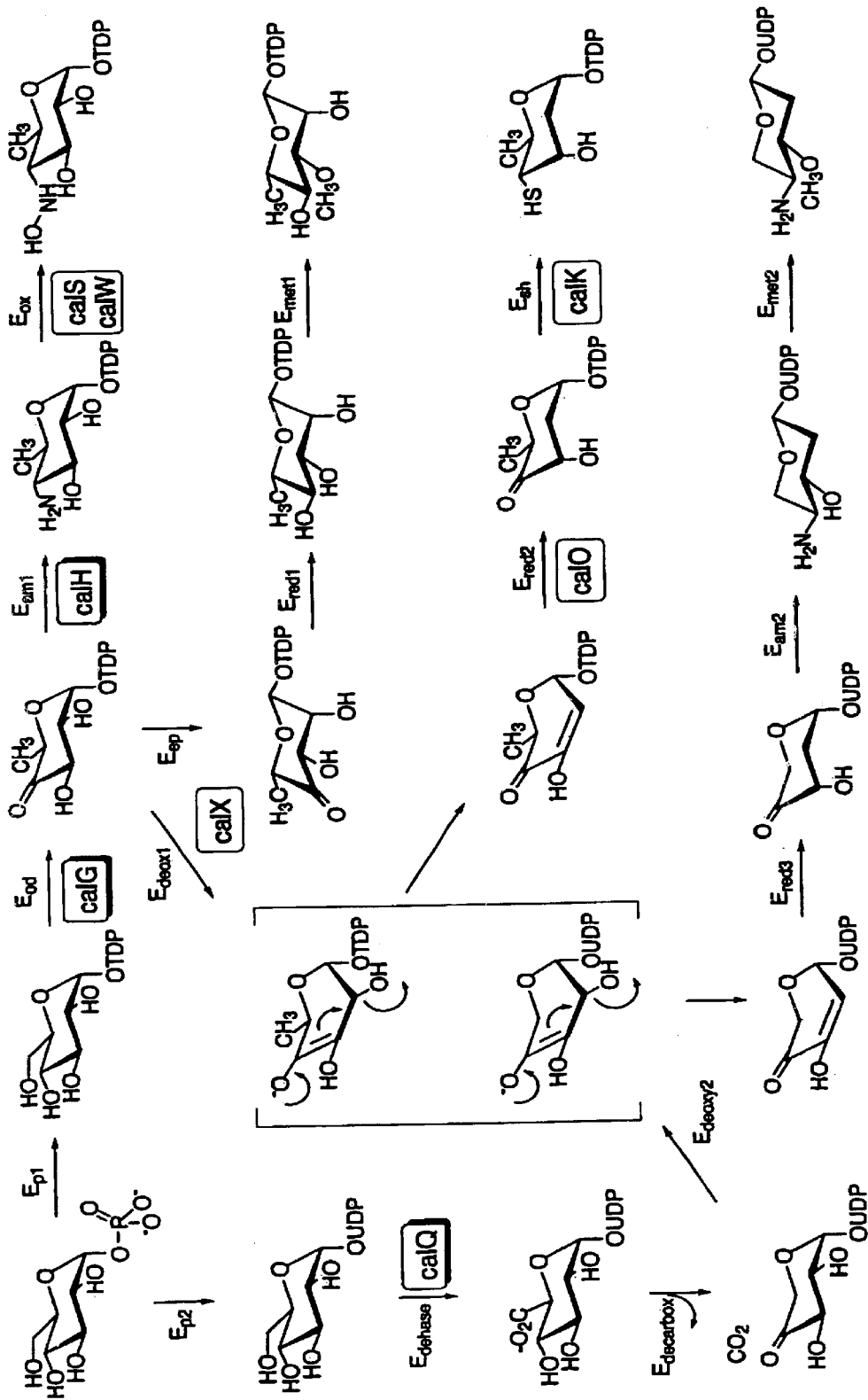

Thus, one aspect of the present invention firther relates to the construction of a composite gene cluster having the ability to make and attach non-natural sugars. The invention further provides an expression vector having a calicheamicin gene operably linked to regulatory sequences to control expression of the calicheamicin protein, and preferably the regulatory sequence is a Streptomyces promoter. The present invention also relates to two newly synthesized sugars, compound (11) and compound (12)(FIG. 7). Compound 11 has the formula:

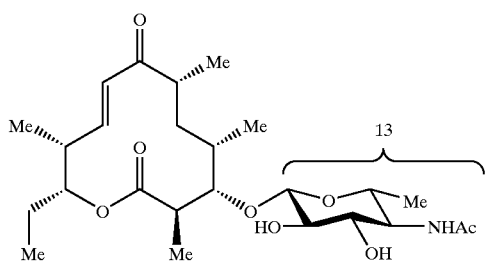

11

The spectral data of compound 11 was as follows:
$^1$H NMR (500 MHz CDCl$_3$, J in hertz) δ 6.75 (1H, dd, J=16.0, 5.5, 9-H) 6.44 (1H, dd, J=16.0, 1.2, 8-H), 5.34 (1H, d, j=8.0, N—H), 4.96 (1H, m, 11-H), 4.27 (1H, d, J=7.5, 1-H), 3.66(1H, dd, J=9.5, 8.0, 4'-H), 3.60 (1H, d, J=10.5, 3-H), 3.50 (1H, 1, J-9.5, 3'H), 3.$^d$ (1H, m, 5'-H), 3.4 (1H, m, 2'-H), 2.84 (1H, dq, J=10.5, 7.5, 2-H), 2.64 (1H, m, 10-H), 2.53 (1H, m, 6-H), 2.06 (3H, s, Me—C=0), 1.7 (1H, m, 12-H), 1.66 (1H, m, 5-H), 1.56 (1H, m. 12-H), 1.4 (1H, M, 5-H), 1.36 (3H, d., J=7.5, 2-Me), 1.25 (311. d, J=6.5, 5'-Me), 1.24 (1H, m. 4-H), 1.21 (3H, d, J=7.5, 6 Me), 1.10 (3H, d, J=6.5, 10-Me), 0.99 (3H, d, J=6.0, 4-Me), 0.91 (3H, t, J=7.2, 12-Me); $^{13}$C NMR (125 MHz, CDCl$_3$) δ 205.3 (C-7), 175.1 (C-1), 171.9 (Me—C—O), 147.1 (C-9), 126.1 (C-8), 103.0 (C-1'), 85.8 (C-3), 75.8 (C-5'), 75.8 (C-3'), 74.1 (C-11) 70.8 (C-2'), 57.6 (C-4'), 45.3 (C-6), 44.0 (C-2), 38.1 (C-10), 34.2 (C-5), 33.6 (C-4), 25.4 (C-12), 23.7 (Me—C—O), 18.1 (C-6'), 17.9 (6 Me), 17.6 (4-Me), 16.4 (2-Me), 10.5 (12-Me), 9.8 (10-Me). High-resolution FAB-MS calculated for C$_{25}$H$_{42}$—NO$_8$(M+H$^+$) 484.2910, found 484.2303.

Compound 12 has the formula:

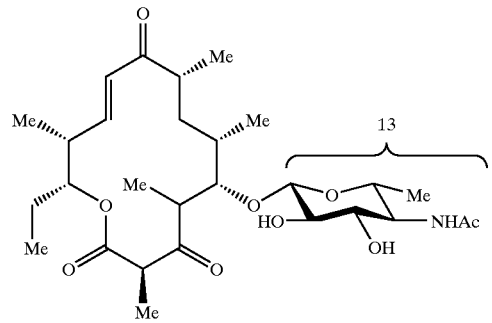

12

The spectral data of compound 12 was as follows:
$^1$H NMR (500 MHz, CDCl$_3$, J in hertz) δ 6.69 (1H, dd, J=16.0, 6.0, 11-H), 6.09 (1H, dd, J=16.0, 1.5, 10-H), 5.35 (1H, d, J=8.5, N—H), 4.96(1H, m, 13-H), 4.36 (1H, d, J=7.5, 1'H), 4.19 (1H, m. 5-H), 3.83 (1H-q, J=6.5, 2-H), 3.68 (1H, dt, J=10.0, 8.5, 4'H), 3.52 (1H, t, J=8.5, 3-'H), 3.50(1H, m, 5-H), 3.42 (1H, t, J=7.5, 2'-H), 2.92 (1H, dq, J=7.0, 5.0, 4-H), 2.81 (1H, m, 8-H), 2.73 (1H, t, J=7.5, 2'-H), 2.06 (3H, a, Me—C—O), 1.8 (1H, m, 6-H), 1.6 (1H, m, 14-H), 1.55 (1H, m. 7-H), 1.37 (3H, d, J=6.5, 2-Me), 1.32 (3H, d, J=7.0, 4-Me), 1.3 (1H, m, H-14), 1.27 (3H, d, J=6.5, 5'-Me), 1.25 (1H, m, 7-H), 1.12 (3H, d, J=6.0, 8-Me), 1.11 (3H, d, J=6.5, 12-Me), 1.07 (3H, d, J=6.0, 6-Me), 0.91 (3H, 1, J-7.2, 1+Me); high resolution FAB MS calculated for C$_{28}$H$_{46}$NO$_2$ (M+H$^+$) 540.3172.found 540.3203.

One aspect of the invention relates to an isolated DNA strand containing the calG gene and having the DNA sequence SEQ ID. NO.: 5. Another aspect of the invention is the protein, CalG, having arnino acid sequence SEQ ID. No.: 6. According to BLAST analysis, calG encodes a 4,6-dehydratase. Dehydratases had been characterized from *E. coli*, Salmonella and Streptomyces, (Thompson, M. et al., *J. Gen. Microbiol.*, 138, 779–786 (1992); Vara, J. A., et al., *J. Biol. Chem.*, 263, 14992–14995 (1988)), and analogous NDP-D-glucose 4,6-dehydratases had been characterized from a variety of organisms. Liu, H.-w., et al., *Ann. Rev. Microbiol.*, 48, 223–256 (1994); Hallis, T. M., et al., *Acc. Chem. Res.*, in press (1999). Based upon these prior studies, it was known that the overall transformation catalyzed by 4,6-dehydratases is an intramolecular oxidation-reduction where an enzyme-bound NAD$^+$ receives the 4-H as a hydride in the oxidative half-reaction and passes the reducing equivalents to C-6 of the dehydration product in the reductive half-reaction. Thus, it appears that CalG is necessary for the formation of the aryltetrasaccharide 4,6-dideoxy-4-hydroxylamino-D-glucose moiety. CalG appears to be a TDP-D-glucose 4,6-dehydratase which catalyzes the conversion of intermediate 13 into intermediate 30. (See FIG. 5). Another aspect of the invention is an expression vector containing calG or a fragment of calG encoding for a bioactive molecule. There is also provided a transformed host cell, preferably bacteria, more preferably, E. coli, containing calG or a fragment of calG encoding for a bioactive molecule.

Moreover, CalG is able to directly mediate the synthesis of the product TDP-4-keto-6-deoxy-alpha-D-glucose as demonstrated by an assay where in the product is known to absorb at 320 nm under basic conditions. In addition this compound was found to co-elute with chemically synthesized TDP-4-keto-6-dideoxy-alpha-D-glucose. CalG has been demonstrated to utilize UDP-glucose as a substrate.

There is also disclosed an isolated DNA strand containing the calS gene. Based on sequence homology with other P450-oxidases, CalS appears to be a P450-oxidase homolog which performs the oxidation of intermediate 39 to intermediate 42(FIG. 5). The oxidation may occur at the nucleotide sugar level or hydroxylamine formation after the sugar has been transferred to the aglycone. There is also provided an expression vector containing the cals gene or a fragment of cals coding for a bioactive molecule. There is also provided a transformed host cell, preferably bacteria, more preferably E. coli, containing calG or a fragment of calG coding for a bioactive molecule.

There is also disclosed an isolated DNA strand containing the calQ gene. Based on sequence homology, CalQ appears to be a UDP-D-glucose-6 dehydrogenase homolog. The CalQ assay is based upon the requirement of this enzyme for two equivalents of NAD+ for activity. Thus, an assay based upon the increase in absorbance (as a result of the conversion of NAD+ to NADH upon the conversion of UDP-alpha-D-glucose to UDP-alpha-D-glucuronic acid). The product was also shown to co-elute with commercially available UDP-glucuronic acid and separately confirmed by high resolution mass spectrometry. This enzyme was also shown to utilize TDP-glucose.

There is also provided an expression vector containing the calQ gene or a fragment of calQ coding for a bioactive molecule. There is also provided a transformed host cell, preferably bacteria, more preferably E. coli, containing calQ or a fragment of calQ coding for a bioactive molecule.

The present invention allows genetic manipulation of the biosynthetic gene cluster to produce calicheamicin analogs. The present invention provides for producing calicheamicin analogs by constructing deletions or substitutions of the genes involved in biosynthesis of the aryltetrasaccharide. The invention further provides for in vitro glycosylation by altering the glycosylation pattern of calicheamicin (via a glycosyltransferase) to produce additional analogs. The invention also provides for alteration of the calicheamicin aglycone by genetic manipulation of the genes encoding the biosynthesis of the warhead. Genetic manipulation, such as producing deletions or substitutions are performed using methods known in the art.

The invention provides for a method of purifying calicheamicin through affinity chromatography. Because of its homology with calicheamicin, CalC functions as a calicheamicin-sequestering/binding protein. Affinity chromatography is performed using methods known in the art.

The invention relates to the expression of the genes located in the biosynthetic gene cluster by using methods known in the art to insert the genes into a suitable expression vector and operably linking the gene to regulatory sequences to control expression of the gene to produce the protein encoded by the inserted gene. The present invention also provides for expression of biologically active proteins by inserting fragments of genes selected from the biosynthetic gene cluster, which encode for biologically active proteins, into a suitable expression vector, using methods known in the art. The genes would be operably linked to regulatory sequences to control their expression.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68° C. for about 3 to 4 hours for fragments of cloned DNA and for about 12 to about 16 hours for total eukaryotic DNA. For lower stringencies the temperature of hybridization is reduced to about 12° C. below the melting temperature (TM) of the duplex. The TM is known to be a function of the G-C content and duplex length as well as the ionic strength of the solution.

As used herein, the term "substantial sequence identity" or "substantial homology" is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not substantially affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include for example, ability to hybridize under defined conditions, or in the case of proteins, immunological crossreactivity, similar enzymatic activity, etc.

Additionally, two nucleotide sequences are "substantially complementary" if the sequences have at least about 40 percent, more preferably, at least about 60 percent and most preferably about 90 percent sequence similarity between them. Two amino acid sequences are "substantially homologous" if they have at least 40%, preferably 70% similarity between the active portions of the polypeptides.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. It is to be understood that the size of the "corresponding portion" will allow for some mismatches in hybridization such that the "corresponding portion" may be smaller or larger than the molecule which hybridizes to it, for example 20–30% larger or smaller, preferably no more than about 12–15% larger or smaller.

The term "functional derivative" of a nucleotide sequence (or poly- or oligonucleotide) is used herein to mean a fragment, variant, homolog, or analog of the nucleotide sequence of interest or of the nucleotide sequence encoding the peptide of interest. A functional derivative may include alternative codons for amino acids, or may code for different amino acids which do not substantially change the function of interest of the peptide encoded by the nucleotide. A functional derivative may retain at least a portion of the function of the nucleotide sequence of interest or of the nucleotide sequence encoding the peptide of interest, which function permits its utility in accordance with the invention. Such function may include the ability to hybridize with at least one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, or 94; the ability to hybridize with a substantially homologous DNA from another organism which DNA encodes at least one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95 or a functional derivative thereof, or with an mRNA transcript thereof, or the ability to encode a protein that is a functional derivative of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95, or the like.

A "fragment" of the gene or nucleotide sequence refers to any subset of the molecule, e.g., a shorter polynucleotide or oligonucleotide. A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different genus or species. An "analog" refers to a non-natural molecule substantially similar to or functioning in relation to either the entire molecule, a variant or a fragment thereof.

"Functional derivatives" of the proteins as described herein are fragments, variants, analogs, or chemical derivatives of at least one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95, and which retain at least a portion of the activity of at least one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95 or retain immunological cross reactivity with an antibody specific for at least one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 95. As used herein, a fragment of the protein refers to any subset of the molecule. Variant peptides may be made by direct chemical synthesis, for example, using methods well known in the art. An analog of a protein refers to a non-natural protein substantially similar to either the entire protein or a fragment thereof. As used herein, a chemical derivative of a protein may contain additional chemical moieties not normally a part of the peptide or peptide fragment. Modifications may be introduced into the a peptide or fragment thereof by reacting targeted amino acid residues of the peptide with an organic derivatizing agent that is capable of reacting with selected side chains or terminal residues.

A protein or peptide according to the invention may be produced by culturing a cell transformed with a nucleotide sequence of this invention (in the sense orientation), allowing the cell to synthesize the protein and then isolating the protein, either as a free protein or as a fusion protein, depending on the cloning protocol used, from either the culture medium or from cell extracts. Alternatively, the protein can be produced in a cell-free system. Ranu, et al., Meth. Enzymol., 60:459–484, (1979).

As can be appreciated from the disclosure above, the present invention has a wide variety of applications. Accordingly, the following examples are offered by way of illustration, not by way of limitation.

EXAMPLES

Example 1

To rapidly elucidate the nucleotide sequence, thermocycle sequencing was accomplished from pUC- or pBluescript-based subclones (using M13 primers and primer walking) as well as directly from isolated cosmids (via primer walking). Nucleotide sequence data was acquired using two Applied Biosystems automated 310 genetic analyzers and sequences were subsequently assembled using the Applied Biosystems AutoAssembler™ DNA sequence assembly software. Dear, S., et al., *Nucl Acids Res.*, 14, 3907–3911 (1991); Huang, X., *Genomics*, 14, 18–25 (1992). Orf assignments were accomplished using a combination of the computational programs MacVector™ 6.0 and Brujene. MacVector is a commercially available software package which provides the ability to construct a Micromonospora codon bias table (from known Micromonospora sequences) and subsequently use this codon bias table to search for optimal orfs. Fickett, J. W., *Nucleic Acids Research*, 10, 5303–5318 (1982). Alternatively, the shareware program Brujene was specifically designed for streptomycetes and assigns priority to orfs that illustrate a consistency high G/C% in the wobble position.

Example 2

Isolating and Characterizing calC

To isolate the gene(s) responsible for calicheamicin resistance in Micromonospora, clones conferring calicheamicin resistance were selected by growth of a Micromonospora genomic bifunctional cosmid library on LB plates containing ampicillin (50 µg ml$^{-1}$) and calicheamicin (0.25 µg ml$^{-1}$). In this selection, six clones (3a, 4a, 4b, 10a, 13a and 16a) displayed resistance to calicheamicin. Restriction mapping of these clones localized the desired phenotype to a ~2kb PstI-SacI fragment of DNA. (FIG. 2). Maximum tolerated concentrations of calicheamicin on the LB plates was ascertained. The results are as follows:

| Cosmid or Plasmid | Maximum tolerated concentration of calicheamicin |
|---|---|
| cosmids 3a, 4a, 10a, 13a, and 16a | 0.5 µg ml$^{-1}$ |
| pJT1214 and pJT1232 | 5.0 µg ml$^{-1}$ |
| pRE7 | 20.0 µg ml$^{-1}$ |
| induced pRE7 | 50.0 µg ml$^{-1}$ |
| pJT1224, pAP6, Pre1, and control plasmids pUC18, pBluescript, and pMAL-C2 | <0.01 µg ml$^{-1}$ |

Nucleotide sequence analysis of the PstI-SacI fragment suggested that it contained two possible orfs. The proximal 1 kb of this fragment carried the single orf calD while the distal 1 kb presented orf calC. Computer translation of calC and subsequent BLAST analysis revealed no homology with known proteins, while the translation of calD to its respective protein, CalD, revealed the presence of three amino acid motifs typically conserved in S-adenosylmethionein-utilizing O-methyltransferases. Therefore, it was hypothesized that calD was not responsible for calicheamicin resistance. To rule out calD as being responsible for calicheamicin resistance, a subclone was engineered (pJT1224) to contain an intact calD, but the truncated calC gene. This subclone was not able to confer resistance to calicheamicin. Next, a subclone containing the calC region was constructed (pJT1232). This clone conferred calicheamicin resistance, as indicated in the above chart.

To ascertain the amino acid sequence of CalC and learn its properties, calC was cloned into a pMAL-C2 vector. (pMAL-C2 by itself could not confer calicheamicin resistance. See above chart.) The resulting plasmid, pRE7, which contained calC, conferred resistance to calicheamicin. See above chart. Plasmid pRE7 was then induced with isopropyl Beta-D-thiogalactoside ("IPTG") to overexpress CalC. Induced pRE7 conferred resistance to calicheamicin and produced a maltose-binding protein CalC fusion protein (mbp-CalC). This resulting overexpression of CalC increased calicheamicin resistance $10^2$-fold in vivo. See above chart.

Example 3

Expression of Protein CalC

The protein mbp-CalC was overexpressed and purified for further analysis. The mbp-CalC was purified from pRE7/*E. coli* to homogeneity as judged by SDS-PAGE. An overnight LB culture (containing 50 mg ml$^{-1}$ ampicillin and 50 ng ml$^{-1}$ calicheamicin from a fresh pRE7/*E. coli* colony was grown at 37° C., 250 rpm to an $A_{600}$=0.5, induced with 0.5 mM IPTG and growth continued overnight. Cells were harvested (4,000×g, 4° C., 20 minutes), resuspended in buffer A (50 mM Tris-Cl, pH 7.5, 200 mM NaCl, 1 mM EDTA) and disrupted by sonication. The cell debris was removed by centrifugation (5,000×g, 4° C., 20 minutes). The supernatant was applied to an amylose affinity column (1.5×7.0 cm, 1 mL $min^{-1}$). The desired mbp-CalC protein was eluted with buffer A containing 10 mM maltose. The eluate was concentrated and chromatographed on an S-300 column (50 mM Tris-Cl, pH 7.5, 200 mM NaCl). Active fractions were used immediately or frozen at −80° C. for storage.

Example 4

Verification of CalC's Calicheamicin Resistance

Given that calicheamicin leads to double strand DNA cleavage and CalC provides calicheamicin-resistance in vivo, it was expected that the addition of CalC to an in vitro calicheamicin-induced DNA cleavage assay would inhibit DNA cleavage. To test this theory, preliminary assays were performed with supercoiled pBlusecript plasmid DNA ("pBS") as the template, and dithiothreitol ("DTT") as the reductive initiator. In a typical assay, purified mbp-CalC (15.0 nM) and 30.0 nM calicheamicin were preincubated for 15 min. in a total volume of 25 $\mu$L 40 mM Tris-Cl, pH 7.5, at 37° C. Then 2.5 $\mu$L 10 mM DTT stock solution was added to the assay solution, and the assay was incubated an additional 1 hour at 37° C. DNA fragmentation was assessed by electrophoresis on a 1% agarose gel stained with ethidium bromide. Using this assay, it was found that mbp-CalC could completely inhibit calicheamicin-induced DNA cleavage at concentrations nearing $10^3$-fold excess of calicheamicin. Preincubation of mbp-CalC and DTT, protein removal via forced dialysis, and the subsequent use of the DTT solution as reductant did not noticeably affect the amount of DNA cleavage.

As indicated in FIG. 4(*b*), no DNA cleavage was observed in the absence of DTT or calicheamicin (lanes a and b), while efficient cleavage was demonstrated in the presence of DTT and calicheamicin (lane c). As expected, the addition of mbp-CalC completely inhibited calicheamicin-induced DNA cleavage (lane f) while the addition of mbp alone (lane d) as a control, failed to inhibit calicheamicin-induced DNA cleavage. Furthermore, preincubation of mbp-CalC with DTT (not shown), or apo-mbp-CalC (lacking the Fe cofactor)(lane e), also failed to inhibit calicheamicin-induced DNA cleavage. However, the addition of $Fe^{+2}$ or $Fe^{+3}$ to the apo-mbp-CalC assay could reconstitute CalC activity (lane g). Reconstitution of apo-mbp-CalC was accomplished by preincubation with 1 mM $FeSO_4$ ($Fe^{+2}$) or $FeCl_3$ ($Fe^{+3}$) prior to the activity assay as previously described.

Example 5

Production of Methymycin/Pikromycin-calicheamicin Hybrid Compounds

The 1.2 kb calH gene was amplified by polymerase chain reaction (PCR) from $pJST1192_{kpn7}$, which is a subclone containing a 7.0 kb KpnI fragment of cosmid 13a. The amplified gene was cloned into the EcoRI/XbaI site of the expression vector pDHS617. This expression vector contains an apramycin resistance marker. The plasmid pDHS617 was derived from pOJ1446 (Bierman, M. et al., *Gene* 1992, 116, 43–49). A promoter sequence from the *S. venezuela* methymycin/pikromycin cluster was incorporated in the plasmid to drive the expression of foreign genes in *S. venezuela*. The resulting plasmid, pLZ-C242 (containing the catH gene insert and the promoter sequence) was introduced by conjugal transfer using *E. coli* S 17-1 into a previously constructed *S. venezuela* mutant, desI. (Borisova, S. et al., *Org. Left.* 1999. 1. 133–136). In the DesI mutant, the desI was replaced by the neomycin resistance gene, which confers resistance to kanamycin The PLS-C242-containing *S. venezuela*-DesI colonies were identified on the basis of their resistance to apramycin antibiotic. One of these positive colonies, DesI/calH-1 was grown in 100 ml of seed medium at 29° C. for 48 hours and then inoculated and grown in five Liters of vegetative medium. Cane, D. E., et al., *J. Am. Chem. Soc.*, 1993, 115, 522–526. The culture was centrifuged to remove cellular debris and mycella. The supernatant was adjusted to pH 9.5 with concentrated KOH, followed by chloroform extraction. The crude products (700 mg) were subjected to flash chromatography on silica gel 'using a gradient of 1–20% methanol in chloroform. A major product, 10-deoxymethynolide (ca. 400 mg), and a mixture of two minor macrolide compounds were obtained. The two macrolides were further purified by HPLC on a $C_{18}$ column using an isocratic mobile phase of acetonitrile/$H_2O$ (1:1). They were later identified as compound (11) and compound (12)(FIG. 7) by spectral anaylses.

Example 6

Molecular Break Light Assay

The invention further provides for a method of assaying the calicheamicin-induced DNA cleavage and its CalC mediated inhibition using the molecular break light assay. Two molecular break lights for the experiments are shown in FIG. 13. Break light A was comprised of a 10-base pair stem which contained the known calicheamicin recognition sequence 5'-TCCT-3', while break light B carried the BamHI endonuclease recognition sequence 5'-GGATCC-3'. The length of break light B also considered the requirement of a 3 base pair overhang required for BamHI recognition and the stem of break light A was adjusted to a comparable length and melting temperature. The loop of both probes consisted of a $T_4$ loop to ensure non-hybridizing interactions. The 5'-fluorophore of both probes was fluorescein (FAM, absorbance$_{max}$=485 nm, emission$_{max}$=517 nm) while the corresponding 3'-quencher was 4-(4'-dimethylaminophenylazo)benzoic acid (DABCYL). Previous studies have shown DABCYL to serve as a universal quencher in molecular beacons and there is significant spectral overlap ($1.02 \times 10^{-15}$ $M^{-1}$ $cm^3$) between the emission spectrum of FAM and the absorption spectrum of DABCYL. In a typical molecular beacon, the quenching efficiency of this pair via FRET has been shown to be essentially complete (99.9%), providing a significant enhancement of the signal to noise ratio as compared to typical complementary oligonucleotide pair FRET-based assays.

Figure 14B:
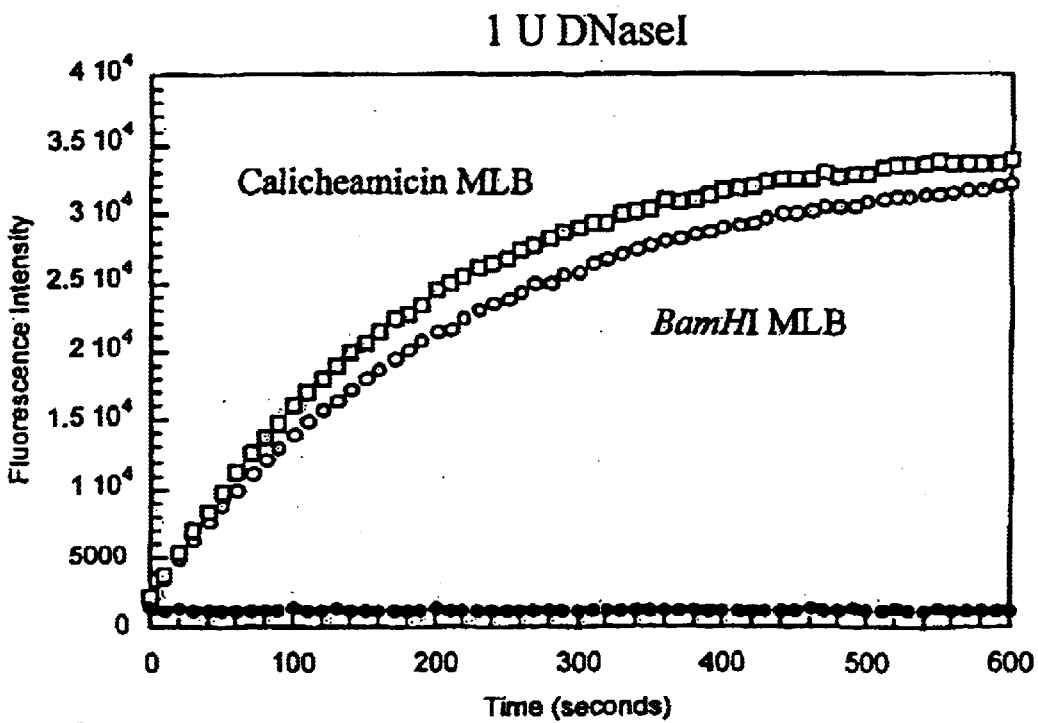

Enzymalic Cleavage as Proof of Principle. The first test was to demonstrate the specificity of the designed molecular break lights via enzymatic cleavage. Specifically, only break light B should cleave in the presence of the restriction endonuclease BamHI while both A and B should be digested by the non-specific nuclease DNaseI. As anticipated, FIG. 14a reveals a time dependent and [BamHI]-dependent increase of fluorescence only with B while A shows no change at 37° C. FIG. 14b illustrates an increase of fluorescence over time with either break light A or B when digested with DNaseI which is also [DNaseI]-dependent. In comparison, control samples containing break lights alone or break lights in the presence of BSA gave no change in fluorescence over >2 hr at 37° C. Given the lack of fluorescence in the absence of enzyme, the designed break lights show no appreciable melting at the designated assay temperature. Furthermore, these experiments clearly demonstrate the specificity of cleavage by BamHI for B and, for the first time, illustrate the principle application of molecular break lights to assess DNA cleavage.

Interestingly, the fluorescence maximum intensity obtained upon complete BamHI cleavage was only 75% that observed in the presence of DNaseI at the same concentration of molecular break light. Furthermore, after the BamHI reaction was complete, the addition of BamHI showed no change while the addition of DNaseI resulted in additional cleavage to give the expected 100% fluorescence maximum. This observation suggests the poly-guanidine tail left attached to FAM upon BamHI digestion quenches the fluorescent signal by ~25%. Consistent with this finding, PAGE analysis of the reaction products confirmed the presence of a 3-base overhang after excess treatment with BamHI which is completely degraded upon DNaseI digestion. As a result, the fluorescence maxium observed with excess BamHI was designated 100% cleavage for the BamHI kinetic studies described below.

Enediyne-Catalyzed Cleavage. Previous assays for enediyne cleavage of DNA relied upon discontinuous assays using radioactive DNA probes, electrophoresis and subsequent phosphoimager analysis. In contrast, by using break lights one can directly follow the extent of DNA cleavage by a specific enediyne in real time with high sensitivity. To demonstrate, FIGS. 15a, b and FIGS. 16a, c, d illustrate cleavage of break light A with varying concentrations of either (1) naturally-occurring enediynes including esperamicin, (2), non-enediyne small molecule agents (such as bleomycin (3) methidiumpropyl-Fe-EDTA, (4), and Fe-EDTA, (5)) as well as the restriction endonuclease BamHI) in the presence of excess reductive activator DTT. Under the conditions described, this assay allows the detection of 1 in the pM range. This sensitivity compares to that of the biochemical induction assay (BIA), the method of choice in detecting DNA-damaging agents. Furthermore, the sensitivity can be significantly enhanced by simply increasing the concentration of the molecular break light in the assay as demonstrated with the iron-dependent agents. The observed maximum fluorescence obtained upon cleavage of 3.2 nM break light A with either 1 or 2 was identical to that observed with DNaseI, consistent with complete degradation of the oligonucleotide. As controls, incubation of molecular break light A with either DTT or enediyne alone revealed no change in fluorescence. Furthermore, although there is some debate regarding the "specificity" of 1, molecular break light B was cleaved by 1 at an identical rate. This supports the view that the specificity of 1 is more dependent upon context and perhaps less so on DNA sequence. It should also be noted that 1 leads to predominately double-stranded cleavage while 2 provides single-stranded nicks and the current molecular break light assay can not distinguish these two phenomena.

Interestingly, two distinct rates were observed in the enediyne molecular break light assay. The first (0–50 seconds) is a lag time most likely attributed to the enediyne activation while the second (50–200 seconds) is indicative to the initial velocity of DNA cleavage. To confirm this, assays were also established in which DTT and enediyne were first preincubated for 1–5 min followed by initiation via the addition of the substrate oligonucleotide. In these preincubation experiments, the previously observed "lag time" attributed to activation was no longer evident while the initial velocity of DNA cleavage was identical to that determined in the standard assay. Preincubation for longer periods (>30 min) revealed the same phenomenon, suggesting "activated" enediynes are perhaps more stable in an aqueous aerobic environment than previously estimated.

CalC inhibits calicheamicin mediated DNA cleavage. As illustrated in FIG. 17, CalC directly inhibits of calicheamicin-mediated DNA cleavage in the break light assay. 3.6 pM break light A is coincubated with 3.5 nM calicheamicin with increasing amounts of CalC (0.0 nm, 1.3 nm, 2.6 nm, 3.9 nm, 5.2 nm). Complete inhibition of calicheamicin is achieved with roughly 2-fold excess of CalC. CalC has no effect on esperamicin-induced cleavage of DNA (data not shown).

All publications, patents and patent applications referred to herein are incorporated in this application by reference in their entirety to the same extent as if each individual publicaion, patent or patent application was specifically and individually indicated to be incorporated by reference in its entirety.

What is claimed is:

1. An isolated nucleic acid molecule, wherein said nucleic acid molecule comprises SEQ ID No. 35.

2. An expression vector comprising said nucleic acid molecule of claim 1.

3. The expression vector of claim 2, wherein said nucleic acid molecule is operably linked to regulatory sequences to control expression of said nucleic acid molecule.

4. The expression vector of claim 3, wherein the regulatory sequence is a Streptomyces promoter.

5. A host cell transformed with the nucleic acid molecule of claim 1.

6. A host cell transformed with the expression vector of claim 2.

7. A host cell transformed with the expression vector of claim 3.

8. The host cell of claim 5, wherein the host cell is a bacterium, yeast, insect, plant, fungi, or mammalian cell.

9. The host cell of claim 8, wherein said bacterium is *E. coli* or Streptomyces.

10. A cosmid comprising a nucleic acid molecule from the calicheamicin biosynthetic gene cluster from *Micromonospora echinospora*, wherein said nucleic acid molecule comprises SEQ ID No. 35.

11. A method of expressing a protein comprising the steps of transfecting a host cell with the expression vector of claim 2, and incubating said cell for a length of time and under conditions sufficient for expression of said protein wherein said protein comprises SEQ ID No. 36.

12. The method of claim 11, wherein said host cell is a bacterial, yeast, insect, plant, fungal, or mammalian cell.

13. An isolated nucleic acid molecule coding for an amino acid sequence comprising SEQ ID No. 36.

14. The isolated nucleic acid molecule of claim 1, wherein said nucleic acid molecule comprises the entire calicheamicin gene cluster from *Micromonospora echinospora*.

15. The cosmid of claim 10, wherein said cosmid comprises the entire calicheamicin gene cluster from *Micromotiospora echinospora*.

* * * * *

UNITED STATES PATENT AND TRADEMARK OFFICE
CERTIFICATE OF CORRECTION

PATENT NO. : 6,733,998 B1  
DATED : May 11, 2004  
INVENTOR(S) : Thorson, Jon, A.

It is certified that error appears in the above-identified patent and that said Letters Patent is hereby corrected as shown below:

Column 11,
Line 33, change "(♦)" to -- (●) --;

Column 17,
Line 65, change "(1H," to -- (III, --.

Signed and Sealed this

Thirtieth Day of November, 2004

JON W. DUDAS
*Director of the United States Patent and Trademark Office*

SEQUENCE LISTING

<160> NUMBER OF SEQ ID NOS: 95

<210> SEQ ID NO 1
<211> LENGTH: 546
<212> TYPE: DNA
<213> ORGANISM: Bacteria
<220> FEATURE:
<221> NAME/KEY: CDS
<222> LOCATION: (1)...(546)

<400> SEQUENCE: 1

```
atg act cag gag aag acc gca ccg gcc gcg aag agc acg acc acc aag      48
Met Thr Gln Glu Lys Thr Ala Pro Ala Ala Lys Ser Thr Thr Thr Lys
 1               5                  10                  15 agc acc gcc gcg aag aag ccg aag ccc ccg aac tac gac ccg ttc gtc      96
Ser Thr Ala Ala Lys Lys Pro Lys Pro Pro Asn Tyr Asp Pro Phe Val
                20                  25                  30 cgg cac agc gtc act gtc aag gcc gac cgc aag acc gcc ttc aag acg     144
Arg His Ser Val Thr Val Lys Ala Asp Arg Lys Thr Ala Phe Lys Thr
            35                  40                  45 ttc ctc gaa ggc ttt ccg gag tgg tgg ccg aac aac ttc cgc acc acc     192
Phe Leu Glu Gly Phe Pro Glu Trp Trp Pro Asn Asn Phe Arg Thr Thr
        50                  55                  60 aag gtc ggg gcc ccg ctg ggc gtc gac aag aag ggc ggc cgc tgg tac     240
Lys Val Gly Ala Pro Leu Gly Val Asp Lys Lys Gly Gly Arg Trp Tyr
 65                  70                  75                  80 gag atc gac gag cag ggc gag gag cac acc ttc ggc ctg atc cgg aag     288
Glu Ile Asp Glu Gln Gly Glu Glu His Thr Phe Gly Leu Ile Arg Lys
                 85                  90                  95 gtg gac gag ccg gac acg ctg gtc atc ggc tgg cgg ctc aac ggc ttc     336
Val Asp Glu Pro Asp Thr Leu Val Ile Gly Trp Arg Leu Asn Gly Phe
            100                 105                 110 ggc cgg atc gac ccg gac aac tcg agc gag ttc acc gtg acc ttc gtg     384
Gly Arg Ile Asp Pro Asp Asn Ser Ser Glu Phe Thr Val Thr Phe Val
        115                 120                 125 gcc gac ggc cag aag aag acc cgg gtg gac gtc gag cac acc cac ttc     432
Ala Asp Gly Gln Lys Lys Thr Arg Val Asp Val Glu His Thr His Phe
    130                 135                 140 gac cgg atg ggc acc aag cac gcc aag cgg gtc cgc aac ggc atg gac     480
Asp Arg Met Gly Thr Lys His Ala Lys Arg Val Arg Asn Gly Met Asp
145                 150                 155                 160 aag ggc tgg ccg acg atc ctc cag tcg ttc cag gac aag atc gac gag     528
Lys Gly Trp Pro Thr Ile Leu Gln Ser Phe Gln Asp Lys Ile Asp Glu
                165                 170                 175 gaa ggg gcg aag aag tga                                             546
Glu Gly Ala Lys Lys *
            180
```

<210> SEQ ID NO 2
<211> LENGTH: 181
<212> TYPE: PRT
<213> ORGANISM: Bacteria

<400> SEQUENCE: 2

```
Met Thr Gln Glu Lys Thr Ala Pro Ala Ala Lys Ser Thr Thr Thr Lys
 1               5                  10                  15

Ser Thr Ala Ala Lys Lys Pro Lys Pro Pro Asn Tyr Asp Pro Phe Val
                20                  25                  30

Arg His Ser Val Thr Val Lys Ala Asp Arg Lys Thr Ala Phe Lys Thr
            35                  40                  45
```

```
Phe Leu Glu Gly Phe Pro Glu Trp Trp Pro Asn Asn Phe Arg Thr Thr
    50                  55                  60

Lys Val Gly Ala Pro Leu Gly Val Asp Lys Lys Gly Arg Trp Tyr
 65                  70                  75                  80

Glu Ile Asp Glu Gln Gly Glu His Thr Phe Gly Leu Ile Arg Lys
                 85                  90                  95

Val Asp Glu Pro Asp Thr Leu Val Ile Gly Trp Arg Leu Asn Gly Phe
                100                 105                 110

Gly Arg Ile Asp Pro Asp Asn Ser Ser Glu Phe Thr Val Thr Phe Val
            115                 120                 125

Ala Asp Gly Gln Lys Lys Thr Arg Val Asp Val Glu His Thr His Phe
            130                 135                 140

Asp Arg Met Gly Thr Lys His Ala Lys Arg Val Arg Asn Gly Met Asp
145                 150                 155                 160

Lys Gly Trp Pro Thr Ile Leu Gln Ser Phe Gln Asp Lys Ile Asp Glu
                165                 170                 175

Glu Gly Ala Lys Lys
            180
```

<210> SEQ ID NO 3
<211> LENGTH: 1155
<212> TYPE: DNA
<213> ORGANISM: Bacteria
<220> FEATURE:
<221> NAME/KEY: CDS
<222> LOCATION: (1)...(1155)

<400> SEQUENCE: 3

```
atg gca act agc gag agg ggt gtc atg atc ccg ctg tcc aag gtc gcc        48
Met Ala Thr Ser Glu Arg Gly Val Met Ile Pro Leu Ser Lys Val Ala
 1               5                  10                  15 atg tct ccg gac gtc agc acc cgc gtc tcc gcc gtc ctg agc agt ggc        96
Met Ser Pro Asp Val Ser Thr Arg Val Ser Ala Val Leu Ser Ser Gly
                20                  25                  30 cgg ctg gag cac ggg ccg acc gtc gcc gag tac gag gcg gcc gtg ggc       144
Arg Leu Glu His Gly Pro Thr Val Ala Glu Tyr Glu Ala Ala Val Gly
            35                  40                  45 agt cgt atc ggc aac ccc cgg gtg gtc tcg gtc aac tgc ggc acg gcc       192
Ser Arg Ile Gly Asn Pro Arg Val Val Ser Val Asn Cys Gly Thr Ala
 50                  55                  60 ggg ctc cac ctg gcg ctg agc ctc gcc gcg cgg ccg ggg gcc ggc gag       240
Gly Leu His Leu Ala Leu Ser Leu Ala Ala Arg Pro Gly Ala Gly Glu
 65                  70                  75                  80 tcg gag cac gac ggc ccg ggc gag gtg ctc acc acg ccg ctg acc ttc       288
Ser Glu His Asp Gly Pro Gly Glu Val Leu Thr Thr Pro Leu Thr Phe
                85                  90                  95 gag ggc acg aac tgg ccg atc ctc gcc aac ggg ctg cgc atc cgg tgg       336
Glu Gly Thr Asn Trp Pro Ile Leu Ala Asn Gly Leu Arg Ile Arg Trp
                100                 105                 110 gtg gac gtc gac ccg gcc acc ctc aac atg gac ctc gac gac ctg gcc       384
Val Asp Val Asp Pro Ala Thr Leu Asn Met Asp Leu Asp Asp Leu Ala
            115                 120                 125 gcg aag atc tcg ccc gcc acc cgg gcc atc gtg gtg gtc cac tgg ctc       432
Ala Lys Ile Ser Pro Ala Thr Arg Ala Ile Val Val Val His Trp Leu
            130                 135                 140 ggc tac ccg gtg gac ctc aac cgg ctg cgc gcc gtc gtg gac cgg gcc       480
Gly Tyr Pro Val Asp Leu Asn Arg Leu Arg Ala Val Val Asp Arg Ala
145                 150                 155                 160
```

```
acg gcg gga tac gac cgc cgc ccg ctg gtc gtg gag gac tgc gcg cag        528
Thr Ala Gly Tyr Asp Arg Arg Pro Leu Val Val Glu Asp Cys Ala Gln
            165                 170                 175 gcg tgg ggc gcc acc tac cgg ggc gcg ccg ctg ggc acg cac ggc aac        576
Ala Trp Gly Ala Thr Tyr Arg Gly Ala Pro Leu Gly Thr His Gly Asn
        180                 185                 190 gtc tgc gtg tac agc acc ggc gcg atc aag atc ctg acg acc ggc agc        624
Val Cys Val Tyr Ser Thr Gly Ala Ile Lys Ile Leu Thr Thr Gly Ser
    195                 200                 205 ggc ggc ttc gtc gtg ctg ccc gac gac gac ctg tac gac cgg ctc cgg        672
Gly Gly Phe Val Val Leu Pro Asp Asp Asp Leu Tyr Asp Arg Leu Arg
210                 215                 220 ctg cgc cgc tgg ctc ggc atc gag cgg gcg tcg gac cgg atc acc ggc        720
Leu Arg Arg Trp Leu Gly Ile Glu Arg Ala Ser Asp Arg Ile Thr Gly
225                 230                 235                 240 gac tac gac gtc gcc gag tgg ggc tac cgg ttc atc ctc aac gag atc        768
Asp Tyr Asp Val Ala Glu Trp Gly Tyr Arg Phe Ile Leu Asn Glu Ile
                245                 250                 255 ggc ggg gcg atc ggc ctg tcc aac ctg gaa cgc gtc gac gag ctg ctg        816
Gly Gly Ala Ile Gly Leu Ser Asn Leu Glu Arg Val Asp Glu Leu Leu
            260                 265                 270 cgc cgg cac cgg gag aac gcc gcg ttc tac gac aag gaa ctg gcc ggc        864
Arg Arg His Arg Glu Asn Ala Ala Phe Tyr Asp Lys Glu Leu Ala Gly
        275                 280                 285 atc gac ggc gtc gag cag acc gag cgg gcc gac gac cgg gag ccc gcg        912
Ile Asp Gly Val Glu Gln Thr Glu Arg Ala Asp Asp Arg Glu Pro Ala
    290                 295                 300 ttc tgg atg tac ccg ctg aag gtc cgc gac cgt ccc gcc ttc atg cgc        960
Phe Trp Met Tyr Pro Leu Lys Val Arg Asp Arg Pro Ala Phe Met Arg
305                 310                 315                 320 cgg ctg ctc gac gcc ggc atc gcc acc agc gtc gtg tcg cgc cgc aac       1008
Arg Leu Leu Asp Ala Gly Ile Ala Thr Ser Val Val Ser Arg Arg Asn
                325                 330                 335 gac gcg cac agc tgc gtc gcg tcg gcc cgc acc acc ctg ccc ggg ctg       1056
Asp Ala His Ser Cys Val Ala Ser Ala Arg Thr Thr Leu Pro Gly Leu
            340                 345                 350 gac cgg gtg gcg gac cgc gtg gtc cac atc ccg gtg ggc tgg tgg ctc       1104
Asp Arg Val Ala Asp Arg Val Val His Ile Pro Val Gly Trp Trp Leu
        355                 360                 365 acc gag gac gac cgc tcc cac gtc gtc gaa acg atc aag tcc ggc tgg       1152
Thr Glu Asp Asp Arg Ser His Val Val Glu Thr Ile Lys Ser Gly Trp
    370                 375                 380 tga                                                                    1155
*

<210> SEQ ID NO 4
<211> LENGTH: 384
<212> TYPE: PRT
<213> ORGANISM: Bacteria

<400> SEQUENCE: 4

Met Ala Thr Ser Glu Arg Gly Val Met Ile Pro Leu Ser Lys Val Ala
  1               5                  10                  15

Met Ser Pro Asp Val Ser Thr Arg Val Ser Ala Val Leu Ser Ser Gly
             20                  25                  30

Arg Leu Glu His Gly Pro Thr Val Ala Glu Tyr Glu Ala Ala Val Gly
         35                  40                  45

Ser Arg Ile Gly Asn Pro Arg Val Val Ser Val Asn Cys Gly Thr Ala
     50                  55                  60
```

```
Gly Leu His Leu Ala Leu Ser Leu Ala Ala Arg Pro Gly Ala Gly Glu
 65                  70                  75                  80

Ser Glu His Asp Gly Pro Gly Glu Val Leu Thr Thr Pro Leu Thr Phe
             85                  90                  95

Glu Gly Thr Asn Trp Pro Ile Leu Ala Asn Gly Leu Arg Ile Arg Trp
            100                 105                 110

Val Asp Val Asp Pro Ala Thr Leu Asn Met Asp Leu Asp Asp Leu Ala
        115                 120                 125

Ala Lys Ile Ser Pro Ala Thr Arg Ala Ile Val Val His Trp Leu
130                 135                 140

Gly Tyr Pro Val Asp Leu Asn Arg Leu Arg Ala Val Val Asp Arg Ala
145                 150                 155                 160

Thr Ala Gly Tyr Asp Arg Arg Pro Leu Val Glu Asp Cys Ala Gln
                165                 170                 175

Ala Trp Gly Ala Thr Tyr Arg Gly Ala Pro Leu Gly Thr His Gly Asn
            180                 185                 190

Val Cys Val Tyr Ser Thr Gly Ala Ile Lys Ile Leu Thr Thr Gly Ser
        195                 200                 205

Gly Gly Phe Val Val Leu Pro Asp Asp Asp Leu Tyr Asp Arg Leu Arg
        210                 215                 220

Leu Arg Arg Trp Leu Gly Ile Glu Arg Ala Ser Asp Arg Ile Thr Gly
225                 230                 235                 240

Asp Tyr Asp Val Ala Glu Trp Gly Tyr Arg Phe Ile Leu Asn Glu Ile
                245                 250                 255

Gly Gly Ala Ile Gly Leu Ser Asn Leu Glu Arg Val Asp Glu Leu Leu
            260                 265                 270

Arg Arg His Arg Glu Asn Ala Ala Phe Tyr Asp Lys Glu Leu Ala Gly
        275                 280                 285

Ile Asp Gly Val Glu Gln Thr Glu Arg Ala Asp Arg Glu Pro Ala
290                 295                 300

Phe Trp Met Tyr Pro Leu Lys Val Arg Asp Arg Pro Ala Phe Met Arg
305                 310                 315                 320

Arg Leu Leu Asp Ala Gly Ile Ala Thr Ser Val Val Ser Arg Asn
                325                 330                 335

Asp Ala His Ser Cys Val Ala Ser Ala Arg Thr Thr Leu Pro Gly Leu
            340                 345                 350

Asp Arg Val Ala Asp Arg Val Val His Ile Pro Val Gly Trp Trp Leu
        355                 360                 365

Thr Glu Asp Asp Arg Ser His Val Val Glu Thr Ile Lys Ser Gly Trp
370                 375                 380

<210> SEQ ID NO 5
<211> LENGTH: 990
<212> TYPE: DNA
<213> ORGANISM: Bacteria
<220> FEATURE:
<221> NAME/KEY: CDS
<222> LOCATION: (1)...(990)
<223> OTHER INFORMATION: biosynthetic gene

<400> SEQUENCE: 5 gtg ccc aga tcc ctg gtc acc ggc ggc ttc ggc ttc gtc ggc agt cac      48
Val Pro Arg Ser Leu Val Thr Gly Gly Phe Gly Phe Val Gly Ser His
 1               5                  10                  15 gtc gtc gaa cgg ctg gtc cgc cgg ggt gac gag gtc gtc gtc tac gac      96
Val Val Glu Arg Leu Val Arg Arg Gly Asp Glu Val Val Val Tyr Asp
            20                  25                  30
```

```
ctc gcc gac ccg ccg ccc gac ctg gag cac ccg ccg ggc gcg atc cgg        144
Leu Ala Asp Pro Pro Pro Asp Leu Glu His Pro Pro Gly Ala Ile Arg
         35                  40                  45 cac gtc cgc ggc gac gtc cgg gac gcc gac ggg ctg gcg gcc gcc gcc        192
His Val Arg Gly Asp Val Arg Asp Ala Asp Gly Leu Ala Ala Ala Ala
 50                  55                  60 acc ggc gtg gac gag gtc tac cac ctc gcg gcg gtc gtc ggc gtc gac        240
Thr Gly Val Asp Glu Val Tyr His Leu Ala Ala Val Val Gly Val Asp
 65                  70                  75                  80 cgg tac ctc agc cgg ccg ctg gac gtg gtc gag atc aac gtg gac ggc        288
Arg Tyr Leu Ser Arg Pro Leu Asp Val Val Glu Ile Asn Val Asp Gly
             85                  90                  95 acc cgg aac gcg ttg cgc gcc gca ctg cgc gcc ggt gcc cgg gtc gtg        336
Thr Arg Asn Ala Leu Arg Ala Ala Leu Arg Ala Gly Ala Arg Val Val
                100                 105                 110 gtg tcc agc acc agc gag gtg tac ggg cgc aat ccg cgg gtg ccg tgg        384
Val Ser Ser Thr Ser Glu Val Tyr Gly Arg Asn Pro Arg Val Pro Trp
            115                 120                 125 cgg gag gac gac gac cgg gtg ctc ggc agc acg gcg acg gac cgg tgg        432
Arg Glu Asp Asp Asp Arg Val Leu Gly Ser Thr Ala Thr Asp Arg Trp
130                 135                 140 tcg tac tcg acg agc aag gcg gcg gcc gag cac ctg gcc ttc gcc ttc        480
Ser Tyr Ser Thr Ser Lys Ala Ala Ala Glu His Leu Ala Phe Ala Phe
145                 150                 155                 160 cac cgg cag gag ggc ctg ccg gtg acg gtg ctg cgg tac ttc aac gtc        528
His Arg Gln Glu Gly Leu Pro Val Thr Val Leu Arg Tyr Phe Asn Val
                165                 170                 175 tac ggc cca cgc cag cgc ccg gcg tac gtc ctc agc cgc acc gtc gcc        576
Tyr Gly Pro Arg Gln Arg Pro Ala Tyr Val Leu Ser Arg Thr Val Ala
            180                 185                 190 cgc ctg ctg cgg ggc gtt ccg ccc gtg gtg tac gac gac ggc cgc cag        624
Arg Leu Leu Arg Gly Val Pro Pro Val Val Tyr Asp Asp Gly Arg Gln
        195                 200                 205 acg cgg tgc ttc acc tgg atc gac gag gcg gcc gag gcg acc ctg ctg        672
Thr Arg Cys Phe Thr Trp Ile Asp Glu Ala Ala Glu Ala Thr Leu Leu
    210                 215                 220 gcc gcc gcc cac ccg cgg gcc gtc ggc gag tgt ttc aac atc ggc agc        720
Ala Ala Ala His Pro Arg Ala Val Gly Glu Cys Phe Asn Ile Gly Ser
225                 230                 235                 240 agc gtg gag acc acc gtc gcc gag gcg gtc cgg ctg gcc ggc acg gtg        768
Ser Val Glu Thr Thr Val Ala Glu Ala Val Arg Leu Ala Gly Thr Val
                245                 250                 255 gcc ggg gtg ccg gtg gcg gcc cag acc gcg gac acc gga gcc ggg ctc        816
Ala Gly Val Pro Val Ala Ala Gln Thr Ala Asp Thr Gly Ala Gly Leu
            260                 265                 270 ggc gcc cgc tac cag gac att ccc cgc cgc gta ccg gac tgc ggc aag        864
Gly Ala Arg Tyr Gln Asp Ile Pro Arg Arg Val Pro Asp Cys Gly Lys
        275                 280                 285 gcc gcc gcg ctg ctg gac tgg cgg gcc cgg gtg ccg ctg gtg acc ggc        912
Ala Ala Ala Leu Leu Asp Trp Arg Ala Arg Val Pro Leu Val Thr Gly
    290                 295                 300 ctg cgc cgg acc gtc gag tgg gcc cgc cgc aac ccg tgg tgg acc gcc        960
Leu Arg Arg Thr Val Glu Trp Ala Arg Arg Asn Pro Trp Trp Thr Ala
305                 310                 315                 320 cag gcc gac gac gga ctg gtc gtc agg tag                                990
Gln Ala Asp Asp Gly Leu Val Val Arg  *
                325
```

<210> SEQ ID NO 6

<211> LENGTH: 329
<212> TYPE: PRT
<213> ORGANISM: Bacteria

<400> SEQUENCE: 6

Met Pro Arg Ser Leu Val Thr Gly Gly Phe Gly Phe Val Gly Ser His
1               5                   10                  15

Val Val Glu Arg Leu Val Arg Arg Gly Asp Glu Val Val Tyr Asp
            20                  25                  30

Leu Ala Asp Pro Pro Pro Asp Leu Glu His Pro Pro Gly Ala Ile Arg
        35                  40                  45

His Val Arg Gly Asp Val Arg Asp Ala Asp Gly Leu Ala Ala Ala Ala
    50                  55                  60

Thr Gly Val Asp Glu Val Tyr His Leu Ala Ala Val Val Gly Val Asp
65                  70                  75                  80

Arg Tyr Leu Ser Arg Pro Leu Asp Val Val Glu Ile Asn Val Asp Gly
                85                  90                  95

Thr Arg Asn Ala Leu Arg Ala Ala Leu Arg Ala Gly Ala Arg Val Val
            100                 105                 110

Val Ser Ser Thr Ser Glu Val Tyr Gly Arg Asn Pro Arg Val Pro Trp
        115                 120                 125

Arg Glu Asp Asp Asp Arg Val Leu Gly Ser Thr Ala Thr Asp Arg Trp
    130                 135                 140

Ser Tyr Ser Thr Ser Lys Ala Ala Ala Glu His Leu Ala Phe Ala Phe
145                 150                 155                 160

His Arg Gln Glu Gly Leu Pro Val Thr Val Leu Arg Tyr Phe Asn Val
                165                 170                 175

Tyr Gly Pro Arg Gln Arg Pro Ala Tyr Val Leu Ser Arg Thr Val Ala
            180                 185                 190

Arg Leu Leu Arg Gly Val Pro Pro Val Val Tyr Asp Asp Gly Arg Gln
        195                 200                 205

Thr Arg Cys Phe Thr Trp Ile Asp Glu Ala Ala Glu Ala Thr Leu Leu
    210                 215                 220

Ala Ala Ala His Pro Arg Ala Val Gly Glu Cys Phe Asn Ile Gly Ser
225                 230                 235                 240

Ser Val Glu Thr Thr Val Ala Glu Ala Val Arg Leu Ala Gly Thr Val
                245                 250                 255

Ala Gly Val Pro Val Ala Ala Gln Thr Ala Asp Thr Gly Ala Gly Leu
            260                 265                 270

Gly Ala Arg Tyr Gln Asp Ile Pro Arg Arg Val Pro Asp Cys Gly Lys
        275                 280                 285

Ala Ala Ala Leu Leu Asp Trp Arg Ala Arg Val Pro Leu Val Thr Gly
    290                 295                 300

Leu Arg Arg Thr Val Glu Trp Ala Arg Arg Asn Pro Trp Trp Thr Ala
305                 310                 315                 320

Gln Ala Asp Asp Gly Leu Val Val Arg
                325

<210> SEQ ID NO 7
<211> LENGTH: 987
<212> TYPE: DNA
<213> ORGANISM: Bacteria
<220> FEATURE:
<221> NAME/KEY: CDS
<222> LOCATION: (1)...(987)

<400> SEQUENCE: 7

```
atg aca acc aat ccg gcc ttg gcc atc gag acc cgc gat ctg gtg aag      48
Met Thr Thr Asn Pro Ala Leu Ala Ile Glu Thr Arg Asp Leu Val Lys
 1               5                  10                  15 gtc ttc ggc cag acg cgc gcg gtc gac gga ctg gac ctg gtg gtg cgg      96
Val Phe Gly Gln Thr Arg Ala Val Asp Gly Leu Asp Leu Val Val Arg
                20                  25                  30 gcc ggg acg atc cac ggg gtg ctg ggc ccg aac ggc gcc ggc aag acg     144
Ala Gly Thr Ile His Gly Val Leu Gly Pro Asn Gly Ala Gly Lys Thr
            35                  40                  45 acg gcc atc aag atg ctc gcc acg ctg atg cga ccc acc tcc ggc acc     192
Thr Ala Ile Lys Met Leu Ala Thr Leu Met Arg Pro Thr Ser Gly Thr
        50                  55                  60 gcg tcc gtg ctg ggg cac gac gtg gtc cgc gag gcc gcc gag gtc cgg     240
Ala Ser Val Leu Gly His Asp Val Val Arg Glu Ala Ala Glu Val Arg
 65                 70                  75                  80 cgc cgc atc ggc ctc acc ggc cag acc atg tcc gtc gac gag gac atg     288
Arg Arg Ile Gly Leu Thr Gly Gln Thr Met Ser Val Asp Glu Asp Met
                85                  90                  95 acc ggc gtg cag aac ctg atc ctc gcc ggc cgc ctg cag ggt ctg cgg     336
Thr Gly Val Gln Asn Leu Ile Leu Ala Gly Arg Leu Gln Gly Leu Arg
            100                 105                 110 cac gcg tcc gcg gcc gcg cgg gcg gag cag ttg atg gag gcg ttc gac     384
His Ala Ser Ala Ala Ala Arg Ala Glu Gln Leu Met Glu Ala Phe Asp
        115                 120                 125 ctc acc gag gtc ggc ggc cgg ctg gtg aag acc ttc tcc ggc ggg cag     432
Leu Thr Glu Val Gly Gly Arg Leu Val Lys Thr Phe Ser Gly Gly Gln
    130                 135                 140 cgg cgg cgc atc gac gtg gcc gcg agc atg gtg gtc acc ccc gag ctg     480
Arg Arg Arg Ile Asp Val Ala Ala Ser Met Val Val Thr Pro Glu Leu
145                 150                 155                 160 ctg ttc ctc gac gag ccg acc acc ggc ctc gac ccg cgc agc cgc agc     528
Leu Phe Leu Asp Glu Pro Thr Thr Gly Leu Asp Pro Arg Ser Arg Ser
                165                 170                 175 gag gtc tgg gag atg atc cgg gcg ctg gtc cgg gac ggg ggc acc gtc     576
Glu Val Trp Glu Met Ile Arg Ala Leu Val Arg Asp Gly Gly Thr Val
            180                 185                 190 ctg ctg acc acg cag tac ctc gac gag gcg gac cac ctc gcc gac gag     624
Leu Leu Thr Thr Gln Tyr Leu Asp Glu Ala Asp His Leu Ala Asp Glu
        195                 200                 205 ctg acg ctc atc gac cac ggc cgc atc gtg gcg cag ggc acc ccg ccg     672
Leu Thr Leu Ile Asp His Gly Arg Ile Val Ala Gln Gly Thr Pro Pro
    210                 215                 220 gag ctg aag gcg agc cgc gcc gcc ggc gtg ctc gac gtg cgg ctg cgt     720
Glu Leu Lys Ala Ser Arg Ala Ala Gly Val Leu Asp Val Arg Leu Arg
225                 230                 235                 240 gac ccc gag cgc cgg gcc gac gcg ggc gcc ctg ctc gcc aag gcc gtc     768
Asp Pro Glu Arg Arg Ala Asp Ala Gly Ala Leu Leu Ala Lys Ala Val
                245                 250                 255 ggc gcc gcc gcc gac ctc gac tcc gat ccg gcg cgg ctg tcg gtg cgg     816
Gly Ala Ala Ala Asp Leu Asp Ser Asp Pro Ala Arg Leu Ser Val Arg
            260                 265                 270 gtg acc gac ccc gac cgg gcg gcg ctg gcc ctg ggc gag ctg gcg cgg     864
Val Thr Asp Pro Asp Arg Ala Ala Leu Ala Leu Gly Glu Leu Ala Arg
        275                 280                 285 gcc ggc atc cac gtc gac gac ttc acg ctc ggc cag ccc tcg ctc gac     912
Ala Gly Ile His Val Asp Asp Phe Thr Leu Gly Gln Pro Ser Leu Asp
    290                 295                 300 acg gtg ttc ctc gcc ctc acc ggt cac tcg acg gtc gac gcc agc gaa     960
Thr Val Phe Leu Ala Leu Thr Gly His Ser Thr Val Asp Ala Ser Glu
```

```
                    305                 310                 315                 320
gaa gag gaa gca gag gta cgg gca tga                                                   987
Glu Glu Glu Ala Glu Val Arg Ala *
                                325
```

<210> SEQ ID NO 8
<211> LENGTH: 328
<212> TYPE: PRT
<213> ORGANISM: Bacteria

<400> SEQUENCE: 8

```
Met Thr Thr Asn Pro Ala Leu Ala Ile Glu Thr Arg Asp Leu Val Lys
 1               5                  10                  15

Val Phe Gly Gln Thr Arg Ala Val Asp Gly Leu Asp Leu Val Val Arg
                20                  25                  30

Ala Gly Thr Ile His Gly Val Leu Gly Pro Asn Gly Ala Gly Lys Thr
            35                  40                  45

Thr Ala Ile Lys Met Leu Ala Thr Leu Met Arg Pro Thr Ser Gly Thr
        50                  55                  60

Ala Ser Val Leu Gly His Asp Val Val Arg Glu Ala Glu Val Arg
65                  70                  75                  80

Arg Arg Ile Gly Leu Thr Gly Gln Thr Met Ser Val Asp Glu Asp Met
                85                  90                  95

Thr Gly Val Gln Asn Leu Ile Leu Ala Gly Arg Leu Gln Gly Leu Arg
            100                 105                 110

His Ala Ser Ala Ala Arg Ala Glu Gln Leu Met Glu Ala Phe Asp
        115                 120                 125

Leu Thr Glu Val Gly Gly Arg Leu Val Lys Thr Phe Ser Gly Gly Gln
    130                 135                 140

Arg Arg Arg Ile Asp Val Ala Ala Ser Met Val Val Thr Pro Glu Leu
145                 150                 155                 160

Leu Phe Leu Asp Glu Pro Thr Thr Gly Leu Asp Pro Arg Ser Arg Ser
                165                 170                 175

Glu Val Trp Glu Met Ile Arg Ala Leu Val Arg Asp Gly Gly Thr Val
            180                 185                 190

Leu Leu Thr Thr Gln Tyr Leu Asp Glu Ala Asp His Leu Ala Asp Glu
        195                 200                 205

Leu Thr Leu Ile Asp His Gly Arg Ile Val Ala Gln Gly Thr Pro Pro
    210                 215                 220

Glu Leu Lys Ala Ser Arg Ala Ala Gly Val Leu Asp Val Arg Leu Arg
225                 230                 235                 240

Asp Pro Glu Arg Arg Ala Asp Ala Gly Ala Leu Leu Ala Lys Ala Val
                245                 250                 255

Gly Ala Ala Ala Asp Leu Asp Ser Asp Pro Ala Arg Leu Ser Val Arg
            260                 265                 270

Val Thr Asp Pro Asp Arg Ala Ala Leu Ala Leu Gly Glu Leu Ala Arg
        275                 280                 285

Ala Gly Ile His Val Asp Asp Phe Thr Leu Gly Gln Pro Ser Leu Asp
    290                 295                 300

Thr Val Phe Leu Ala Leu Thr Gly His Ser Thr Val Asp Ala Ser Glu
305                 310                 315                 320

Glu Glu Glu Ala Glu Val Arg Ala
                325
```

<210> SEQ ID NO 9

-continued

```
<211> LENGTH: 1686
<212> TYPE: DNA
<213> ORGANISM: Bacteria
<220> FEATURE:
<221> NAME/KEY: misc_feature
<222> LOCATION: (1)...(1686)
<223> OTHER INFORMATION: n = A,T,C or G
<221> NAME/KEY: misc_feature
<222> LOCATION: (1)...(1686)
<223> OTHER INFORMATION: n = A,T,C or G
<221> NAME/KEY: CDS
<222> LOCATION: (1)...(1686)

<400> SEQUENCE: 9 atg acg aca ccc agc acc gag gtg cgg ccg ctg ccg gcc gag atc ttc      48
Met Thr Thr Pro Ser Thr Glu Val Arg Pro Leu Pro Ala Glu Ile Phe
1               5                   10                  15 agc cga tcg gtg gcc ggc gcg gaa cgg ccg cca cgc ccc ggc ccg ctg      96
Ser Arg Ser Val Ala Gly Ala Glu Arg Pro Pro Arg Pro Gly Pro Leu
            20                  25                  30 ttc gcc gtc cgc acc ttc gcc tgg cgg aac ctg atc aag ctc cgg tac     144
Phe Ala Val Arg Thr Phe Ala Trp Arg Asn Leu Ile Lys Leu Arg Tyr
        35                  40                  45 gtg cag gac cac ctg ggc acc gcg gtg gtc ttc ccg atc atc ctg acg     192
Val Gln Asp His Leu Gly Thr Ala Val Val Phe Pro Ile Ile Leu Thr
    50                  55                  60 ctg gtc ttc acc tat ctg ctc ggc ggc gcg atc gcc ggc tcg ccc cgg     240
Leu Val Phe Thr Tyr Leu Leu Gly Gly Ala Ile Ala Gly Ser Pro Arg
65                  70                  75                  80 gag tac ctg cag ttc ttc ctt ccc ggc gtg atc gtc ctc tcg ctc gtg     288
Glu Tyr Leu Gln Phe Phe Leu Pro Gly Val Ile Val Leu Ser Leu Val
                85                  90                  95 tcg tcg agc atg atg agc gcc ctg acg ctg aac cgg gac atc gcc acc     336
Ser Ser Ser Met Met Ser Ala Leu Thr Leu Asn Arg Asp Ile Ala Thr
            100                 105                 110 ggc atg ttc gac cgg gtc cgc agc acg ccc atc tgg cag ccc gcg gta     384
Gly Met Phe Asp Arg Val Arg Ser Thr Pro Ile Trp Gln Pro Ala Val
        115                 120                 125 ctg gtc ggg gcg atg gcc ggc gac gcc gtc cgg tac gcc ctg acc tcg     432
Leu Val Gly Ala Met Ala Gly Asp Ala Val Arg Tyr Ala Leu Thr Ser
    130                 135                 140 atc gtg ccg ctg tcg ctc ggc ctg ctc ggc ttc cgg ccg gac ggc         480
Ile Val Pro Leu Ser Leu Gly Leu Leu Gly Phe Arg Pro Asp Gly
145                 150                 155                 160 ggc ctg tcc ggg gtg gtg ctc gcc ctg ctc tac ctg cag ctg ttc acc     528
Gly Leu Ser Gly Val Val Leu Ala Leu Leu Tyr Leu Gln Leu Phe Thr
                165                 170                 175 ttc agc gtc gcc tgg ctg tgg atg ctg ttc gcg gtg ctg atc ccg cag     576
Phe Ser Val Ala Trp Leu Trp Met Leu Phe Ala Val Leu Ile Pro Gln
            180                 185                 190 ccg acc gcc gcc gcc ggc gtg gtg aac ctc ctg cag ttc gtg ctc ctc     624
Pro Thr Ala Ala Ala Gly Val Val Asn Leu Leu Gln Phe Val Leu Leu
        195                 200                 205 ttc ggc agc aac atc ctg gcg ccg tcg cag acg atg ccg ggc tgg ctg     672
Phe Gly Ser Asn Ile Leu Ala Pro Ser Gln Thr Met Pro Gly Trp Leu
    210                 215                 220 gag gcg gtg gtc aag ttg aac ccc gtc acc cac gcc gcg acc gcc acc     720
Glu Ala Val Val Lys Leu Asn Pro Val Thr His Ala Ala Thr Ala Thr
225                 230                 235                 240 cgc ggg ctg ntg cac ggc acg gtg acc tcg ggg gag atg ggc gcn ggc     768
Arg Gly Leu Xaa His Gly Thr Val Thr Ser Gly Glu Met Gly Ala Gly
                245                 250                 255
```

```
ctg ctg acc tgc gcc gtg ctc atc gtg gct gct cgc ccc gcc cac gat       816
Leu Leu Thr Cys Ala Val Leu Ile Val Ala Ala Arg Pro Ala His Asp
        260                 265                 270 ctg gct cta cag ccg caa gca gcg ctg aca ccc ctc ccc gac ggc ccc       864
Leu Ala Leu Gln Pro Gln Ala Ala Leu Thr Pro Leu Pro Asp Gly Pro
            275                 280                 285 ggt gtg ccc cct gtt ctc ctc gca ggg gca ggc ccg ggg ccg tcg cgg       912
Gly Val Pro Pro Val Leu Leu Ala Gly Ala Gly Pro Gly Pro Ser Arg
290                 295                 300 cat ccc gcc gcc ggt cgg cgc tgt gcc ccg gcc gca ccc gga gcc ttt       960
His Pro Ala Ala Gly Arg Arg Cys Ala Pro Ala Ala Pro Gly Ala Phe
305                 310                 315                 320 gcc gcg ccg gcc acc gct gct gcg gcc gta acc gcc cgc tgt gtc ggt      1008
Ala Ala Pro Ala Thr Ala Ala Ala Val Thr Ala Arg Cys Val Gly
            325                 330                 335 cac cgg cgc cgt ggc ggc gca ccg tgt cgg ggc cgg ctg ccc act tgt      1056
His Arg Arg Arg Gly Gly Ala Pro Cys Arg Gly Arg Leu Pro Thr Cys
                340                 345                 350 ggc cgc cgt gcg gtc ggc gga cgg acg gcg gcc ccg gac gga cat gag      1104
Gly Arg Arg Ala Val Gly Gly Arg Thr Ala Ala Pro Asp Gly His Glu
            355                 360                 365 tcc gtc cgg ggc cgc gtc gtg gtc ggt cga gca gct ccc gac cgg cta      1152
Ser Val Arg Gly Arg Val Val Val Gly Arg Ala Ala Pro Asp Arg Leu
370                 375                 380 cga gcc gga gtg gac cag cgc ggc cca ggc ctc gcc gcg ctc ctg cga      1200
Arg Ala Gly Val Asp Gln Arg Gly Pro Gly Leu Ala Ala Leu Leu Arg
385                 390                 395                 400 gat ccg cat cat ctc ggg gct cgg ctc gaa ctc ctc ggc cgc gtc ctc      1248
Asp Pro His His Leu Gly Ala Arg Leu Glu Leu Leu Gly Arg Val Leu
                405                 410                 415 cgg gac cgg gcc gcc cgg cag gtc gcc ccg gat gaa cat acc gag gaa      1296
Arg Asp Arg Ala Ala Arg Gln Val Ala Pro Asp Glu His Thr Glu Glu
            420                 425                 430 gtc gag cgc cat ctc cca gcc gac gcc gac ctc cac gag cat ctg ctc      1344
Val Glu Arg His Leu Pro Ala Asp Ala Asp Leu His Glu His Leu Leu
            435                 440                 445 cga ggt cgt ggc gtg ctc cag ctc cag cag ggt gcc gtc gcc ctc ctc      1392
Arg Gly Arg Gly Val Leu Gln Leu Gln Gln Gly Ala Val Ala Leu Leu
450                 455                 460 gtc agc cgc agc tcc acc tcg ctg tcc ggc ttg ccc tcg tac acc cag      1440
Val Ser Arg Ser Ser Thr Ser Leu Ser Gly Leu Pro Ser Tyr Thr Gln
465                 470                 475                 480 ctg atg gtg agc cgg cgc ggt ggc tcg cag cgc agg atg tcg ccg ctg      1488
Leu Met Val Ser Arg Arg Gly Gly Ser Gln Arg Arg Met Ser Pro Leu
                485                 490                 495 gcg ttg ccc tgc agg gcg aag ttg cca ccc tcg cgg agg tcg ccc ttg      1536
Ala Leu Pro Cys Arg Ala Lys Leu Pro Pro Ser Arg Arg Ser Pro Leu
            500                 505                 510 ggc tcg atg aac cag cgg ttg atg cgg ttc ggg tcg gtg cag gcg ctc      1584
Gly Ser Met Asn Gln Arg Leu Met Arg Phe Gly Ser Val Gln Ala Leu
        515                 520                 525 cag acc tcg tcg acg ggc gcg tcg tac cgt tgc cgg atg atg atg ctg      1632
Gln Thr Ser Ser Thr Gly Ala Ser Tyr Arg Cys Arg Met Met Met Leu
530                 535                 540 cgg gcc tcg ccg gcc ggg atg gtg cgc cgg ccg agg gca cgc tcc gtc      1680
Arg Ala Ser Pro Ala Gly Met Val Arg Arg Pro Arg Ala Arg Ser Val
545                 550                 555                 560 gcc tga                                                               1686
Ala *
```

```
<210> SEQ ID NO 10
<211> LENGTH: 561
<212> TYPE: PRT
<213> ORGANISM: Bacteria
<220> FEATURE:
<221> NAME/KEY: VARIANT
<222> LOCATION: (1)...(561)
<223> OTHER INFORMATION: Xaa = Any Amino Acid
<221> NAME/KEY: VARIANT
<222> LOCATION: (1)...(561)
<223> OTHER INFORMATION: Xaa = Any Amino Acid

<400> SEQUENCE: 10
```

Met Thr Thr Pro Ser Thr Glu Val Arg Pro Leu Pro Ala Glu Ile Phe
 1               5                  10                  15

Ser Arg Ser Val Ala Gly Ala Glu Arg Pro Pro Arg Pro Gly Pro Leu
                20                  25                  30

Phe Ala Val Arg Thr Phe Ala Trp Arg Asn Leu Ile Lys Leu Arg Tyr
            35                  40                  45

Val Gln Asp His Leu Gly Thr Ala Val Val Phe Pro Ile Ile Leu Thr
        50                  55                  60

Leu Val Phe Thr Tyr Leu Leu Gly Gly Ala Ile Ala Gly Ser Pro Arg
65                  70                  75                  80

Glu Tyr Leu Gln Phe Phe Leu Pro Gly Val Ile Val Leu Ser Leu Val
                85                  90                  95

Ser Ser Ser Met Met Ser Ala Leu Thr Leu Asn Arg Asp Ile Ala Thr
            100                 105                 110

Gly Met Phe Asp Arg Val Arg Ser Thr Pro Ile Trp Gln Pro Ala Val
        115                 120                 125

Leu Val Gly Ala Met Ala Gly Asp Ala Val Arg Tyr Ala Leu Thr Ser
130                 135                 140

Ile Val Pro Leu Ser Leu Gly Leu Leu Gly Phe Arg Pro Asp Gly
145                 150                 155                 160

Gly Leu Ser Gly Val Val Leu Ala Leu Leu Tyr Leu Gln Leu Phe Thr
                165                 170                 175

Phe Ser Val Ala Trp Leu Trp Met Leu Phe Ala Val Leu Ile Pro Gln
            180                 185                 190

Pro Thr Ala Ala Ala Gly Val Val Asn Leu Leu Gln Phe Val Leu Leu
        195                 200                 205

Phe Gly Ser Asn Ile Leu Ala Pro Ser Gln Thr Met Pro Gly Trp Leu
    210                 215                 220

Glu Ala Val Val Lys Leu Asn Pro Val Thr His Ala Ala Thr Ala Thr
225                 230                 235                 240

Arg Gly Leu Xaa His Gly Thr Val Thr Ser Gly Glu Met Gly Ala Gly
                245                 250                 255

Leu Leu Thr Cys Ala Val Leu Ile Val Ala Ala Arg Pro Ala His Asp
            260                 265                 270

Leu Ala Leu Gln Pro Gln Ala Ala Leu Thr Pro Leu Pro Asp Gly Pro
        275                 280                 285

Gly Val Pro Pro Val Leu Leu Ala Gly Ala Gly Pro Gly Pro Ser Arg
    290                 295                 300

His Pro Ala Ala Gly Arg Arg Cys Ala Pro Ala Ala Pro Gly Ala Phe
305                 310                 315                 320

Ala Ala Pro Ala Thr Ala Ala Ala Val Thr Ala Arg Cys Val Gly
                325                 330                 335

His Arg Arg Arg Gly Gly Ala Pro Cys Arg Gly Arg Leu Pro Thr Cys

-continued

```
              340                 345                 350
Gly Arg Arg Ala Val Gly Gly Arg Thr Ala Ala Pro Asp Gly His Glu
        355                 360                 365

Ser Val Arg Gly Arg Val Val Gly Arg Ala Ala Pro Asp Arg Leu
    370                 375                 380

Arg Ala Gly Val Asp Gln Arg Gly Pro Gly Leu Ala Ala Leu Leu Arg
385                 390                 395                 400

Asp Pro His His Leu Gly Ala Arg Leu Glu Leu Leu Gly Arg Val Leu
                405                 410                 415

Arg Asp Arg Ala Ala Arg Gln Val Ala Pro Asp Glu His Thr Glu Glu
            420                 425                 430

Val Glu Arg His Leu Pro Ala Asp Ala Asp Leu His Glu His Leu Leu
        435                 440                 445

Arg Gly Arg Gly Val Leu Gln Leu Gln Gln Gly Ala Val Ala Leu Leu
    450                 455                 460

Val Ser Arg Ser Ser Thr Ser Leu Ser Gly Leu Pro Ser Tyr Thr Gln
465                 470                 475                 480

Leu Met Val Ser Arg Arg Gly Gly Ser Gln Arg Met Ser Pro Leu
                485                 490                 495

Ala Leu Pro Cys Arg Ala Lys Leu Pro Pro Ser Arg Arg Ser Pro Leu
            500                 505                 510

Gly Ser Met Asn Gln Arg Leu Met Arg Phe Gly Ser Val Gln Ala Leu
        515                 520                 525

Gln Thr Ser Ser Thr Gly Ala Ser Tyr Arg Cys Arg Met Met Met Leu
    530                 535                 540

Arg Ala Ser Pro Ala Gly Met Val Arg Pro Arg Ala Arg Ser Val
545                 550                 555                 560

Ala
```

```
<210> SEQ ID NO 11
<211> LENGTH: 792
<212> TYPE: DNA
<213> ORGANISM: Bacteria
<220> FEATURE:
<221> NAME/KEY: CDS
<222> LOCATION: (1)...(792)

<400> SEQUENCE: 11
```

```
atg cga tgg agg ctg cgg atg gac agc ggc gac ggt cag gac ctg cgt      48
Met Arg Trp Arg Leu Arg Met Asp Ser Gly Asp Gly Gln Asp Leu Arg
 1               5                  10                  15 gcg ttc gtg cac gac tca ccg gag gag acg gag acc acc cag cgc ctg      96
Ala Phe Val His Asp Ser Pro Glu Glu Thr Glu Thr Thr Gln Arg Leu
                20                  25                  30 acg aag ctc ttg acc aac tct ccg atc ccc acg gag gaa ctg gtc aac     144
Thr Lys Leu Leu Thr Asn Ser Pro Ile Pro Thr Glu Glu Leu Val Asn
            35                  40                  45 aac ctc ccc ctg ttc ctg cgc cgc cac cag atg acc gat ctg ctc tcg     192
Asn Leu Pro Leu Phe Leu Arg Arg His Gln Met Thr Asp Leu Leu Ser
        50                  55                  60 atg gac gcg ctc tac cgt cag gtc ctc gac gtg ccg ggc gtg atc atg     240
Met Asp Ala Leu Tyr Arg Gln Val Leu Asp Val Pro Gly Val Ile Met
 65                  70                  75                  80 gag ttc ggc gtc cgg ttc ggc cgt cac ctc ggc acg ttc gcc gcc ctg     288
Glu Phe Gly Val Arg Phe Gly Arg His Leu Gly Thr Phe Ala Ala Leu
                85                  90                  95 cgc ggt gtc tac gag ccc tac aac ccg ctg cgc cgc atc gtc ggc ttc     336
```

```
                -continued

Arg Gly Val Tyr Glu Pro Tyr Asn Pro Leu Arg Arg Ile Val Gly Phe
            100                 105                 110 gac acc ttc acc ggc ttc ccc gac gtc aac gac gtc gac cgc gtc ggc    384
Asp Thr Phe Thr Gly Phe Pro Asp Val Asn Asp Val Asp Arg Val Gly
            115                 120                 125 ccc acg gcg tac cag ggc cgc ttc gca gtg ccc ggg ggc tat ccg gcg    432
Pro Thr Ala Tyr Gln Gly Arg Phe Ala Val Pro Gly Gly Tyr Pro Ala
        130                 135                 140 tac ctg aaa gag gtg ctg gac gcg cac gag tgc agc gac ttc ttc ggc    480
Tyr Leu Lys Glu Val Leu Asp Ala His Glu Cys Ser Asp Phe Phe Gly
145                 150                 155                 160 cac gtg acg cag cgc agc gtg ctc gtc gag ggg gac gta cgg gag acg    528
His Val Thr Gln Arg Ser Val Leu Val Glu Gly Asp Val Arg Glu Thr
                165                 170                 175 gtg ccg cgc tac ctc gcg gag aac ccg cag acc gtc atc gcg ctg gcg    576
Val Pro Arg Tyr Leu Ala Glu Asn Pro Gln Thr Val Ile Ala Leu Ala
            180                 185                 190 tac ttc gac ctc gac ctc tac gag ccg acg aag gcc gtc ctg gag gcg    624
Tyr Phe Asp Leu Asp Leu Tyr Glu Pro Thr Lys Ala Val Leu Glu Ala
        195                 200                 205 atc cgc ccc tac ctc acc aag ggc agc atc gtc gcc ttc gac gaa ctc    672
Ile Arg Pro Tyr Leu Thr Lys Gly Ser Ile Val Ala Phe Asp Glu Leu
210                 215                 220 gac aat ccg aag tgg ccc ggc gag aac atc gcg atg cgg aag gtg ctc    720
Asp Asn Pro Lys Trp Pro Gly Glu Asn Ile Ala Met Arg Lys Val Leu
225                 230                 235                 240 ggg ctg gac cac gcc ccg ctg cgc ctg ctg ccg ggc cgc ccg gcg ccg    768
Gly Leu Asp His Ala Pro Leu Arg Leu Leu Pro Gly Arg Pro Ala Pro
                245                 250                 255 gcg tac ctg cgg tgg ggc gac tga                                    792
Ala Tyr Leu Arg Trp Gly Asp  *
            260

<210> SEQ ID NO 12
<211> LENGTH: 263
<212> TYPE: PRT
<213> ORGANISM: Bacteria

<400> SEQUENCE: 12

Met Arg Trp Arg Leu Arg Met Asp Ser Gly Asp Gly Gln Asp Leu Arg
1               5                   10                  15

Ala Phe Val His Asp Ser Pro Glu Glu Thr Glu Thr Thr Gln Arg Leu
            20                  25                  30

Thr Lys Leu Leu Thr Asn Ser Pro Ile Pro Thr Glu Glu Leu Val Asn
        35                  40                  45

Asn Leu Pro Leu Phe Leu Arg Arg His Gln Met Thr Asp Leu Leu Ser
    50                  55                  60

Met Asp Ala Leu Tyr Arg Gln Val Leu Asp Val Pro Gly Val Ile Met
65                  70                  75                  80

Glu Phe Gly Val Arg Phe Gly Arg His Leu Gly Thr Phe Ala Ala Leu
                85                  90                  95

Arg Gly Val Tyr Glu Pro Tyr Asn Pro Leu Arg Arg Ile Val Gly Phe
            100                 105                 110

Asp Thr Phe Thr Gly Phe Pro Asp Val Asn Asp Val Asp Arg Val Gly
        115                 120                 125

Pro Thr Ala Tyr Gln Gly Arg Phe Ala Val Pro Gly Gly Tyr Pro Ala
    130                 135                 140

Tyr Leu Lys Glu Val Leu Asp Ala His Glu Cys Ser Asp Phe Phe Gly
```

```
                 145                  150                  155                  160

His Val Thr Gln Arg Ser Val Leu Val Glu Gly Asp Val Arg Glu Thr
                          165                  170                  175

Val Pro Arg Tyr Leu Ala Glu Asn Pro Gln Thr Val Ile Ala Leu Ala
                          180                  185                  190

Tyr Phe Asp Leu Asp Leu Tyr Glu Pro Thr Lys Ala Val Leu Glu Ala
                          195                  200                  205

Ile Arg Pro Tyr Leu Thr Lys Gly Ser Ile Val Ala Phe Asp Glu Leu
                          210                  215                  220

Asp Asn Pro Lys Trp Pro Gly Glu Asn Ile Ala Met Arg Lys Val Leu
         225                  230                  235                  240

Gly Leu Asp His Ala Pro Leu Arg Leu Leu Pro Gly Arg Pro Ala Pro
                          245                  250                  255

Ala Tyr Leu Arg Trp Gly Asp
                          260

<210> SEQ ID NO 13
<211> LENGTH: 738
<212> TYPE: DNA
<213> ORGANISM: Bacteria
<220> FEATURE:
<221> NAME/KEY: CDS
<222> LOCATION: (1)...(738)

<400> SEQUENCE: 13 atg ttc gga ccg gag cac gcc gag gtg tac gag gcc gcc tac cgc ggc        48
Met Phe Gly Pro Glu His Ala Glu Val Tyr Glu Ala Ala Tyr Arg Gly
  1               5                  10                  15 cgc ggc aag agc tgg cac gac gag gcg gcg gac gtg gcc gac cgg atc        96
Arg Gly Lys Ser Trp His Asp Glu Ala Ala Asp Val Ala Asp Arg Ile
             20                  25                  30 cgg gcc gcc cgc ccc gac gcc gcc cgg ctg ctc gac gtc ggc tgc ggc       144
Arg Ala Ala Arg Pro Asp Ala Ala Arg Leu Leu Asp Val Gly Cys Gly
         35                  40                  45 acc ggc gcg cac ctc gag acc ttc gcg acc cgc ttc ccc cac gtg gag       192
Thr Gly Ala His Leu Glu Thr Phe Ala Thr Arg Phe Pro His Val Glu
     50                  55                  60 ggg ctc gaa ctg gcc ccg gcg atg ctg gcg ctc gcc cga cac cgg ctg       240
Gly Leu Glu Leu Ala Pro Ala Met Leu Ala Leu Ala Arg His Arg Leu
 65                  70                  75                  80 ccc ggg gtg cgc ctg cac gcc ggg gac atg cgg acg ttc gac ctt ggc       288
Pro Gly Val Arg Leu His Ala Gly Asp Met Arg Thr Phe Asp Leu Gly
                 85                  90                  95 gtc acg ttc gac gcg gtg acc tgc ctg ttc acc gcg gtc aac ttc ctc       336
Val Thr Phe Asp Ala Val Thr Cys Leu Phe Thr Ala Val Asn Phe Leu
            100                  105                  110 ggc acg gtg gcc gag atg cgg gcg gcc gtg gcc gcg atg tcg gcc cac       384
Gly Thr Val Ala Glu Met Arg Ala Ala Val Ala Ala Met Ser Ala His
        115                  120                  125 ctg gcg ccg ggc ggc gtg ctg gtg ctc gaa ccg tgg tgg ttc ccg gag       432
Leu Ala Pro Gly Gly Val Leu Val Leu Glu Pro Trp Trp Phe Pro Glu
    130                  135                  140 cgg ttc atc gac ggg tac gtc ggc ggc gac ctg gtg cgc gag gag ggc       480
Arg Phe Ile Asp Gly Tyr Val Gly Gly Asp Leu Val Arg Glu Glu Gly
145                  150                  155                  160 cgc acg gtg gcg cgg gtg tcg cgg tcc acc cgg cag gga cgg gtg acg       528
Arg Thr Val Ala Arg Val Ser Arg Ser Thr Arg Gln Gly Arg Val Thr
                 165                  170                  175 cgg atg gag gag cgc tgg ctc gtc ggc gac gcc gcc ggg atc cgg gag       576
```

```
                                                                        -continued Arg Met Glu Glu Arg Trp Leu Val Gly Asp Ala Ala Gly Ile Arg Glu
            180                 185                 190 ttc agc cag gtc ggc ctg ctc acc atg ttc acc cgc gag gag tac gac    624
Phe Ser Gln Val Gly Leu Leu Thr Met Phe Thr Arg Glu Glu Tyr Asp
        195                 200                 205 gcg gcg ttc gcc gct gcc ggc tgc gag tcc gcg tac gtc gag ggc tgg    672
Ala Ala Phe Ala Ala Ala Gly Cys Glu Ser Ala Tyr Val Glu Gly Trp
    210                 215                 220 ctg acc ggc cgg ggc ctt ttc gtg gcg acg cgt acc ggt gga cac gcc    720
Leu Thr Gly Arg Gly Leu Phe Val Ala Thr Arg Thr Gly Gly His Ala
225                 230                 235                 240 acc ccg aca atg gtt tga                                            738
Thr Pro Thr Met Val *
                245

<210> SEQ ID NO 14
<211> LENGTH: 245
<212> TYPE: PRT
<213> ORGANISM: Bacteria

<400> SEQUENCE: 14

Met Phe Gly Pro Glu His Ala Glu Val Tyr Glu Ala Ala Tyr Arg Gly
 1               5                  10                  15

Arg Gly Lys Ser Trp His Asp Glu Ala Ala Asp Val Ala Asp Arg Ile
             20                  25                  30

Arg Ala Ala Arg Pro Asp Ala Ala Arg Leu Leu Asp Val Gly Cys Gly
         35                  40                  45

Thr Gly Ala His Leu Glu Thr Phe Ala Thr Arg Phe Pro His Val Glu
     50                  55                  60

Gly Leu Glu Leu Ala Pro Ala Met Leu Ala Leu Ala Arg His Arg Leu
 65                  70                  75                  80

Pro Gly Val Arg Leu His Ala Gly Asp Met Arg Thr Phe Asp Leu Gly
                 85                  90                  95

Val Thr Phe Asp Ala Val Thr Cys Leu Phe Thr Ala Val Asn Phe Leu
            100                 105                 110

Gly Thr Val Ala Glu Met Arg Ala Ala Val Ala Ala Met Ser Ala His
        115                 120                 125

Leu Ala Pro Gly Gly Val Leu Val Leu Glu Pro Trp Trp Phe Pro Glu
    130                 135                 140

Arg Phe Ile Asp Gly Tyr Val Gly Gly Asp Leu Val Arg Glu Glu Gly
145                 150                 155                 160

Arg Thr Val Ala Arg Val Ser Arg Ser Thr Arg Gln Gly Arg Val Thr
                165                 170                 175

Arg Met Glu Glu Arg Trp Leu Val Gly Asp Ala Ala Gly Ile Arg Glu
            180                 185                 190

Phe Ser Gln Val Gly Leu Leu Thr Met Phe Thr Arg Glu Glu Tyr Asp
        195                 200                 205

Ala Ala Phe Ala Ala Ala Gly Cys Glu Ser Ala Tyr Val Glu Gly Trp
    210                 215                 220

Leu Thr Gly Arg Gly Leu Phe Val Ala Thr Arg Thr Gly Gly His Ala
225                 230                 235                 240

Thr Pro Thr Met Val
                245

<210> SEQ ID NO 15
<211> LENGTH: 1707
<212> TYPE: DNA
```

<213> ORGANISM: Bacteria
<220> FEATURE:
<221> NAME/KEY: CDS
<222> LOCATION: (1)...(1707)

<400> SEQUENCE: 15

| | | | | | | | | | | | | | | | | |
|---|---|---|---|---|---|---|---|---|---|---|---|---|---|---|---|---|
| gtg | ccg | gac | cac | gac | cag | cag | cct | cgc | cac | ggc | ggc | acg | ctg | cgc | tac | 48 |
| Val | Pro | Asp | His | Asp | Gln | Gln | Pro | Arg | His | Gly | Gly | Thr | Leu | Arg | Tyr | |
| 1 | | | | 5 | | | | | 10 | | | | | 15 | | |
| tac | ggg | ccc | ggt | ggc | ctc | gac | cac | ctg | gac | ccc | gcc | gcc | gcg | tac | tac | 96 |
| Tyr | Gly | Pro | Gly | Gly | Leu | Asp | His | Leu | Asp | Pro | Ala | Ala | Ala | Tyr | Tyr | |
| | | | 20 | | | | | 25 | | | | | 30 | | | |
| gcc | ttc | tcc | cac | cag | gtc | atc | cgg | ctc | ttc | gcc | cgg | cag | ctg | ttc | agc | 144 |
| Ala | Phe | Ser | His | Gln | Val | Ile | Arg | Leu | Phe | Ala | Arg | Gln | Leu | Phe | Ser | |
| | | 35 | | | | | 40 | | | | | 45 | | | | |
| tac | ccg | acc | acg | gag | gac | gcc | gcc | gcg | ctg | gtg | ccg | gtg | ccc | gac | gtg | 192 |
| Tyr | Pro | Thr | Thr | Glu | Asp | Ala | Ala | Ala | Leu | Val | Pro | Val | Pro | Asp | Val | |
| 50 | | | | | 55 | | | | | 60 | | | | | | |
| gcc | gcc | gag | ttg | ccc | acg | gtg | gac | aat | ggc | ggg | ctc | agc | gag | gac | ggc | 240 |
| Ala | Ala | Glu | Leu | Pro | Thr | Val | Asp | Asn | Gly | Gly | Leu | Ser | Glu | Asp | Gly | |
| 65 | | | | 70 | | | | | 75 | | | | | 80 | | |
| cgc | acg | tac | acg | atc | cgc | ctg | cgc | gac | ggg | gtc | cgg | tgg | gac | acc | gcc | 288 |
| Arg | Thr | Tyr | Thr | Ile | Arg | Leu | Arg | Asp | Gly | Val | Arg | Trp | Asp | Thr | Ala | |
| | | | | 85 | | | | | 90 | | | | | 95 | | |
| ccg | ccg | cgg | ccg | gtg | acc | gcg | ggg | gac | ttc | gtg | cgc | ggc | ttc | aag | cgg | 336 |
| Pro | Pro | Arg | Pro | Val | Thr | Ala | Gly | Asp | Phe | Val | Arg | Gly | Phe | Lys | Arg | |
| | | | 100 | | | | | 105 | | | | | 110 | | | |
| atg | gcc | aac | ccg | gtc | gcc | ggg | gcc | ggc | gcc | atc | gcc | tac | tac | acg | agc | 384 |
| Met | Ala | Asn | Pro | Val | Ala | Gly | Ala | Gly | Ala | Ile | Ala | Tyr | Tyr | Thr | Ser | |
| | | 115 | | | | | 120 | | | | | 125 | | | | |
| acc | atc | gcc | ggc | atg | gcg | gag | ttc | gcc | gag | ggc | tac | cgc | gcg | cgc | ttc | 432 |
| Thr | Ile | Ala | Gly | Met | Ala | Glu | Phe | Ala | Glu | Gly | Tyr | Arg | Ala | Arg | Phe | |
| 130 | | | | | 135 | | | | | 140 | | | | | | |
| gcc | ggg | cgt | acg | ccc | acc | gcc | gcc | gag | ctg | gcc | gac | tac | cag | aac | ggc | 480 |
| Ala | Gly | Arg | Thr | Pro | Thr | Ala | Ala | Glu | Leu | Ala | Asp | Tyr | Gln | Asn | Gly | |
| 145 | | | | 150 | | | | | 155 | | | | | 160 | | |
| cac | gag | atc | agc | ggg | ctg | tgg | gcc | aag | gac | gac | cgg | acc | ctg | gtg | atc | 528 |
| His | Glu | Ile | Ser | Gly | Leu | Trp | Ala | Lys | Asp | Asp | Arg | Thr | Leu | Val | Ile | |
| | | | | 165 | | | | | 170 | | | | | 175 | | |
| gag | ctg | ctg | cgc | ccc | gcc | aac | gac | atg | ctc | aac | ctg | ctg | gcg | atg | ccg | 576 |
| Glu | Leu | Leu | Arg | Pro | Ala | Asn | Asp | Met | Leu | Asn | Leu | Leu | Ala | Met | Pro | |
| | | | 180 | | | | | 185 | | | | | 190 | | | |
| ttc | gcc | tcc | gcc | gcg | ccc | cgg | gag | ttc | gac | gac | ctc | gtc | ccg | gac | ggt | 624 |
| Phe | Ala | Ser | Ala | Ala | Pro | Arg | Glu | Phe | Asp | Asp | Leu | Val | Pro | Asp | Gly | |
| | | 195 | | | | | 200 | | | | | 205 | | | | |
| ccg | gac | ttc | gcg | cgg | ctg | gtc | cgc | tcc | aac | ggg | ccg | tac | cgg | atc | acc | 672 |
| Pro | Asp | Phe | Ala | Arg | Leu | Val | Arg | Ser | Asn | Gly | Pro | Tyr | Arg | Ile | Thr | |
| 210 | | | | | 215 | | | | | 220 | | | | | | |
| ggc | tac | gcc | cgg | ggc | agc | cac | ctg | acc | atg | gac | cac | aac | ccc | gcc | tgg | 720 |
| Gly | Tyr | Ala | Arg | Gly | Ser | His | Leu | Thr | Met | Asp | His | Asn | Pro | Ala | Trp | |
| 225 | | | | | 230 | | | | | 235 | | | | | 240 | |
| cgg | gcc | gac | gca | gac | ccg | atc | cgc | cgc | cgc | tac | gtg | gac | cgt | atc | gag | 768 |
| Arg | Ala | Asp | Ala | Asp | Pro | Ile | Arg | Arg | Arg | Tyr | Val | Asp | Arg | Ile | Glu | |
| | | | | 245 | | | | | 250 | | | | | 255 | | |
| gtg | cgg | atg | gcg | agg | gtg | agc | gac | gag | cgg | gtc | cgc | gcc | gag | atc | gag | 816 |
| Val | Arg | Met | Ala | Arg | Val | Ser | Asp | Glu | Arg | Val | Arg | Ala | Glu | Ile | Glu | |
| | | | 260 | | | | | 265 | | | | | 270 | | | |
| agc | ggg | gcg | gcc | gac | ctg | tcg | tgg | ggc | gcc | gcc | gtg | ggc | agg | ccc | cgc | 864 |
| Ser | Gly | Ala | Ala | Asp | Leu | Ser | Trp | Gly | Ala | Ala | Val | Gly | Arg | Pro | Arg | |
| | | 275 | | | | | 280 | | | | | 285 | | | | |

| | | |
|---|---|---|
| cgg cgt acg gcg gcc gac cgg aac ctc ggc tgg gcg ctg aac ccc tac<br>Arg Arg Thr Ala Ala Asp Arg Asn Leu Gly Trp Ala Leu Asn Pro Tyr<br>290                           295                     300 | | 912 |
| ctg gcg ttc aac ctg cac agc ccg cac gag cgg ggg gcg ctg cgc gac<br>Leu Ala Phe Asn Leu His Ser Pro His Glu Arg Gly Ala Leu Arg Asp<br>305                   310                     315                 320 | | 960 |
| cgg acc gtc cgg ctg gcg atc gcg tac gcc gtc gac aag gcg cgg ctc<br>Arg Thr Val Arg Leu Ala Ile Ala Tyr Ala Val Asp Lys Ala Arg Leu<br>                    325                     330                     335 | | 1008 |
| gtc cgg ttc ttc gac gac atg aac atc ggc acg gtg acc cgc ccc gcg<br>Val Arg Phe Phe Asp Asp Met Asn Ile Gly Thr Val Thr Arg Pro Ala<br>                340                     345                     350 | | 1056 |
| cac acg gcc atc ccg ccg ggc aac ttc ggc cac cgc gag tac gac ccg<br>His Thr Ala Ile Pro Pro Gly Asn Phe Gly His Arg Glu Tyr Asp Pro<br>355                   360                     365 | | 1104 |
| tac ccg acg ccg ggg gac cgg ggc gac cgg gcg cgc tgc cgg gag ctg<br>Tyr Pro Thr Pro Gly Asp Arg Gly Asp Arg Ala Arg Cys Arg Glu Leu<br>               370                     375                     380 | | 1152 |
| ctc gcc gag gcc ggg tac ccc gac ggg ctg cgg ctc acc atg atc tac<br>Leu Ala Glu Ala Gly Tyr Pro Asp Gly Leu Arg Leu Thr Met Ile Tyr<br>385                   390                     395                 400 | | 1200 |
| cgg atc gac gcg gtg cac ggc cag gtg gcc aag gcg atc gcc gag gac<br>Arg Ile Asp Ala Val His Gly Gln Val Ala Lys Ala Ile Ala Glu Asp<br>                    405                     410                     415 | | 1248 |
| ctg ggc gcg ggc ggc gtc gac gtc cgg ctg gtc gag atc gac cag acc<br>Leu Gly Ala Gly Gly Val Asp Val Arg Leu Val Glu Ile Asp Gln Thr<br>                420                     425                     430 | | 1296 |
| gac gag tac tac cgc atc ctc cag gac ccg gcc cgc gcg gcg gcg ggg<br>Asp Glu Tyr Tyr Arg Ile Leu Gln Asp Pro Ala Arg Ala Ala Ala Gly<br>         435                     440                     445 | | 1344 |
| gag tgg gac atc acg ccg gcc gcc tgg atg ccg gac tgg ttc ggc aac<br>Glu Trp Asp Ile Thr Pro Ala Ala Trp Met Pro Asp Trp Phe Gly Asn<br>450                   455                     460 | | 1392 |
| aac ggg cgg tcg tac gtc cag ccg atg ttc cag tcc aac acc ggc gtc<br>Asn Gly Arg Ser Tyr Val Gln Pro Met Phe Gln Ser Asn Thr Gly Val<br>465                   470                     475                 480 | | 1440 |
| ggc acg gcc aac tac ggc ggc tac cac aac ccg ctc gtc gac gag ctg<br>Gly Thr Ala Asn Tyr Gly Gly Tyr His Asn Pro Leu Val Asp Glu Leu<br>                    485                     490                     495 | | 1488 |
| atc gac cgc gcg ttg tcc gcc cgg acg gag gcc gag gcg gag gag ctg<br>Ile Asp Arg Ala Leu Ser Ala Arg Thr Glu Ala Glu Ala Glu Glu Leu<br>               500                     505                     510 | | 1536 |
| tgg cac cgg gtc gac cgg cag gtg ctg cag gac gtg gcg atc gtg ccg<br>Trp His Arg Val Asp Arg Gln Val Leu Gln Asp Val Ala Ile Val Pro<br>              515                     520                     525 | | 1584 |
| atc ctg gcc tgc gag ccg acc atc gag cac ctg acc agt tcc cgg gtg<br>Ile Leu Ala Cys Glu Pro Thr Ile Glu His Leu Thr Ser Ser Arg Val<br>530                   535                     540 | | 1632 |
| cgg ggg gcg atc ccg ctg ccg cac gtg gac cgc tgg tac gac gcg gcg<br>Arg Gly Ala Ile Pro Leu Pro His Val Asp Arg Trp Tyr Asp Ala Ala<br>545                   550                     555                 560 | | 1680 |
| aac ctc tgg ctg gac ccg ccc gac tga<br>Asn Leu Trp Leu Asp Pro Pro Asp  *<br>                   565 | | 1707 |

<210> SEQ ID NO 16
<211> LENGTH: 568
<212> TYPE: PRT
<213> ORGANISM: Bacteria

<400> SEQUENCE: 16

-continued

```
Val Pro Asp His Asp Gln Gln Pro Arg His Gly Gly Thr Leu Arg Tyr
 1               5                  10                  15

Tyr Gly Pro Gly Gly Leu Asp His Leu Asp Pro Ala Ala Ala Tyr Tyr
            20                  25                  30

Ala Phe Ser His Gln Val Ile Arg Leu Phe Ala Arg Gln Leu Phe Ser
            35                  40                  45

Tyr Pro Thr Thr Glu Asp Ala Ala Leu Val Pro Val Pro Asp Val
 50                  55                  60

Ala Ala Glu Leu Pro Thr Val Asp Asn Gly Gly Leu Ser Glu Asp Gly
 65                  70                  75                  80

Arg Thr Tyr Thr Ile Arg Leu Arg Asp Gly Val Arg Trp Asp Thr Ala
                85                  90                  95

Pro Pro Arg Pro Val Thr Ala Gly Asp Phe Val Arg Gly Phe Lys Arg
                100                 105                 110

Met Ala Asn Pro Val Ala Gly Ala Gly Ala Ile Ala Tyr Tyr Thr Ser
                115                 120                 125

Thr Ile Ala Gly Met Ala Glu Phe Ala Glu Gly Tyr Arg Ala Arg Phe
 130                 135                 140

Ala Gly Arg Thr Pro Thr Ala Ala Glu Leu Ala Asp Tyr Gln Asn Gly
145                 150                 155                 160

His Glu Ile Ser Gly Leu Trp Ala Lys Asp Asp Arg Thr Leu Val Ile
                165                 170                 175

Glu Leu Leu Arg Pro Ala Asn Asp Met Leu Asn Leu Leu Ala Met Pro
                180                 185                 190

Phe Ala Ser Ala Ala Pro Arg Glu Phe Asp Asp Leu Val Pro Asp Gly
                195                 200                 205

Pro Asp Phe Ala Arg Leu Val Arg Ser Asn Gly Pro Tyr Arg Ile Thr
 210                 215                 220

Gly Tyr Ala Arg Gly Ser His Leu Thr Met Asp His Asn Pro Ala Trp
225                 230                 235                 240

Arg Ala Asp Ala Asp Pro Ile Arg Arg Tyr Val Asp Arg Ile Glu
                245                 250                 255

Val Arg Met Ala Arg Val Ser Asp Glu Arg Val Arg Ala Glu Ile Glu
                260                 265                 270

Ser Gly Ala Ala Asp Leu Ser Trp Gly Ala Ala Val Gly Arg Pro Arg
275                 280                 285

Arg Arg Thr Ala Ala Asp Arg Asn Leu Gly Trp Ala Leu Asn Pro Tyr
290                 295                 300

Leu Ala Phe Asn Leu His Ser Pro His Glu Arg Gly Ala Leu Arg Asp
305                 310                 315                 320

Arg Thr Val Arg Leu Ala Ile Ala Tyr Ala Val Asp Lys Ala Arg Leu
                325                 330                 335

Val Arg Phe Phe Asp Asp Met Asn Ile Gly Thr Val Thr Arg Pro Ala
                340                 345                 350

His Thr Ala Ile Pro Pro Gly Asn Phe Gly His Arg Glu Tyr Asp Pro
                355                 360                 365

Tyr Pro Thr Pro Gly Asp Arg Gly Asp Arg Ala Arg Cys Arg Glu Leu
 370                 375                 380

Leu Ala Glu Ala Gly Tyr Pro Asp Gly Leu Arg Leu Thr Met Ile Tyr
385                 390                 395                 400

Arg Ile Asp Ala Val His Gly Gln Val Ala Lys Ala Ile Ala Glu Asp
                405                 410                 415
```

```
Leu Gly Ala Gly Gly Val Asp Val Arg Leu Val Glu Ile Asp Gln Thr
            420                 425                 430

Asp Glu Tyr Tyr Arg Ile Leu Gln Asp Pro Ala Arg Ala Ala Ala Gly
        435                 440                 445

Glu Trp Asp Ile Thr Pro Ala Ala Trp Met Pro Asp Trp Phe Gly Asn
    450                 455                 460

Asn Gly Arg Ser Tyr Val Gln Pro Met Phe Gln Ser Asn Thr Gly Val
465                 470                 475                 480

Gly Thr Ala Asn Tyr Gly Gly Tyr His Asn Pro Leu Val Asp Glu Leu
                485                 490                 495

Ile Asp Arg Ala Leu Ser Ala Arg Thr Glu Ala Glu Ala Glu Glu Leu
            500                 505                 510

Trp His Arg Val Asp Arg Gln Val Leu Gln Asp Val Ala Ile Val Pro
        515                 520                 525

Ile Leu Ala Cys Glu Pro Thr Ile Glu His Leu Thr Ser Ser Arg Val
        530                 535                 540

Arg Gly Ala Ile Pro Leu Pro His Val Asp Arg Trp Tyr Asp Ala Ala
545                 550                 555                 560

Asn Leu Trp Leu Asp Pro Pro Asp
                565

<210> SEQ ID NO 17
<211> LENGTH: 999
<212> TYPE: DNA
<213> ORGANISM: Bacteria
<220> FEATURE:
<221> NAME/KEY: CDS
<222> LOCATION: (1)...(999)

<400> SEQUENCE: 17 atg gac agg ttg cag tcg gcg ctg gcc ctc tac gag gag gcg atg ggc      48
Met Asp Arg Leu Gln Ser Ala Leu Ala Leu Tyr Glu Glu Ala Met Gly
 1               5                  10                  15 tac acg tac gcg gca gcc ctg cgg gcc gcc gcc gcc gtc ggc gtc gcc      96
Tyr Thr Tyr Ala Ala Ala Leu Arg Ala Ala Ala Ala Val Gly Val Ala
            20                  25                  30 gac cac ctg gtc gac ggc ccc cgt acg ccc gcc gag ctg gcc gcc gcg     144
Asp His Leu Val Asp Gly Pro Arg Thr Pro Ala Glu Leu Ala Ala Ala
        35                  40                  45 acg ggc acc gac gcg gac gcg ctc cgc cgg gtg ctg cgc ctg ctg gcg     192
Thr Gly Thr Asp Ala Asp Ala Leu Arg Arg Val Leu Arg Leu Leu Ala
    50                  55                  60 gtc cgc gac gtg gtc cgc gag tcc gac ggc cgg ttc gcg ctg acc gac     240
Val Arg Asp Val Val Arg Glu Ser Asp Gly Arg Phe Ala Leu Thr Asp
65                  70                  75                  80 aag ggc gcg gcg ctg cgg tcg gac tcg ccg gtg ccc gcg cgg gcc ggc     288
Lys Gly Ala Ala Leu Arg Ser Asp Ser Pro Val Pro Ala Arg Ala Gly
                85                  90                  95 atc ctc atg ttc acc gac acg atg ttc tgg acg atg agt cac cgg gtg     336
Ile Leu Met Phe Thr Asp Thr Met Phe Trp Thr Met Ser His Arg Val
            100                 105                 110 gcg agc gcg ctg ggg ccg gag cga ccc gcc ttc gcc gac atc ttc ggt     384
Ala Ser Ala Leu Gly Pro Glu Arg Pro Ala Phe Ala Asp Ile Phe Gly
        115                 120                 125 agc tcg ctg gac gcc tac ttc gac ggc gac gcc gag gtc gag gcg ctc     432
Ser Ser Leu Asp Ala Tyr Phe Asp Gly Asp Ala Glu Val Glu Ala Leu
    130                 135                 140 tac tac gag ggc atg gaa acg gtc agc gcg gcg gag cac ctc att ctc     480
Tyr Tyr Glu Gly Met Glu Thr Val Ser Ala Ala Glu His Leu Ile Leu
```

```
                    145                 150                 155                 160
gcc cgc gcc ggt gac ttc ccc gcc acc ggc acc gtg gcg gac gtc ggc       528
Ala Arg Ala Gly Asp Phe Pro Ala Thr Gly Thr Val Ala Asp Val Gly
                165                 170                 175 ggc ggc cgg ggc ggc ttc ctg ctc acc gtc cta cgc gag cac ccc ggc       576
Gly Gly Arg Gly Gly Phe Leu Leu Thr Val Leu Arg Glu His Pro Gly
            180                 185                 190 ctg cag ggc gtg ctg ctg gac cgc gcg gag gtg gtc gcc cgg cac cgg       624
Leu Gln Gly Val Leu Leu Asp Arg Ala Glu Val Val Ala Arg His Arg
        195                 200                 205 ctg gac gcc ccg gac gtg gcg ggg cgc tgg aag gtt gtc gag ggc gac       672
Leu Asp Ala Pro Asp Val Ala Gly Arg Trp Lys Val Val Glu Gly Asp
    210                 215                 220 ttc ctc cgc gag gtg ccc cac gcc gac gtg cac gtg ctc aag cgc atc       720
Phe Leu Arg Glu Val Pro His Ala Asp Val His Val Leu Lys Arg Ile
225                 230                 235                 240 ctg cac aac tgg ggc gac gag gac agc gtc cgg atc ctg acg aac tgc       768
Leu His Asn Trp Gly Asp Glu Asp Ser Val Arg Ile Leu Thr Asn Cys
                245                 250                 255 cgc cgg gtc atg ccc gcg cac ggc cgg gtg ctc gtg atc gac gcg gtc       816
Arg Arg Val Met Pro Ala His Gly Arg Val Leu Val Ile Asp Ala Val
            260                 265                 270 gtc ccc gag ggc aac gac gcg cac cag agc aag gag atg gac ttc atg       864
Val Pro Glu Gly Asn Asp Ala His Gln Ser Lys Glu Met Asp Phe Met
        275                 280                 285 atg ctc gcc gcg cgc acc ggc cag gaa cgc acc gcc gcc gag ctg gag       912
Met Leu Ala Ala Arg Thr Gly Gln Glu Arg Thr Ala Ala Glu Leu Glu
    290                 295                 300 ccg ttg ttc acc gcg gcc ggg ctg cgc ctg gac cgg gtc gtc ggc acc       960
Pro Leu Phe Thr Ala Ala Gly Leu Arg Leu Asp Arg Val Val Gly Thr
305                 310                 315                 320 tcg tcg gtc atg tcc atc gcg gtc ggc gtg ccg gcc tga                   999
Ser Ser Val Met Ser Ile Ala Val Gly Val Pro Ala *
                325                 330

<210> SEQ ID NO 18
<211> LENGTH: 332
<212> TYPE: PRT
<213> ORGANISM: Bacteria

<400> SEQUENCE: 18

Met Asp Arg Leu Gln Ser Ala Leu Ala Leu Tyr Glu Glu Ala Met Gly
 1               5                  10                  15

Tyr Thr Tyr Ala Ala Ala Leu Arg Ala Ala Ala Ala Val Gly Val Ala
                20                  25                  30

Asp His Leu Val Asp Gly Pro Arg Thr Pro Ala Glu Leu Ala Ala Ala
            35                  40                  45

Thr Gly Thr Asp Ala Asp Ala Leu Arg Arg Val Leu Arg Leu Leu Ala
        50                  55                  60

Val Arg Asp Val Val Arg Glu Ser Asp Gly Arg Phe Ala Leu Thr Asp
65                  70                  75                  80

Lys Gly Ala Ala Leu Arg Ser Asp Ser Pro Val Pro Ala Arg Ala Gly
                85                  90                  95

Ile Leu Met Phe Thr Asp Thr Met Phe Trp Thr Met Ser His Arg Val
                100                 105                 110

Ala Ser Ala Leu Gly Pro Glu Arg Pro Ala Phe Ala Asp Ile Phe Gly
            115                 120                 125

Ser Ser Leu Asp Ala Tyr Phe Asp Gly Asp Ala Glu Val Glu Ala Leu
```

-continued

```
                130                 135                 140
Tyr Tyr Glu Gly Met Glu Thr Val Ser Ala Ala Glu His Leu Ile Leu
145                 150                 155                 160

Ala Arg Ala Gly Asp Phe Pro Ala Thr Gly Thr Val Ala Asp Val Gly
                165                 170                 175

Gly Gly Arg Gly Gly Phe Leu Leu Thr Val Leu Arg Glu His Pro Gly
            180                 185                 190

Leu Gln Gly Val Leu Leu Asp Arg Ala Glu Val Val Ala Arg His Arg
            195                 200                 205

Leu Asp Ala Pro Asp Val Ala Gly Arg Trp Lys Val Val Glu Gly Asp
    210                 215                 220

Phe Leu Arg Glu Val Pro His Ala Asp Val His Val Leu Lys Arg Ile
225                 230                 235                 240

Leu His Asn Trp Gly Asp Glu Asp Ser Val Arg Ile Leu Thr Asn Cys
                245                 250                 255

Arg Arg Val Met Pro Ala His Gly Arg Val Leu Val Ile Asp Ala Val
                260                 265                 270

Val Pro Glu Gly Asn Asp Ala His Gln Ser Lys Glu Met Asp Phe Met
            275                 280                 285

Met Leu Ala Ala Arg Thr Gly Gln Glu Arg Thr Ala Ala Glu Leu Glu
290                 295                 300

Pro Leu Phe Thr Ala Ala Gly Leu Arg Leu Asp Arg Val Val Gly Thr
305                 310                 315                 320

Ser Ser Val Met Ser Ile Ala Val Gly Val Pro Ala
                325                 330

<210> SEQ ID NO 19
<211> LENGTH: 1323
<212> TYPE: DNA
<213> ORGANISM: Bacteria
<220> FEATURE:
<221> NAME/KEY: CDS
<222> LOCATION: (1)...(1323)

<400> SEQUENCE: 19 gtg agc cgt acc gtg gag tcc cct ggc ccg gcc acc gtg tcg gcg tca      48
Val Ser Arg Thr Val Glu Ser Pro Gly Pro Ala Thr Val Ser Ala Ser
 1               5                  10                  15 ccg gcg cag agt ccg ctg cgc acc gcg tcc tgg gcc cgc atc cgc gag      96
Pro Ala Gln Ser Pro Leu Arg Thr Ala Ser Trp Ala Arg Ile Arg Glu
            20                  25                  30 ctg ttc gcc ctg gac ccg acg acc gtg cac ctc aac acg ggg acg gtc     144
Leu Phe Ala Leu Asp Pro Thr Thr Val His Leu Asn Thr Gly Thr Val
        35                  40                  45 ggc gcc atg ccg tac gag gtg ctg gac acc gtg gac cgg gtg acc cgc     192
Gly Ala Met Pro Tyr Glu Val Leu Asp Thr Val Asp Arg Val Thr Arg
    50                  55                  60 cag tgg acc ggc ggc ctg ctc gac gtc tac cgc ccg gcg atg ttc acc     240
Gln Trp Thr Gly Gly Leu Leu Asp Val Tyr Arg Pro Ala Met Phe Thr
65                  70                  75                  80 gag tac cgg gac gcc atc gcg aag acg ttc ggc gtg gac ggc gac gag     288
Glu Tyr Arg Asp Ala Ile Ala Lys Thr Phe Gly Val Asp Gly Asp Glu
                85                  90                  95 atc gtg atc tgc cac aac gcc acc gag ggg gtc gcc cgg gtc atc cac     336
Ile Val Ile Cys His Asn Ala Thr Glu Gly Val Ala Arg Val Ile His
            100                 105                 110 ggc ctc gac ctg cgc gag ggc gac gag gtg gtg acg acg acg cac gag     384
Gly Leu Asp Leu Arg Glu Gly Asp Glu Val Val Thr Thr Thr His Glu
```

```
                    115                 120                     125
tgc tac tcc gtg ctg tcc aac ttc aac ctg ctg cgc aac cgg ttc ggg        432
Cys Tyr Ser Val Leu Ser Asn Phe Asn Leu Leu Arg Asn Arg Phe Gly
    130                 135                 140 gtg gtg ctg aag acc gtc acc ccg ccg tcc ggc cac gag gtg cgc gcg        480
Val Val Leu Lys Thr Val Thr Pro Pro Ser Gly His Glu Val Arg Ala
145                 150                 155                 160 gag gag atc gtc gag ctg gtc gag gcc gcc atc acg ccc cgg acg aag        528
Glu Glu Ile Val Glu Leu Val Glu Ala Ala Ile Thr Pro Arg Thr Lys
                165                 170                 175 gtg ctc tcg ttc gcc gcg atc acc ctc ttc acc ggg acg atg ttc ccc        576
Val Leu Ser Phe Ala Ala Ile Thr Leu Phe Thr Gly Thr Met Phe Pro
            180                 185                 190 atc cgg cag ctc tgc gag ctg gcg cac cgg cac ggg ctg acc acc gtc        624
Ile Arg Gln Leu Cys Glu Leu Ala His Arg His Gly Leu Thr Thr Val
        195                 200                 205 atc gac ggc gcg ctg atc ccc ggc atg ctc gac tgc gac ctg cgc gcg        672
Ile Asp Gly Ala Leu Ile Pro Gly Met Leu Asp Cys Asp Leu Arg Ala
    210                 215                 220 acc ggg gcg gac ttc atc acc tgc tcc ggg tcg aag ttc cag tgc ggc        720
Thr Gly Ala Asp Phe Ile Thr Cys Ser Gly Ser Lys Phe Gln Cys Gly
225                 230                 235                 240 ccg ctc ggc acc ggc ctg atc tac gtc cgc aac aag gtc gtc ccc gag        768
Pro Leu Gly Thr Gly Leu Ile Tyr Val Arg Asn Lys Val Val Pro Glu
                245                 250                 255 cac aac ccc ctg ccg ctg ccc acg ttc tgg ccg ctc atc tcg acc tgg        816
His Asn Pro Leu Pro Leu Pro Thr Phe Trp Pro Leu Ile Ser Thr Trp
            260                 265                 270 tac ccg atg atg ggc agc ccg ccg cgg acc agc acc gcc gtg gag        864
Tyr Pro Met Met Gly Ser Pro Pro Arg Thr Ser Thr Ala Val Glu
        275                 280                 285 agc tac aac atg ggc gac ttc ctg cag agc gcc ggc agc gcc aac ctg        912
Ser Tyr Asn Met Gly Asp Phe Leu Gln Ser Ala Gly Ser Ala Asn Leu
    290                 295                 300 gcg cgg ggc gcc gcc ctg gcc cgg gcc ttc gag ctg tgg gac gac atc        960
Ala Arg Gly Ala Ala Leu Ala Arg Ala Phe Glu Leu Trp Asp Asp Ile
305                 310                 315                 320 ggc cgc gac cgc atc gag gcg tac atc atg gac ctc gcc gag tac gcc       1008
Gly Arg Asp Arg Ile Glu Ala Tyr Ile Met Asp Leu Ala Glu Tyr Ala
                325                 330                 335 cgc ggc cgg ctc atc gac gcg ttc ggc gtc gag gcc atg tac tcc ccc       1056
Arg Gly Arg Leu Ile Asp Ala Phe Gly Val Glu Ala Met Tyr Ser Pro
            340                 345                 350 ggc gcc gac ccg cgg ctg cgc tcg ccg ctc ctc gcg ttc aac ccg ttc       1104
Gly Ala Asp Pro Arg Leu Arg Ser Pro Leu Leu Ala Phe Asn Pro Phe
        355                 360                 365 cgg cgg ccg gag gac gcc tgg aac atc aag aag ttc atc ggc ttc gtc       1152
Arg Arg Pro Glu Asp Ala Trp Asn Ile Lys Lys Phe Ile Gly Phe Val
    370                 375                 380 aag cgc ctg gag acc gag cac cgg atc tgg acc cgc tgg acg gag ttc       1200
Lys Arg Leu Glu Thr Glu His Arg Ile Trp Thr Arg Trp Thr Glu Phe
385                 390                 395                 400 gac gtg ccc ggc tcc ccg cac cag cac tac gcg gcg cgc atc acc acg       1248
Asp Val Pro Gly Ser Pro His Gln His Tyr Ala Ala Arg Ile Thr Thr
                405                 410                 415 cac ctg ttc aac acc cgg gaa gag atc gac cac acc gta cgg acg atg       1296
His Leu Phe Asn Thr Arg Glu Glu Ile Asp His Thr Val Arg Thr Met
            420                 425                 430 gtc cgc ctg gcc gag gag atg tct tga                                    1323
Val Arg Leu Ala Glu Glu Met Ser
```

```
Val Arg Leu Ala Glu Glu Met Ser   *
        435                 440

<210> SEQ ID NO 20
<211> LENGTH: 440
<212> TYPE: PRT
<213> ORGANISM: Bacteria

<400> SEQUENCE: 20

Val Ser Arg Thr Val Glu Ser Pro Gly Pro Ala Thr Val Ser Ala Ser
 1               5                  10                  15

Pro Ala Gln Ser Pro Leu Arg Thr Ala Ser Trp Ala Arg Ile Arg Glu
            20                  25                  30

Leu Phe Ala Leu Asp Pro Thr Thr Val His Leu Asn Thr Gly Thr Val
        35                  40                  45

Gly Ala Met Pro Tyr Glu Val Leu Asp Thr Val Asp Arg Val Thr Arg
    50                  55                  60

Gln Trp Thr Gly Gly Leu Leu Asp Val Tyr Arg Pro Ala Met Phe Thr
65                  70                  75                  80

Glu Tyr Arg Asp Ala Ile Ala Lys Thr Phe Gly Val Asp Gly Asp Glu
                85                  90                  95

Ile Val Ile Cys His Asn Ala Thr Glu Gly Val Ala Arg Val Ile His
            100                 105                 110

Gly Leu Asp Leu Arg Glu Gly Asp Glu Val Val Thr Thr His Glu
        115                 120                 125

Cys Tyr Ser Val Leu Ser Asn Phe Asn Leu Leu Arg Asn Arg Phe Gly
    130                 135                 140

Val Val Leu Lys Thr Val Thr Pro Pro Ser Gly His Glu Val Arg Ala
145                 150                 155                 160

Glu Glu Ile Val Glu Leu Val Glu Ala Ala Ile Thr Pro Arg Thr Lys
                165                 170                 175

Val Leu Ser Phe Ala Ala Ile Thr Leu Phe Thr Gly Thr Met Phe Pro
            180                 185                 190

Ile Arg Gln Leu Cys Glu Leu Ala His Arg His Gly Leu Thr Thr Val
        195                 200                 205

Ile Asp Gly Ala Leu Ile Pro Gly Met Leu Asp Cys Asp Leu Arg Ala
    210                 215                 220

Thr Gly Ala Asp Phe Ile Thr Cys Ser Gly Ser Lys Phe Gln Cys Gly
225                 230                 235                 240

Pro Leu Gly Thr Gly Leu Ile Tyr Val Arg Asn Lys Val Val Pro Glu
                245                 250                 255

His Asn Pro Leu Pro Leu Pro Thr Phe Trp Pro Leu Ile Ser Thr Trp
            260                 265                 270

Tyr Pro Met Met Gly Ser Pro Pro Arg Thr Ser Thr Ala Val Glu
        275                 280                 285

Ser Tyr Asn Met Gly Asp Phe Leu Gln Ser Ala Gly Ser Ala Asn Leu
    290                 295                 300

Ala Arg Gly Ala Ala Leu Ala Arg Ala Phe Glu Leu Trp Asp Asp Ile
305                 310                 315                 320

Gly Arg Asp Arg Ile Glu Ala Tyr Ile Met Asp Leu Ala Glu Tyr Ala
                325                 330                 335

Arg Gly Arg Leu Ile Asp Ala Phe Gly Val Glu Ala Met Tyr Ser Pro
            340                 345                 350

Gly Ala Asp Pro Arg Leu Arg Ser Pro Leu Leu Ala Phe Asn Pro Phe
        355                 360                 365
```

```
Arg Arg Pro Glu Asp Ala Trp Asn Ile Lys Lys Phe Ile Gly Phe Val
    370                 375                 380

Lys Arg Leu Glu Thr Glu His Arg Ile Trp Thr Arg Trp Thr Glu Phe
385                 390                 395                 400

Asp Val Pro Gly Ser Pro His Gln His Tyr Ala Ala Arg Ile Thr Thr
                405                 410                 415

His Leu Phe Asn Thr Arg Glu Glu Ile Asp His Thr Val Arg Thr Met
                420                 425                 430

Val Arg Leu Ala Glu Glu Met Ser
            435                 440

<210> SEQ ID NO 21
<211> LENGTH: 1683
<212> TYPE: DNA
<213> ORGANISM: Bacteria
<220> FEATURE:
<221> NAME/KEY: CDS
<222> LOCATION: (1)...(1683)

<400> SEQUENCE: 21 gtg acg cag gcg cgc agt gca acg acg acg aac gac acc cgg ctg cgg      48
Val Thr Gln Ala Arg Ser Ala Thr Thr Thr Asn Asp Thr Arg Leu Arg
1               5                   10                  15 ggc acc ctg cgg ctg ctc ggg ccc gcc gcc gtc cac cag gcg gac ccg      96
Gly Thr Leu Arg Leu Leu Gly Pro Ala Ala Val His Gln Ala Asp Pro
                20                  25                  30 gcc gcc gcc tgg tcg ccg gcc gag cgc cag ttg ctc cgg ctg tgc acc     144
Ala Ala Ala Trp Ser Pro Ala Glu Arg Gln Leu Leu Arg Leu Cys Thr
            35                  40                  45 cgg cag ctg atc agc tac cgc ccg gaa ccc gac ccg ggc gac tgg cgc     192
Arg Gln Leu Ile Ser Tyr Arg Pro Glu Pro Asp Pro Gly Asp Trp Arg
        50                  55                  60 gcc ctc gcg ccg gtc gcc gac ctg gcc acc gac gtc ccc tcg acc tac     240
Ala Leu Ala Pro Val Ala Asp Leu Ala Thr Asp Val Pro Ser Thr Tyr
65                  70                  75                  80 aac gcc ggc ctg ggc gcc agc cac cgc agc tac gtg gtg cac ctg cgc     288
Asn Ala Gly Leu Gly Ala Ser His Arg Ser Tyr Val Val His Leu Arg
                85                  90                  95 ccc ggg gtg ctc tgg gac acg ccg acc ccc cgc ccg gtg acg gcg cac     336
Pro Gly Val Leu Trp Asp Thr Pro Thr Pro Arg Pro Val Thr Ala His
                100                 105                 110 gac gtc gta cgc ggc ttc aag cgg ctg gcc aac ccg ctc acc cga cac     384
Asp Val Val Arg Gly Phe Lys Arg Leu Ala Asn Pro Leu Thr Arg His
            115                 120                 125 ccc gcg ctg gcg tac ttc cgg ggc acc ctg cgg ggc atg ggc cgg tac     432
Pro Ala Leu Ala Tyr Phe Arg Gly Thr Leu Arg Gly Met Gly Arg Tyr
        130                 135                 140 tgc gac gag tac gcg gcg gcg gtc gcc ggc cac ccg gtc acc gcg gcg     480
Cys Asp Glu Tyr Ala Ala Ala Val Ala Gly His Pro Val Thr Ala Ala
145                 150                 155                 160 ctc ctc gcc ggc ttc cag gac gcc cac gag atc ccc ggc gtg ttc gcc     528
Leu Leu Ala Gly Phe Gln Asp Ala His Glu Ile Pro Gly Val Phe Ala
                165                 170                 175 gtc gac gac gag acg gtg gtc ttc gag ctg gac cgt ccg gcg ctg gac     576
Val Asp Asp Glu Thr Val Val Phe Glu Leu Asp Arg Pro Ala Leu Asp
                180                 185                 190 ttc gtc gac atg ctg gcg cag agc ggc gcc tcc ccg gcc ccg gtg gag     624
Phe Val Asp Met Leu Ala Gln Ser Gly Ala Ser Pro Ala Pro Val Glu
            195                 200                 205
```

| | | |
|---|---|---|
| tac gac gca cac ctg ccg gga agc gcc ggc ctg cac gag cac ctg gtc<br>Tyr Asp Ala His Leu Pro Gly Ser Ala Gly Leu His Glu His Leu Val<br>210                        215                        220 | 672 |
| gcc aac ggc ccg tac cgc gtc gtg tcg tgg cgc ccc ggg ggc acc atc<br>Ala Asn Gly Pro Tyr Arg Val Val Ser Trp Arg Pro Gly Gly Thr Ile<br>225                        230                        235                        240 | 720 |
| cgg ctg gag ccg aac ccg gcg tgg cgg gcg gag acc gac ccg atc cgc<br>Arg Leu Glu Pro Asn Pro Ala Trp Arg Ala Glu Thr Asp Pro Ile Arg<br>                        245                        250                        255 | 768 |
| gag cgg cgg ttc gac gcc gtc gag ttc cgc gtc gcc atg ggc ggg ccg<br>Glu Arg Arg Phe Asp Ala Val Glu Phe Arg Val Ala Met Gly Gly Pro<br>                    260                        265                        270 | 816 |
| cgc gaa ctg gcc gac cgg ctc gcc gcc gac gac gcc gac ctg ccg tgg<br>Arg Glu Leu Ala Asp Arg Leu Ala Ala Asp Asp Ala Asp Leu Pro Trp<br>                275                        280                        285 | 864 |
| ggc gtg ccg atc ggc ccg gtg ccc ggt cag cgg ctc gac ccg tgc ctg<br>Gly Val Pro Ile Gly Pro Val Pro Gly Gln Arg Leu Asp Pro Cys Leu<br>290                        295                        300 | 912 |
| gtg ttc aac ctg cgc gac ccc gcc aac ccg gcc gtc gcc gac gcc gcg<br>Val Phe Asn Leu Arg Asp Pro Ala Asn Pro Ala Val Ala Asp Ala Ala<br>305                        310                        315                        320 | 960 |
| gtg cgc cgg gtc gtc gcc ggg gcg gtc gac cgg gcg gcg ctg gtg cgc<br>Val Arg Arg Val Val Ala Gly Ala Val Asp Arg Ala Ala Leu Val Arg<br>                        325                        330                        335 | 1008 |
| atc gcc cgg gcc gcc gac ccg tgg tcc gag gtc cgc gcc gcc cac acc<br>Ile Ala Arg Ala Ala Asp Pro Trp Ser Glu Val Arg Ala Ala His Thr<br>                    340                        345                        350 | 1056 |
| gtc gtg ccg ccc ggc aac gac ggg cac cgg cag ccc gac ccg ctc acc<br>Val Val Pro Pro Gly Asn Asp Gly His Arg Gln Pro Asp Pro Leu Thr<br>                355                        360                        365 | 1104 |
| gac ccg att ccc gac gcc gac gcg gac ccg cgc gag cgg ctc gcc gcc<br>Asp Pro Ile Pro Asp Ala Asp Ala Asp Pro Arg Glu Arg Leu Ala Ala<br>370                        375                        380 | 1152 |
| gcg ggg cac ccg gac ggg ctc acc ctg acc gcg gtg cac ccc gac acg<br>Ala Gly His Pro Asp Gly Leu Thr Leu Thr Ala Val His Pro Asp Thr<br>385                        390                        395                        400 | 1200 |
| gcc gag gac ctg gcg ctg gcc cgc tcg tgg gcg gcc gac ctc ggc gcc<br>Ala Glu Asp Leu Ala Leu Ala Arg Ser Trp Ala Ala Asp Leu Gly Ala<br>                    405                        410                        415 | 1248 |
| gcc ggc atc gac gta cgc ctg gtc gcg ctc gac gac gcc aac cac cgg<br>Ala Gly Ile Asp Val Arg Leu Val Ala Leu Asp Asp Ala Asn His Arg<br>                        420                        425                        430 | 1296 |
| gcc ctg ctc gcc gcc acg ggc gac gcg ccc ggc ctg cga tgg gac ctg<br>Ala Leu Leu Ala Ala Thr Gly Asp Ala Pro Gly Leu Arg Trp Asp Leu<br>                435                        440                        445 | 1344 |
| gcg acc gcc acg ttc acc gcg ccg tgg gcc tac ggc aac gcc cgg gtg<br>Ala Thr Ala Thr Phe Thr Ala Pro Trp Ala Tyr Gly Asn Ala Arg Val<br>450                        455                        460 | 1392 |
| ttc ctg caa ccg ctg gtc ggc gag gga ccc ggc aac ccc ggc ggc tac<br>Phe Leu Gln Pro Leu Val Gly Glu Gly Pro Gly Asn Pro Gly Gly Tyr<br>465                        470                        475                        480 | 1440 |
| cgc gac ccc ggg gtt gac cgg gtg gtc gag cgc gcg ctg gac gcg gcc<br>Arg Asp Pro Gly Val Asp Arg Val Val Glu Arg Ala Leu Asp Ala Ala<br>                    485                        490                        495 | 1488 |
| gac ccg cgc gag gcg gtc gcc ctg tgg cag gag gtg gag cgg cgg ctg<br>Asp Pro Arg Glu Ala Val Ala Leu Trp Gln Glu Val Glu Arg Arg Leu<br>                500                        505                        510 | 1536 |
| ctc gcc gac gcc gcg gtc gta ccc ctg ctg ttc cgg cgg gcc acg gac<br>Leu Ala Asp Ala Ala Val Val Pro Leu Leu Phe Arg Arg Ala Thr Asp<br>515                        520                        525 | 1584 |

-continued

```
gcc gcg ccg cgc ggg ccc cgg gtg cgg cgc gcg acc gcc ctg ccg gcg      1632
Ala Ala Pro Arg Gly Pro Arg Val Arg Arg Ala Thr Ala Leu Pro Ala
    530                 535                 540 ctc gcc ggc ctg ccc gac ctc gcc gac gtg cgg ctc ggg gtg gac cgg      1680
Leu Ala Gly Leu Pro Asp Leu Ala Asp Val Arg Leu Gly Val Asp Arg
545                 550                 555                 560 tga                                                                  1683
 *
```

<210> SEQ ID NO 22
<211> LENGTH: 560
<212> TYPE: PRT
<213> ORGANISM: Bacteria

<400> SEQUENCE: 22

```
Val Thr Gln Ala Arg Ser Ala Thr Thr Asn Asp Thr Arg Leu Arg
 1               5                  10                  15

Gly Thr Leu Arg Leu Leu Gly Pro Ala Ala Val His Gln Ala Asp Pro
                20                  25                  30

Ala Ala Ala Trp Ser Pro Ala Glu Arg Gln Leu Leu Arg Leu Cys Thr
            35                  40                  45

Arg Gln Leu Ile Ser Tyr Arg Pro Glu Pro Asp Pro Gly Asp Trp Arg
50                  55                  60

Ala Leu Ala Pro Val Ala Asp Leu Ala Thr Asp Val Pro Ser Thr Tyr
65                  70                  75                  80

Asn Ala Gly Leu Gly Ala Ser His Arg Ser Tyr Val Val His Leu Arg
                85                  90                  95

Pro Gly Val Leu Trp Asp Thr Pro Thr Pro Arg Pro Val Thr Ala His
            100                 105                 110

Asp Val Val Arg Gly Phe Lys Arg Leu Ala Asn Pro Leu Thr Arg His
        115                 120                 125

Pro Ala Leu Ala Tyr Phe Arg Gly Thr Leu Arg Gly Met Gly Arg Tyr
    130                 135                 140

Cys Asp Glu Tyr Ala Ala Ala Val Ala Gly His Pro Val Thr Ala Ala
145                 150                 155                 160

Leu Leu Ala Gly Phe Gln Asp Ala His Glu Ile Pro Gly Val Phe Ala
                165                 170                 175

Val Asp Asp Glu Thr Val Val Phe Glu Leu Asp Arg Pro Ala Leu Asp
            180                 185                 190

Phe Val Asp Met Leu Ala Gln Ser Gly Ala Ser Pro Ala Pro Val Glu
        195                 200                 205

Tyr Asp Ala His Leu Pro Gly Ser Ala Gly Leu His Glu His Leu Val
    210                 215                 220

Ala Asn Gly Pro Tyr Arg Val Val Ser Trp Arg Pro Gly Gly Thr Ile
225                 230                 235                 240

Arg Leu Glu Pro Asn Pro Ala Trp Arg Ala Glu Thr Asp Pro Ile Arg
                245                 250                 255

Glu Arg Arg Phe Asp Ala Val Glu Phe Arg Val Ala Met Gly Gly Pro
            260                 265                 270

Arg Glu Leu Ala Asp Arg Leu Ala Ala Asp Ala Asp Leu Pro Trp
        275                 280                 285

Gly Val Pro Ile Gly Pro Val Pro Gly Gln Arg Leu Asp Pro Cys Leu
    290                 295                 300

Val Phe Asn Leu Arg Asp Pro Ala Asn Pro Ala Val Ala Asp Ala Ala
305                 310                 315                 320
```

```
Val Arg Arg Val Val Ala Gly Ala Val Asp Arg Ala Ala Leu Val Arg
            325                 330                 335

Ile Ala Arg Ala Ala Asp Pro Trp Ser Glu Val Arg Ala Ala His Thr
            340                 345                 350

Val Val Pro Pro Gly Asn Asp Gly His Arg Gln Pro Asp Pro Leu Thr
            355                 360                 365

Asp Pro Ile Pro Asp Ala Asp Ala Asp Pro Arg Glu Arg Leu Ala Ala
            370                 375                 380

Ala Gly His Pro Asp Gly Leu Thr Leu Thr Ala Val His Pro Asp Thr
385                 390                 395                 400

Ala Glu Asp Leu Ala Leu Ala Arg Ser Trp Ala Ala Asp Leu Gly Ala
            405                 410                 415

Ala Gly Ile Asp Val Arg Leu Val Ala Leu Asp Asp Ala Asn His Arg
            420                 425                 430

Ala Leu Leu Ala Ala Thr Gly Asp Ala Pro Gly Leu Arg Trp Asp Leu
            435                 440                 445

Ala Thr Ala Thr Phe Thr Ala Pro Trp Ala Tyr Gly Asn Ala Arg Val
            450                 455                 460

Phe Leu Gln Pro Leu Val Gly Glu Gly Pro Gly Asn Pro Gly Gly Tyr
465                 470                 475                 480

Arg Asp Pro Gly Val Asp Arg Val Val Glu Arg Ala Leu Asp Ala Ala
            485                 490                 495

Asp Pro Arg Glu Ala Val Ala Leu Trp Gln Glu Val Glu Arg Arg Leu
            500                 505                 510

Leu Ala Asp Ala Ala Val Val Pro Leu Leu Phe Arg Arg Ala Thr Asp
            515                 520                 525

Ala Ala Pro Arg Gly Pro Arg Val Arg Arg Ala Thr Ala Leu Pro Ala
            530                 535                 540

Leu Ala Gly Leu Pro Asp Leu Ala Asp Val Arg Leu Gly Val Asp Arg
545                 550                 555                 560

<210> SEQ ID NO 23
<211> LENGTH: 1248
<212> TYPE: DNA
<213> ORGANISM: Bacteria
<220> FEATURE:
<221> NAME/KEY: CDS
<222> LOCATION: (1)...(1248)

<400> SEQUENCE: 23 gtg acc ggt gcc gcc gcc gac gcg gtg gtc gcc gac tac ctc gcg ctc      48
Val Thr Gly Ala Ala Ala Asp Ala Val Val Ala Asp Tyr Leu Ala Leu
 1               5                  10                  15 ggg ctg cgg atg ggt cgg ctc gtc gag ggc tac gtc gac tgc tgg ttc      96
Gly Leu Arg Met Gly Arg Leu Val Glu Gly Tyr Val Asp Cys Trp Phe
            20                  25                  30 ggc gac cgg gcc ctc gcc gag cgg gtc gcc gcg gag ccg gcg ccg gac     144
Gly Asp Arg Ala Leu Ala Glu Arg Val Ala Ala Glu Pro Ala Pro Asp
        35                  40                  45 ccg gcg gag ctg gcc gga cag gcc cgc gac ctg ctg cgc cgc ctg ggc     192
Pro Ala Glu Leu Ala Gly Gln Ala Arg Asp Leu Leu Arg Arg Leu Gly
    50                  55                  60 gac gcg gac ctc gac gcg gag cgg cgg cgg ttc ctc gcc gcg cag ctg     240
Asp Ala Asp Leu Asp Ala Glu Arg Arg Arg Phe Leu Ala Ala Gln Leu
65                  70                  75                  80 acc gcg gtg gag tgc gcg gcc cgg cgg gcg gcg ggt gag cag atc ggc     288
Thr Ala Val Glu Cys Ala Ala Arg Arg Ala Ala Gly Glu Gln Ile Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 85  |     |     |     |     | 90  |     |     |     |     | 95  |     |     |
| ttc | ctg | gcc | gag | gtg | gag | acc | tac | ttc | gac | gtc | gag | gtg | cgc | ctc | ggc | 336 |
| Phe | Leu | Ala | Glu | Val | Glu | Thr | Tyr | Phe | Asp | Val | Glu | Val | Arg | Leu | Gly |     |
|     |     |     |     | 100 |     |     |     |     | 105 |     |     |     |     | 110 |     |     |
| gac | ccg | gac | cgg | tac | gcc | gcc | gcg | cac | gac | gcc | atc | gac | gcg | ctg | ctg | 384 |
| Asp | Pro | Asp | Arg | Tyr | Ala | Ala | Ala | His | Asp | Ala | Ile | Asp | Ala | Leu | Leu |     |
|     |     |     | 115 |     |     |     |     | 120 |     |     |     |     | 125 |     |     |     |
| ccg | ggc | acc | ggc | ccg | ctg | atg | gac | aag | gtc | gag | gcg | ttc | tac | gcc | cgc | 432 |
| Pro | Gly | Thr | Gly | Pro | Leu | Met | Asp | Lys | Val | Glu | Ala | Phe | Tyr | Ala | Arg |     |
|     | 130 |     |     |     |     | 135 |     |     |     |     | 140 |     |     |     |     |     |
| aac | gtg | gtg | ccg | ccg | gag | cgg | ctg | ggc | cac | gcc | gtg | cgg | gcc | gtc | gcc | 480 |
| Asn | Val | Val | Pro | Pro | Glu | Arg | Leu | Gly | His | Ala | Val | Arg | Ala | Val | Ala |     |
| 145 |     |     |     |     | 150 |     |     |     |     | 155 |     |     |     |     | 160 |     |
| gac | gcg | ctg | cgc | gcc | cgt | gcc | cgg | ccg | atg | ctc | ggg | ctg | ccc | gag | gcc | 528 |
| Asp | Ala | Leu | Arg | Ala | Arg | Ala | Arg | Pro | Met | Leu | Gly | Leu | Pro | Glu | Ala |     |
|     |     |     |     | 165 |     |     |     |     | 170 |     |     |     |     | 175 |     |     |
| gag | cgg | gtc | gac | atc | gag | gtg | gtc | cgc | gac | cgg | ccg | tgg | aac | gcg | ttc | 576 |
| Glu | Arg | Val | Asp | Ile | Glu | Val | Val | Arg | Asp | Arg | Pro | Trp | Asn | Ala | Phe |     |
|     |     |     | 180 |     |     |     |     | 185 |     |     |     |     | 190 |     |     |     |
| aac | cgg | tac | cac | ggc | ggc | ttc | cgt | tcc | acg | gtg | acg | ctg | aac | gag | acg | 624 |
| Asn | Arg | Tyr | His | Gly | Gly | Phe | Arg | Ser | Thr | Val | Thr | Leu | Asn | Glu | Thr |     |
|     | 195 |     |     |     |     | 200 |     |     |     |     | 205 |     |     |     |     |     |
| gcc | ggc | cgg | acc | atc | gcc | gtg | ctg | ccg | ctg | atg | gcc | acc | cac | gag | gcg | 672 |
| Ala | Gly | Arg | Thr | Ile | Ala | Val | Leu | Pro | Leu | Met | Ala | Thr | His | Glu | Ala |     |
| 210 |     |     |     |     | 215 |     |     |     |     | 220 |     |     |     |     |     |     |
| tac | ccg | ggc | cac | cac | acc | gag | cac | tgc | ctc | aag | gag | gcc | ggg | ctg | gtg | 720 |
| Tyr | Pro | Gly | His | His | Thr | Glu | His | Cys | Leu | Lys | Glu | Ala | Gly | Leu | Val |     |
| 225 |     |     |     |     | 230 |     |     |     |     | 235 |     |     |     |     | 240 |     |
| ctc | gac | cgg | ggc | tgg | gac | gag | cac | cgc | atc | gcc | ctg | gtc | aac | acc | ccg | 768 |
| Leu | Asp | Arg | Gly | Trp | Asp | Glu | His | Arg | Ile | Ala | Leu | Val | Asn | Thr | Pro |     |
|     |     |     |     | 245 |     |     |     |     | 250 |     |     |     |     | 255 |     |     |
| cag | tgc | ctg | gtg | gcg | gag | ggc | acc | gcc | gag | cac | gcc | gcg | gcg | gcg | ctg | 816 |
| Gln | Cys | Leu | Val | Ala | Glu | Gly | Thr | Ala | Glu | His | Ala | Ala | Ala | Ala | Leu |     |
|     |     |     | 260 |     |     |     |     | 265 |     |     |     |     | 270 |     |     |     |
| ctc | ggg | ccc | ggc | tgg | gga | cgg | tgg | acc | acc | gag | gtg | ctg | gcc | ggc | gag | 864 |
| Leu | Gly | Pro | Gly | Trp | Gly | Arg | Trp | Thr | Thr | Glu | Val | Leu | Ala | Gly | Glu |     |
|     | 275 |     |     |     |     | 280 |     |     |     |     | 285 |     |     |     |     |     |
| ggg | gtg | ccc | gtc | gag | ggc | gac | ctc | gtc | gag | cgg | atg | gtg | ggg | ctc | gtc | 912 |
| Gly | Val | Pro | Val | Glu | Gly | Asp | Leu | Val | Glu | Arg | Met | Val | Gly | Leu | Val |     |
|     | 290 |     |     |     |     | 295 |     |     |     |     | 300 |     |     |     |     |     |
| aac | gag | ctg | atg | ccg | gcc | cgg | cag | gac | gcg | gcg | atc | ctg | ctg | cac | gac | 960 |
| Asn | Glu | Leu | Met | Pro | Ala | Arg | Gln | Asp | Ala | Ala | Ile | Leu | Leu | His | Asp |     |
| 305 |     |     |     |     | 310 |     |     |     |     | 315 |     |     |     |     | 320 |     |
| cgg | ggg | gcg | tcg | atc | gac | gac | gcg | gtg | gag | cac | ctg | cac | cgg | tgg | ctg | 1008 |
| Arg | Gly | Ala | Ser | Ile | Asp | Asp | Ala | Val | Glu | His | Leu | His | Arg | Trp | Leu |     |
|     |     |     |     | 325 |     |     |     |     | 330 |     |     |     |     | 335 |     |     |
| ctg | ctg | ccg | cgg | gac | cgg | gcc | gag | cag | atc | gcc | acc | ttc | ctg | acc | gac | 1056 |
| Leu | Leu | Pro | Arg | Asp | Arg | Ala | Glu | Gln | Ile | Ala | Thr | Phe | Leu | Thr | Asp |     |
|     |     |     | 340 |     |     |     |     | 345 |     |     |     |     | 350 |     |     |     |
| ccg | ctg | tgg | cgg | gcc | tac | tcc | gtg | acg | tac | atc | gag | ggg | gcc | cgg | ctg | 1104 |
| Pro | Leu | Trp | Arg | Ala | Tyr | Ser | Val | Thr | Tyr | Ile | Glu | Gly | Ala | Arg | Leu |     |
|     |     | 355 |     |     |     |     | 360 |     |     |     |     | 365 |     |     |     |     |
| gtc | ggc | ggg | tgg | ctc | gcc | gcc | cgg | ccg | gcc | ggc | gag | ccg | ctc | gtc | gcg | 1152 |
| Val | Gly | Gly | Trp | Leu | Ala | Ala | Arg | Pro | Ala | Gly | Glu | Pro | Leu | Val | Ala |     |
|     | 370 |     |     |     |     | 375 |     |     |     |     | 380 |     |     |     |     |     |
| cgg | tac | cgc | acc | ctg | ctg | gcg | gag | cag | ctc | ctt | ccc | gcg | cag | ctc | cgc | 1200 |
| Arg | Tyr | Arg | Thr | Leu | Leu | Ala | Glu | Gln | Leu | Leu | Pro | Ala | Gln | Leu | Arg |     |
| 385 |     |     |     |     | 390 |     |     |     |     | 395 |     |     |     |     | 400 |     |
| gac | ggc | acg | gtc | ccc | gcg | ggc | gcg | ccg | ccc | gtg | ccc | gcg | gcc | cgc | tga | 1248 |

-continued

Asp Gly Thr Val Pro Ala Gly Ala Pro Val Pro Ala Ala Arg *
            405                 410                 415

<210> SEQ ID NO 24
<211> LENGTH: 415
<212> TYPE: PRT
<213> ORGANISM: Bacteria

<400> SEQUENCE: 24

Val Thr Gly Ala Ala Ala Asp Ala Val Ala Asp Tyr Leu Ala Leu
1               5                   10                  15

Gly Leu Arg Met Gly Arg Leu Val Glu Gly Tyr Val Asp Cys Trp Phe
            20                  25                  30

Gly Asp Arg Ala Leu Ala Glu Arg Val Ala Ala Glu Pro Ala Pro Asp
            35                  40                  45

Pro Ala Glu Leu Ala Gly Gln Ala Arg Asp Leu Leu Arg Arg Leu Gly
            50                  55                  60

Asp Ala Asp Leu Asp Ala Glu Arg Arg Phe Leu Ala Ala Gln Leu
65                  70                  75                  80

Thr Ala Val Glu Cys Ala Ala Arg Arg Ala Ala Gly Glu Gln Ile Gly
                85                  90                  95

Phe Leu Ala Glu Val Glu Thr Tyr Phe Asp Val Glu Val Arg Leu Gly
            100                 105                 110

Asp Pro Asp Arg Tyr Ala Ala His Asp Ala Ile Asp Ala Leu Leu
            115                 120                 125

Pro Gly Thr Gly Pro Leu Met Asp Lys Val Glu Ala Phe Tyr Ala Arg
            130                 135                 140

Asn Val Val Pro Pro Glu Arg Leu Gly His Ala Val Arg Ala Val Ala
145                 150                 155                 160

Asp Ala Leu Arg Ala Arg Ala Arg Pro Met Leu Gly Leu Pro Glu Ala
                165                 170                 175

Glu Arg Val Asp Ile Glu Val Val Arg Asp Arg Pro Trp Asn Ala Phe
            180                 185                 190

Asn Arg Tyr His Gly Gly Phe Arg Ser Thr Val Thr Leu Asn Glu Thr
            195                 200                 205

Ala Gly Arg Thr Ile Ala Val Leu Pro Leu Met Ala Thr His Glu Ala
            210                 215                 220

Tyr Pro Gly His His Thr Glu His Cys Leu Lys Glu Ala Gly Leu Val
225                 230                 235                 240

Leu Asp Arg Gly Trp Asp Glu His Arg Ile Ala Leu Val Asn Thr Pro
                245                 250                 255

Gln Cys Leu Val Ala Glu Gly Thr Ala Glu His Ala Ala Ala Leu
            260                 265                 270

Leu Gly Pro Gly Trp Gly Arg Trp Thr Thr Glu Val Leu Ala Gly Glu
            275                 280                 285

Gly Val Pro Val Glu Gly Asp Leu Val Glu Arg Met Val Gly Leu Val
            290                 295                 300

Asn Glu Leu Met Pro Ala Arg Gln Asp Ala Ala Ile Leu Leu His Asp
305                 310                 315                 320

Arg Gly Ala Ser Ile Asp Asp Ala Val Glu His Leu His Arg Trp Leu
                325                 330                 335

Leu Leu Pro Arg Asp Arg Ala Glu Gln Ile Ala Thr Phe Leu Thr Asp
            340                 345                 350

Pro Leu Trp Arg Ala Tyr Ser Val Thr Tyr Ile Glu Gly Ala Arg Leu
            355                 360                 365

```
Val Gly Gly Trp Leu Ala Ala Arg Pro Ala Gly Glu Pro Leu Val Ala
    370                 375                 380

Arg Tyr Arg Thr Leu Leu Ala Glu Gln Leu Leu Pro Ala Gln Leu Arg
385                 390                 395                 400

Asp Gly Thr Val Pro Ala Gly Ala Pro Val Pro Ala Ala Arg
                405                 410                 415

<210> SEQ ID NO 25
<211> LENGTH: 1194
<212> TYPE: DNA
<213> ORGANISM: Bacteria
<220> FEATURE:
<221> NAME/KEY: CDS
<222> LOCATION: (1)...(1194)

<400> SEQUENCE: 25 atg gcc cac ctc ctg atc gtc aac gtc gcc agc cac ggc ctg atc ctg      48
Met Ala His Leu Leu Ile Val Asn Val Ala Ser His Gly Leu Ile Leu
  1               5                  10                  15 ccc acc ctc acc gtg gtc acc gag ctg gtc cgg cgc ggg cac cgg gtc      96
Pro Thr Leu Thr Val Val Thr Glu Leu Val Arg Arg Gly His Arg Val
             20                  25                  30 agc tac gtc acc gcc ggc ggg ttc gcg gag ccg gtc cgt gcc gcc ggc     144
Ser Tyr Val Thr Ala Gly Gly Phe Ala Glu Pro Val Arg Ala Ala Gly
         35                  40                  45 gcg acg gtg gtg ccc tac cag tcg gag atc atc gac gcg gac gcc gcc     192
Ala Thr Val Val Pro Tyr Gln Ser Glu Ile Ile Asp Ala Asp Ala Ala
     50                  55                  60 gag gtg ttc ggc tcg gac gac ctc ggc gtc cgt ccc cac ctg atg tac     240
Glu Val Phe Gly Ser Asp Asp Leu Gly Val Arg Pro His Leu Met Tyr
 65                  70                  75                  80 ctg cgg gag aac gtc tcg gtg ctc cgg gcc acc gcc gag gcg ctc gac     288
Leu Arg Glu Asn Val Ser Val Leu Arg Ala Thr Ala Glu Ala Leu Asp
                 85                  90                  95 ggc gac gtg ccg gac ctg gtc ctc tac gac gac ttc ccg ttc atc gcc     336
Gly Asp Val Pro Asp Leu Val Leu Tyr Asp Asp Phe Pro Phe Ile Ala
            100                 105                 110 ggg cag ttg ctg gcc gcc cgc tgg cgg cgg ccg gcc gtc cgg ctc agc     384
Gly Gln Leu Leu Ala Ala Arg Trp Arg Arg Pro Ala Val Arg Leu Ser
        115                 120                 125 gcg gcg ttc gcg tcg aac gag cac tac tcg ttc tcc cag gac atg gtc     432
Ala Ala Phe Ala Ser Asn Glu His Tyr Ser Phe Ser Gln Asp Met Val
    130                 135                 140 acc ctg gcc ggc acg atc gac ccg ctc gac ctg ccg gtg ttc cgc gac     480
Thr Leu Ala Gly Thr Ile Asp Pro Leu Asp Leu Pro Val Phe Arg Asp
145                 150                 155                 160 acc ctg cgg gac ctg ctc gcc gag cac ggc ctg tcc cgg tcg gtc gtg     528
Thr Leu Arg Asp Leu Leu Ala Glu His Gly Leu Ser Arg Ser Val Val
                165                 170                 175 gac tgc tgg aac cac gtg gag caa ctc aac ctg gtc ttc gtc ccg aag     576
Asp Cys Trp Asn His Val Glu Gln Leu Asn Leu Val Phe Val Pro Lys
            180                 185                 190 gcg ttc cag atc gcc ggc gac acc ttc gac gac cgc ttc gtc ttc gtc     624
Ala Phe Gln Ile Ala Gly Asp Thr Phe Asp Asp Arg Phe Val Phe Val
        195                 200                 205 ggg ccg tgc ttc gac gac cgg cgg ttc ctc ggc gag tgg acc cgc ccg     672
Gly Pro Cys Phe Asp Asp Arg Arg Phe Leu Gly Glu Trp Thr Arg Pro
    210                 215                 220 gcc gac gac ctg ccg gtg gtg ctg gtg tcg ctc ggc acc acc ttc aac     720
Ala Asp Asp Leu Pro Val Val Leu Val Ser Leu Gly Thr Thr Phe Asn
```

```
                225                 230                 235                 240 gac cgg ccc gga ttc ttc cgc gac tgc gcg cgg gcg ttc gac ggc cag         768
Asp Arg Pro Gly Phe Phe Arg Asp Cys Ala Arg Ala Phe Asp Gly Gln
                    245                 250                 255 ccg tgg cac gtg gtg atg acg ctg ggc ggc cag gtc gac ccg gcg gct         816
Pro Trp His Val Val Met Thr Leu Gly Gly Gln Val Asp Pro Ala Ala
            260                 265                 270 ctc ggc gac ctg ccc ccc aac gtg gag gcg cac cgc tgg gtc ccg cac         864
Leu Gly Asp Leu Pro Pro Asn Val Glu Ala His Arg Trp Val Pro His
        275                 280                 285 gtg aag gtg ctc gaa cag gcg acg gtc tgc gtg acg cac ggc ggc atg         912
Val Lys Val Leu Glu Gln Ala Thr Val Cys Val Thr His Gly Gly Met
    290                 295                 300 ggc acc ctc atg gag gcg ctc tac tgg ggg cgc ccg ctg gtg gtc gtg         960
Gly Thr Leu Met Glu Ala Leu Tyr Trp Gly Arg Pro Leu Val Val Val
305                 310                 315                 320 ccg cag tcc ttc gac gtg cag ccg atg gcc cgg cgg gtc gac cag ctc        1008
Pro Gln Ser Phe Asp Val Gln Pro Met Ala Arg Arg Val Asp Gln Leu
                325                 330                 335 ggc ctc ggc gcg gtg ctg ccc ggg gag aag gcc gac ggc gac acg ctg        1056
Gly Leu Gly Ala Val Leu Pro Gly Glu Lys Ala Asp Gly Asp Thr Leu
            340                 345                 350 ctc gcc gcc gtc ggg gcc gtc gcg gcc gac ccc gcg ctc ctc gcc cgg        1104
Leu Ala Ala Val Gly Ala Val Ala Ala Asp Pro Ala Leu Leu Ala Arg
        355                 360                 365 gtc gag gcc atg cgg ggc cac gtc cgc cgg gcc ggg ggc gcg gcc cgg        1152
Val Glu Ala Met Arg Gly His Val Arg Arg Ala Gly Gly Ala Ala Arg
    370                 375                 380 gcc gcc gac gcc gtg gag gcg tac ctg gcc cgc gcc cgc tga               1194
Ala Ala Asp Ala Val Glu Ala Tyr Leu Ala Arg Ala Arg *
385                 390                 395

<210> SEQ ID NO 26
<211> LENGTH: 397
<212> TYPE: PRT
<213> ORGANISM: Bacteria

<400> SEQUENCE: 26

Met Ala His Leu Leu Ile Val Asn Val Ala Ser His Gly Leu Ile Leu
1               5                   10                  15

Pro Thr Leu Thr Val Thr Glu Leu Val Arg Arg Gly His Arg Val
            20                  25                  30

Ser Tyr Val Thr Ala Gly Gly Phe Ala Glu Pro Val Arg Ala Ala Gly
        35                  40                  45

Ala Thr Val Val Pro Tyr Gln Ser Glu Ile Ile Asp Ala Asp Ala Ala
    50                  55                  60

Glu Val Phe Gly Ser Asp Asp Leu Gly Val Arg Pro His Leu Met Tyr
65                  70                  75                  80

Leu Arg Glu Asn Val Ser Val Leu Arg Ala Thr Ala Glu Ala Leu Asp
                85                  90                  95

Gly Asp Val Pro Asp Leu Val Leu Tyr Asp Asp Phe Pro Phe Ile Ala
            100                 105                 110

Gly Gln Leu Leu Ala Ala Arg Trp Arg Arg Pro Ala Val Arg Leu Ser
        115                 120                 125

Ala Ala Phe Ala Ser Asn Glu His Tyr Ser Phe Ser Gln Asp Met Val
    130                 135                 140

Thr Leu Ala Gly Thr Ile Asp Pro Leu Asp Leu Pro Val Phe Arg Asp
145                 150                 155                 160
```

```
                Thr Leu Arg Asp Leu Leu Ala Glu His Gly Leu Ser Arg Ser Val Val
                            165                 170                 175

Asp Cys Trp Asn His Val Glu Gln Leu Asn Leu Val Phe Val Pro Lys
                            180                 185                 190

Ala Phe Gln Ile Ala Gly Asp Thr Phe Asp Arg Phe Val Phe Val
                            195                 200                 205

Gly Pro Cys Phe Asp Arg Arg Phe Leu Gly Glu Trp Thr Arg Pro
                            210                 215                 220

Ala Asp Asp Leu Pro Val Val Leu Val Ser Leu Gly Thr Thr Phe Asn
                225                 230                 235                 240

Asp Arg Pro Gly Phe Phe Arg Asp Cys Ala Arg Ala Phe Asp Gly Gln
                            245                 250                 255

Pro Trp His Val Val Met Thr Leu Gly Gly Gln Val Asp Pro Ala Ala
                            260                 265                 270

Leu Gly Asp Leu Pro Pro Asn Val Glu Ala His Arg Trp Val Pro His
                            275                 280                 285

Val Lys Val Leu Glu Gln Ala Thr Val Cys Val Thr His Gly Gly Met
                            290                 295                 300

Gly Thr Leu Met Glu Ala Leu Tyr Trp Gly Arg Pro Leu Val Val Val
                305                 310                 315                 320

Pro Gln Ser Phe Asp Val Gln Pro Met Ala Arg Arg Val Asp Gln Leu
                            325                 330                 335

Gly Leu Gly Ala Val Leu Pro Gly Glu Lys Ala Asp Gly Asp Thr Leu
                            340                 345                 350

Leu Ala Ala Val Gly Ala Val Ala Ala Asp Pro Ala Leu Leu Ala Arg
                            355                 360                 365

Val Glu Ala Met Arg Gly His Val Arg Arg Ala Gly Gly Ala Ala Arg
                            370                 375                 380

Ala Ala Asp Ala Val Glu Ala Tyr Leu Ala Arg Ala Arg
                385                 390                 395

<210> SEQ ID NO 27
<211> LENGTH: 993
<212> TYPE: DNA
<213> ORGANISM: Bacteria
<220> FEATURE:
<221> NAME/KEY: CDS
<222> LOCATION: (1)...(993)

<400> SEQUENCE: 27 gtg tcg tcg ctg cat gtc cgg ctc gga cgg acc ggc ctg cgg gtc agc        48
Val Ser Ser Leu His Val Arg Leu Gly Arg Thr Gly Leu Arg Val Ser
 1               5                  10                  15 cgg gtc gcc atc ggg acc gtc aac ttc ggc ggc cgg gtc gac gag gcc        96
Arg Val Ala Ile Gly Thr Val Asn Phe Gly Gly Arg Val Asp Glu Ala
            20                  25                  30 gac gcc cac cgg ctg ctc gac cac gcc gtc gcg cag ggg gtc aac ctg       144
Asp Ala His Arg Leu Leu Asp His Ala Val Ala Gln Gly Val Asn Leu
        35                  40                  45 gtc gac acc gcc gac atc tac ggc tgg cgg gtg cac cgg ggc tgg acc       192
Val Asp Thr Ala Asp Ile Tyr Gly Trp Arg Val His Arg Gly Trp Thr
    50                  55                  60 gag gag atg atc ggg cgc tgg ctc gcc aag gac ccg gcc cgg cgg gac       240
Glu Glu Met Ile Gly Arg Trp Leu Ala Lys Asp Pro Ala Arg Arg Asp
65                  70                  75                  80 gag gtg gtc ctc gcg acc aag gtc ggc aat ccc atg ggg gac ggc ccc       288
Glu Val Val Leu Ala Thr Lys Val Gly Asn Pro Met Gly Asp Gly Pro
```

-continued

|  | 85 |  |  |  | 90 |  |  |  | 95 |  |  |  |  |
|---|---|---|---|---|---|---|---|---|---|---|---|---|---|
| aac | gcc | cgg | ggc | ctg | tcg | gcc | cga | cac | gtc | gtc | gcc | gcc | tgc gag gcg | 336 |
| Asn | Ala | Arg | Gly | Leu | Ser | Ala | Arg | His | Val | Val | Ala | Ala | Cys Glu Ala |
|  |  |  | 100 |  |  |  |  | 105 |  |  |  | 110 |  |

```
aac gcc cgg ggc ctg tcg gcc cga cac gtc gtc gcc gcc tgc gag gcg      336
Asn Ala Arg Gly Leu Ser Ala Arg His Val Val Ala Ala Cys Glu Ala
            100             105             110 tcg ctg cgc cgg ctc cag acc gac gcc atc gac ctc tac cag atg cac      384
Ser Leu Arg Arg Leu Gln Thr Asp Ala Ile Asp Leu Tyr Gln Met His
            115             120             125 cac gtc gac cgg gag gtc ggc tgg gac gag atc tgg cag gcc atg gag      432
His Val Asp Arg Glu Val Gly Trp Asp Glu Ile Trp Gln Ala Met Glu
130             135             140 cag ctc gtc cgg cag ggc aag gtc cgc tac gtc ggg tcc tcg aac ttc      480
Gln Leu Val Arg Gln Gly Lys Val Arg Tyr Val Gly Ser Ser Asn Phe
145             150             155             160 gcc ggc tgg gac ctg gtg agc gcc cag gag gcc gcg cgc cgg cac cgg      528
Ala Gly Trp Asp Leu Val Ser Ala Gln Glu Ala Ala Arg Arg His Arg
            165             170             175 ctc ctc ggg ctg gcc agc gag cag tgc gtc tac aac ctg gtc agc cgg      576
Leu Leu Gly Leu Ala Ser Glu Gln Cys Val Tyr Asn Leu Val Ser Arg
            180             185             190 tac gtc gaa ctg gag gtg ctc ccc gcc gcc gtc gcc gag ggc atc ggg      624
Tyr Val Glu Leu Glu Val Leu Pro Ala Ala Val Ala Glu Gly Ile Gly
            195             200             205 gtg ctc gtc tgg tcg ccg ctg cac ggc ggg ctg ctc ggc ggc gtg ctg      672
Val Leu Val Trp Ser Pro Leu His Gly Gly Leu Leu Gly Gly Val Leu
210             215             220 cgg aag ctg gcc gac ggc acc gcg gtc aag tcc gcg cag gga cgg gcc      720
Arg Lys Leu Ala Asp Gly Thr Ala Val Lys Ser Ala Gln Gly Arg Ala
225             230             235             240 gcc gag gcg gtc gag cgg cac cgc gcg aca ctc gcc gcg tac gag acg      768
Ala Glu Ala Val Glu Arg His Arg Ala Thr Leu Ala Ala Tyr Glu Thr
            245             250             255 ttc tgc gcc gag gcc ggc cgc gac ccg gcg gag gtc ggc atg gcc tgg      816
Phe Cys Ala Glu Ala Gly Arg Asp Pro Ala Glu Val Gly Met Ala Trp
            260             265             270 gtg ctg cac cgc ccg gcg gtg acc gcc gcg gtc gtc ggt ccg cgt acc      864
Val Leu His Arg Pro Ala Val Thr Ala Ala Val Val Gly Pro Arg Thr
            275             280             285 ccc gaa cac ctg gac ggc gcc ctg cgg gcc ctg cac cgg ccg ctg tcg      912
Pro Glu His Leu Asp Gly Ala Leu Arg Ala Leu His Arg Pro Leu Ser
            290             295             300 gcg gcg gag ctc gcc cgg ctc gac gag ctg ttc ccg ccg ctc ggc cgg      960
Ala Ala Glu Leu Ala Arg Leu Asp Glu Leu Phe Pro Pro Leu Gly Arg
305             310             315             320 ggc ggc gcc gcc ccg gac gcc tgg atg tcc tga                          993
Gly Gly Ala Ala Pro Asp Ala Trp Met Ser *
            325             330
```

<210> SEQ ID NO 28
<211> LENGTH: 330
<212> TYPE: PRT
<213> ORGANISM: Bacteria

<400> SEQUENCE: 28

```
Val Ser Ser Leu His Val Arg Leu Gly Arg Thr Gly Leu Arg Val Ser
 1               5                  10                  15

Arg Val Ala Ile Gly Thr Val Asn Phe Gly Gly Arg Val Asp Glu Ala
                20                  25                  30

Asp Ala His Arg Leu Leu Asp His Ala Val Ala Gln Gly Val Asn Leu
            35                  40                  45
```

-continued

```
Val Asp Thr Ala Asp Ile Tyr Gly Trp Arg Val His Arg Gly Trp Thr
 50                  55                  60

Glu Glu Met Ile Gly Arg Trp Leu Ala Lys Asp Pro Ala Arg Arg Asp
 65                  70                  75                  80

Glu Val Val Leu Ala Thr Lys Val Gly Asn Pro Met Gly Asp Gly Pro
                 85                  90                  95

Asn Ala Arg Gly Leu Ser Ala Arg His Val Val Ala Ala Cys Glu Ala
                100                 105                 110

Ser Leu Arg Arg Leu Gln Thr Asp Ala Ile Asp Leu Tyr Gln Met His
            115                 120                 125

His Val Asp Arg Glu Val Gly Trp Asp Glu Ile Trp Gln Ala Met Glu
130                 135                 140

Gln Leu Val Arg Gln Gly Lys Val Arg Tyr Val Gly Ser Ser Asn Phe
145                 150                 155                 160

Ala Gly Trp Asp Leu Val Ser Ala Gln Glu Ala Ala Arg Arg His Arg
                165                 170                 175

Leu Leu Gly Leu Ala Ser Glu Gln Cys Val Tyr Asn Leu Val Ser Arg
                180                 185                 190

Tyr Val Glu Leu Glu Val Leu Pro Ala Ala Val Ala Glu Gly Ile Gly
            195                 200                 205

Val Leu Val Trp Ser Pro Leu His Gly Gly Leu Leu Gly Gly Val Leu
210                 215                 220

Arg Lys Leu Ala Asp Gly Thr Ala Val Lys Ser Ala Gln Gly Arg Ala
225                 230                 235                 240

Ala Glu Ala Val Glu Arg His Arg Ala Thr Leu Ala Ala Tyr Glu Thr
                245                 250                 255

Phe Cys Ala Glu Ala Gly Arg Asp Pro Ala Glu Val Gly Met Ala Trp
                260                 265                 270

Val Leu His Arg Pro Ala Val Thr Ala Ala Val Gly Pro Arg Thr
            275                 280                 285

Pro Glu His Leu Asp Gly Ala Leu Arg Ala Leu His Arg Pro Leu Ser
            290                 295                 300

Ala Ala Glu Leu Ala Arg Leu Asp Glu Leu Phe Pro Pro Leu Gly Arg
305                 310                 315                 320

Gly Gly Ala Ala Pro Asp Ala Trp Met Ser
                325                 330

<210> SEQ ID NO 29
<211> LENGTH: 543
<212> TYPE: DNA
<213> ORGANISM: Bacteria
<220> FEATURE:
<221> NAME/KEY: CDS
<222> LOCATION: (1)...(543)

<400> SEQUENCE: 29 gga tcc cgg cag gga tat ggg agg atc gcc cac cac aac atc cac ttt     48
Gly Ser Arg Gln Gly Tyr Gly Arg Ile Ala His His Asn Ile His Phe
 1               5                  10                  15 gga cgg tcc tgg aag ggc acc ttc gat gag gtc atc cgg cgt ggc gag     96
Gly Arg Ser Trp Lys Gly Thr Phe Asp Glu Val Ile Arg Arg Gly Glu
                20                  25                  30 ctg atg agc gac ccg tcc ctg ctg gtg acc aac ccg agc cgg acg gac    144
Leu Met Ser Asp Pro Ser Leu Leu Val Thr Asn Pro Ser Arg Thr Asp
            35                  40                  45 ccg tcc gtg gcg ccc gcc ggc cgg cac acc tac tac gtg ctc gcg ccg    192
Pro Ser Val Ala Pro Ala Gly Arg His Thr Tyr Tyr Val Leu Ala Pro
```

```
                  50                  55                   60
gtg ccc aac ctc cac cgg gcg ccg ttc gac tgg cgg ggc gac ctc acc       240
Val Pro Asn Leu His Arg Ala Pro Phe Asp Trp Arg Gly Asp Leu Thr
 65                  70                  75                   80 gac cgc tac gcc gac cag ctc gtc ggg acc ctg gag gag cgc ggc tac       288
Asp Arg Tyr Ala Asp Gln Leu Val Gly Thr Leu Glu Glu Arg Gly Tyr
                 85                  90                   95 gtc ggc ttc ggc gcc ggc gtc gag gtg ctg cgg gcg gtc acc ccg gcc       336
Val Gly Phe Gly Ala Gly Val Glu Val Leu Arg Ala Val Thr Pro Ala
                100                 105                  110 gag tgg gcg gag cag ggg atg gcc gcc ggc acc ccg ttc gcc gcc gcg       384
Glu Trp Ala Glu Gln Gly Met Ala Ala Gly Thr Pro Phe Ala Ala Ala
            115                 120                  125 cac agc ttc ttc cag acc ggc ccg ttc cgc ccg tcg aac ctg cac cgg       432
His Ser Phe Phe Gln Thr Gly Pro Phe Arg Pro Ser Asn Leu His Arg
        130                 135                 140 acg ctg ccg aac gtg gtc ttc gtc ggc tcc ggc acc cag ccc ggt gtc       480
Thr Leu Pro Asn Val Val Phe Val Gly Ser Gly Thr Gln Pro Gly Val
145                 150                 155                  160 ggc gtg ccg atg gtg ctc atc tcc ggc aag ctc gcc gcc ggc cgc atc       528
Gly Val Pro Met Val Leu Ile Ser Gly Lys Leu Ala Ala Gly Arg Ile
                165                 170                  175 acc ggg aga tcc tga                                                   543
Thr Gly Arg Ser  *
            180

<210> SEQ ID NO 30
<211> LENGTH: 180
<212> TYPE: PRT
<213> ORGANISM: Bacteria

<400> SEQUENCE: 30

Gly Ser Arg Gln Gly Tyr Gly Arg Ile Ala His His Asn Ile His Phe
 1                5                  10                   15

Gly Arg Ser Trp Lys Gly Thr Phe Asp Glu Val Ile Arg Arg Gly Glu
             20                  25                  30

Leu Met Ser Asp Pro Ser Leu Leu Val Thr Asn Pro Ser Arg Thr Asp
         35                  40                  45

Pro Ser Val Ala Pro Ala Gly Arg His Thr Tyr Tyr Val Leu Ala Pro
 50                  55                  60

Val Pro Asn Leu His Arg Ala Pro Phe Asp Trp Arg Gly Asp Leu Thr
 65                  70                  75                  80

Asp Arg Tyr Ala Asp Gln Leu Val Gly Thr Leu Glu Glu Arg Gly Tyr
                 85                  90                  95

Val Gly Phe Gly Ala Gly Val Glu Val Leu Arg Ala Val Thr Pro Ala
            100                 105                 110

Glu Trp Ala Glu Gln Gly Met Ala Ala Gly Thr Pro Phe Ala Ala Ala
        115                 120                 125

His Ser Phe Phe Gln Thr Gly Pro Phe Arg Pro Ser Asn Leu His Arg
    130                 135                 140

Thr Leu Pro Asn Val Val Phe Val Gly Ser Gly Thr Gln Pro Gly Val
145                 150                 155                 160

Gly Val Pro Met Val Leu Ile Ser Gly Lys Leu Ala Ala Gly Arg Ile
                165                 170                 175

Thr Gly Arg Ser
            180
```

-continued

```
<210> SEQ ID NO 31
<211> LENGTH: 1362
<212> TYPE: DNA
<213> ORGANISM: Bacteria
<220> FEATURE:
<221> NAME/KEY: CDS
<222> LOCATION: (1)...(1362)

<400> SEQUENCE: 31
```

| | | | | | | | | | | | | | | | | |
|---|---|---|---|---|---|---|---|---|---|---|---|---|---|---|---|---|
| atg | ccg | ttc | ctt | ccc | gac | ccg | ggc | gaa | ccg | tcc | ccg | ctg | aag | gtg | gtc | 48 |
| Met | Pro | Phe | Leu | Pro | Asp | Pro | Gly | Glu | Pro | Ser | Pro | Leu | Lys | Val | Val | |
| 1 | | | | 5 | | | | | 10 | | | | | 15 | | |
| atc | gcc | ggc | gcc | ggc | tac | gtc | ggc | acc | tgt | ctc | gcc | gtc | acc | ctc | gcc | 96 |
| Ile | Ala | Gly | Ala | Gly | Tyr | Val | Gly | Thr | Cys | Leu | Ala | Val | Thr | Leu | Ala | |
| | | | | 20 | | | | | 25 | | | | | 30 | | |
| ggc | cgc | ggc | gcc | gag | gtg | gtc | gcg | gtc | gac | agc | gac | ccg | ggc | acc | gtc | 144 |
| Gly | Arg | Gly | Ala | Glu | Val | Val | Ala | Val | Asp | Ser | Asp | Pro | Gly | Thr | Val | |
| | | 35 | | | | | 40 | | | | | 45 | | | | |
| gcg | gac | ctg | cgg | gcc | ggc | cgg | tgc | cgg | ctg | ccc | gag | ccc | ggc | ctg | gcc | 192 |
| Ala | Asp | Leu | Arg | Ala | Gly | Arg | Cys | Arg | Leu | Pro | Glu | Pro | Gly | Leu | Ala | |
| | 50 | | | | | 55 | | | | | 60 | | | | | |
| ggc | gcc | gtc | cgg | gac | ctc | gcc | gcg | acc | gga | cgg | ctg | acg | gcg | agc | acg | 240 |
| Gly | Ala | Val | Arg | Asp | Leu | Ala | Ala | Thr | Gly | Arg | Leu | Thr | Ala | Ser | Thr | |
| 65 | | | | | 70 | | | | | 75 | | | | | 80 | |
| tcg | tac | gac | ccg | gtc | ggc | gcg | gcg | gac | gtg | gtg | atc | gtg | acg | gtc | ggc | 288 |
| Ser | Tyr | Asp | Pro | Val | Gly | Ala | Ala | Asp | Val | Val | Ile | Val | Thr | Val | Gly | |
| | | | | 85 | | | | | 90 | | | | | 95 | | |
| acc | ccg | acc | gac | gcc | ggc | cac | gag | atg | gtc | acc | gac | cag | ctc | gtc | gcg | 336 |
| Thr | Pro | Thr | Asp | Ala | Gly | His | Glu | Met | Val | Thr | Asp | Gln | Leu | Val | Ala | |
| | | | | 100 | | | | | 105 | | | | | 110 | | |
| gcg | tgc | gag | cag | atc | gcc | ccg | cgg | ctg | cgc | gcc | ggg | caa | ctg | gtg | atc | 384 |
| Ala | Cys | Glu | Gln | Ile | Ala | Pro | Arg | Leu | Arg | Ala | Gly | Gln | Leu | Val | Ile | |
| | | 115 | | | | | 120 | | | | | 125 | | | | |
| ctc | aag | tcg | acg | gtc | tcc | ccg | ggc | acc | acc | cgg | acc | ctc | gtc | gcg | ccc | 432 |
| Leu | Lys | Ser | Thr | Val | Ser | Pro | Gly | Thr | Thr | Arg | Thr | Leu | Val | Ala | Pro | |
| | 130 | | | | | 135 | | | | | 140 | | | | | |
| ctg | ctg | gag | agc | ggc | ggg | ctg | gtg | cac | gag | cgc | gac | ttc | ggg | ctg | gcc | 480 |
| Leu | Leu | Glu | Ser | Gly | Gly | Leu | Val | His | Glu | Arg | Asp | Phe | Gly | Leu | Ala | |
| 145 | | | | | 150 | | | | | 155 | | | | | 160 | |
| ttc | tgc | ccg | gag | cgg | ctc | gcc | gag | ggg | gtg | gcg | ctg | gcg | cag | gtg | cgg | 528 |
| Phe | Cys | Pro | Glu | Arg | Leu | Ala | Glu | Gly | Val | Ala | Leu | Ala | Gln | Val | Arg | |
| | | | | 165 | | | | | 170 | | | | | 175 | | |
| acg | ctg | ccg | gtg | gtg | gtg | ggt | ggg | tgc | ggc | ccg | cgc | agc | gcc | gcc | gcg | 576 |
| Thr | Leu | Pro | Val | Val | Val | Gly | Gly | Cys | Gly | Pro | Arg | Ser | Ala | Ala | Ala | |
| | | | | 180 | | | | | 185 | | | | | 190 | | |
| gcc | gaa | cgg | ttc | tgg | cgg | tcc | gcg | ctc | ggc | gtc | gac | gtc | cgg | cag | gtg | 624 |
| Ala | Glu | Arg | Phe | Trp | Arg | Ser | Ala | Leu | Gly | Val | Asp | Val | Arg | Gln | Val | |
| | | 195 | | | | | 200 | | | | | 205 | | | | |
| ccg | tcg | gcc | gag | tcc | gcc | gag | gtg | gtc | aag | ctc | gcg | acc | aac | tgg | tgg | 672 |
| Pro | Ser | Ala | Glu | Ser | Ala | Glu | Val | Val | Lys | Leu | Ala | Thr | Asn | Trp | Trp | |
| | 210 | | | | | 215 | | | | | 220 | | | | | |
| atc | gac | gcg | aac | gtg | gcg | atc | gcc | aac | gaa | ctc | gcc | cgg | tac | tgc | gcg | 720 |
| Ile | Asp | Ala | Asn | Val | Ala | Ile | Ala | Asn | Glu | Leu | Ala | Arg | Tyr | Cys | Ala | |
| 225 | | | | | 230 | | | | | 235 | | | | | 240 | |
| gtg | ctg | ggg | gtg | gac | gtc | ctc | gac | gtg | atc | ggc | gcg | gcg | aac | acc | ctg | 768 |
| Val | Leu | Gly | Val | Asp | Val | Leu | Asp | Val | Ile | Gly | Ala | Ala | Asn | Thr | Leu | |
| | | | | 245 | | | | | 250 | | | | | 255 | | |
| ccc | aag | ggc | agc | agc | atg | gtg | aac | ctg | ctg | ctg | ccg | ggg | gtg | ggt | gtc | 816 |
| Pro | Lys | Gly | Ser | Ser | Met | Val | Asn | Leu | Leu | Leu | Pro | Gly | Val | Gly | Val | |
| | | | | 260 | | | | | 265 | | | | | 270 | | |
| ggc | ggc | tcc | tgc | ctg | acg | aag | gac | ccg | tgg | atg | gcg | tgg | cgg | gac | ggc | 864 |

```
                Gly Gly Ser Cys Leu Thr Lys Asp Pro Trp Met Ala Trp Arg Asp Gly
                            275                 280                 285 cgg gac cgg ggc gtg ccc ctg cgc acg gtc gag acg gcc cgc gcg gtc      912
Arg Asp Arg Gly Val Pro Leu Arg Thr Val Glu Thr Ala Arg Ala Val
    290                 295                 300 aac gac gac atg ccc cgc cac acc gcc gcc gtc atc gcc gac gag ctg      960
Asn Asp Asp Met Pro Arg His Thr Ala Ala Val Ile Ala Asp Glu Leu
305                 310                 315                 320 gtc aag ctg gga cgg gat cgg aac gac acg acg atc gcc gtg ctc ggc     1008
Val Lys Leu Gly Arg Asp Arg Asn Asp Thr Thr Ile Ala Val Leu Gly
                325                 330                 335 gcg gcg ttc aag aac gac acc ggc gac gtc cgc aac acc ccg gtg cgc     1056
Ala Ala Phe Lys Asn Asp Thr Gly Asp Val Arg Asn Thr Pro Val Arg
            340                 345                 350 ggg gtc gtg gcg gcg ctg cgc gac agc ggc ttc cgg gtc cgg atc ttc     1104
Gly Val Val Ala Ala Leu Arg Asp Ser Gly Phe Arg Val Arg Ile Phe
        355                 360                 365 gac ccg ctg gcc gat ccc gcc gag atc gtc gcc cgg ttc ggc acc gcg     1152
Asp Pro Leu Ala Asp Pro Ala Glu Ile Val Ala Arg Phe Gly Thr Ala
    370                 375                 380 ccg gcg gcg agc ctg gac gag gcg gtg agc ggg gcg ggc tgc ctg gcc     1200
Pro Ala Ala Ser Leu Asp Glu Ala Val Ser Gly Ala Gly Cys Leu Ala
385                 390                 395                 400 ttc ctc gcc ggg cac cgc cag ttc cac gag ctc gac ttc ggc gcc ctg     1248
Phe Leu Ala Gly His Arg Gln Phe His Glu Leu Asp Phe Gly Ala Leu
                405                 410                 415 gcc gag cgg gtg gac gag ccc tgc ctg gtc ttc gac ggc cgc atg cac     1296
Ala Glu Arg Val Asp Glu Pro Cys Leu Val Phe Asp Gly Arg Met His
            420                 425                 430 ctc ccg ccg gcg cgc atc cgc gag ctg cac cgg ttc ggc ttc gcc tac     1344
Leu Pro Pro Ala Arg Ile Arg Glu Leu His Arg Phe Gly Phe Ala Tyr
        435                 440                 445 cgc ggc att gga agg tga                                              1362
Arg Gly Ile Gly Arg  *
    450

<210> SEQ ID NO 32
<211> LENGTH: 453
<212> TYPE: PRT
<213> ORGANISM: Bacteria

<400> SEQUENCE: 32

Met Pro Phe Leu Pro Asp Pro Gly Glu Pro Ser Pro Leu Lys Val Val
 1               5                  10                  15

Ile Ala Gly Ala Gly Tyr Val Gly Thr Cys Leu Ala Val Thr Leu Ala
            20                  25                  30

Gly Arg Gly Ala Glu Val Val Ala Val Asp Ser Asp Pro Gly Thr Val
        35                  40                  45

Ala Asp Leu Arg Ala Gly Arg Cys Arg Leu Pro Glu Pro Gly Leu Ala
    50                  55                  60

Gly Ala Val Arg Asp Leu Ala Thr Gly Arg Leu Thr Ala Ser Thr
65                  70                  75                  80

Ser Tyr Asp Pro Val Gly Ala Ala Asp Val Val Ile Val Thr Val Gly
                85                  90                  95

Thr Pro Thr Asp Ala Gly His Glu Met Val Thr Asp Gln Leu Val Ala
            100                 105                 110

Ala Cys Glu Gln Ile Ala Pro Arg Leu Arg Ala Gly Gln Leu Val Ile
        115                 120                 125
```

```
Leu Lys Ser Thr Val Ser Pro Gly Thr Thr Arg Thr Leu Val Ala Pro
    130                 135                 140

Leu Leu Glu Ser Gly Gly Leu Val His Glu Arg Asp Phe Gly Leu Ala
145                 150                 155                 160

Phe Cys Pro Glu Arg Leu Ala Glu Gly Val Ala Leu Ala Gln Val Arg
                165                 170                 175

Thr Leu Pro Val Val Gly Gly Cys Gly Pro Arg Ser Ala Ala Ala
                180                 185                 190

Ala Glu Arg Phe Trp Arg Ser Ala Leu Gly Val Asp Val Arg Gln Val
            195                 200                 205

Pro Ser Ala Glu Ser Ala Glu Val Val Lys Leu Ala Thr Asn Trp Trp
    210                 215                 220

Ile Asp Ala Asn Val Ala Ile Ala Asn Glu Leu Ala Arg Tyr Cys Ala
225                 230                 235                 240

Val Leu Gly Val Asp Val Leu Asp Val Ile Gly Ala Ala Asn Thr Leu
                245                 250                 255

Pro Lys Gly Ser Ser Met Val Asn Leu Leu Pro Gly Val Gly Val
                260                 265                 270

Gly Gly Ser Cys Leu Thr Lys Asp Pro Trp Met Ala Trp Arg Asp Gly
            275                 280                 285

Arg Asp Arg Gly Val Pro Leu Arg Thr Val Glu Thr Ala Arg Ala Val
    290                 295                 300

Asn Asp Asp Met Pro Arg His Thr Ala Ala Val Ile Ala Asp Glu Leu
305                 310                 315                 320

Val Lys Leu Gly Arg Asp Arg Asn Asp Thr Thr Ile Ala Val Leu Gly
                325                 330                 335

Ala Ala Phe Lys Asn Asp Thr Gly Asp Val Arg Asn Thr Pro Val Arg
                340                 345                 350

Gly Val Val Ala Ala Leu Arg Asp Ser Gly Phe Arg Val Arg Ile Phe
            355                 360                 365

Asp Pro Leu Ala Asp Pro Ala Glu Ile Val Ala Arg Phe Gly Thr Ala
    370                 375                 380

Pro Ala Ala Ser Leu Asp Glu Ala Val Ser Gly Ala Gly Cys Leu Ala
385                 390                 395                 400

Phe Leu Ala Gly His Arg Gln Phe His Glu Leu Asp Phe Gly Ala Leu
                405                 410                 415

Ala Glu Arg Val Asp Glu Pro Cys Leu Val Phe Asp Gly Arg Met His
            420                 425                 430

Leu Pro Pro Ala Arg Ile Arg Glu Leu His Arg Phe Gly Phe Ala Tyr
    435                 440                 445

Arg Gly Ile Gly Arg
    450

<210> SEQ ID NO 33
<211> LENGTH: 843
<212> TYPE: DNA
<213> ORGANISM: Bacteria
<220> FEATURE:
<221> NAME/KEY: CDS
<222> LOCATION: (1)...(843)

<400> SEQUENCE: 33 atg gag cag tcc cgg gag gcg gct gcg gcg cgg gcc atc gac tac atg    48
Met Glu Gln Ser Arg Glu Ala Ala Ala Ala Arg Ala Ile Asp Tyr Met
 1               5                  10                  15 cgc cgg cac ctg tcg gag ccg ctg cag ctg gcc gac ctg gcc cgg gtt    96
```

-continued

```
                Arg Arg His Leu Ser Glu Pro Leu Gln Leu Ala Asp Leu Ala Arg Val
                         20                  25                  30 gtc ccc ttc agc ccg ttc cac ttc cac cgg ctg ttc cgc gac gtg acc        144
Val Pro Phe Ser Pro Phe His Phe His Arg Leu Phe Arg Asp Val Thr
         35                  40                  45 acg atg acc ccg gcc cgc ttc ctc gcc gcg ctg cgg atg gcg gag gcc        192
Thr Met Thr Pro Ala Arg Phe Leu Ala Ala Leu Arg Met Ala Glu Ala
     50                  55                  60 cgc cgg atg ctg ctg cac tcc ggc ctg acg gtg acc gcg atc agc ggc        240
Arg Arg Met Leu Leu His Ser Gly Leu Thr Val Thr Ala Ile Ser Gly
 65                  70                  75                  80 cac gtc ggc tac acg agc gcg ggg acc ttc acc acc cag ttc tcc cgg        288
His Val Gly Tyr Thr Ser Ala Gly Thr Phe Thr Thr Gln Phe Ser Arg
                 85                  90                  95 ctg gtc ggc acg tcg ccg ggg cac ttc cgg cag atg tcc cgg ctg ctg        336
Leu Val Gly Thr Ser Pro Gly His Phe Arg Gln Met Ser Arg Leu Leu
            100                 105                 110 gcc ggc cgg ccc tgc cac gtc ctg gcg ggc tgg ctg cgc aac gcc gtc        384
Ala Gly Arg Pro Cys His Val Leu Ala Gly Trp Leu Arg Asn Ala Val
        115                 120                 125 acg gag gtc acc cga ccc cgg ctg gtg ctg cac gtg ccc gag agc gag        432
Thr Glu Val Thr Arg Pro Arg Leu Val Leu His Val Pro Glu Ser Glu
    130                 135                 140 ccc ggc gac ctg gtg ctg gtc ggc ctg cgg gcc gac ggg gag gcc gcg        480
Pro Gly Asp Leu Val Leu Val Gly Leu Arg Ala Asp Gly Glu Ala Ala
145                 150                 155                 160 gac gcg tcg acc acg tgg gcg gtg gcg gcc gac ggc gcg cag gtc ccg        528
Asp Ala Ser Thr Thr Trp Ala Val Ala Ala Asp Gly Ala Gln Val Pro
                165                 170                 175 gtg gtg gcg cgg ccg ggc ccg tac cag gcc cgg gtc gtg ctg gtc cgg        576
Val Val Ala Arg Pro Gly Pro Tyr Gln Ala Arg Val Val Leu Val Arg
            180                 185                 190 ggc gac agc acg ctg acc cgc gcc ctg gtg gac gag gag ccc acc agc        624
Gly Asp Ser Thr Leu Thr Arg Ala Leu Val Asp Glu Glu Pro Thr Ser
        195                 200                 205 cat ctg gtc ggc acc gcc gaa ctg gtg ctg ccc cag gac ggc tgc gcg        672
His Leu Val Gly Thr Ala Glu Leu Val Leu Pro Gln Asp Gly Cys Ala
    210                 215                 220 gcc gtc ccg gtc acc acc gcg ccg ccg cgg ccg acc gac ccg ccg gcg        720
Ala Val Pro Val Thr Thr Ala Pro Pro Arg Pro Thr Asp Pro Pro Ala
225                 230                 235                 240 ctg gcc ctc ggc ccg gtg tgc cgg ctc gtc gag acg ttc acg cgg ctg        768
Leu Ala Leu Gly Pro Val Cys Arg Leu Val Glu Thr Phe Thr Arg Leu
                245                 250                 255 gcc ggc ccg tcg ggc cgg ccg ggt ccg gcc tgg tcg gcc ggc cgc acc        816
Ala Gly Pro Ser Gly Arg Pro Gly Pro Ala Trp Ser Ala Gly Arg Thr
            260                 265                 270 gcg ctg gcc gcg gcg gcc atc gcg tga                                    843
Ala Leu Ala Ala Ala Ala Ile Ala *
        275                 280

<210> SEQ ID NO 34
<211> LENGTH: 280
<212> TYPE: PRT
<213> ORGANISM: Bacteria

<400> SEQUENCE: 34

Met Glu Gln Ser Arg Glu Ala Ala Ala Arg Ala Ile Asp Tyr Met
 1               5                  10                  15

Arg Arg His Leu Ser Glu Pro Leu Gln Leu Ala Asp Leu Ala Arg Val
```

```
                  20                  25                  30

Val Pro Phe Ser Pro Phe His Phe Arg Leu Phe Arg Asp Val Thr
        35                  40                  45

Thr Met Thr Pro Ala Arg Phe Leu Ala Ala Leu Arg Met Ala Glu Ala
 50                  55                  60

Arg Arg Met Leu Leu His Ser Gly Leu Thr Val Thr Ala Ile Ser Gly
 65                  70                  75                  80

His Val Gly Tyr Thr Ser Ala Gly Thr Phe Thr Thr Gln Phe Ser Arg
                 85                  90                  95

Leu Val Gly Thr Ser Pro Gly His Phe Arg Gln Met Ser Arg Leu Leu
            100                 105                 110

Ala Gly Arg Pro Cys His Val Leu Ala Gly Trp Leu Arg Asn Ala Val
            115                 120                 125

Thr Glu Val Thr Arg Pro Arg Leu Val Leu His Val Pro Glu Ser Glu
        130                 135                 140

Pro Gly Asp Leu Val Leu Val Gly Leu Arg Ala Asp Gly Glu Ala Ala
145                 150                 155                 160

Asp Ala Ser Thr Thr Trp Ala Val Ala Ala Asp Gly Ala Gln Val Pro
                165                 170                 175

Val Val Ala Arg Pro Gly Pro Tyr Gln Ala Arg Val Val Leu Val Arg
            180                 185                 190

Gly Asp Ser Thr Leu Thr Arg Ala Leu Val Asp Glu Glu Pro Thr Ser
            195                 200                 205

His Leu Val Gly Thr Ala Glu Leu Val Leu Pro Gln Asp Gly Cys Ala
        210                 215                 220

Ala Val Pro Val Thr Thr Ala Pro Pro Arg Pro Thr Asp Pro Pro Ala
225                 230                 235                 240

Leu Ala Leu Gly Pro Val Cys Arg Leu Val Glu Thr Phe Thr Arg Leu
                245                 250                 255

Ala Gly Pro Ser Gly Arg Pro Gly Pro Ala Trp Ser Ala Gly Arg Thr
            260                 265                 270

Ala Leu Ala Ala Ala Ala Ile Ala
        275                 280

<210> SEQ ID NO 35
<211> LENGTH: 1209
<212> TYPE: DNA
<213> ORGANISM: Bacteria
<220> FEATURE:
<221> NAME/KEY: CDS
<222> LOCATION: (1)...(1209)

<400> SEQUENCE: 35 gtg ctg gtc gat gcc gtg acc gcg ttc gat ccc acc gac gcc gac gtg      48
Val Leu Val Asp Ala Val Thr Ala Phe Asp Pro Thr Asp Ala Asp Val
 1               5                  10                  15 cgg cgt gac ccc tac ccg tcc tac cac tgg ctg ctg cgg cac gac ccg      96
Arg Arg Asp Pro Tyr Pro Ser Tyr His Trp Leu Leu Arg His Asp Pro
                20                  25                  30 gtg cac cgt ggc gcc cac cgg gtc tgg tac gtc tcc cgc ttc gcg gac     144
Val His Arg Gly Ala His Arg Val Trp Tyr Val Ser Arg Phe Ala Asp
         35                  40                  45 gtg cgc gcg gtg ctc ggc gac gag cgc ttc gcc cgg acc ggc atc cgc     192
Val Arg Ala Val Leu Gly Asp Glu Arg Phe Ala Arg Thr Gly Ile Arg
 50                  55                  60 cgg ttc tgg acc gac ctc gtc ggg ccc ggg ctg ctc gcc gag atc gtc     240
Arg Phe Trp Thr Asp Leu Val Gly Pro Gly Leu Leu Ala Glu Ile Val
                65                  70                  75
```

|       |       |       |       |       |       |       |       |       |       |       |       |       |       |       |       | |
|---|---|---|---|---|---|---|---|---|---|---|---|---|---|---|---|---|
| 65 | | | | | 70 | | | | | 75 | | | | | 80 | |
| ggc | gac | atc | atc | ctg | ttc | cag | gac | gag | ccc | gac | cac | ggc | cgg | ctg | cgc | 288 |
| Gly | Asp | Ile | Ile | Leu | Phe | Gln | Asp | Glu | Pro | Asp | His | Gly | Arg | Leu | Arg | |
| | | | | | | | 85 | | | | | 90 | | | 95 | |
| ggg | gtg | gtc | ggc | ccg | gcg | ttc | tcg | ccg | tcc | gcg | ctg | cgc | cgg | ctg | gaa | 336 |
| Gly | Val | Val | Gly | Pro | Ala | Phe | Ser | Pro | Ser | Ala | Leu | Arg | Arg | Leu | Glu | |
| | | | 100 | | | | | 105 | | | | | 110 | | | |
| ccg | gtg | atc | gcc | ggc | acc | gtg | gac | gac | ctg | ctg | cgg | ccc | gcc | ctg | gcc | 384 |
| Pro | Val | Ile | Ala | Gly | Thr | Val | Asp | Asp | Leu | Leu | Arg | Pro | Ala | Leu | Ala | |
| | | | 115 | | | | | 120 | | | | | 125 | | | |
| cgg | ggc | gcg | atg | gac | gtg | gtc | gac | gag | ctg | gcg | tac | ccg | ctg | gcg | ctg | 432 |
| Arg | Gly | Ala | Met | Asp | Val | Val | Asp | Glu | Leu | Ala | Tyr | Pro | Leu | Ala | Leu | |
| | 130 | | | | | 135 | | | | | 140 | | | | | |
| cgc | gcg | gtc | ctc | ggc | ctg | ctc | ggc | ctg | ccc | gcc | gcc | gac | tgg | ggg | gcg | 480 |
| Arg | Ala | Val | Leu | Gly | Leu | Leu | Gly | Leu | Pro | Ala | Ala | Asp | Trp | Gly | Ala | |
| 145 | | | | | 150 | | | | | 155 | | | | | 160 | |
| gtc | ggg | cgc | tgg | tcg | cgc | gac | gtg | gga | cgg | acc | ctg | gac | cgg | ggc | gcc | 528 |
| Val | Gly | Arg | Trp | Ser | Arg | Asp | Val | Gly | Arg | Thr | Leu | Asp | Arg | Gly | Ala | |
| | | | | 165 | | | | | 170 | | | | | 175 | | |
| agc | gcc | gag | gac | atg | cgc | cgc | ggc | cac | gcg | gcg | atc | gcc | gag | ttc | gcc | 576 |
| Ser | Ala | Glu | Asp | Met | Arg | Arg | Gly | His | Ala | Ala | Ile | Ala | Glu | Phe | Ala | |
| | | | 180 | | | | | 185 | | | | | 190 | | | |
| gac | tac | gtg | gag | cgg | gcc | ctc | gcg | agg | cgg | cgg | cgt | gag | ggc | ggc | gag | 624 |
| Asp | Tyr | Val | Glu | Arg | Ala | Leu | Ala | Arg | Arg | Arg | Arg | Glu | Gly | Gly | Glu | |
| | | | 195 | | | | | 200 | | | | | 205 | | | |
| gac | ctg | ctg | gcg | ttg | atg | ctc | gac | gcc | cac | gac | cgc | ggc | ctg | atg | agt | 672 |
| Asp | Leu | Leu | Ala | Leu | Met | Leu | Asp | Ala | His | Asp | Arg | Gly | Leu | Met | Ser | |
| | 210 | | | | | 215 | | | | | 220 | | | | | |
| cgc | aac | gag | atc | gtc | agc | acg | gtg | gtc | acg | ttc | atc | ttc | acc | ggc | cac | 720 |
| Arg | Asn | Glu | Ile | Val | Ser | Thr | Val | Val | Thr | Phe | Ile | Phe | Thr | Gly | His | |
| 225 | | | | | 230 | | | | | 235 | | | | | 240 | |
| gag | acg | gtg | gcc | agc | cag | gtg | ggc | aac | gcc | gtg | ctg | agc | ctg | ctg | gcg | 768 |
| Glu | Thr | Val | Ala | Ser | Gln | Val | Gly | Asn | Ala | Val | Leu | Ser | Leu | Leu | Ala | |
| | | | | 245 | | | | | 250 | | | | | 255 | | |
| cac | ccg | gac | cag | ctc | gac | ctg | ctc | cgg | cgc | cgg | ccg | gac | ctg | ctg | gcc | 816 |
| His | Pro | Asp | Gln | Leu | Asp | Leu | Leu | Arg | Arg | Arg | Pro | Asp | Leu | Leu | Ala | |
| | | | 260 | | | | | 265 | | | | | 270 | | | |
| cag | gcc | gtc | gag | gag | tgc | ctg | cgg | tac | gac | ccg | tcg | gtg | cag | tcc | aac | 864 |
| Gln | Ala | Val | Glu | Glu | Cys | Leu | Arg | Tyr | Asp | Pro | Ser | Val | Gln | Ser | Asn | |
| | | 275 | | | | | 280 | | | | | 285 | | | | |
| acc | cgg | cag | ctc | gac | gtc | gac | gtg | gag | ctg | cgc | ggt | cgg | cgg | ctg | cgc | 912 |
| Thr | Arg | Gln | Leu | Asp | Val | Asp | Val | Glu | Leu | Arg | Gly | Arg | Arg | Leu | Arg | |
| | | 290 | | | | | 295 | | | | | 300 | | | | |
| cgc | gac | gac | gtc | gtg | gtc | gtc | ctg | gcc | ggc | gcg | gcg | aac | cgg | gac | ccg | 960 |
| Arg | Asp | Asp | Val | Val | Val | Val | Leu | Ala | Gly | Ala | Ala | Asn | Arg | Asp | Pro | |
| 305 | | | | | 310 | | | | | 315 | | | | | 320 | |
| cgg | cgg | tac | gac | cgg | ccc | gac | gat | ttc | gac | atc | gag | cgg | gat | ccg | gtc | 1008 |
| Arg | Arg | Tyr | Asp | Arg | Pro | Asp | Asp | Phe | Asp | Ile | Glu | Arg | Asp | Pro | Val | |
| | | | | 325 | | | | | 330 | | | | | 335 | | |
| ccg | tcg | atg | tcc | ttc | ggc | gcg | ggg | atg | cgc | tac | tgc | ctc | ggg | tcc | tac | 1056 |
| Pro | Ser | Met | Ser | Phe | Gly | Ala | Gly | Met | Arg | Tyr | Cys | Leu | Gly | Ser | Tyr | |
| | | | 340 | | | | | 345 | | | | | 350 | | | |
| ctc | gcc | cgt | acg | cag | ctg | cgc | gcc | gcg | gtg | gcc | gcc | ctg | gcc | cga | ctg | 1104 |
| Leu | Ala | Arg | Thr | Gln | Leu | Arg | Ala | Ala | Val | Ala | Ala | Leu | Ala | Arg | Leu | |
| | | 355 | | | | | 360 | | | | | 365 | | | | |
| ccg | ggc | ctg | cgg | ctg | ggc | tgc | gcg | tcg | gac | gcc | ctg | gcc | tat | cag | ccg | 1152 |
| Pro | Gly | Leu | Arg | Leu | Gly | Cys | Ala | Ser | Asp | Ala | Leu | Ala | Tyr | Gln | Pro | |
| | 370 | | | | | 375 | | | | | 380 | | | | | |
| cgc | acc | atg | ttc | cgg | ggc | ctg | gcc | agc | ctg | ccg | atc | gcg | ttc | acg | ccg | 1200 |

```
Arg Thr Met Phe Arg Gly Leu Ala Ser Leu Pro Ile Ala Phe Thr Pro
385                 390                 395                 400 ggc ggt tga                                                              1209
Gly Gly *
```

<210> SEQ ID NO 36
<211> LENGTH: 402
<212> TYPE: PRT
<213> ORGANISM: Bacteria

<400> SEQUENCE: 36

```
Val Leu Val Asp Ala Val Thr Ala Phe Asp Pro Thr Asp Ala Asp Val
 1               5                  10                  15

Arg Arg Asp Pro Tyr Pro Ser Tyr His Trp Leu Leu Arg His Asp Pro
            20                  25                  30

Val His Arg Gly Ala His Arg Val Trp Tyr Val Ser Arg Phe Ala Asp
        35                  40                  45

Val Arg Ala Val Leu Gly Asp Glu Arg Phe Ala Arg Thr Gly Ile Arg
    50                  55                  60

Arg Phe Trp Thr Asp Leu Val Gly Pro Gly Leu Leu Ala Glu Ile Val
65                  70                  75                  80

Gly Asp Ile Ile Leu Phe Gln Asp Glu Pro Asp His Gly Arg Leu Arg
                85                  90                  95

Gly Val Val Gly Pro Ala Phe Ser Pro Ser Ala Leu Arg Arg Leu Glu
            100                 105                 110

Pro Val Ile Ala Gly Thr Val Asp Asp Leu Leu Arg Pro Ala Leu Ala
        115                 120                 125

Arg Gly Ala Met Asp Val Val Asp Glu Leu Ala Tyr Pro Leu Ala Leu
    130                 135                 140

Arg Ala Val Leu Gly Leu Leu Gly Leu Pro Ala Ala Asp Trp Gly Ala
145                 150                 155                 160

Val Gly Arg Trp Ser Arg Asp Val Gly Arg Thr Leu Asp Arg Gly Ala
                165                 170                 175

Ser Ala Glu Asp Met Arg Arg Gly His Ala Ala Ile Ala Glu Phe Ala
            180                 185                 190

Asp Tyr Val Glu Arg Ala Leu Ala Arg Arg Arg Glu Gly Gly Glu
        195                 200                 205

Asp Leu Leu Ala Leu Met Leu Asp Ala His Asp Arg Gly Leu Met Ser
    210                 215                 220

Arg Asn Glu Ile Val Ser Thr Val Val Thr Phe Ile Phe Thr Gly His
225                 230                 235                 240

Glu Thr Val Ala Ser Gln Val Gly Asn Ala Val Leu Ser Leu Leu Ala
                245                 250                 255

His Pro Asp Gln Leu Asp Leu Leu Arg Arg Pro Asp Leu Leu Ala
            260                 265                 270

Gln Ala Val Glu Glu Cys Leu Arg Tyr Asp Pro Ser Val Gln Ser Asn
        275                 280                 285

Thr Arg Gln Leu Asp Val Asp Val Glu Leu Arg Gly Arg Arg Leu Arg
    290                 295                 300

Arg Asp Asp Val Val Val Leu Ala Gly Ala Ala Asn Arg Asp Pro
305                 310                 315                 320

Arg Arg Tyr Asp Arg Pro Asp Phe Asp Ile Glu Arg Asp Pro Val
                325                 330                 335

Pro Ser Met Ser Phe Gly Ala Gly Met Arg Tyr Cys Leu Gly Ser Tyr
            340                 345                 350
```

```
Leu Ala Arg Thr Gln Leu Arg Ala Val Ala Ala Leu Ala Arg Leu
            355                 360                 365

Pro Gly Leu Arg Leu Gly Cys Ala Ser Asp Ala Leu Ala Tyr Gln Pro
        370                 375                 380

Arg Thr Met Phe Arg Gly Leu Ala Ser Leu Pro Ile Ala Phe Thr Pro
385                 390                 395                 400

Gly Gly

<210> SEQ ID NO 37
<211> LENGTH: 1263
<212> TYPE: DNA
<213> ORGANISM: Bacteria
<220> FEATURE:
<221> NAME/KEY: CDS
<222> LOCATION: (1)...(1263)

<400> SEQUENCE: 37 atg agc cac ccc gaa ccc gag tac gac gtg atc gtc gtg ggc ggc ggc      48
Met Ser His Pro Glu Pro Glu Tyr Asp Val Ile Val Val Gly Gly Gly
  1               5                  10                  15 ccg gcc gga tcg agc acg gcc ggt ctg ctc gcc cag gag ggc cac cgg      96
Pro Ala Gly Ser Ser Thr Ala Gly Leu Leu Ala Gln Glu Gly His Arg
                 20                  25                  30 gtc ctg ctg ctg gag cgc gag aag ttc ccc cgc tac cac atc ggc gag     144
Val Leu Leu Leu Glu Arg Glu Lys Phe Pro Arg Tyr His Ile Gly Glu
             35                  40                  45 tcc ctg atc agc ggc gtc acc ctc acc ctg gac gcg ctc ggc gta cgc     192
Ser Leu Ile Ser Gly Val Thr Leu Thr Leu Asp Ala Leu Gly Val Arg
         50                  55                  60 gag cgg atg gcg gag ctg cgc ttc cag atc aaa cac ggc ggc agc ctg     240
Glu Arg Met Ala Glu Leu Arg Phe Gln Ile Lys His Gly Gly Ser Leu
 65                  70                  75                  80 ctg tgg ggg gcc gat cag acc gcc ccg tgg tcg ttc cgg ttc cgg gag     288
Leu Trp Gly Ala Asp Gln Thr Ala Pro Trp Ser Phe Arg Phe Arg Glu
                 85                  90                  95 atc cgc gac gcc cgg ttc gac tac tcg tgg cag gtc cgg cgt gcc gaa     336
Ile Arg Asp Ala Arg Phe Asp Tyr Ser Trp Gln Val Arg Arg Ala Glu
            100                 105                 110 ttc gac gcg atg ctg ctg gac cgg gcg cgg gaa ctg ggc gtg gtg gtg     384
Phe Asp Ala Met Leu Leu Asp Arg Ala Arg Glu Leu Gly Val Val Val
        115                 120                 125 gtc gag gga gcc acc gtc cgg ggg ccg ctg acc gac ggc gag cgg gtc     432
Val Glu Gly Ala Thr Val Arg Gly Pro Leu Thr Asp Gly Glu Arg Val
    130                 135                 140 gcg ggc gtc agc tac cag ttc cgg ggt gag gcc gac ccg atc gac gcc     480
Ala Gly Val Ser Tyr Gln Phe Arg Gly Glu Ala Asp Pro Ile Asp Ala
145                 150                 155                 160 cgc gcc gcg atc gtg gtc gac gcg tcg ggg cag cag cgc tgg ctc ggc     528
Arg Ala Ala Ile Val Val Asp Ala Ser Gly Gln Gln Arg Trp Leu Gly
                165                 170                 175 cgg cac ttc ggg ttg gtc tcc tgg cac gac gac ctg cgc aac atg gcg     576
Arg His Phe Gly Leu Val Ser Trp His Asp Asp Leu Arg Asn Met Ala
            180                 185                 190 gcg tgg agc tac tac gcc ggg gcg ctg cgc tac ccc ggc gat cac gag     624
Ala Trp Ser Tyr Tyr Ala Gly Ala Leu Arg Tyr Pro Gly Asp His Glu
        195                 200                 205 ggc gac ctg ctc gtc gag agc tgc gcc cag ggt tgg ctc tgg tac gcg     672
Gly Asp Leu Leu Val Glu Ser Cys Ala Gln Gly Trp Leu Trp Tyr Ala
    210                 215                 220
```

```
ccg ctg agc ccc acc ctg acc ggg atc ggg tac gtc acc ccg tcg gac        720
Pro Leu Ser Pro Thr Leu Thr Gly Ile Gly Tyr Val Thr Pro Ser Asp
225                 230                 235                 240 cgg ttc gcc gag acc ggc ctt ccc ccg gat cag ttg ctg gag aaa cag        768
Arg Phe Ala Glu Thr Gly Leu Pro Pro Asp Gln Leu Leu Glu Lys Gln
            245                 250                 255 atc gcg gag tcg aac gag gtc tcc tgg ctc acc gcc ggc gcg cgg cgg        816
Ile Ala Glu Ser Asn Glu Val Ser Trp Leu Thr Ala Gly Ala Arg Arg
        260                 265                 270 gtc gac gtc tac cgc acc gcg cgg gac tgg tcg tac gcg tgc agc cag        864
Val Asp Val Tyr Arg Thr Ala Arg Asp Trp Ser Tyr Ala Cys Ser Gln
    275                 280                 285 ttc tcc ggg ccg ggc tgg gtg ctg gtc ggt gac gcc gcc gcc ttc atc        912
Phe Ser Gly Pro Gly Trp Val Leu Val Gly Asp Ala Ala Ala Phe Ile
290                 295                 300 gac ccc ctg ctg tcc tcc ggc gtg acg ctg gcg atg cgc ggc gcg ctc        960
Asp Pro Leu Leu Ser Ser Gly Val Thr Leu Ala Met Arg Gly Ala Leu
305                 310                 315                 320 agc ctg tcc cgg gcg gtg cac gag gca ctg gcc gcg ccg gag aag gag       1008
Ser Leu Ser Arg Ala Val His Glu Ala Leu Ala Ala Pro Glu Lys Glu
            325                 330                 335 cgc cat ctc atg cag gtg tac gag gac cgc tac cgg gac ttc ctc gcc       1056
Arg His Leu Met Gln Val Tyr Glu Asp Arg Tyr Arg Asp Phe Leu Ala
        340                 345                 350 gcc ctg ctg gat ctg atc cgg ttc ttc tac gac ggc gcg cac ggc cgc       1104
Ala Leu Leu Asp Leu Ile Arg Phe Phe Tyr Asp Gly Ala His Gly Arg
    355                 360                 365 gac gag ttg cac ctg cgc gcc cag gcc atc gtg gac ccg gac cgg ctg       1152
Asp Glu Leu His Leu Arg Ala Gln Ala Ile Val Asp Pro Asp Arg Leu
370                 375                 380 atg cct ccg aag atc tcg ttc gtc tcc ctg ctg tcg ggg ctg gcg cgg       1200
Met Pro Pro Lys Ile Ser Phe Val Ser Leu Leu Ser Gly Leu Ala Arg
385                 390                 395                 400 ggc gac gag acg ctc gac cgc agc cct cgg acg gcc att gac cga ccg       1248
Gly Asp Glu Thr Leu Asp Arg Ser Pro Arg Thr Ala Ile Asp Arg Pro
            405                 410                 415 tca gac gct ata taa                                                   1263
Ser Asp Ala Ile  *
            420

<210> SEQ ID NO 38
<211> LENGTH: 420
<212> TYPE: PRT
<213> ORGANISM: Bacteria

<400> SEQUENCE: 38

Met Ser His Pro Glu Pro Glu Tyr Asp Val Ile Val Val Gly Gly Gly
1               5                   10                  15

Pro Ala Gly Ser Ser Thr Ala Gly Leu Leu Ala Gln Glu Gly His Arg
            20                  25                  30

Val Leu Leu Leu Glu Arg Glu Lys Phe Pro Arg Tyr His Ile Gly Glu
        35                  40                  45

Ser Leu Ile Ser Gly Val Thr Leu Thr Leu Asp Ala Leu Gly Val Arg
    50                  55                  60

Glu Arg Met Ala Glu Leu Arg Phe Gln Ile Lys His Gly Gly Ser Leu
65                  70                  75                  80

Leu Trp Gly Ala Asp Gln Thr Ala Pro Trp Ser Phe Arg Phe Arg Glu
            85                  90                  95

Ile Arg Asp Ala Arg Phe Asp Tyr Ser Trp Gln Val Arg Arg Ala Glu
```

-continued

```
            100                 105                 110
Phe Asp Ala Met Leu Asp Arg Ala Arg Glu Leu Gly Val Val
            115                 120                 125
Val Glu Gly Ala Thr Val Arg Gly Pro Leu Thr Asp Gly Glu Arg Val
130                 135                 140
Ala Gly Val Ser Tyr Gln Phe Arg Gly Glu Ala Asp Pro Ile Asp Ala
145                 150                 155                 160
Arg Ala Ala Ile Val Val Asp Ala Ser Gly Gln Gln Arg Trp Leu Gly
                165                 170                 175
Arg His Phe Gly Leu Val Ser Trp His Asp Asp Leu Arg Asn Met Ala
                180                 185                 190
Ala Trp Ser Tyr Tyr Ala Gly Ala Leu Arg Tyr Pro Gly Asp His Glu
                195                 200                 205
Gly Asp Leu Leu Val Glu Ser Cys Ala Gln Gly Trp Leu Trp Tyr Ala
            210                 215                 220
Pro Leu Ser Pro Thr Leu Thr Gly Ile Gly Tyr Val Thr Pro Ser Asp
225                 230                 235                 240
Arg Phe Ala Glu Thr Gly Leu Pro Pro Asp Gln Leu Leu Glu Lys Gln
                245                 250                 255
Ile Ala Glu Ser Asn Glu Val Ser Trp Leu Thr Ala Gly Ala Arg Arg
                260                 265                 270
Val Asp Val Tyr Arg Thr Ala Arg Asp Trp Ser Tyr Ala Cys Ser Gln
                275                 280                 285
Phe Ser Gly Pro Gly Trp Val Leu Val Gly Asp Ala Ala Phe Ile
            290                 295                 300
Asp Pro Leu Leu Ser Ser Gly Val Thr Leu Ala Met Arg Gly Ala Leu
305                 310                 315                 320
Ser Leu Ser Arg Ala Val His Glu Ala Leu Ala Pro Glu Lys Glu
                325                 330                 335
Arg His Leu Met Gln Val Tyr Glu Asp Arg Tyr Arg Asp Phe Leu Ala
                340                 345                 350
Ala Leu Leu Asp Leu Ile Arg Phe Phe Tyr Asp Gly Ala His Gly Arg
                355                 360                 365
Asp Glu Leu His Leu Arg Ala Gln Ala Ile Val Asp Pro Asp Arg Leu
            370                 375                 380
Met Pro Pro Lys Ile Ser Phe Val Ser Leu Leu Ser Gly Leu Ala Arg
385                 390                 395                 400
Gly Asp Glu Thr Leu Asp Arg Ser Pro Arg Thr Ala Ile Asp Arg Pro
                405                 410                 415
Ser Asp Ala Ile
            420
```

<210> SEQ ID NO 39
<211> LENGTH: 1137
<212> TYPE: DNA
<213> ORGANISM: B
<220> FEATURE:
<221> NAME/KEY: CDS
<222> LOCATION: (1)...(1137)

<400> SEQUENCE: 39

```
atg cgc gtg ctg ttc gtc tcc tcc ccc ggt atc ggc cac ctc ttc ccg    48
Met Arg Val Leu Phe Val Ser Ser Pro Gly Ile Gly His Leu Phe Pro
 1               5                  10                  15 ctg atc cag ctc gcc tgg ggc ttc cgc acg gcc ggc cac gac gtg ctg    96
Leu Ile Gln Leu Ala Trp Gly Phe Arg Thr Ala Gly His Asp Val Leu
```

-continued

| | | | | | | | | | | | | | | | | |
|---|---|---|---|---|---|---|---|---|---|---|---|---|---|---|---|---|
| | | 20 | | | | 25 | | | | 30 | | | | | | |
| atc | gcg | gtc | gcc | gag | cac | gcc | gac | cgg | gcc | gcc | gcc | gcg | ggc | ctg | gag | 144 |
| Ile | Ala | Val | Ala | Glu | His | Ala | Asp | Arg | Ala | Ala | Ala | Ala | Gly | Leu | Glu | |
| | | 35 | | | | 40 | | | | 45 | | | | | | |
| gtc | gtc | gac | gtg | gcg | ccc | gac | tac | agc | gcg | gtc | aag | gtc | ttc | gag | cag | 192 |
| Val | Val | Asp | Val | Ala | Pro | Asp | Tyr | Ser | Ala | Val | Lys | Val | Phe | Glu | Gln | |
| | | 50 | | | | 55 | | | | 60 | | | | | | |
| gtg | gcc | aag | gac | aac | ccg | cgc | ttc | gcc | gag | acc | gtc | gcc | acg | cgt | ccc | 240 |
| Val | Ala | Lys | Asp | Asn | Pro | Arg | Phe | Ala | Glu | Thr | Val | Ala | Thr | Arg | Pro | |
| 65 | | | | 70 | | | | 75 | | | | 80 | | | | |
| gcg | atc | gat | ctg | gag | gag | tgg | ggc | gtg | cag | atc | gcg | gcg | gtg | aac | cgc | 288 |
| Ala | Ile | Asp | Leu | Glu | Glu | Trp | Gly | Val | Gln | Ile | Ala | Ala | Val | Asn | Arg | |
| | | | | 85 | | | | 90 | | | | 95 | | | | |
| ccg | ctg | gtc | gac | ggg | acc | atg | gcg | ctg | gtc | gac | gac | tac | cgt | ccc | gac | 336 |
| Pro | Leu | Val | Asp | Gly | Thr | Met | Ala | Leu | Val | Asp | Asp | Tyr | Arg | Pro | Asp | |
| | | | 100 | | | | 105 | | | | 110 | | | | | |
| ctg | gtg | gtc | tac | gag | cag | ggc | gcc | acc | gtc | ggc | ctg | ctg | gcc | gcc | gac | 384 |
| Leu | Val | Val | Tyr | Glu | Gln | Gly | Ala | Thr | Val | Gly | Leu | Leu | Ala | Ala | Asp | |
| | | | 115 | | | | 120 | | | | 125 | | | | | |
| cgc | gcc | ggg | gtg | ccg | gca | gtg | cag | cgc | aac | cag | agc | gcc | tgg | cgg | acc | 432 |
| Arg | Ala | Gly | Val | Pro | Ala | Val | Gln | Arg | Asn | Gln | Ser | Ala | Trp | Arg | Thr | |
| | 130 | | | | 135 | | | | 140 | | | | | | | |
| cgg | ggc | atg | cac | cgc | tcg | atc | gcg | tcc | ttc | ctg | acc | gac | ctg | atg | gac | 480 |
| Arg | Gly | Met | His | Arg | Ser | Ile | Ala | Ser | Phe | Leu | Thr | Asp | Leu | Met | Asp | |
| 145 | | | | 150 | | | | 155 | | | | 160 | | | | |
| aag | cac | cag | gtc | agc | ctg | ccc | gag | ccg | gtg | gcg | acg | atc | gag | tcg | ttc | 528 |
| Lys | His | Gln | Val | Ser | Leu | Pro | Glu | Pro | Val | Ala | Thr | Ile | Glu | Ser | Phe | |
| | | | | 165 | | | | 170 | | | | 175 | | | | |
| ccg | ccg | agc | ctg | ctg | ctg | gag | gcg | gag | ccc | gag | ggc | tgg | ttc | atg | cgc | 576 |
| Pro | Pro | Ser | Leu | Leu | Leu | Glu | Ala | Glu | Pro | Glu | Gly | Trp | Phe | Met | Arg | |
| | | | 180 | | | | 185 | | | | 190 | | | | | |
| tgg | gtg | ccg | tac | ggc | ggc | ggc | gcc | gtc | ctc | ggc | gac | cgg | ctg | ccg | ccg | 624 |
| Trp | Val | Pro | Tyr | Gly | Gly | Gly | Ala | Val | Leu | Gly | Asp | Arg | Leu | Pro | Pro | |
| | | 195 | | | | 200 | | | | 205 | | | | | | |
| gtg | ccc | gcc | cgg | ccc | gag | gtg | gcg | atc | acc | atg | ggc | acc | atc | gag | ctc | 672 |
| Val | Pro | Ala | Arg | Pro | Glu | Val | Ala | Ile | Thr | Met | Gly | Thr | Ile | Glu | Leu | |
| | 210 | | | | 215 | | | | 220 | | | | | | | |
| cag | gcg | ttc | ggc | atc | ggc | gcc | gtg | gag | ccc | atc | atc | gcc | gcc | gcc | ggc | 720 |
| Gln | Ala | Phe | Gly | Ile | Gly | Ala | Val | Glu | Pro | Ile | Ile | Ala | Ala | Ala | Gly | |
| 225 | | | | 230 | | | | 235 | | | | 240 | | | | |
| gag | gtg | gac | gcc | gac | ttc | gtg | ctc | gcc | ctc | ggc | gac | ctc | gac | atc | agc | 768 |
| Glu | Val | Asp | Ala | Asp | Phe | Val | Leu | Ala | Leu | Gly | Asp | Leu | Asp | Ile | Ser | |
| | | | | 245 | | | | 250 | | | | 255 | | | | |
| ccg | ctg | ggc | acg | ttg | ccg | cgc | aac | gtc | cgg | gcg | gtc | ggc | tgg | acg | ccg | 816 |
| Pro | Leu | Gly | Thr | Leu | Pro | Arg | Asn | Val | Arg | Ala | Val | Gly | Trp | Thr | Pro | |
| | | | 260 | | | | 265 | | | | 270 | | | | | |
| ctg | cac | acc | ctg | ctg | cgt | acc | tgc | acc | gcg | gtg | gtg | cac | cac | ggc | ggg | 864 |
| Leu | His | Thr | Leu | Leu | Arg | Thr | Cys | Thr | Ala | Val | Val | His | His | Gly | Gly | |
| | | 275 | | | | 280 | | | | 285 | | | | | | |
| ggc | ggc | acg | gtg | atg | acc | gcc | atc | gac | gcc | ggc | atc | ccg | cag | ctg | ctc | 912 |
| Gly | Gly | Thr | Val | Met | Thr | Ala | Ile | Asp | Ala | Gly | Ile | Pro | Gln | Leu | Leu | |
| | | 290 | | | | 295 | | | | 300 | | | | | | |
| gcc | ccg | gac | ccg | cgc | gac | cag | ttc | cag | cac | acc | gcc | cgg | gag | gcc | gtc | 960 |
| Ala | Pro | Asp | Pro | Arg | Asp | Gln | Phe | Gln | His | Thr | Ala | Arg | Glu | Ala | Val | |
| 305 | | | | 310 | | | | 315 | | | | 320 | | | | |
| agc | cgg | cgc | ggc | atc | ggc | ctg | gtc | agc | acg | tcg | gac | aag | gtc | gac | gcg | 1008 |
| Ser | Arg | Arg | Gly | Ile | Gly | Leu | Val | Ser | Thr | Ser | Asp | Lys | Val | Asp | Ala | |
| | | | 325 | | | | 330 | | | | 335 | | | | | |
| gac | ctg | ctg | cgc | cgg | ctg | atc | ggg | gac | gag | tcg | ctg | cgc | acc | gcg | gcc | 1056 |

```
Asp Leu Leu Arg Arg Leu Ile Gly Asp Glu Ser Leu Arg Thr Ala Ala
            340                 345                 350 cgg gag gta cgc gag gag atg gtc gcg ctg ccc acg ccg gcg gag acg        1104
Arg Glu Val Arg Glu Glu Met Val Ala Leu Pro Thr Pro Ala Glu Thr
            355                 360                 365 gtg cgg cgc atc gtc gag cgc atc tcg ggt tga                            1137
Val Arg Arg Ile Val Glu Arg Ile Ser Gly *
            370                 375
```

<210> SEQ ID NO 40
<211> LENGTH: 378
<212> TYPE: PRT
<213> ORGANISM: Bacteria

<400> SEQUENCE: 40

```
Met Arg Val Leu Phe Val Ser Ser Pro Gly Ile Gly His Leu Phe Pro
  1               5                  10                  15

Leu Ile Gln Leu Ala Trp Gly Phe Arg Thr Ala Gly His Asp Val Leu
             20                  25                  30

Ile Ala Val Ala Glu His Ala Asp Arg Ala Ala Ala Gly Leu Glu
         35                  40                  45

Val Val Asp Val Ala Pro Asp Tyr Ser Ala Val Lys Val Phe Glu Gln
 50                  55                  60

Val Ala Lys Asp Asn Pro Arg Phe Ala Glu Thr Val Ala Thr Arg Pro
 65                  70                  75                  80

Ala Ile Asp Leu Glu Glu Trp Gly Val Gln Ile Ala Ala Val Asn Arg
                 85                  90                  95

Pro Leu Val Asp Gly Thr Met Ala Leu Val Asp Asp Tyr Arg Pro Asp
            100                 105                 110

Leu Val Val Tyr Glu Gln Gly Ala Thr Val Gly Leu Leu Ala Ala Asp
            115                 120                 125

Arg Ala Gly Val Pro Ala Val Gln Arg Asn Gln Ser Ala Trp Arg Thr
        130                 135                 140

Arg Gly Met His Arg Ser Ile Ala Ser Phe Leu Thr Asp Leu Met Asp
145                 150                 155                 160

Lys His Gln Val Ser Leu Pro Glu Pro Val Ala Thr Ile Glu Ser Phe
                165                 170                 175

Pro Pro Ser Leu Leu Leu Glu Ala Glu Pro Glu Gly Trp Phe Met Arg
            180                 185                 190

Trp Val Pro Tyr Gly Gly Gly Ala Val Leu Gly Asp Arg Leu Pro Pro
            195                 200                 205

Val Pro Ala Arg Pro Glu Val Ala Ile Thr Met Gly Thr Ile Glu Leu
    210                 215                 220

Gln Ala Phe Gly Ile Gly Ala Val Glu Pro Ile Ile Ala Ala Gly
225                 230                 235                 240

Glu Val Asp Ala Asp Phe Val Leu Ala Leu Gly Asp Leu Asp Ile Ser
                245                 250                 255

Pro Leu Gly Thr Leu Pro Arg Asn Val Arg Ala Val Gly Trp Thr Pro
            260                 265                 270

Leu His Thr Leu Leu Arg Thr Cys Thr Ala Val Val His His Gly Gly
        275                 280                 285

Gly Gly Thr Val Met Thr Ala Ile Asp Ala Gly Ile Pro Gln Leu Leu
    290                 295                 300

Ala Pro Asp Pro Arg Asp Gln Phe Gln His Thr Ala Arg Glu Ala Val
305                 310                 315                 320
```

```
Ser Arg Arg Gly Ile Gly Leu Val Ser Thr Ser Asp Lys Val Asp Ala
            325                 330                 335

Asp Leu Leu Arg Arg Leu Ile Gly Asp Glu Ser Leu Arg Thr Ala Ala
            340                 345                 350

Arg Glu Val Arg Glu Glu Met Val Ala Leu Pro Thr Pro Ala Glu Thr
            355                 360                 365

Val Arg Arg Ile Val Glu Arg Ile Ser Gly
        370                 375

<210> SEQ ID NO 41
<211> LENGTH: 1035
<212> TYPE: DNA
<213> ORGANISM: Bacteria
<220> FEATURE:
<221> NAME/KEY: CDS
<222> LOCATION: (1)...(1035)

<400> SEQUENCE: 41
```

| | | | | | | | | | | | | | | | | |
|---|---|---|---|---|---|---|---|---|---|---|---|---|---|---|---|---|
| atg | cgc | acc | gcc | gga | acg | tac | atc | cgt | ggg | atc | ggg | gcc | tac | ctt | cct | 48 |
| Met | Arg | Thr | Ala | Gly | Thr | Tyr | Ile | Arg | Gly | Ile | Gly | Ala | Tyr | Leu | Pro | |
| 1 | | | | 5 | | | | | 10 | | | | | 15 | | |
| gag | acc | gtc | acc | gtc | gag | gaa | gcc | gtc | gcc | cag | ggc | ctg | tac | ccg | cag | 96 |
| Glu | Thr | Val | Thr | Val | Glu | Glu | Ala | Val | Ala | Gln | Gly | Leu | Tyr | Pro | Gln | |
| | | | 20 | | | | | 25 | | | | | 30 | | | |
| gag | gac | atc | gag | acg | cac | ggg | ctg | ggc | ggg | gcc | gcg | atc | gcc | ggc | gaa | 144 |
| Glu | Asp | Ile | Glu | Thr | His | Gly | Leu | Gly | Gly | Ala | Ala | Ile | Ala | Gly | Glu | |
| | | 35 | | | | | 40 | | | | | 45 | | | | |
| ctg | ccc | gcg | ccg | gac | atg | gcg | ctg | cgg | gcc | gcg | cag | gac | gcc | ctc | aag | 192 |
| Leu | Pro | Ala | Pro | Asp | Met | Ala | Leu | Arg | Ala | Ala | Gln | Asp | Ala | Leu | Lys | |
| 50 | | | | | 55 | | | | | 60 | | | | | | |
| gag | agc | gag | ctg | ggc | cgc | ggc | gac | atc | gac | ctg | ctc | tac | gcg | gcc | | 240 |
| Glu | Ser | Glu | Leu | Gly | Arg | Gly | Asp | Ile | Asp | Leu | Leu | Tyr | Ala | Ala | | |
| 65 | | | | 70 | | | | | 75 | | | | | 80 | | |
| gcc | tgg | cac | cag | ggc | ccc | gag | ggc | tgg | ctg | gcg | cac | tcc | tac | atc | cag | 288 |
| Ala | Trp | His | Gln | Gly | Pro | Glu | Gly | Trp | Leu | Ala | His | Ser | Tyr | Ile | Gln | |
| | | | | 85 | | | | | 90 | | | | | 95 | | |
| cac | tac | ctg | ctc | ggc | ggg | gtg | ccc | cgg | gcg | acc | gag | atc | cgg | cag | ggc | 336 |
| His | Tyr | Leu | Leu | Gly | Gly | Val | Pro | Arg | Ala | Thr | Glu | Ile | Arg | Gln | Gly | |
| | | | 100 | | | | | 105 | | | | | 110 | | | |
| tgc | aac | ggc | atg | ttc | acc | atg | ctc | gaa | ctc | gcg | gcc | agc | tac | ctg | aag | 384 |
| Cys | Asn | Gly | Met | Phe | Thr | Met | Leu | Glu | Leu | Ala | Ala | Ser | Tyr | Leu | Lys | |
| | | 115 | | | | | 120 | | | | | 125 | | | | |
| gcc | gcg | ccg | gaa | cgc | aag | gcg | gcg | atg | ctc | gtc | gcc | gcc | gac | aac | tac | 432 |
| Ala | Ala | Pro | Glu | Arg | Lys | Ala | Ala | Met | Leu | Val | Ala | Ala | Asp | Asn | Tyr | |
| | 130 | | | | | 135 | | | | | 140 | | | | | |
| ggc | acc | ccg | ctg | ctg | gac | cgc | tgg | cgc | acc | aac | ctc | ggc | ttc | atc | ctc | 480 |
| Gly | Thr | Pro | Leu | Leu | Asp | Arg | Trp | Arg | Thr | Asn | Leu | Gly | Phe | Ile | Leu | |
| 145 | | | | | 150 | | | | | 155 | | | | | 160 | |
| ggc | gac | gcc | gcc | tcc | gcg | gtg | gtg | ctg | agc | acc | gag | agc | ggc | ttc | gtc | 528 |
| Gly | Asp | Ala | Ala | Ser | Ala | Val | Val | Leu | Ser | Thr | Glu | Ser | Gly | Phe | Val | |
| | | | | 165 | | | | | 170 | | | | | 175 | | |
| gag | ctg | atg | tcg | gtc | tgc | tcc | atc | acc | gtg | ccg | gag | gcc | gag | gag | gtg | 576 |
| Glu | Leu | Met | Ser | Val | Cys | Ser | Ile | Thr | Val | Pro | Glu | Ala | Glu | Glu | Val | |
| | | | 180 | | | | | 185 | | | | | 190 | | | |
| cac | cgc | ggc | ggc | gag | ccg | atg | ttc | ccg | ccc | ggc | gcg | acg | ctc | gcc | aag | 624 |
| His | Arg | Gly | Gly | Glu | Pro | Met | Phe | Pro | Pro | Gly | Ala | Thr | Leu | Ala | Lys | |
| | | 195 | | | | | 200 | | | | | 205 | | | | |
| gag | ctc | gac | ttc | ggc | gcc | cgg | ctc | ttc | tac | cac | atc | acc | gag | cag | acc | 672 |
| Glu | Leu | Asp | Phe | Gly | Ala | Arg | Leu | Phe | Tyr | His | Ile | Thr | Glu | Gln | Thr | |
| | 210 | | | | | 215 | | | | | 220 | | | | | |

-continued

```
ccc gtg ctc gcc gtg ctc ggc gag gcg cag gag acg atg acc acc gtc      720
Pro Val Leu Ala Val Leu Gly Glu Ala Gln Glu Thr Met Thr Thr Val
225                 230                 235                 240 gcc gag cag gcg ctc gcc gag gcc ggc atc ggc acg gga gac ctg gcc      768
Ala Glu Gln Ala Leu Ala Glu Ala Gly Ile Gly Thr Gly Asp Leu Ala
                245                 250                 255 aag gtc tcc ttc atg aac tac tcc cgc gag gtg gtc gag cag cgc tgc      816
Lys Val Ser Phe Met Asn Tyr Ser Arg Glu Val Val Glu Gln Arg Cys
            260                 265                 270 atg gcg ccc ctg ggg ctg ggg atg gag aag tcc acc tgg gac ttc ggg      864
Met Ala Pro Leu Gly Leu Gly Met Glu Lys Ser Thr Trp Asp Phe Gly
        275                 280                 285 cgg atg atc ggg cac tgc ggc gcc agc gac cac ctg ctc gcc ctg cac      912
Arg Met Ile Gly His Cys Gly Ala Ser Asp His Leu Leu Ala Leu His
    290                 295                 300 cac tcg ctg cgg gcc ggt gag gtc gcc gcc ggc gac cac gtg ctg tgg      960
His Ser Leu Arg Ala Gly Glu Val Ala Ala Gly Asp His Val Leu Trp
305                 310                 315                 320 ctg gcg atg ggc ccc ggc gtg gag ttc acc gcc gcc gtc ctg cgc gta     1008
Leu Ala Met Gly Pro Gly Val Glu Phe Thr Ala Ala Val Leu Arg Val
                325                 330                 335 ctg gac aac ccc tac gtc gag cgc tga                                 1035
Leu Asp Asn Pro Tyr Val Glu Arg *
            340
```

<210> SEQ ID NO 42
<211> LENGTH: 344
<212> TYPE: PRT
<213> ORGANISM: Bacteria

<400> SEQUENCE: 42

```
Met Arg Thr Ala Gly Thr Tyr Ile Arg Gly Ile Gly Ala Tyr Leu Pro
 1               5                  10                  15

Glu Thr Val Thr Val Glu Ala Val Ala Gln Gly Leu Tyr Pro Gln
                20                  25                  30

Glu Asp Ile Glu Thr His Gly Leu Gly Gly Ala Ile Ala Gly Glu
            35                  40                  45

Leu Pro Ala Pro Asp Met Ala Leu Arg Ala Ala Gln Asp Ala Leu Lys
 50                  55                  60

Glu Ser Glu Leu Gly Arg Gly Asp Ile Asp Leu Leu Leu Tyr Ala Ala
 65                  70                  75                  80

Ala Trp His Gln Gly Pro Glu Gly Trp Leu Ala His Ser Tyr Ile Gln
                85                  90                  95

His Tyr Leu Leu Gly Gly Val Pro Arg Ala Thr Glu Ile Arg Gln Gly
            100                 105                 110

Cys Asn Gly Met Phe Thr Met Leu Glu Leu Ala Ala Ser Tyr Leu Lys
        115                 120                 125

Ala Ala Pro Glu Arg Lys Ala Ala Met Leu Val Ala Ala Asp Asn Tyr
    130                 135                 140

Gly Thr Pro Leu Leu Asp Arg Trp Arg Thr Asn Leu Gly Phe Ile Leu
145                 150                 155                 160

Gly Asp Ala Ala Ser Ala Val Val Leu Ser Thr Glu Ser Gly Phe Val
                165                 170                 175

Glu Leu Met Ser Val Cys Ser Ile Thr Val Pro Glu Ala Glu Val
            180                 185                 190

His Arg Gly Gly Glu Pro Met Phe Pro Pro Gly Ala Thr Leu Ala Lys
        195                 200                 205
```

```
Glu Leu Asp Phe Gly Ala Arg Leu Phe Tyr His Ile Thr Glu Gln Thr
    210                 215                 220

Pro Val Leu Ala Val Leu Gly Glu Ala Gln Glu Thr Met Thr Thr Val
225                 230                 235                 240

Ala Glu Gln Ala Leu Ala Glu Ala Gly Ile Gly Thr Gly Asp Leu Ala
                245                 250                 255

Lys Val Ser Phe Met Asn Tyr Ser Arg Glu Val Val Glu Gln Arg Cys
            260                 265                 270

Met Ala Pro Leu Gly Leu Gly Met Glu Lys Ser Thr Trp Asp Phe Gly
        275                 280                 285

Arg Met Ile Gly His Cys Gly Ala Ser Asp His Leu Leu Ala Leu His
    290                 295                 300

His Ser Leu Arg Ala Gly Glu Val Ala Ala Gly Asp His Val Leu Trp
305                 310                 315                 320

Leu Ala Met Gly Pro Gly Val Glu Phe Thr Ala Ala Val Leu Arg Val
                325                 330                 335

Leu Asp Asn Pro Tyr Val Glu Arg
            340

<210> SEQ ID NO 43
<211> LENGTH: 1347
<212> TYPE: DNA
<213> ORGANISM: .
<220> FEATURE:
<221> NAME/KEY: CDS
<222> LOCATION: (1)...(1347)

<400> SEQUENCE: 43 gtg acc ggg cgc gac gac cgg ccc gac ggc gct cgg ccg gtc cca ccc     48
Val Thr Gly Arg Asp Asp Arg Pro Asp Gly Ala Arg Pro Val Pro Pro
  1               5                  10                  15 ggg cca gcg gtc acg ccc ggg cca gcg gtc acg ccc ggg ccg ccg gtc     96
Gly Pro Ala Val Thr Pro Gly Pro Ala Val Thr Pro Gly Pro Pro Val
             20                  25                  30 acg cca ggg cgg gcg gcg gac gga ccg gcc gag gcc ggg agc gcg gcc    144
Thr Pro Gly Arg Ala Ala Asp Gly Pro Ala Glu Ala Gly Ser Ala Ala
         35                  40                  45 ggg atc gac gcg ttt ccg ctg ccc cgc cgg tgc ccg ttc ggc ccg ccg    192
Gly Ile Asp Ala Phe Pro Leu Pro Arg Arg Cys Pro Phe Gly Pro Pro
     50                  55                  60 gcc gag tac gcc cgg ctg cgg acc gag cgg ccg gtc gcc cgg ctg ccc    240
Ala Glu Tyr Ala Arg Leu Arg Thr Glu Arg Pro Val Ala Arg Leu Pro
 65                  70                  75                  80 atg ctc ggc ggc aac acg gcc tgg gtg gtg tcc cgg tac gcc gac gtc    288
Met Leu Gly Gly Asn Thr Ala Trp Val Val Ser Arg Tyr Ala Asp Val
                 85                  90                  95 aag cgg gtg ctc agc gac ccg cgg atg agc gcg gac cgg cgc cgg gcc    336
Lys Arg Val Leu Ser Asp Pro Arg Met Ser Ala Asp Arg Arg Arg Ala
            100                 105                 110 ggt ttt ccg cgg ttc gcg ccg acc acc gag agc cag cgg cag gcc tcg    384
Gly Phe Pro Arg Phe Ala Pro Thr Thr Glu Ser Gln Arg Gln Ala Ser
        115                 120                 125 ttc gcg aac ttc cgc ccc ccg ctg aac tgg atg gac ccg ccg gag cac    432
Phe Ala Asn Phe Arg Pro Pro Leu Asn Trp Met Asp Pro Pro Glu His
    130                 135                 140 acc gcc gcc cgc cgc cag atc gtc gac gag ttc gcc gcg cgg cgg gta    480
Thr Ala Ala Arg Arg Gln Ile Val Asp Glu Phe Ala Ala Arg Arg Val
145                 150                 155                 160 cga cag ctg cgg ccg ctg gtc gag cgg gtg gtg gac gag cac ctc gac    528
```

```
Arg Gln Leu Arg Pro Leu Val Glu Arg Val Asp Glu His Leu Asp
                165                 170                 175 gcc atg acg gcc ggg cgg tcg agc gcc gac ctg gtg ccg tcg ttc agc          576
Ala Met Thr Ala Gly Arg Ser Ser Ala Asp Leu Val Pro Ser Phe Ser
            180                 185                 190 tat ccg gtg ccg tcg cgg gtg atc tgc gag atg ctc ggc gtg ccg tac          624
Tyr Pro Val Pro Ser Arg Val Ile Cys Glu Met Leu Gly Val Pro Tyr
        195                 200                 205 ggc gaa cac gcg ttc ttc gag cgc cgg tcc acc cgg atg ctg agt cgc          672
Gly Glu His Ala Phe Phe Glu Arg Arg Ser Thr Arg Met Leu Ser Arg
    210                 215                 220 ggc gtg ccc gcg gac gag cgg gcc cgg tgc gcc cgc gag atc cgc gag          720
Gly Val Pro Ala Asp Glu Arg Ala Arg Cys Ala Arg Glu Ile Arg Glu
225                 230                 235                 240 ttc ctc gac ggc gtg gtg acc gac aag gag cgg cac ccc ggc gac gac          768
Phe Leu Asp Gly Val Val Thr Asp Lys Glu Arg His Pro Gly Asp Asp
                245                 250                 255 gtg ctc agc cgg ctg ctc gcc gcg cag cgc gcg gcc ggc gag ccc gac          816
Val Leu Ser Arg Leu Leu Ala Ala Gln Arg Ala Ala Gly Glu Pro Asp
            260                 265                 270 cac gag gcc gtg gtg agc atg gcc ttc gtg ctg ctg gtc gcc ggg cac          864
His Glu Ala Val Val Ser Met Ala Phe Val Leu Leu Val Ala Gly His
        275                 280                 285 gtc acg acg tcg aac atg atc tcg ctg agc gtg ctg gcc ctg ttg acc          912
Val Thr Thr Ser Asn Met Ile Ser Leu Ser Val Leu Ala Leu Leu Thr
    290                 295                 300 cat ccg gag cgg ctc gcc cgc ctg cgc gcc gag ccg gac cgg ttc ccc          960
His Pro Glu Arg Leu Ala Arg Leu Arg Ala Glu Pro Asp Arg Phe Pro
305                 310                 315                 320 gcc gcc gtc gag gag ctg ctg cgg tac ttc acc atc gtc gag gcg gcg         1008
Ala Ala Val Glu Glu Leu Leu Arg Tyr Phe Thr Ile Val Glu Ala Ala
                325                 330                 335 acc gcg cgg acc gcg acc gcc gac gtg acg gtc ggt ggg gtc acc atc         1056
Thr Ala Arg Thr Ala Thr Ala Asp Val Thr Val Gly Gly Val Thr Ile
            340                 345                 350 cgg gcc ggg gag ggg gtg gtg gcg ctg ggc cag gcc gcc aac cgg gac         1104
Arg Ala Gly Glu Gly Val Val Ala Leu Gly Gln Ala Ala Asn Arg Asp
        355                 360                 365 ccg gcg gcg ttc gac cgg ccg gac gag ttc gac ccg gac cgc gac gcc         1152
Pro Ala Ala Phe Asp Arg Pro Asp Glu Phe Asp Pro Asp Arg Asp Ala
    370                 375                 380 cgg cac cac ctc gcc ttc ggc tac gga cga cac atc tgc ccc ggc cag         1200
Arg His His Leu Ala Phe Gly Tyr Gly Arg His Ile Cys Pro Gly Gln
385                 390                 395                 400 cac ctg gcc cgg ctg gaa ctg gac gtc gcg ctg agc cgg ctg gtc cgg         1248
His Leu Ala Arg Leu Glu Leu Asp Val Ala Leu Ser Arg Leu Val Arg
                405                 410                 415 cgg ctg ccc ggg ctg cgg ttg acc gtg gac gtg gac gac ctg ccg ctc         1296
Arg Leu Pro Gly Leu Arg Leu Thr Val Asp Val Asp Asp Leu Pro Leu
            420                 425                 430 aag gag gac ggc aac atc ttc ggc ctg cac gcg ctg ccg gtc gcc tgg         1344
Lys Glu Asp Gly Asn Ile Phe Gly Leu His Ala Leu Pro Val Ala Trp
        435                 440                 445 tga                                                                      1347
*

<210> SEQ ID NO 44
<211> LENGTH: 448
<212> TYPE: PRT
<213> ORGANISM: Bacteria
```

<400> SEQUENCE: 44

| | | | | | | | | | | | | | | |
|---|---|---|---|---|---|---|---|---|---|---|---|---|---|---|
|Val|Thr|Gly|Arg|Asp|Asp|Arg|Pro|Asp|Gly|Ala|Arg|Pro|Val|Pro|Pro|
|1| | |5| | | | |10| | | | |15| | |
|Gly|Pro|Ala|Val|Thr|Pro|Gly|Pro|Ala|Val|Thr|Pro|Gly|Pro|Pro|Val|
| | | |20| | | |25| | | |30| | | | |
|Thr|Pro|Gly|Arg|Ala|Ala|Asp|Gly|Pro|Ala|Glu|Ala|Gly|Ser|Ala|Ala|
| | |35| | | |40| | | |45| | | | | |
|Gly|Ile|Asp|Ala|Phe|Pro|Leu|Pro|Arg|Arg|Cys|Pro|Phe|Gly|Pro|Pro|
| |50| | | |55| | | |60| | | | | | |
|Ala|Glu|Tyr|Ala|Arg|Leu|Arg|Thr|Glu|Arg|Pro|Val|Ala|Arg|Leu|Pro|
|65| | | |70| | | |75| | | |80| | | |
|Met|Leu|Gly|Gly|Asn|Thr|Ala|Trp|Val|Val|Ser|Arg|Tyr|Ala|Asp|Val|
| | | |85| | | |90| | | |95| | | | |
|Lys|Arg|Val|Leu|Ser|Asp|Pro|Arg|Met|Ser|Ala|Asp|Arg|Arg|Arg|Ala|
| | | |100| | | |105| | | |110| | | | |
|Gly|Phe|Pro|Arg|Phe|Ala|Pro|Thr|Thr|Glu|Ser|Gln|Arg|Gln|Ala|Ser|
| | |115| | | |120| | | |125| | | | | |
|Phe|Ala|Asn|Phe|Arg|Pro|Pro|Leu|Asn|Trp|Met|Asp|Pro|Pro|Glu|His|
|130| | | |135| | | |140| | | | | | | |
|Thr|Ala|Ala|Arg|Arg|Gln|Ile|Val|Asp|Glu|Phe|Ala|Ala|Arg|Arg|Val|
|145| | | |150| | | |155| | | |160| | | |
|Arg|Gln|Leu|Arg|Pro|Leu|Val|Glu|Arg|Val|Asp|Glu|His|Leu|Asp|
| | | |165| | | |170| | | |175| | | | |
|Ala|Met|Thr|Ala|Gly|Arg|Ser|Ser|Ala|Asp|Leu|Val|Pro|Ser|Phe|Ser|
| | |180| | | |185| | | |190| | | | | |
|Tyr|Pro|Val|Pro|Ser|Arg|Val|Ile|Cys|Glu|Met|Leu|Gly|Val|Pro|Tyr|
| | |195| | | |200| | | |205| | | | | |
|Gly|Glu|His|Ala|Phe|Phe|Glu|Arg|Arg|Ser|Thr|Arg|Met|Leu|Ser|Arg|
| |210| | | |215| | | |220| | | | | | |
|Gly|Val|Pro|Ala|Asp|Glu|Arg|Ala|Arg|Cys|Ala|Arg|Glu|Ile|Arg|Glu|
|225| | | |230| | | |235| | | |240| | | |
|Phe|Leu|Asp|Gly|Val|Val|Thr|Asp|Lys|Glu|Arg|His|Pro|Gly|Asp|Asp|
| | | |245| | | |250| | | |255| | | | |
|Val|Leu|Ser|Arg|Leu|Leu|Ala|Ala|Gln|Arg|Ala|Ala|Gly|Glu|Pro|Asp|
| | |260| | | |265| | | |270| | | | | |
|His|Glu|Ala|Val|Val|Ser|Met|Ala|Phe|Val|Leu|Leu|Val|Ala|Gly|His|
| |275| | | |280| | | |285| | | | | | |
|Val|Thr|Thr|Ser|Asn|Met|Ile|Ser|Leu|Ser|Val|Leu|Ala|Leu|Leu|Thr|
| |290| | | |295| | | |300| | | | | | |
|His|Pro|Glu|Arg|Leu|Ala|Arg|Leu|Arg|Ala|Glu|Pro|Asp|Arg|Phe|Pro|
|305| | | |310| | | |315| | | |320| | | |
|Ala|Ala|Val|Glu|Glu|Leu|Leu|Arg|Tyr|Phe|Thr|Ile|Val|Glu|Ala|Ala|
| | | |325| | | |330| | | |335| | | | |
|Thr|Ala|Arg|Thr|Ala|Thr|Ala|Asp|Val|Thr|Val|Gly|Gly|Val|Thr|Ile|
| | |340| | | |345| | | |350| | | | | |
|Arg|Ala|Gly|Glu|Gly|Val|Val|Ala|Leu|Gly|Gln|Ala|Ala|Asn|Arg|Asp|
| |355| | | |360| | | |365| | | | | | |
|Pro|Ala|Phe|Asp|Arg|Pro|Asp|Glu|Phe|Asp|Pro|Asp|Arg|Asp|Ala|
| |370| | | |375| | | |380| | | | | | |
|Arg|His|His|Leu|Ala|Phe|Gly|Tyr|Gly|Arg|His|Ile|Cys|Pro|Gly|Gln|
|385| | | |390| | | |395| | | |400| | | |
|His|Leu|Ala|Arg|Leu|Glu|Leu|Asp|Val|Ala|Leu|Ser|Arg|Leu|Val|Arg|

|     |     |     |     |     | 405 |     |     |     |     | 410 |     |     |     |     | 415 |     |     |
| --- | --- | --- | --- | --- | --- | --- | --- | --- | --- | --- | --- | --- | --- | --- | --- | --- | --- |
| Arg | Leu | Pro | Gly | Leu | Arg | Leu | Thr | Val | Asp | Val | Asp | Asp | Leu | Pro | Leu |     |     |
|     |     |     | 420 |     |     |     |     | 425 |     |     |     | 430 |     |     |     |     |     |

Lys Glu Asp Gly Asn Ile Phe Gly Leu His Ala Leu Pro Val Ala Trp
          435                   440                   445

<210> SEQ ID NO 45
<211> LENGTH: 588
<212> TYPE: DNA
<213> ORGANISM: Bacteria
<220> FEATURE:
<221> NAME/KEY: CDS
<222> LOCATION: (1)...(588)

<400> SEQUENCE: 45

| cgg | ccc | cac | cca | tgg | cga | ccc | ggc | agg | tcc | cgc | tgc | gcg | agg | tgc | gcg | 48 |
| --- | --- | --- | --- | --- | --- | --- | --- | --- | --- | --- | --- | --- | --- | --- | --- | --- |
| Arg | Pro | His | Pro | Trp | Arg | Pro | Gly | Arg | Ser | Arg | Cys | Ala | Arg | Cys | Ala |    |
| 1   |     |     |     | 5   |     |     |     |     | 10  |     |     |     |     | 15  |     |    |

| act | ggt | acc | gcg | ccg | acg | acg | aga | tcc | gcc | acc | gct | ccg | gcc | ggt | tct | 96 |
| --- | --- | --- | --- | --- | --- | --- | --- | --- | --- | --- | --- | --- | --- | --- | --- | --- |
| Thr | Gly | Thr | Ala | Pro | Thr | Thr | Arg | Ser | Ala | Thr | Ala | Pro | Ala | Gly | Ser |    |
|     |     |     | 20  |     |     |     |     | 25  |     |     |     |     | 30  |     |     |    |

| tcc | gca | tcg | tcg | gcc | ggc | ggg | tgc | ggg | cca | gca | acc | gcg | agg | tgt | ccc | 144 |
| --- | --- | --- | --- | --- | --- | --- | --- | --- | --- | --- | --- | --- | --- | --- | --- | --- |
| Ser | Ala | Ser | Ser | Ala | Gly | Gly | Cys | Gly | Pro | Ala | Thr | Ala | Arg | Cys | Pro |     |
|     | 35  |     |     |     |     | 40  |     |     |     |     | 45  |     |     |     |     |     |

| agt | ggt | gcc | agc | cgt | tgc | tgg | cac | cgt | gcg | gga | cgg | gtc | tgg | tgg | cgt | 192 |
| --- | --- | --- | --- | --- | --- | --- | --- | --- | --- | --- | --- | --- | --- | --- | --- | --- |
| Ser | Gly | Ala | Ser | Arg | Cys | Trp | His | Arg | Ala | Gly | Arg | Val | Trp | Trp | Arg |     |
| 50  |     |     |     |     | 55  |     |     |     |     | 60  |     |     |     |     |     |     |

| tcg | tcg | tcc | gac | gca | tcg | acg | gcg | tgc | tgc | acg | tgc | tcg | ccc | acg | ccg | 240 |
| --- | --- | --- | --- | --- | --- | --- | --- | --- | --- | --- | --- | --- | --- | --- | --- | --- |
| Ser | Ser | Ser | Asp | Ala | Ser | Thr | Ala | Cys | Cys | Thr | Cys | Ser | Pro | Thr | Pro |     |
| 65  |     |     |     |     | 70  |     |     |     |     | 75  |     |     |     |     | 80  |     |

| acc | tgc | ggc | ccg | gct | acc | ggg | aca | ccg | tcg | agc | tgg | gac | cga | ccg | tgc | 288 |
| --- | --- | --- | --- | --- | --- | --- | --- | --- | --- | --- | --- | --- | --- | --- | --- | --- |
| Thr | Cys | Gly | Pro | Ala | Thr | Gly | Thr | Pro | Ser | Ser | Trp | Asp | Arg | Pro | Cys |     |
|     |     |     |     | 85  |     |     |     |     | 90  |     |     |     |     | 95  |     |     |

| agt | gca | ccc | cgg | gac | aac | ttc | acc | ggc | ccg | gcc | cgg | gac | ggc | cgc | ccg | 336 |
| --- | --- | --- | --- | --- | --- | --- | --- | --- | --- | --- | --- | --- | --- | --- | --- | --- |
| Ser | Ala | Pro | Arg | Asp | Asn | Phe | Thr | Gly | Pro | Ala | Arg | Asp | Gly | Arg | Pro |     |
|     |     |     | 100 |     |     |     |     | 105 |     |     |     |     | 110 |     |     |     |

| gcg | tac | ctc | gac | ctg | gtg | ctc | tcc | gac | gag | gtc | cgc | gtg | cac | tac | gac | 384 |
| --- | --- | --- | --- | --- | --- | --- | --- | --- | --- | --- | --- | --- | --- | --- | --- | --- |
| Ala | Tyr | Leu | Asp | Leu | Val | Leu | Ser | Asp | Glu | Val | Arg | Val | His | Tyr | Asp |     |
|     |     | 115 |     |     |     |     | 120 |     |     |     |     | 125 |     |     |     |     |

| gtg | ctg | cag | tcg | gag | gag | ggc | ggg | cgg | ttc | cac | cac | gcg | gtg | acc | cgg | 432 |
| --- | --- | --- | --- | --- | --- | --- | --- | --- | --- | --- | --- | --- | --- | --- | --- | --- |
| Val | Leu | Gln | Ser | Glu | Glu | Gly | Gly | Arg | Phe | His | His | Ala | Val | Thr | Arg |     |
| 130 |     |     |     |     | 135 |     |     |     |     | 140 |     |     |     |     |     |     |

| cac | atg | gtg | gtg | gag | gtg | ggc | ccg | gac | ttc | ccc | acc | gcg | aca | ccg | ccg | 480 |
| --- | --- | --- | --- | --- | --- | --- | --- | --- | --- | --- | --- | --- | --- | --- | --- | --- |
| His | Met | Val | Val | Glu | Val | Gly | Pro | Asp | Phe | Pro | Thr | Ala | Thr | Pro | Pro |     |
| 145 |     |     |     | 150 |     |     |     |     | 155 |     |     |     |     | 160 |     |     |

| gac | tac | acc | tgg | ctg | acc | ctg | cgc | cag | ttg | acc | gcc | gtg | gcg | gcc | ttc | 528 |
| --- | --- | --- | --- | --- | --- | --- | --- | --- | --- | --- | --- | --- | --- | --- | --- | --- |
| Asp | Tyr | Thr | Trp | Leu | Thr | Leu | Arg | Gln | Leu | Thr | Ala | Val | Ala | Ala | Phe |     |
|     |     |     | 165 |     |     |     |     | 170 |     |     |     |     | 175 |     |     |     |

| agc | tat | cag | gtc | aac | atc | gag | gcg | cgc | agc | ctc | ctg | tgc | ctg | cgg | 576 |
| --- | --- | --- | --- | --- | --- | --- | --- | --- | --- | --- | --- | --- | --- | --- | --- |
| Ser | Tyr | Gln | Val | Asn | Ile | Glu | Ala | Arg | Ser | Leu | Leu | Cys | Leu | Arg |     |
|     |     | 180 |     |     |     |     | 185 |     |     |     |     | 190 |     |     |     |

| gcg | ctg | cgg | tga | 588 |
| --- | --- | --- | --- | --- |
| Ala | Leu | Arg | *   |     |
|     | 195 |     |     |     |

<210> SEQ ID NO 46
<211> LENGTH: 195
<212> TYPE: PRT
<213> ORGANISM: Bacteria

<400> SEQUENCE: 46

```
Arg Pro His Pro Trp Arg Pro Gly Arg Ser Arg Cys Ala Arg Cys Ala
  1               5                  10                  15

Thr Gly Thr Ala Pro Thr Thr Arg Ser Ala Thr Ala Pro Ala Gly Ser
             20                  25                  30

Ser Ala Ser Ser Ala Gly Gly Cys Gly Pro Ala Thr Ala Arg Cys Pro
         35                  40                  45

Ser Gly Ala Ser Arg Cys Trp His Arg Ala Gly Arg Val Trp Trp Arg
     50                  55                  60

Ser Ser Ser Asp Ala Ser Thr Ala Cys Cys Thr Cys Ser Pro Thr Pro
 65              70                  75                  80

Thr Cys Gly Pro Ala Thr Gly Thr Pro Ser Ser Trp Asp Arg Pro Cys
                 85                  90                  95

Ser Ala Pro Arg Asp Asn Phe Thr Gly Pro Ala Arg Asp Gly Arg Pro
             100                 105                 110

Ala Tyr Leu Asp Leu Val Leu Ser Asp Glu Val Arg Val His Tyr Asp
         115                 120                 125

Val Leu Gln Ser Glu Glu Gly Gly Arg Phe His His Ala Val Thr Arg
     130                 135                 140

His Met Val Val Glu Val Gly Pro Asp Phe Pro Thr Ala Thr Pro Pro
145                 150                 155                 160

Asp Tyr Thr Trp Leu Thr Leu Arg Gln Leu Thr Ala Val Ala Ala Phe
                 165                 170                 175

Ser Tyr Gln Val Asn Ile Glu Ala Arg Ser Leu Leu Leu Cys Leu Arg
             180                 185                 190

Ala Leu Arg
        195

<210> SEQ ID NO 47
<211> LENGTH: 591
<212> TYPE: DNA
<213> ORGANISM: Bacteria
<220> FEATURE:
<221> NAME/KEY: CDS
<222> LOCATION: (1)...(591)

<400> SEQUENCE: 47 atg acc cgg gac gat ccc gcc gac aac ccg tac cag gtg gcc gtc atc      48
Met Thr Arg Asp Asp Pro Ala Asp Asn Pro Tyr Gln Val Ala Val Ile
 1               5                  10                  15 ggc atc ggt tgc cgg ctg ccc agc gac gtc gac acc ccg gac gcc ctc      96
Gly Ile Gly Cys Arg Leu Pro Ser Asp Val Asp Thr Pro Asp Ala Leu
             20                  25                  30 tgg gag ctg cta ctc aag ggc ggc cag acc gcc ggc gag atc ccg gcg     144
Trp Glu Leu Leu Leu Lys Gly Gly Gln Thr Ala Gly Glu Ile Pro Ala
         35                  40                  45 cag cgc tgg cgc gcc tac cgg gag cgc ggc ccc gag tac gag gcg gtc     192
Gln Arg Trp Arg Ala Tyr Arg Glu Arg Gly Pro Glu Tyr Glu Ala Val
     50                  55                  60 ctg cgc gac acc gtc acc gcc ggc agc tac ctg cgt gac gtc gcg ggc     240
Leu Arg Asp Thr Val Thr Ala Gly Ser Tyr Leu Arg Asp Val Ala Gly
 65                  70                  75                  80 ttc gac ccc gag ttc ttc ggc ctg tcg ccc cgg gag gcg gcc gag atg     288
Phe Asp Pro Glu Phe Phe Gly Leu Ser Pro Arg Glu Ala Ala Glu Met
                 85                  90                  95 gac ccg cag cag cgg atc ctg ctc gag gtc ggc tgg gag gcc ctg gag     336
Asp Pro Gln Gln Arg Ile Leu Leu Glu Val Gly Trp Glu Ala Leu Glu
             100                 105                 110 cac gcc ggc ctg cca ccc acc cgg ctg gcc ggc acc gac acg ggc gtc     384
```

```
His Ala Gly Leu Pro Pro Thr Arg Leu Ala Gly Thr Asp Thr Gly Val
        115                 120                 125 ttc gtc ggg gac agc acc acc gac tac ggc gac cgg ctg ctg gag gac       432
Phe Val Gly Asp Ser Thr Thr Asp Tyr Gly Asp Arg Leu Leu Glu Asp
130                 135                 140 ctg ccg acc gtc gag gcg tac acc ggg atc ggc gcg gcc acc tgc gcc       480
Leu Pro Thr Val Glu Ala Tyr Thr Gly Ile Gly Ala Ala Thr Cys Ala
145                 150                 155                 160 ctg gcc aac cgc atc tcc tac gcg ctg gac ctg cac ggc ccg agc gtc       528
Leu Ala Asn Arg Ile Ser Tyr Ala Leu Asp Leu His Gly Pro Ser Val
                165                 170                 175 gcc gag gac acg gtc tgc tcg gcg tcg ctg gtc gcg gtg cac ctg gcc       576
Ala Glu Asp Thr Val Cys Ser Ala Ser Leu Val Ala Val His Leu Ala
            180                 185                 190 tgc cag agc ctg ctg                                                   591
Cys Gln Ser Leu Leu
        195

<210> SEQ ID NO 48
<211> LENGTH: 197
<212> TYPE: PRT
<213> ORGANISM: Bacteria

<400> SEQUENCE: 48

Met Thr Arg Asp Asp Pro Ala Asp Asn Pro Tyr Gln Val Ala Val Ile
1               5                   10                  15

Gly Ile Gly Cys Arg Leu Pro Ser Asp Val Asp Thr Pro Asp Ala Leu
            20                  25                  30

Trp Glu Leu Leu Leu Lys Gly Gly Gln Thr Ala Gly Glu Ile Pro Ala
        35                  40                  45

Gln Arg Trp Arg Ala Tyr Arg Glu Arg Gly Pro Glu Tyr Glu Ala Val
    50                  55                  60

Leu Arg Asp Thr Val Thr Ala Gly Ser Tyr Leu Arg Asp Val Ala Gly
65                  70                  75                  80

Phe Asp Pro Glu Phe Phe Gly Leu Ser Pro Arg Glu Ala Ala Glu Met
                85                  90                  95

Asp Pro Gln Gln Arg Ile Leu Leu Glu Val Gly Trp Glu Ala Leu Glu
            100                 105                 110

His Ala Gly Leu Pro Pro Thr Arg Leu Ala Gly Thr Asp Thr Gly Val
        115                 120                 125

Phe Val Gly Asp Ser Thr Thr Asp Tyr Gly Asp Arg Leu Leu Glu Asp
130                 135                 140

Leu Pro Thr Val Glu Ala Tyr Thr Gly Ile Gly Ala Ala Thr Cys Ala
145                 150                 155                 160

Leu Ala Asn Arg Ile Ser Tyr Ala Leu Asp Leu His Gly Pro Ser Val
                165                 170                 175

Ala Glu Asp Thr Val Cys Ser Ala Ser Leu Val Ala Val His Leu Ala
            180                 185                 190

Cys Gln Ser Leu Leu
        195

<210> SEQ ID NO 49
<211> LENGTH: 618
<212> TYPE: DNA
<213> ORGANISM: Bacteria
<220> FEATURE:
<221> NAME/KEY: CDS
<222> LOCATION: (1)...(618)
```

```
<400> SEQUENCE: 49 atc ccc gag gag gcc ggg cag ctc agc atc gcg ggg gtg gcc gag ttg      48
Ile Pro Glu Glu Ala Gly Gln Leu Ser Ile Ala Gly Val Ala Glu Leu
1               5                   10                  15 gtg gcc cgc cgc gcc gac ccg ccc gga cac acc gag aac agc gtg ctc      96
Val Ala Arg Arg Ala Asp Pro Pro Gly His Thr Glu Asn Ser Val Leu
                20                  25                  30 atc gcc gcg ccg ctg ccg ctg gtc tgg gac gtc acc aac gac gtg gcc     144
Ile Ala Ala Pro Leu Pro Leu Val Trp Asp Val Thr Asn Asp Val Ala
            35                  40                  45 ggc tgg ccc gag ctg ttc acc gag tac gcc cgg gcg gag atc ctg gac     192
Gly Trp Pro Glu Leu Phe Thr Glu Tyr Ala Arg Ala Glu Ile Leu Asp
        50                  55                  60 ggc gac ggc gac acc gtg cgg ttc cgg ctc acc atg cac ccc gac gag     240
Gly Asp Gly Asp Thr Val Arg Phe Arg Leu Thr Met His Pro Asp Glu
65                  70                  75                  80 aac ggg gtg gcg tgg agc tgg gtc agc gaa cgc acg gcc gac ccg gcc     288
Asn Gly Val Ala Trp Ser Trp Val Ser Glu Arg Thr Ala Asp Pro Ala
                85                  90                  95 acc cgg cag gtg cgc gcc cgg cgg gtg gag acc ggg ccg ttc gag tac     336
Thr Arg Gln Val Arg Ala Arg Arg Val Glu Thr Gly Pro Phe Glu Tyr
                100                 105                 110 atg cgc atc cac tgg cgc tac gcg gag gag ccc ggc ggc acg cgg atg     384
Met Arg Ile His Trp Arg Tyr Ala Glu Glu Pro Gly Gly Thr Arg Met
            115                 120                 125 acg tgg gtg cag gac ttc gcg atg aag ccg acc gcg ccg gtg gac aac     432
Thr Trp Val Gln Asp Phe Ala Met Lys Pro Thr Ala Pro Val Asp Asn
        130                 135                 140 gcc ggc atg acc gac cgg atc aac gcc aac agc gcc gtg cag ctc gcc     480
Ala Gly Met Thr Asp Arg Ile Asn Ala Asn Ser Ala Val Gln Leu Ala
145                 150                 155                 160 gtc atc cgg gac aag atc gaa cgc ctg gcc cgc gag gga acg gct ggc     528
Val Ile Arg Asp Lys Ile Glu Arg Leu Ala Arg Glu Gly Thr Ala Gly
                165                 170                 175 ccg gcc ccc gcc gcc gcg gcc gcc acc acg ccc ggc ccg gcc ccg gcc     576
Pro Ala Pro Ala Ala Ala Ala Ala Thr Thr Pro Gly Pro Ala Pro Ala
                180                 185                 190 gcg cgc acc gcc gac gag gcg acg gga gcc ggc gat gag tga             618
Ala Arg Thr Ala Asp Glu Ala Thr Gly Ala Gly Asp Glu *
            195                 200                 205

<210> SEQ ID NO 50
<211> LENGTH: 205
<212> TYPE: PRT
<213> ORGANISM: Bacteria

<400> SEQUENCE: 50

Ile Pro Glu Glu Ala Gly Gln Leu Ser Ile Ala Gly Val Ala Glu Leu
1               5                   10                  15

Val Ala Arg Arg Ala Asp Pro Pro Gly His Thr Glu Asn Ser Val Leu
                20                  25                  30

Ile Ala Ala Pro Leu Pro Leu Val Trp Asp Val Thr Asn Asp Val Ala
            35                  40                  45

Gly Trp Pro Glu Leu Phe Thr Glu Tyr Ala Arg Ala Glu Ile Leu Asp
        50                  55                  60

Gly Asp Gly Asp Thr Val Arg Phe Arg Leu Thr Met His Pro Asp Glu
65                  70                  75                  80

Asn Gly Val Ala Trp Ser Trp Val Ser Glu Arg Thr Ala Asp Pro Ala
                85                  90                  95
```

```
Thr Arg Gln Val Arg Ala Arg Val Glu Thr Gly Pro Phe Glu Tyr
            100                 105                 110

Met Arg Ile His Trp Arg Tyr Ala Glu Glu Pro Gly Gly Thr Arg Met
        115                 120                 125

Thr Trp Val Gln Asp Phe Ala Met Lys Pro Thr Ala Pro Val Asp Asn
130                 135                 140

Ala Gly Met Thr Asp Arg Ile Asn Ala Asn Ser Ala Val Gln Leu Ala
145                 150                 155                 160

Val Ile Arg Asp Lys Ile Glu Arg Leu Ala Arg Glu Gly Thr Ala Gly
                165                 170                 175

Pro Ala Pro Ala Ala Ala Ala Thr Thr Pro Gly Pro Ala Pro Ala
            180                 185                 190

Ala Arg Thr Ala Asp Glu Ala Thr Gly Ala Gly Asp Glu
        195                 200                 205

<210> SEQ ID NO 51
<211> LENGTH: 405
<212> TYPE: DNA
<213> ORGANISM: Bacteria
<220> FEATURE:
<221> NAME/KEY: CDS
<222> LOCATION: (1)...(405)

<400> SEQUENCE: 51 atg agt gac cag acc ctg cgg ctg gtc gcc gcc gcc gtc gcg ccg          48
Met Ser Asp Gln Thr Leu Arg Leu Val Ala Ala Ala Val Ala Pro
1               5                   10                  15 gac agc cgc cgt ggc ggc gag ctg cgg gtg ctg ctc ggc ccg aag acc      96
Asp Ser Arg Arg Gly Gly Glu Leu Arg Val Leu Leu Gly Pro Lys Thr
            20                  25                  30 gtc ggc agc acg tcc ggc ttc atg ggg gtg gcg acg ctg cgc ccg ggg     144
Val Gly Ser Thr Ser Gly Phe Met Gly Val Ala Thr Leu Arg Pro Gly
        35                  40                  45 gag cgg atc gcc gag cac tac cat ccc tac agc gag gag ttc ctg tac    192
Glu Arg Ile Ala Glu His Tyr His Pro Tyr Ser Glu Glu Phe Leu Tyr
    50                  55                  60 gtc gcc cgg ggc gcg atc acc gcc gac ctg gac gac gag ccg gtg ccg    240
Val Ala Arg Gly Ala Ile Thr Ala Asp Leu Asp Asp Glu Pro Val Pro
65                  70                  75                  80 ctg gcc gcc ggg gag gcg ctg ttc gtg ccg cgc tac gtc cgg cac cgg    288
Leu Ala Ala Gly Glu Ala Leu Phe Val Pro Arg Tyr Val Arg His Arg
                85                  90                  95 ctg cgc aac acc ggc gac gag ccg gcc gag gtg gtc ttc cac ctc ggt    336
Leu Arg Asn Thr Gly Asp Glu Pro Ala Glu Val Val Phe His Leu Gly
            100                 105                 110 ccc ctc gcc ccc cgg ccc gaa ctc ggc cac gtc gac acc gag ctc gtc    384
Pro Leu Ala Pro Arg Pro Glu Leu Gly His Val Asp Thr Glu Leu Val
        115                 120                 125 gag caa cgg ggc ggg tcg tga                                         405
Glu Gln Arg Gly Gly Ser *
    130

<210> SEQ ID NO 52
<211> LENGTH: 134
<212> TYPE: PRT
<213> ORGANISM: Bacteria

<400> SEQUENCE: 52

Met Ser Asp Gln Thr Leu Arg Leu Val Ala Ala Ala Val Ala Pro
1               5                   10                  15
```

```
Asp Ser Arg Arg Gly Gly Glu Leu Arg Val Leu Leu Gly Pro Lys Thr
            20                  25                  30

Val Gly Ser Thr Ser Gly Phe Met Gly Val Ala Thr Leu Arg Pro Gly
        35                  40                  45

Glu Arg Ile Ala Glu His Tyr His Pro Tyr Ser Glu Phe Leu Tyr
    50                  55                  60

Val Ala Arg Gly Ala Ile Thr Ala Asp Leu Asp Asp Glu Pro Val Pro
 65                  70                  75                  80

Leu Ala Ala Gly Glu Ala Leu Phe Val Pro Arg Tyr Val Arg His Arg
                85                  90                  95

Leu Arg Asn Thr Gly Asp Glu Pro Ala Glu Val Val Phe His Leu Gly
            100                 105                 110

Pro Leu Ala Pro Arg Pro Glu Leu Gly His Val Asp Thr Glu Leu Val
        115                 120                 125

Glu Gln Arg Gly Gly Ser
        130

<210> SEQ ID NO 53
<211> LENGTH: 1137
<212> TYPE: DNA
<213> ORGANISM: Bacteria
<220> FEATURE:
<221> NAME/KEY: CDS
<222> LOCATION: (1)...(1137)

<400> SEQUENCE: 53 gtg acc ggg cgc cgc acg gtg gtg acc ggc gtc ggg gtg gtc gcc ccc      48
Val Thr Gly Arg Arg Thr Val Val Thr Gly Val Gly Val Val Ala Pro
 1               5                  10                  15 ggc ggc gcc agc cgg gac cgg ttc tgg aag gcc atc acc gag ggg cgc      96
Gly Gly Ala Ser Arg Asp Arg Phe Trp Lys Ala Ile Thr Glu Gly Arg
             20                  25                  30 acc gcg acc cgc cgg atc acc ttc ttc gac ccg tcc gcg ttc cgg tcg     144
Thr Ala Thr Arg Arg Ile Thr Phe Phe Asp Pro Ser Ala Phe Arg Ser
         35                  40                  45 cag atc gcc gcc gag tgc gac ttc gac ccg gtc gcc gcc ggc ctc tcc     192
Gln Ile Ala Ala Glu Cys Asp Phe Asp Pro Val Ala Ala Gly Leu Ser
     50                  55                  60 gag gcc gag cgg cgg cgc gcc gac cgg tac gtg cag ttc gcg ctc gcc     240
Glu Ala Glu Arg Arg Arg Ala Asp Arg Tyr Val Gln Phe Ala Leu Ala
 65                  70                  75                  80 tgc tcc gcc gag gcg gtc gcc gac gcc ggg ctg gag ctc acc gac gcc     288
Cys Ser Ala Glu Ala Val Ala Asp Ala Gly Leu Glu Leu Thr Asp Ala
                 85                  90                  95 gag cgg gac cgc gcc ggg gtg gtg ctc ggc acc gcc gtc ggc ggc acc     336
Glu Arg Asp Arg Ala Gly Val Val Leu Gly Thr Ala Val Gly Gly Thr
            100                 105                 110 atg gcc ctg gag cag gag tac gtc acg gtc agc gac acc ggc cgc cgg     384
Met Ala Leu Glu Gln Glu Tyr Val Thr Val Ser Asp Thr Gly Arg Arg
        115                 120                 125 tgg ctg gtc gac gcc gcg cgc ggc ggc ccg tac ctc tac cag gcg ctg     432
Trp Leu Val Asp Ala Ala Arg Gly Gly Pro Tyr Leu Tyr Gln Ala Leu
    130                 135                 140 gtg ccg agc agc ctg gcc gcc gac gtg gcc tgc cgg cac ggg ctg cac     480
Val Pro Ser Ser Leu Ala Ala Asp Val Ala Cys Arg His Gly Leu His
145                 150                 155                 160 ggc ccc gcg cag gtg gtc tcc acc ggc tgc acc tcg ggc atc gac gcc     528
Gly Pro Ala Gln Val Val Ser Thr Gly Cys Thr Ser Gly Ile Asp Ala
                165                 170                 175
```

-continued

```
atc ggg tac gcc cac cag ctc atc gcc gac ggc gag gcc gac atc gtg      576
Ile Gly Tyr Ala His Gln Leu Ile Ala Asp Gly Glu Ala Asp Ile Val
            180                 185                 190 ctg gcc ggg gcg gcg gac tcg cct atc tcc ccg gtg acc gtc gcg tcc      624
Leu Ala Gly Ala Ala Asp Ser Pro Ile Ser Pro Val Thr Val Ala Ser
        195                 200                 205 ttc gac gcg atc aag gcg acc agt ccc gac aac gac gat ccg gcg cac      672
Phe Asp Ala Ile Lys Ala Thr Ser Pro Asp Asn Asp Asp Pro Ala His
    210                 215                 220 gcc tcc cgc ccg ttc gac gcc gac cgg cac ggc ttc gtc ctc gcc gag      720
Ala Ser Arg Pro Phe Asp Ala Asp Arg His Gly Phe Val Leu Ala Glu
225                 230                 235                 240 ggc gcg gcg gtg ctg gtg ctg gag gag gcc ggg cac gcc cgg cgg cgc      768
Gly Ala Ala Val Leu Val Leu Glu Glu Ala Gly His Ala Arg Arg Arg
                245                 250                 255 ggc gcc cac gtc tac tgc gag gtc gcc ggc tac gcc agc cgc agc aac      816
Gly Ala His Val Tyr Cys Glu Val Ala Gly Tyr Ala Ser Arg Ser Asn
            260                 265                 270 ggc tac cac atg acg ggg ctg cgg ccc gac ggg ctg gag atg ggg ctg      864
Gly Tyr His Met Thr Gly Leu Arg Pro Asp Gly Leu Glu Met Gly Leu
        275                 280                 285 gcc atc tcg gcc gcg ctc aag cag ggc cgg atc gcc ccc gag cag gtc      912
Ala Ile Ser Ala Ala Leu Lys Gln Gly Arg Ile Ala Pro Glu Gln Val
    290                 295                 300 tcc tac atc agc gcg cac ggt tcc ggc acc cgg cag aac gac cgg cac      960
Ser Tyr Ile Ser Ala His Gly Ser Gly Thr Arg Gln Asn Asp Arg His
305                 310                 315                 320 gag acc gcc gcg ttc aag cgg gcc ctc ggg cag gcc gcg tac cgg gtg     1008
Glu Thr Ala Ala Phe Lys Arg Ala Leu Gly Gln Ala Ala Tyr Arg Val
                325                 330                 335 ccg atc agc tcg atc aag tcg atg gtc ggg cac tcg ctc ggc gcg atc     1056
Pro Ile Ser Ser Ile Lys Ser Met Val Gly His Ser Leu Gly Ala Ile
            340                 345                 350 ggc tcg atc gag atg gcc gcc tgc gcc ctg gcc gtc gag ttc ggc gtg     1104
Gly Ser Ile Glu Met Ala Ala Cys Ala Leu Ala Val Glu Phe Gly Val
        355                 360                 365 gtg ccg ccg acg gcc aac tgg acc acc cgg gat                         1137
Val Pro Pro Thr Ala Asn Trp Thr Thr Arg Asp
    370                 375
```

<210> SEQ ID NO 54
<211> LENGTH: 379
<212> TYPE: PRT
<213> ORGANISM: Bacteria

<400> SEQUENCE: 54

```
Val Thr Gly Arg Arg Thr Val Thr Gly Val Gly Val Val Ala Pro
 1               5                  10                  15

Gly Gly Ala Ser Arg Asp Arg Phe Trp Lys Ala Ile Thr Glu Gly Arg
                20                  25                  30

Thr Ala Thr Arg Arg Ile Thr Phe Phe Asp Pro Ser Ala Phe Arg Ser
            35                  40                  45

Gln Ile Ala Ala Glu Cys Asp Phe Asp Pro Val Ala Ala Gly Leu Ser
    50                  55                  60

Glu Ala Glu Arg Arg Arg Ala Asp Arg Tyr Val Gln Phe Ala Leu Ala
65                  70                  75                  80

Cys Ser Ala Glu Ala Val Ala Asp Ala Gly Leu Glu Leu Thr Asp Ala
                85                  90                  95
```

```
Glu Arg Asp Arg Ala Gly Val Val Leu Gly Thr Ala Val Gly Gly Thr
            100                 105                 110

Met Ala Leu Glu Gln Glu Tyr Val Thr Val Ser Asp Thr Gly Arg Arg
        115                 120                 125

Trp Leu Val Asp Ala Ala Arg Gly Gly Pro Tyr Leu Tyr Gln Ala Leu
        130                 135                 140

Val Pro Ser Ser Leu Ala Ala Asp Val Ala Cys Arg His Gly Leu His
145                 150                 155                 160

Gly Pro Ala Gln Val Val Ser Thr Gly Cys Thr Ser Gly Ile Asp Ala
                165                 170                 175

Ile Gly Tyr Ala His Gln Leu Ile Ala Asp Gly Glu Ala Asp Ile Val
            180                 185                 190

Leu Ala Gly Ala Ala Asp Ser Pro Ile Ser Pro Val Thr Val Ala Ser
        195                 200                 205

Phe Asp Ala Ile Lys Ala Thr Ser Pro Asp Asn Asp Pro Ala His
210                 215                 220

Ala Ser Arg Pro Phe Asp Ala Asp Arg His Gly Phe Val Leu Ala Glu
225                 230                 235                 240

Gly Ala Ala Val Leu Val Leu Glu Glu Ala Gly His Ala Arg Arg Arg
                245                 250                 255

Gly Ala His Val Tyr Cys Glu Val Ala Gly Tyr Ala Ser Arg Ser Asn
            260                 265                 270

Gly Tyr His Met Thr Gly Leu Arg Pro Asp Gly Leu Glu Met Gly Leu
        275                 280                 285

Ala Ile Ser Ala Ala Leu Lys Gln Gly Arg Ile Ala Pro Glu Gln Val
        290                 295                 300

Ser Tyr Ile Ser Ala His Gly Ser Gly Thr Arg Gln Asn Asp Arg His
305                 310                 315                 320

Glu Thr Ala Ala Phe Lys Arg Ala Leu Gly Gln Ala Ala Tyr Arg Val
                325                 330                 335

Pro Ile Ser Ser Ile Lys Ser Met Val Gly His Ser Leu Gly Ala Ile
            340                 345                 350

Gly Ser Ile Glu Met Ala Ala Cys Ala Leu Ala Val Glu Phe Gly Val
        355                 360                 365

Val Pro Pro Thr Ala Asn Trp Thr Thr Arg Asp
        370                 375

<210> SEQ ID NO 55
<211> LENGTH: 969
<212> TYPE: DNA
<213> ORGANISM: Bacteria
<220> FEATURE:
<221> NAME/KEY: CDS
<222> LOCATION: (1)...(969)

<400> SEQUENCE: 55 atg ccc gcc aat tgg cga acc att cgt caa tac gcc ctg acg ccg ggg      48
Met Pro Ala Asn Trp Arg Thr Ile Arg Gln Tyr Ala Leu Thr Pro Gly
 1               5                  10                  15 atg gcc cag acc acc ttc gcg acc cgg ggc ttc cgc gcc cgg gac gag      96
Met Ala Gln Thr Thr Phe Ala Thr Arg Gly Phe Arg Ala Arg Asp Glu
                20                  25                  30 ccg acc cgc gag cgg ctg gag tcg gtc ggc gcc cac ttc ctc acc ggc     144
Pro Thr Arg Glu Arg Leu Glu Ser Val Gly Ala His Phe Leu Thr Gly
            35                  40                  45 tac ggg cac gcc gtc ggc gcc cgg ggc ccg gac gag gcc gtc ggg gcg     192
Tyr Gly His Ala Val Gly Ala Arg Gly Pro Asp Glu Ala Val Gly Ala
```

-continued

```
        50                  55                  60
ctg gag acc gtc gcg ccg gac ctg cgc ggg ttc gcg tac gag ggc gcg     240
Leu Glu Thr Val Ala Pro Asp Leu Arg Gly Phe Ala Tyr Glu Gly Ala
 65                  70                  75                  80 gcg atg ggc ctc gcc gtc ctg gac ggg ctg acc ggt ggc cgc cgg atc     288
Ala Met Gly Leu Ala Val Leu Asp Gly Leu Thr Gly Gly Arg Arg Ile
                 85                  90                  95 gcc cgg ttc ctg gcc ggg ccg gcc gcc cgg cac gtg tac atg gtc cat     336
Ala Arg Phe Leu Ala Gly Pro Ala Ala Arg His Val Tyr Met Val His
            100                 105                 110 gtc ggg gtg ggc tgg gcg atg gcc cgc ctg ccc cgc tgg cgt cgg cac     384
Val Gly Val Gly Trp Ala Met Ala Arg Leu Pro Arg Trp Arg Arg His
        115                 120                 125 gcg atc caa ccc gcc gac cgg ctg ctg ggc tgg ctg gcg ctg gac ggc     432
Ala Ile Gln Pro Ala Asp Arg Leu Leu Gly Trp Leu Ala Leu Asp Gly
    130                 135                 140 tac gga ttc cac cag gcg tac ttc cac acc cgg cgg tac gtg tgg tcg     480
Tyr Gly Phe His Gln Ala Tyr Phe His Thr Arg Arg Tyr Val Trp Ser
145                 150                 155                 160 cac cgg cgt gac gag gtg ctg ccc tgg ccc ggc gac ccg atc ggg cgg     528
His Arg Arg Asp Glu Val Leu Pro Trp Pro Gly Asp Pro Ile Gly Arg
                165                 170                 175 tgg acc ggg cgc gtc gtg gac cag ggc atc ggc cgc gcg ctg tgg ttc     576
Trp Thr Gly Arg Val Val Asp Gln Gly Ile Gly Arg Ala Leu Trp Phe
            180                 185                 190 gtc gag ggc gcc gac acc gac cgg atc gcc gac acc gtc gac ggc ttc     624
Val Glu Gly Ala Asp Thr Asp Arg Ile Ala Asp Thr Val Asp Gly Phe
        195                 200                 205 ccg ccg gac cgg cac gag gac ctg tac agc ggg gtg gcg ctg gcc gcc     672
Pro Pro Asp Arg His Glu Asp Leu Tyr Ser Gly Val Ala Leu Ala Ala
    210                 215                 220 acg tac gcc ggg ggg gcg ccg ccc gag gac ctg cgg cgg ctg cgc gag     720
Thr Tyr Ala Gly Gly Ala Pro Pro Glu Asp Leu Arg Arg Leu Arg Glu
225                 230                 235                 240 cgc ggc gga gcc tac gcc ccg gcg atg gcc cag ggc agc gcc ttc gcg     768
Arg Gly Gly Ala Tyr Ala Pro Ala Met Ala Gln Gly Ser Ala Phe Ala
                245                 250                 255 gcg gag gcc cgg gag cgc gcc ggg ctg acc acc gcg cac acc gcg gtc     816
Ala Glu Ala Arg Glu Arg Ala Gly Leu Thr Thr Ala His Thr Ala Val
            260                 265                 270 gcc acc gac gtc ttc tgc ggc gcg cca ccg gcc gag gcg gcg gcg gtc     864
Ala Thr Asp Val Phe Cys Gly Ala Pro Pro Ala Glu Ala Ala Ala Val
        275                 280                 285 acc cag gcc gcg ctg gcc gac ctc gac cgg gac ggg ccg gag ccg gcc     912
Thr Gln Ala Ala Leu Ala Asp Leu Asp Arg Asp Gly Pro Glu Pro Ala
    290                 295                 300 tac ctg gtg tgg cgg cag cgg atc gcc aag cag ttc gtg acg ctg ggg     960
Tyr Leu Val Trp Arg Gln Arg Ile Ala Lys Gln Phe Val Thr Leu Gly
305                 310                 315                 320 agg tgc tga                                                         969
Arg Cys *
```

<210> SEQ ID NO 56
<211> LENGTH: 322
<212> TYPE: PRT
<213> ORGANISM: Bacteria

<400> SEQUENCE: 56

```
Met Pro Ala Asn Trp Arg Thr Ile Arg Gln Tyr Ala Leu Thr Pro Gly
 1               5                  10                  15
```

```
Met Ala Gln Thr Thr Phe Ala Thr Arg Gly Phe Arg Ala Arg Asp Glu
             20                  25                  30

Pro Thr Arg Glu Arg Leu Glu Ser Val Gly Ala His Phe Leu Thr Gly
         35                  40                  45

Tyr Gly His Ala Val Gly Ala Arg Gly Pro Asp Glu Ala Val Gly Ala
     50                  55                  60

Leu Glu Thr Val Ala Pro Asp Leu Arg Gly Phe Ala Tyr Glu Gly Ala
 65                  70                  75                  80

Ala Met Gly Leu Ala Val Leu Asp Gly Leu Thr Gly Gly Arg Arg Ile
                 85                  90                  95

Ala Arg Phe Leu Ala Gly Pro Ala Ala Arg His Val Tyr Met Val His
            100                 105                 110

Val Gly Val Gly Trp Ala Met Ala Arg Leu Pro Arg Trp Arg Arg His
        115                 120                 125

Ala Ile Gln Pro Ala Asp Arg Leu Leu Gly Trp Leu Ala Leu Asp Gly
    130                 135                 140

Tyr Gly Phe His Gln Ala Tyr Phe His Thr Arg Arg Tyr Val Trp Ser
145                 150                 155                 160

His Arg Arg Asp Glu Val Leu Pro Trp Pro Gly Asp Pro Ile Gly Arg
                165                 170                 175

Trp Thr Gly Arg Val Val Asp Gln Gly Ile Gly Arg Ala Leu Trp Phe
            180                 185                 190

Val Glu Gly Ala Asp Thr Asp Arg Ile Ala Asp Thr Val Asp Gly Phe
        195                 200                 205

Pro Pro Asp Arg His Glu Asp Leu Tyr Ser Gly Val Ala Leu Ala Ala
    210                 215                 220

Thr Tyr Ala Gly Gly Ala Pro Pro Glu Asp Leu Arg Arg Leu Arg Glu
225                 230                 235                 240

Arg Gly Gly Ala Tyr Ala Pro Ala Met Ala Gln Gly Ser Ala Phe Ala
                245                 250                 255

Ala Glu Ala Arg Glu Arg Ala Gly Leu Thr Thr Ala His Thr Ala Val
            260                 265                 270

Ala Thr Asp Val Phe Cys Gly Ala Pro Pro Ala Glu Ala Ala Ala Val
        275                 280                 285

Thr Gln Ala Ala Leu Ala Asp Leu Asp Arg Asp Gly Pro Glu Pro Ala
    290                 295                 300

Tyr Leu Val Trp Arg Gln Arg Ile Ala Lys Gln Phe Val Thr Leu Gly
305                 310                 315                 320

Arg Cys

<210> SEQ ID NO 57
<211> LENGTH: 1956
<212> TYPE: DNA
<213> ORGANISM: Bacteria
<220> FEATURE:
<221> NAME/KEY: CDS
<222> LOCATION: (1)...(1956)

<400> SEQUENCE: 57 atg ttc cgc cgg cag ttg gcc ggg ctg gtc gcg ctg gtg ctg ctc acc      48
Met Phe Arg Arg Gln Leu Ala Gly Leu Val Ala Leu Val Leu Leu Thr
  1               5                  10                  15 ggc atg tac gtg ctg gtc cgg cag ccg gag gcg aac gcc gac gag cgg      96
Gly Met Tyr Val Leu Val Arg Gln Pro Glu Ala Asn Ala Asp Glu Arg
             20                  25                  30
```

-continued

| | | |
|---|---|---|
| cgc gcc atg gcg gag ccg tac cgg ttc acg ccg atg tcg ctg ccg atg<br>Arg Ala Met Ala Glu Pro Tyr Arg Phe Thr Pro Met Ser Leu Pro Met<br>            35                        40                        45 | 144 |
| ccg ggc ggc ctg ccg cag cag tcg atc cgc cgg gtc aac ggc gcg tac<br>Pro Gly Gly Leu Pro Gln Gln Ser Ile Arg Arg Val Asn Gly Ala Tyr<br>     50                        55                        60 | 192 |
| cag cac ctg gcg gcg tgg atc tcc tcc gtc ggc gcc ggc gcc gcg atg<br>Gln His Leu Ala Ala Trp Ile Ser Ser Val Gly Ala Gly Ala Ala Met<br>65                       70                        75                        80 | 240 |
| aac gac ctg gac ggt gac gga ctg gcc aac gac ctg tgc gtc acc gac<br>Asn Asp Leu Asp Gly Asp Gly Leu Ala Asn Asp Leu Cys Val Thr Asp<br>                85                        90                        95 | 288 |
| cca cgc gtc gac cgc gtc gtg gtg acc ccg gcc ccg acc gcc ggc gcc<br>Pro Arg Val Asp Arg Val Val Val Thr Pro Ala Pro Thr Ala Gly Ala<br>          100                        105                      110 | 336 |
| gac cgc tac cag ccg ttc gtg ctg gac ccg gcg ccg ctg ccg atg aac<br>Asp Arg Tyr Gln Pro Phe Val Leu Asp Pro Ala Pro Leu Pro Met Asn<br>               115                        120                      125 | 384 |
| ccg tac gtc gcc ccg atg ggc tgc ctg ccc ggc gac ctc aac gcc gac<br>Pro Tyr Val Ala Pro Met Gly Cys Leu Pro Gly Asp Leu Asn Ala Asp<br>         130                        135                      140 | 432 |
| ggc cgc acc gac ctg ctc gtg tac tgg tgg ggc cgg acc ccg gtc gtc<br>Gly Arg Thr Asp Leu Leu Val Tyr Trp Trp Gly Arg Thr Pro Val Val<br>145                       150                        155                      160 | 480 |
| ttc ctg gcc cgg gcg gac gcg acc ggg ctg tcc cgg gcc gcc tac cac<br>Phe Leu Ala Arg Ala Asp Ala Thr Gly Leu Ser Arg Ala Ala Tyr His<br>               165                        170                      175 | 528 |
| ccc gtc gag ctg gtg ccg ggc gcg gcg acc ggc ggt agc cgg tac gac<br>Pro Val Glu Leu Val Pro Gly Ala Ala Thr Gly Gly Ser Arg Tyr Asp<br>         180                        185                      190 | 576 |
| ggg ccg aag tgg aac acc aac gcc gcg acg ctg gcc gac ttc gac ggc<br>Gly Pro Lys Trp Asn Thr Asn Ala Ala Thr Leu Ala Asp Phe Asp Gly<br>               195                        200                      205 | 624 |
| gac ggg cac ctg gac gtc tac atc ggc aac tac ttc ccc gac agc gcc<br>Asp Gly His Leu Asp Val Tyr Ile Gly Asn Tyr Phe Pro Asp Ser Ala<br>         210                        215                      220 | 672 |
| gtc ctc gac gac acc gtc cac ggc ggg gtg gcg atg aac cgg tcc atg<br>Val Leu Asp Asp Thr Val His Gly Gly Val Ala Met Asn Arg Ser Met<br>225                       230                        235                      240 | 720 |
| tcc aac ggc ctc aac ggc ggc gag gac cac gtg ttc cgg tgg acc ggc<br>Ser Asn Gly Leu Asn Gly Gly Glu Asp His Val Phe Arg Trp Thr Gly<br>               245                        250                      255 | 768 |
| ggc acc gcc ggc gcc acg ccg agc gcc tcc ttc gcc gag gtc ccg gac<br>Gly Thr Ala Gly Ala Thr Pro Ser Ala Ser Phe Ala Glu Val Pro Asp<br>         260                        265                      270 | 816 |
| gtc ttc gac acc aag gtc tcc cgg ggc tgg acg ctc gcc gtc gcc gcg<br>Val Phe Asp Thr Lys Val Ser Arg Gly Trp Thr Leu Ala Val Ala Ala<br>               275                        280                      285 | 864 |
| aac gac ctc gac ggc gac caa ctg ccc gag ctg tac gtg gcc aac gac<br>Asn Asp Leu Asp Gly Asp Gln Leu Pro Glu Leu Tyr Val Ala Asn Asp<br>290                       295                        300 | 912 |
| ttc ggg ccg gac cgg ctg ctg cac aac cgg tcg gag cgg ggg cgg atc<br>Phe Gly Pro Asp Arg Leu Leu His Asn Arg Ser Glu Arg Gly Arg Ile<br>305                     310                        315                      320 | 960 |
| gcc ttc gcg ccg gtc gag agc ccc ggg ctg ccc ggc ctg acc ccc aag<br>Ala Phe Ala Pro Val Glu Ser Pro Gly Leu Pro Gly Leu Thr Pro Lys<br>               325                        330                      335 | 1008 |
| tca aag cgg ctc ggc cac gac tcg ttc aag ggc atg ggc gtg gac ttc<br>Ser Lys Arg Leu Gly His Asp Ser Phe Lys Gly Met Gly Val Asp Phe<br>         340                        345                      350 | 1056 |

```
ggc gac atc gac ggc gac ggc atg ttc gac ctg tac gtc ggc aac atc      1104
Gly Asp Ile Asp Gly Asp Gly Met Phe Asp Leu Tyr Val Gly Asn Ile
            355                 360                 365 acc acc tcc ttc ggc atc cag gag agc aac ttc gcc ttc gtc aac acc      1152
Thr Thr Ser Phe Gly Ile Gln Glu Ser Asn Phe Ala Phe Val Asn Thr
    370                 375                 380 gcc gcc gac acc gcc gcg ctg cgc gcc gcg ctg tgg gcc ggc gag gcg      1200
Ala Ala Asp Thr Ala Ala Leu Arg Ala Ala Leu Trp Ala Gly Glu Ala
385                 390                 395                 400 ccg tgg cac gac cgc agc gcc gag ctg ggc ctg gcc tgg agc ggg tgg      1248
Pro Trp His Asp Arg Ser Ala Glu Leu Gly Leu Ala Trp Ser Gly Trp
                405                 410                 415 agc tgg gac gtc aag ttc ggc gac ttc acc aac cgc ggc gac ccg gcg      1296
Ser Trp Asp Val Lys Phe Gly Asp Phe Thr Asn Arg Gly Asp Pro Ala
            420                 425                 430 atc gtg cag acc tcc ggc ttc gtc aag ggc gag gtc aac cgc tgg gcg      1344
Ile Val Gln Thr Ser Gly Phe Val Lys Gly Glu Val Asn Arg Trp Ala
    435                 440                 445 cag ttg cag gag gcg gcc acc gcc aac gac gac ctg ctc gcc aac ccc      1392
Gln Leu Gln Glu Ala Ala Thr Ala Asn Asp Asp Leu Leu Ala Asn Pro
450                 455                 460 cgc tgg tgg ccg aag gtc gag cag ggc gac gac atc gcc ggc ggc cag      1440
Arg Trp Trp Pro Lys Val Glu Gln Gly Asp Asp Ile Ala Gly Gly Gln
465                 470                 475                 480 cac ctc gcc ttc cac gtc cgg ggc gcc gac ggc cgc tac gag gac ctc      1488
His Leu Ala Phe His Val Arg Gly Ala Asp Gly Arg Tyr Glu Asp Leu
                485                 490                 495 agc cac gaa ctg ggc ctg gcc gac cgg gtg ccc agc cgg ggc atc gcc      1536
Ser His Glu Leu Gly Leu Ala Asp Arg Val Pro Ser Arg Gly Ile Ala
            500                 505                 510 acc gcc gac gcc gac ggc gac ggg cgc ctc gac ctc gtc gtc gcc cgg      1584
Thr Ala Asp Ala Asp Gly Asp Gly Arg Leu Asp Leu Val Val Ala Arg
    515                 520                 525 cag tgg gac gcg ccg gtc ttc tac cgc aac gac agc ccg gac acc ggt      1632
Gln Trp Asp Ala Pro Val Phe Tyr Arg Asn Asp Ser Pro Asp Thr Gly
530                 535                 540 tcc ttc ctc acc ctg cgg ctg ctg cac gag cag gcg ccg gcc gcc ggc      1680
Ser Phe Leu Thr Leu Arg Leu Leu His Glu Gln Ala Pro Ala Ala Gly
545                 550                 555                 560 ccc ctc gcc ggg gcg ggg tcg ccg gtc gtc ggc gcg cag gtc cgg gtg      1728
Pro Leu Ala Gly Ala Gly Ser Pro Val Val Gly Ala Gln Val Arg Val
                565                 570                 575 acc acg ccg gac ggc cgg gtg ctc atc gac cgg gtc gac ggc ggc agc      1776
Thr Thr Pro Asp Gly Arg Val Leu Ile Asp Arg Val Asp Gly Gly Ser
            580                 585                 590 ggc cac tcg ggc cgg cgc agc aac gag gtg tcg ctc ggt ctc gac gac      1824
Gly His Ser Gly Arg Arg Ser Asn Glu Val Ser Leu Gly Leu Asp Asp
    595                 600                 605 gtg acc ggc ccg gtg tcg gtc cac ctc acc tgg cgg gac cgg tcc ggc      1872
Val Thr Gly Pro Val Ser Val His Leu Thr Trp Arg Asp Arg Ser Gly
610                 615                 620 gcc ccg cac gag cag gag ctg acg ctg gcc ccc ggt cga cac acc ctc      1920
Ala Pro His Glu Gln Glu Leu Thr Leu Ala Pro Gly Arg His Thr Leu
625                 630                 635                 640 acc ctc ggt tcg cag gct cgg gag gtc tcg cga tga                      1956
Thr Leu Gly Ser Gln Ala Arg Glu Val Ser Arg *
                645                 650
```

<210> SEQ ID NO 58

```
<211> LENGTH: 651
<212> TYPE: PRT
<213> ORGANISM: Bacteria

<400> SEQUENCE: 58
```

| | | | | | | | | | | | | | | |
|---|---|---|---|---|---|---|---|---|---|---|---|---|---|---|
|Met|Phe|Arg|Arg|Gln|Leu|Ala|Gly|Leu|Val|Ala|Leu|Val|Leu|Leu|Thr|
|1| | | |5| | | | |10| | | | |15| |

Gly Met Tyr Val Leu Val Arg Gln Pro Glu Ala Asn Ala Asp Glu Arg
            20                  25                  30

Arg Ala Met Ala Glu Pro Tyr Arg Phe Thr Pro Met Ser Leu Pro Met
        35                  40                  45

Pro Gly Gly Leu Pro Gln Gln Ser Ile Arg Arg Val Asn Gly Ala Tyr
    50                  55                  60

Gln His Leu Ala Ala Trp Ile Ser Ser Val Gly Ala Gly Ala Ala Met
65                  70                  75                  80

Asn Asp Leu Asp Gly Asp Gly Leu Ala Asn Asp Leu Cys Val Thr Asp
                85                  90                  95

Pro Arg Val Asp Arg Val Val Val Thr Pro Ala Pro Thr Ala Gly Ala
            100                 105                 110

Asp Arg Tyr Gln Pro Phe Val Leu Asp Pro Ala Pro Leu Pro Met Asn
        115                 120                 125

Pro Tyr Val Ala Pro Met Gly Cys Leu Pro Gly Asp Leu Asn Ala Asp
    130                 135                 140

Gly Arg Thr Asp Leu Leu Val Tyr Trp Trp Gly Arg Thr Pro Val Val
145                 150                 155                 160

Phe Leu Ala Arg Ala Asp Ala Thr Gly Leu Ser Arg Ala Ala Tyr His
                165                 170                 175

Pro Val Glu Leu Val Pro Gly Ala Ala Thr Gly Gly Ser Arg Tyr Asp
            180                 185                 190

Gly Pro Lys Trp Asn Thr Asn Ala Ala Thr Leu Ala Asp Phe Asp Gly
        195                 200                 205

Asp Gly His Leu Asp Val Tyr Ile Gly Asn Tyr Phe Pro Asp Ser Ala
    210                 215                 220

Val Leu Asp Asp Thr Val His Gly Gly Val Ala Met Asn Arg Ser Met
225                 230                 235                 240

Ser Asn Gly Leu Asn Gly Gly Glu Asp His Val Phe Arg Trp Thr Gly
                245                 250                 255

Gly Thr Ala Gly Ala Thr Pro Ser Ala Ser Phe Ala Glu Val Pro Asp
            260                 265                 270

Val Phe Asp Thr Lys Val Ser Arg Gly Trp Thr Leu Ala Val Ala Ala
        275                 280                 285

Asn Asp Leu Asp Gly Asp Gln Leu Pro Glu Leu Tyr Val Ala Asn Asp
    290                 295                 300

Phe Gly Pro Asp Arg Leu Leu His Asn Arg Ser Glu Arg Gly Arg Ile
305                 310                 315                 320

Ala Phe Ala Pro Val Glu Ser Pro Gly Leu Pro Gly Leu Thr Pro Lys
                325                 330                 335

Ser Lys Arg Leu Gly His Asp Ser Phe Lys Gly Met Gly Val Asp Phe
            340                 345                 350

Gly Asp Ile Asp Gly Asp Gly Met Phe Asp Leu Tyr Val Gly Asn Ile
        355                 360                 365

Thr Thr Ser Phe Gly Ile Gln Glu Ser Asn Phe Ala Phe Val Asn Thr
    370                 375                 380

Ala Ala Asp Thr Ala Ala Leu Arg Ala Ala Leu Trp Ala Gly Glu Ala

```
                    385                 390                 395                 400
Pro Trp His Asp Arg Ser Ala Glu Leu Gly Leu Ala Trp Ser Gly Trp
                405                 410                 415

Ser Trp Asp Val Lys Phe Gly Asp Phe Thr Asn Arg Gly Asp Pro Ala
                420                 425                 430

Ile Val Gln Thr Ser Gly Phe Val Lys Gly Glu Val Asn Arg Trp Ala
                435                 440                 445

Gln Leu Gln Glu Ala Ala Thr Ala Asn Asp Asp Leu Leu Ala Asn Pro
        450                 455                 460

Arg Trp Trp Pro Lys Val Glu Gln Gly Asp Asp Ile Ala Gly Gly Gln
465                 470                 475                 480

His Leu Ala Phe His Val Arg Gly Ala Asp Gly Arg Tyr Glu Asp Leu
                485                 490                 495

Ser His Glu Leu Gly Leu Ala Asp Arg Val Pro Ser Arg Gly Ile Ala
                500                 505                 510

Thr Ala Asp Ala Asp Gly Asp Gly Arg Leu Asp Leu Val Val Ala Arg
                515                 520                 525

Gln Trp Asp Ala Pro Val Phe Tyr Arg Asn Asp Ser Pro Asp Thr Gly
        530                 535                 540

Ser Phe Leu Thr Leu Arg Leu Leu His Glu Gln Ala Pro Ala Ala Gly
545                 550                 555                 560

Pro Leu Ala Gly Ala Gly Ser Pro Val Val Gly Ala Gln Val Arg Val
                565                 570                 575

Thr Thr Pro Asp Gly Arg Val Leu Ile Asp Arg Val Asp Gly Gly Ser
                580                 585                 590

Gly His Ser Gly Arg Arg Ser Asn Glu Val Ser Leu Gly Leu Asp Asp
                595                 600                 605

Val Thr Gly Pro Val Ser Val His Leu Thr Trp Arg Asp Arg Ser Gly
                610                 615                 620

Ala Pro His Glu Gln Glu Leu Thr Leu Ala Pro Gly Arg His Thr Leu
625                 630                 635                 640

Thr Leu Gly Ser Gln Ala Arg Glu Val Ser Arg
                645                 650

<210> SEQ ID NO 59
<211> LENGTH: 630
<212> TYPE: DNA
<213> ORGANISM: Bacteria
<220> FEATURE:
<221> NAME/KEY: CDS
<222> LOCATION: (1)...(630)

<400> SEQUENCE: 59 atg ggc gaa acg gga cgt cag ttg gcc gtc gtc acg gcg gac gcc gac      48
Met Gly Glu Thr Gly Arg Gln Leu Ala Val Val Thr Ala Asp Ala Asp
 1               5                  10                  15 gtc gtg gag gcg gag ctg gtg gac gac gag acg gcc ggc gcc tcc gtc      96
Val Val Glu Ala Glu Leu Val Asp Asp Glu Thr Ala Gly Ala Ser Val
                20                  25                  30 gtc gtc cac acg gac cgc gac cgg cac ctc tcc ccc gag acc gtc gcc     144
Val Val His Thr Asp Arg Asp Arg His Leu Ser Pro Glu Thr Val Ala
            35                  40                  45 gcc atc gcg gcg agc gtc gcc gac tcc acc cgc cgc gcg tac ggc acc     192
Ala Ile Ala Ala Ser Val Ala Asp Ser Thr Arg Arg Ala Tyr Gly Thr
        50                  55                  60 gac cgg gcc gcg ttc gcc gcc tgg tgc gcc gag gag gac cgc acg gcc     240
Asp Arg Ala Ala Phe Ala Ala Trp Cys Ala Glu Glu Asp Arg Thr Ala
```

```
                65                  70                  75                  80
gtc ccc gcg tcg gcg gag acg atg gcg gag tgg gtg cgg cac ctg acc          288
Val Pro Ala Ser Ala Glu Thr Met Ala Glu Trp Val Arg His Leu Thr
                85                  90                  95 gtc acg ccc cgc ccc cgg acg cag cga ccg gcc ggg ccg tcg acc atc          336
Val Thr Pro Arg Pro Arg Thr Gln Arg Pro Ala Gly Pro Ser Thr Ile
            100                 105                 110 gag cgg gcc atg tcc gcc gtg acc acc tgg cac gag gag cag gga cgg          384
Glu Arg Ala Met Ser Ala Val Thr Thr Trp His Glu Glu Gln Gly Arg
            115                 120                 125 ccg aag ccg aac atg cgc ggc gcc cgg gcc gtc ctc aac gcc tac aag          432
Pro Lys Pro Asn Met Arg Gly Ala Arg Ala Val Leu Asn Ala Tyr Lys
        130                 135                 140 gac cgg ctc gcc gtg gag aag gcg gag gcc gcg cag gcc cgc cag gcg          480
Asp Arg Leu Ala Val Glu Lys Ala Glu Ala Ala Gln Ala Arg Gln Ala
145                 150                 155                 160 acc gcc gcc ctc ccc ccg cag atc cgc gcc atg ctc gcc ggg gtc gac          528
Thr Ala Ala Leu Pro Pro Gln Ile Arg Ala Met Leu Ala Gly Val Asp
                165                 170                 175 cgg acc acc ctc gcc ggg aag cgg aac gcg gcc tgg tcc tcc tcg gtt          576
Arg Thr Thr Leu Ala Gly Lys Arg Asn Ala Ala Trp Ser Ser Ser Val
                180                 185                 190 cgc cac ggc ggc cgc gtc ctc cga gct ggt cgc agc tgg acg tcg aca          624
Arg His Gly Gly Arg Val Leu Arg Ala Gly Arg Ser Trp Thr Ser Thr
                195                 200                 205 cgg tga                                                                   630
Arg *

<210> SEQ ID NO 60
<211> LENGTH: 209
<212> TYPE: PRT
<213> ORGANISM: Bacteria

<400> SEQUENCE: 60

Met Gly Glu Thr Gly Arg Gln Leu Ala Val Val Thr Ala Asp Ala Asp
1               5                   10                  15

Val Val Glu Ala Glu Leu Val Asp Asp Glu Thr Ala Gly Ala Ser Val
                20                  25                  30

Val Val His Thr Asp Arg Asp Arg His Leu Ser Pro Glu Thr Val Ala
            35                  40                  45

Ala Ile Ala Ala Ser Val Ala Asp Ser Thr Arg Arg Ala Tyr Gly Thr
        50                  55                  60

Asp Arg Ala Ala Phe Ala Ala Trp Cys Ala Glu Glu Asp Arg Thr Ala
65                  70                  75                  80

Val Pro Ala Ser Ala Glu Thr Met Ala Glu Trp Val Arg His Leu Thr
                85                  90                  95

Val Thr Pro Arg Pro Arg Thr Gln Arg Pro Ala Gly Pro Ser Thr Ile
            100                 105                 110

Glu Arg Ala Met Ser Ala Val Thr Thr Trp His Glu Glu Gln Gly Arg
            115                 120                 125

Pro Lys Pro Asn Met Arg Gly Ala Arg Ala Val Leu Asn Ala Tyr Lys
        130                 135                 140

Asp Arg Leu Ala Val Glu Lys Ala Glu Ala Ala Gln Ala Arg Gln Ala
145                 150                 155                 160

Thr Ala Ala Leu Pro Pro Gln Ile Arg Ala Met Leu Ala Gly Val Asp
                165                 170                 175

Arg Thr Thr Leu Ala Gly Lys Arg Asn Ala Ala Trp Ser Ser Ser Val
```

-continued

```
                180                 185                 190
Arg His Gly Gly Arg Val Leu Arg Ala Gly Arg Ser Trp Thr Ser Thr
            195                 200                 205
Arg

<210> SEQ ID NO 61
<211> LENGTH: 1566
<212> TYPE: DNA
<213> ORGANISM: Bacteria
<220> FEATURE:
<221> NAME/KEY: CDS
<222> LOCATION: (1)...(1566)

<400> SEQUENCE: 61 gtg ttc ttc gag gac tgc acc ctc gcg gag gcc acc tat ccc acg ctg      48
Val Phe Phe Glu Asp Cys Thr Leu Ala Glu Ala Thr Tyr Pro Thr Leu
 1               5                  10                  15 ttc gcc ggg gtg gac gtc gtg ccg tcc agc gtc gac ctc cag cgc gtg      96
Phe Ala Gly Val Asp Val Val Pro Ser Ser Val Asp Leu Gln Arg Val
             20                  25                  30 gag tac gaa cgg ccc atc ggc gcg gag cag ggc ctc gcc gcc gcc ctg     144
Glu Tyr Glu Arg Pro Ile Gly Ala Glu Gln Gly Leu Ala Ala Ala Leu
         35                  40                  45 gcg cag gag gcg gag gag gcc ggc ggc cgc tcc ccg tac gac gtg acc     192
Ala Gln Glu Ala Glu Glu Ala Gly Gly Arg Ser Pro Tyr Asp Val Thr
     50                  55                  60 ctg atc gac gcc gcg ccg tcc ctc ggg ctg gtc acc gtt gcc gca ctc     240
Leu Ile Asp Ala Ala Pro Ser Leu Gly Leu Val Thr Val Ala Ala Leu
 65                  70                  75                  80 acc gcc gcc gac gag gcc ctg gtg ccc atc aag gtc ggc ggc ctg gac     288
Thr Ala Ala Asp Glu Ala Leu Val Pro Ile Lys Val Gly Gly Leu Asp
                 85                  90                  95 atg aag gcc atg gcg tcc ctc cac aag acg ctc cgc agc gtc cag cgg     336
Met Lys Ala Met Ala Ser Leu His Lys Thr Leu Arg Ser Val Gln Arg
            100                 105                 110 aag acg aac ccg aag ctg agc gtc ggg gcc gtc ctg ctg acc gcg tgg     384
Lys Thr Asn Pro Lys Leu Ser Val Gly Ala Val Leu Leu Thr Ala Trp
        115                 120                 125 gac aag agc acg ttt gcc cgg cag ctc gcc acg aag gtg agc gag gac     432
Asp Lys Ser Thr Phe Ala Arg Gln Leu Ala Thr Lys Val Ser Glu Asp
    130                 135                 140 tac ccg gag gcg gcc gtc gtg ccg atc cgg cgc agc atc cgc gcg tcg     480
Tyr Pro Glu Ala Ala Val Val Pro Ile Arg Arg Ser Ile Arg Ala Ser
145                 150                 155                 160 gag gcc ccg ctc tcc gag gag ccg atc cgc ctg tac gcg ccc gag gcg     528
Glu Ala Pro Leu Ser Glu Glu Pro Ile Arg Leu Tyr Ala Pro Glu Ala
                165                 170                 175 gcc ccg gcc ggg gac tac gac cag tgc ggc cgc cgt cct cct gcc ggg     576
Ala Pro Ala Gly Asp Tyr Asp Gln Cys Gly Arg Arg Pro Pro Ala Gly
            180                 185                 190 gag ggc tgc cgc gtg agc cgc cgc tcc ctc gcc ctc ccg tcg acc agg     624
Glu Gly Cys Arg Val Ser Arg Arg Ser Leu Ala Leu Pro Ser Thr Arg
        195                 200                 205 agc acc gag ccg gac cac gcc gac gag ctg gag gcc gcc ccc gaa gag     672
Ser Thr Glu Pro Asp His Ala Asp Glu Leu Glu Ala Ala Pro Glu Glu
    210                 215                 220 aag ctc gcg gcc gcg cgg tcc gcc ggg gtg gtc gcc tcg ctg acc ggc     720
Lys Leu Ala Ala Ala Arg Ser Ala Gly Val Val Ala Ser Leu Thr Gly
225                 230                 235                 240 gcg gac ctg tcg acg ccc ctc acc gtg gcg cag ctc ccc acg ccg tac     768
```

```
Ala Asp Leu Ser Thr Pro Leu Thr Val Ala Gln Leu Pro Thr Pro Tyr
                245                 250                 255 gac gtc gcg gag acc gtc acg gcg ccg ctg aac gac cag gag cgc ggt        816
Asp Val Ala Glu Thr Val Thr Ala Pro Leu Asn Asp Gln Glu Arg Gly
            260                 265                 270 tac ctg gac gtg tgc gag cag gcc ctc cac ggc ttc cgg aag tcc gtc        864
Tyr Leu Asp Val Cys Glu Gln Ala Leu His Gly Phe Arg Lys Ser Val
                275                 280                 285 gtc gtc gcg ggc aag gcc ctg gag gtc atc aac cgc ggc cgc ctc tac        912
Val Val Ala Gly Lys Ala Leu Glu Val Ile Asn Arg Gly Arg Leu Tyr
290                 295                 300 cgg gag acg cac gag acg ttc gcg gac tac gtg acg gag gtg tgg gac        960
Arg Glu Thr His Glu Thr Phe Ala Asp Tyr Val Thr Glu Val Trp Asp
305                 310                 315                 320 atg aag cgg gcc cac gcc tat cgg atg atc gag ggg tgg cga ccg gcc       1008
Met Lys Arg Ala His Ala Tyr Arg Met Ile Glu Gly Trp Arg Pro Ala
                325                 330                 335 gac ctc gtg tct cca att gga gac atc aac gag ggc cag gcc cgc gag       1056
Asp Leu Val Ser Pro Ile Gly Asp Ile Asn Glu Gly Gln Ala Arg Glu
            340                 345                 350 ctg gcg ccc gtg ctc aag gag tac ggg ccc gag gtg acc gtc acc ctg       1104
Leu Ala Pro Val Leu Lys Glu Tyr Gly Pro Glu Val Thr Val Thr Leu
        355                 360                 365 tac cgg ggg gtc aag gag ctg cgc ggc gac cgg cgg gtg acg gct gcg       1152
Tyr Arg Gly Val Lys Glu Leu Arg Gly Asp Arg Arg Val Thr Ala Ala
370                 375                 380 gac ctc tcg gag gcc cgg gca gcg ctg cct ccg ccg aag cac ctc gcc       1200
Asp Leu Ser Glu Ala Arg Ala Ala Leu Pro Pro Pro Lys His Leu Ala
385                 390                 395                 400 cgg ccg gac cag gtg cgc gac gtc ctc acc gtg gcg gcc gcc gag ggc       1248
Arg Pro Asp Gln Val Arg Asp Val Leu Thr Val Ala Ala Ala Glu Gly
                405                 410                 415 cgc gcg ccc cgg ctc gcc ccg gcc gag ccg aag gtg ccg gcc cag gcc       1296
Arg Ala Pro Arg Leu Ala Pro Ala Glu Pro Lys Val Pro Ala Gln Ala
            420                 425                 430 gcc gac gag cac cag gcc gag cag gtc gac gag ggc ggc gta agt cag       1344
Ala Asp Glu His Gln Ala Glu Gln Val Asp Glu Gly Gly Val Ser Gln
        435                 440                 445 gac cag gtc gac gag ggc gcg gag gcc atc gcc acc ctg gag gcc gcc       1392
Asp Gln Val Asp Glu Gly Ala Glu Ala Ile Ala Thr Leu Glu Ala Ala
450                 455                 460 gtg gcc cag caa cgg cag atc tat gac cgg gtg ggc ggc ggg act ctc       1440
Val Ala Gln Gln Arg Gln Ile Tyr Asp Arg Val Gly Gly Gly Thr Leu
465                 470                 475                 480 gcg gcc gcc ctg ctg tac gac cca ggc cgg ggt gac cat ctg cgc cgc       1488
Ala Ala Ala Leu Leu Tyr Asp Pro Gly Arg Gly Asp His Leu Arg Arg
                485                 490                 495 gag ctg cgg cag tac gcg cag cgg acg gcg tac cgg gca cgg gat acc       1536
Glu Leu Arg Gln Tyr Ala Gln Arg Thr Ala Tyr Arg Ala Arg Asp Thr
            500                 505                 510 tcc ggt gag cag gtg gcc gac gac gcg taa                               1566
Ser Gly Glu Gln Val Ala Asp Asp Ala *
        515                 520

<210> SEQ ID NO 62
<211> LENGTH: 521
<212> TYPE: PRT
<213> ORGANISM: Bacteria

<400> SEQUENCE: 62
```

-continued

```
Val Phe Phe Glu Asp Cys Thr Leu Ala Glu Ala Thr Tyr Pro Thr Leu
 1               5                  10                 15

Phe Ala Gly Val Asp Val Val Pro Ser Ser Val Asp Leu Gln Arg Val
            20                  25                 30

Glu Tyr Glu Arg Pro Ile Gly Ala Glu Gln Gly Leu Ala Ala Ala Leu
         35                  40                 45

Ala Gln Glu Ala Glu Ala Gly Gly Arg Ser Pro Tyr Asp Val Thr
 50                  55                 60

Leu Ile Asp Ala Ala Pro Ser Leu Gly Leu Val Thr Val Ala Ala Leu
 65                  70                 75                  80

Thr Ala Ala Asp Glu Ala Leu Val Pro Ile Lys Val Gly Gly Leu Asp
                 85                  90                 95

Met Lys Ala Met Ala Ser Leu His Lys Thr Leu Arg Ser Val Gln Arg
                100                 105                110

Lys Thr Asn Pro Lys Leu Ser Val Gly Ala Val Leu Leu Thr Ala Trp
                115                 120                125

Asp Lys Ser Thr Phe Ala Arg Gln Leu Ala Thr Lys Val Ser Glu Asp
                130                 135                140

Tyr Pro Glu Ala Ala Val Val Pro Ile Arg Arg Ser Ile Arg Ala Ser
145                 150                 155                160

Glu Ala Pro Leu Ser Glu Glu Pro Ile Arg Leu Tyr Ala Pro Glu Ala
                165                 170                175

Ala Pro Ala Gly Asp Tyr Asp Gln Cys Gly Arg Arg Pro Pro Ala Gly
                180                 185                190

Glu Gly Cys Arg Val Ser Arg Arg Ser Leu Ala Leu Pro Ser Thr Arg
                195                 200                205

Ser Thr Glu Pro Asp His Ala Asp Glu Leu Glu Ala Ala Pro Glu Glu
210                 215                 220

Lys Leu Ala Ala Ala Arg Ser Ala Gly Val Val Ala Ser Leu Thr Gly
225                 230                 235                240

Ala Asp Leu Ser Thr Pro Leu Thr Val Ala Gln Leu Pro Thr Pro Tyr
                245                 250                255

Asp Val Ala Glu Thr Val Thr Ala Pro Leu Asn Asp Gln Glu Arg Gly
                260                 265                270

Tyr Leu Asp Val Cys Glu Gln Ala Leu His Gly Phe Arg Lys Ser Val
                275                 280                285

Val Val Ala Gly Lys Ala Leu Glu Val Ile Asn Arg Gly Arg Leu Tyr
                290                 295                300

Arg Glu Thr His Glu Thr Phe Ala Asp Tyr Val Thr Glu Val Trp Asp
305                 310                 315                320

Met Lys Arg Ala His Ala Tyr Arg Met Ile Glu Gly Trp Arg Pro Ala
                325                 330                335

Asp Leu Val Ser Pro Ile Gly Asp Ile Asn Glu Gly Gln Ala Arg Glu
                340                 345                350

Leu Ala Pro Val Leu Lys Glu Tyr Gly Pro Glu Val Thr Val Thr Leu
                355                 360                365

Tyr Arg Gly Val Lys Glu Leu Arg Gly Asp Arg Arg Val Thr Ala Ala
                370                 375                380

Asp Leu Ser Glu Ala Arg Ala Leu Pro Pro Lys His Leu Ala
385                 390                 395                400

Arg Pro Asp Gln Val Arg Asp Val Leu Thr Val Ala Ala Ala Glu Gly
                405                 410                415

Arg Ala Pro Arg Leu Ala Pro Ala Glu Pro Lys Val Pro Ala Gln Ala
```

```
            420             425             430
Ala Asp Glu His Gln Ala Glu Gln Val Asp Glu Gly Gly Val Ser Gln
            435             440             445

Asp Gln Val Asp Glu Gly Ala Glu Ala Ile Ala Thr Leu Glu Ala Ala
        450             455             460

Val Ala Gln Gln Arg Gln Ile Tyr Asp Arg Val Gly Gly Thr Leu
465             470             475             480

Ala Ala Ala Leu Leu Tyr Asp Pro Gly Arg Gly Asp His Leu Arg Arg
                485             490             495

Glu Leu Arg Gln Tyr Ala Gln Arg Thr Ala Tyr Arg Ala Arg Asp Thr
            500             505             510

Ser Gly Glu Gln Val Ala Asp Asp Ala
            515             520
```

<210> SEQ ID NO 63
<211> LENGTH: 528
<212> TYPE: DNA
<213> ORGANISM: Bacteria
<220> FEATURE:
<221> NAME/KEY: CDS
<222> LOCATION: (1)...(528)

<400> SEQUENCE: 63

```
atg gga gag gcg cga gtg ccg acg agg aag cgc ggg ccg aac atg gcc    48
Met Gly Glu Ala Arg Val Pro Thr Arg Lys Arg Gly Pro Asn Met Ala
1               5                   10                  15 ctg gtc aac atg gac acc gga gag gcg gtg tcc gcc agg ccg cgg act    96
Leu Val Asn Met Asp Thr Gly Glu Ala Val Ser Ala Arg Pro Arg Thr
            20                  25                  30 ccg cac cag ttc gac ggg aag ggg tac acc ttg cag gcc gta ggc agc    144
Pro His Gln Phe Asp Gly Lys Gly Tyr Thr Leu Gln Ala Val Gly Ser
        35                  40                  45 gac gtc ccc ctg tac tcc ctc ggg ctg gcc gca gcg gag tgg gcg acg    192
Asp Val Pro Leu Tyr Ser Leu Gly Leu Ala Ala Ala Glu Trp Ala Thr
    50                  55                  60 ctc gaa tgg ctc cgc gaa cac gga ggc gcg gcc gga tac gtc ccg gtc    240
Leu Glu Trp Leu Arg Glu His Gly Gly Ala Ala Gly Tyr Val Pro Val
65                  70                  75                  80 acg ccc gag gag ctg ggc gag gac gtc ggc gcc agc aag gac acc tgc    288
Thr Pro Glu Glu Leu Gly Glu Asp Val Gly Ala Ser Lys Asp Thr Cys
                85                  90                  95 cgg aag gcc ctt aac cgg ctg gtc aag ctc ggg ctt gtg gtc aag ccg    336
Arg Lys Ala Leu Asn Arg Leu Val Lys Leu Gly Leu Val Val Lys Pro
            100                 105                 110 ggc ccg cga tcc ggc tct tac cag ctg aac ccc ctc cga tac tgg gag    384
Gly Pro Arg Ser Gly Ser Tyr Gln Leu Asn Pro Leu Arg Tyr Trp Glu
        115                 120                 125 gga gcc ggg agc acg cag gtc aac gcc tgc cgc cgc atg gcg ccg ccg    432
Gly Ala Gly Ser Thr Gln Val Asn Ala Cys Arg Arg Met Ala Pro Pro
    130                 135                 140 cgt gtg gcc ccg gac gac aag gcc atg acc agg tcc gcc agc aag ccc    480
Arg Val Ala Pro Asp Asp Lys Ala Met Thr Arg Ser Ala Ser Lys Pro
145                 150                 155                 160 aag acc atc ccg gct acc cgc cgc cgc gcc gca gga gag acg cga tga    528
Lys Thr Ile Pro Ala Thr Arg Arg Arg Ala Ala Gly Glu Thr Arg *
                165                 170                 175
```

<210> SEQ ID NO 64
<211> LENGTH: 175
<212> TYPE: PRT

<213> ORGANISM: Bacteria

<400> SEQUENCE: 64

```
Met Gly Glu Ala Arg Val Pro Thr Arg Lys Arg Gly Pro Asn Met Ala
1               5                   10                  15

Leu Val Asn Met Asp Thr Gly Glu Ala Val Ser Ala Arg Pro Arg Thr
            20                  25                  30

Pro His Gln Phe Asp Gly Lys Gly Tyr Thr Leu Gln Ala Val Gly Ser
        35                  40                  45

Asp Val Pro Leu Tyr Ser Leu Gly Leu Ala Ala Glu Trp Ala Thr
    50                  55                  60

Leu Glu Trp Leu Arg Glu His Gly Gly Ala Ala Gly Tyr Val Pro Val
65              70                  75                  80

Thr Pro Glu Glu Leu Gly Glu Asp Val Gly Ala Ser Lys Asp Thr Cys
                85                  90                  95

Arg Lys Ala Leu Asn Arg Leu Val Lys Leu Gly Leu Val Val Lys Pro
            100                 105                 110

Gly Pro Arg Ser Gly Ser Tyr Gln Leu Asn Pro Leu Arg Tyr Trp Glu
        115                 120                 125

Gly Ala Gly Ser Thr Gln Val Asn Ala Cys Arg Arg Met Ala Pro Pro
    130                 135                 140

Arg Val Ala Pro Asp Asp Lys Ala Met Thr Arg Ser Ala Ser Lys Pro
145                 150                 155                 160

Lys Thr Ile Pro Ala Thr Arg Arg Ala Ala Gly Glu Thr Arg
                165                 170                 175
```

<210> SEQ ID NO 65
<211> LENGTH: 420
<212> TYPE: DNA
<213> ORGANISM: Bacteria
<220> FEATURE:
<221> NAME/KEY: CDS
<222> LOCATION: (1)...(420)

<400> SEQUENCE: 65

```
atg acg acc atg ccc gta gaa ggc ttc aac ccg gag cgc gac ctg acc      48
Met Thr Thr Met Pro Val Glu Gly Phe Asn Pro Glu Arg Asp Leu Thr
1               5                   10                  15 gcc ccg tcg ctg tac tcg ctg aac ctg tcc gct gct cag cac tgc acg      96
Ala Pro Ser Leu Tyr Ser Leu Asn Leu Ser Ala Ala Gln His Cys Thr
            20                  25                  30 ctc gcg tgg gtg gag gac cac ggc ggc ctg ttt gac gtc atc ccc gta     144
Leu Ala Trp Val Glu Asp His Gly Gly Leu Phe Asp Val Ile Pro Val
        35                  40                  45 ccg gtc gaa acc gtc gcc gag gac tgc ggc aac tcc gtc tcc acg gtg     192
Pro Val Glu Thr Val Ala Glu Asp Cys Gly Asn Ser Val Ser Thr Val
    50                  55                  60 cac gag gct ctc gcc cgc ctg gag gcc ctg aac ctc ctc gtg cgg acc     240
His Glu Ala Leu Ala Arg Leu Glu Ala Leu Asn Leu Leu Val Arg Thr
65              70                  75                  80 tcc gcc ggc ctc tac cgg atc aac gcc cgg tac tac ttc acg ctg cac     288
Ser Ala Gly Leu Tyr Arg Ile Asn Ala Arg Tyr Tyr Phe Thr Leu His
                85                  90                  95 ccc gag ctg cgc gag atg atc acc gcc gcc ctc acg gac ccc ccg gtc     336
Pro Glu Leu Arg Glu Met Ile Thr Ala Ala Leu Thr Asp Pro Pro Val
            100                 105                 110 acc ccg gac gac cgt gcc cgc gcg ccc cgc aag gtc agc aac acc gac     384
Thr Pro Asp Asp Arg Ala Arg Ala Pro Arg Lys Val Ser Asn Thr Asp
        115                 120                 125
```

```
gct cgc cgc cgc cgg acg atc cgc ccc gtc tct tga                    420
Ala Arg Arg Arg Arg Thr Ile Arg Pro Val Ser *
    130                 135
```

<210> SEQ ID NO 66
<211> LENGTH: 139
<212> TYPE: PRT
<213> ORGANISM: Bacteria

<400> SEQUENCE: 66

```
Met Thr Thr Met Pro Val Glu Gly Phe Asn Pro Glu Arg Asp Leu Thr
 1               5                  10                  15

Ala Pro Ser Leu Tyr Ser Leu Asn Leu Ser Ala Ala Gln His Cys Thr
            20                  25                  30

Leu Ala Trp Val Glu Asp His Gly Gly Leu Phe Asp Val Ile Pro Val
        35                  40                  45

Pro Val Glu Thr Val Ala Glu Asp Cys Gly Asn Ser Val Ser Thr Val
    50                  55                  60

His Glu Ala Leu Ala Arg Leu Glu Ala Leu Asn Leu Leu Val Arg Thr
65                  70                  75                  80

Ser Ala Gly Leu Tyr Arg Ile Asn Ala Arg Tyr Tyr Phe Thr Leu His
                85                  90                  95

Pro Glu Leu Arg Glu Met Ile Thr Ala Ala Leu Thr Asp Pro Pro Val
            100                 105                 110

Thr Pro Asp Asp Arg Ala Arg Ala Pro Arg Lys Val Ser Asn Thr Asp
        115                 120                 125

Ala Arg Arg Arg Arg Thr Ile Arg Pro Val Ser
    130                 135
```

<210> SEQ ID NO 67
<211> LENGTH: 564
<212> TYPE: DNA
<213> ORGANISM: Bacteria
<220> FEATURE:
<221> NAME/KEY: CDS
<222> LOCATION: (1)...(564)

<400> SEQUENCE: 67

```
gtg cca gac ggt cag ttg ccg ccc tgt acg gga gga agc tcg aag cct     48
Val Pro Asp Gly Gln Leu Pro Pro Cys Thr Gly Gly Ser Ser Lys Pro
 1               5                  10                  15 tca ggc tgc tcg tgt cca tcg cca acg agc gtc tgc gtc acg gcc agg     96
Ser Gly Cys Ser Cys Pro Ser Pro Thr Ser Val Cys Val Thr Ala Arg
            20                  25                  30 acg tcg ccc ttc gcg tcg tac tgg acg gtc cgg tac agc atc aca ggc    144
Thr Ser Pro Phe Ala Ser Tyr Trp Thr Val Arg Tyr Ser Ile Thr Gly
        35                  40                  45 ttg ctc gcg gag ggc gga agg ccg aag tct tcg cac tcg aac cag gcg    192
Leu Leu Ala Glu Gly Gly Arg Pro Lys Ser Ser His Ser Asn Gln Ala
    50                  55                  60 agc atc cga gcg gtc agg gtg cgc tcc agc cgg acg cac ccc gga atc    240
Ser Ile Arg Ala Val Arg Val Arg Ser Ser Arg Thr His Pro Gly Ile
65                  70                  75                  80 gtg ggg gcc aca ggc gtt aga gcc agg tcc ggc gag acg cgc ggc ggc    288
Val Gly Ala Thr Gly Val Arg Ala Arg Ser Gly Glu Thr Arg Gly Gly
                85                  90                  95 ggg atc ggg agc cca aga cct ggc gca agc ctc cgc acc gtc tca ctc    336
Gly Ile Gly Ser Pro Arg Pro Gly Ala Ser Leu Arg Thr Val Ser Leu
            100                 105                 110
```

```
acg acg gcc acc ggg tca cca agg ctg gtc agg tcg aac cac tcg ccc      384
Thr Thr Ala Thr Gly Ser Pro Arg Leu Val Arg Ser Asn His Ser Pro
        115                 120                 125 cgc cgg ttg tgc tca cgg aac tcc tgg tgg agc gcc ccc tca agg gcg      432
Arg Arg Leu Cys Ser Arg Asn Ser Trp Trp Ser Ala Pro Ser Arg Ala
130                 135                 140 cgg ccg ccc tcg cac gtc cac agc acc gac agc gtc agc ggc aga ccg      480
Arg Pro Pro Ser His Val His Ser Thr Asp Ser Val Ser Gly Arg Pro
145                 150                 155                 160 gtc tgc atc gtg cgg act ctc ctc tcc acg tct gtc gtg gtg ccg atc      528
Val Cys Ile Val Arg Thr Leu Leu Ser Thr Ser Val Val Val Pro Ile
                165                 170                 175 ttc acc agg tct agg ccc tcg gct cct aag aga tag                      564
Phe Thr Arg Ser Arg Pro Ser Ala Pro Lys Arg *
            180                 185

<210> SEQ ID NO 68
<211> LENGTH: 187
<212> TYPE: PRT
<213> ORGANISM: Bacteria

<400> SEQUENCE: 68

Val Pro Asp Gly Gln Leu Pro Pro Cys Thr Gly Gly Ser Ser Lys Pro
1               5                   10                  15

Ser Gly Cys Ser Cys Pro Ser Pro Thr Ser Val Cys Val Thr Ala Arg
            20                  25                  30

Thr Ser Pro Phe Ala Ser Tyr Trp Thr Val Arg Tyr Ser Ile Thr Gly
        35                  40                  45

Leu Leu Ala Glu Gly Gly Arg Pro Lys Ser Ser His Ser Asn Gln Ala
    50                  55                  60

Ser Ile Arg Ala Val Arg Val Arg Ser Ser Arg Thr His Pro Gly Ile
65                  70                  75                  80

Val Gly Ala Thr Gly Val Arg Ala Arg Ser Gly Glu Thr Arg Gly Gly
                85                  90                  95

Gly Ile Gly Ser Pro Arg Pro Gly Ala Ser Leu Arg Thr Val Ser Leu
            100                 105                 110

Thr Thr Ala Thr Gly Ser Pro Arg Leu Val Arg Ser Asn His Ser Pro
        115                 120                 125

Arg Arg Leu Cys Ser Arg Asn Ser Trp Trp Ser Ala Pro Ser Arg Ala
130                 135                 140

Arg Pro Pro Ser His Val His Ser Thr Asp Ser Val Ser Gly Arg Pro
145                 150                 155                 160

Val Cys Ile Val Arg Thr Leu Leu Ser Thr Ser Val Val Val Pro Ile
                165                 170                 175

Phe Thr Arg Ser Arg Pro Ser Ala Pro Lys Arg
            180                 185

<210> SEQ ID NO 69
<211> LENGTH: 798
<212> TYPE: DNA
<213> ORGANISM: Bacteria
<220> FEATURE:
<221> NAME/KEY: CDS
<222> LOCATION: (1)...(798)

<400> SEQUENCE: 69 atg gcg act agg cgg aag ggc cgc cct ggc ggc tat gag gaa atc gcc      48
Met Ala Thr Arg Arg Lys Gly Arg Pro Gly Gly Tyr Glu Glu Ile Ala
1               5                   10                  15
```

```
gcg cac ttt cgg cgg ctc atg gac tcg ggc gag ttg tcc cct ggc gac      96
Ala His Phe Arg Arg Leu Met Asp Ser Gly Glu Leu Ser Pro Gly Asp
            20                  25                  30 ccg ctg ccc tcc atg cgc gac gtg tgc gac cag ttc ggt tcg gcg atc     144
Pro Leu Pro Ser Met Arg Asp Val Cys Asp Gln Phe Gly Ser Ala Ile
        35                  40                  45 acg acg gtg aac cgg gcg ttc cgg ctc ctc cag gag gag ggc cgg acg     192
Thr Thr Val Asn Arg Ala Phe Arg Leu Leu Gln Glu Glu Gly Arg Thr
    50                  55                  60 gtc tcc aag ccg ggc gtg ggc acg atc gtc cgg gac atg tcc cgg gtt     240
Val Ser Lys Pro Gly Val Gly Thr Ile Val Arg Asp Met Ser Arg Val
65                  70                  75                  80 cgg gtg ccg ttc agt acg tac ggc gac gtc ctg gcg ccg ggc ggc gat     288
Arg Val Pro Phe Ser Thr Tyr Gly Asp Val Leu Ala Pro Gly Gly Asp
                85                  90                  95 aag ggc ccg tgg gag cgt gcg acg gcc gcg cag ggc ctt gac ggc cgg     336
Lys Gly Pro Trp Glu Arg Ala Thr Ala Ala Gln Gly Leu Asp Gly Arg
            100                 105                 110 atg ctc gtg gag gcg ccc gag gag gtc ggg gcc ccg gcg gac gtc gcc     384
Met Leu Val Glu Ala Pro Glu Glu Val Gly Ala Pro Ala Asp Val Ala
        115                 120                 125 gcg cgc ctc ggc atc gag ccg ggc gcc ctg gtc gtc cac cgg cgg cgc     432
Ala Arg Leu Gly Ile Glu Pro Gly Ala Leu Val Val His Arg Arg Arg
    130                 135                 140 cgc gcc acg atc ggc gag gac gtc gtc cag ctc caa gac gcc tgg tac     480
Arg Ala Thr Ile Gly Glu Asp Val Val Gln Leu Gln Asp Ala Trp Tyr
145                 150                 155                 160 ccg ctg gag atc gcc cgg gcc gcc ggc ctg gac cgg ccg ggg aag gtc     528
Pro Leu Glu Ile Ala Arg Ala Ala Gly Leu Asp Arg Pro Gly Lys Val
                165                 170                 175 gtg ggt ggt gtc ctc ggt gcc atg acg ggc gcc ggc ctt tcg ccg acg     576
Val Gly Gly Val Leu Gly Ala Met Thr Gly Ala Gly Leu Ser Pro Thr
            180                 185                 190 tcc acc gac cac gac gtc gag gtg tgg gtg ccg tcc gcg cag caa gcc     624
Ser Thr Asp His Asp Val Glu Val Trp Val Pro Ser Ala Gln Gln Ala
        195                 200                 205 gcg gaa ctc tcc ctc ggc tcc cgc gtg tcg gtc ctg gtc gtc gag cgc     672
Ala Glu Leu Ser Leu Gly Ser Arg Val Ser Val Leu Val Val Glu Arg
    210                 215                 220 gtc acc tac gac gcg acg gtc cgt gtc ctg gaa ctg acc cgt cac acg     720
Val Thr Tyr Asp Ala Thr Val Arg Val Leu Glu Leu Thr Arg His Thr
225                 230                 235                 240 ggc gcg gct gac agg ctg acg ctg acc tac aag ggc ctg cca ctc cgg     768
Gly Ala Ala Asp Arg Leu Thr Leu Thr Tyr Lys Gly Leu Pro Leu Arg
                245                 250                 255 gcg acc gga gcc gag ggg agc acg tca tga                             798
Ala Thr Gly Ala Glu Gly Ser Thr Ser *
            260                 265
```

<210> SEQ ID NO 70
<211> LENGTH: 265
<212> TYPE: PRT
<213> ORGANISM: Bacteria

<400> SEQUENCE: 70

```
Met Ala Thr Arg Arg Lys Gly Arg Pro Gly Gly Tyr Glu Glu Ile Ala
1               5                   10                  15

Ala His Phe Arg Arg Leu Met Asp Ser Gly Glu Leu Ser Pro Gly Asp
            20                  25                  30

Pro Leu Pro Ser Met Arg Asp Val Cys Asp Gln Phe Gly Ser Ala Ile
```

-continued

```
                35                  40                  45
Thr Thr Val Asn Arg Ala Phe Arg Leu Leu Gln Glu Glu Gly Arg Thr
         50                  55                  60

Val Ser Lys Pro Gly Val Gly Thr Ile Val Arg Asp Met Ser Arg Val
 65                  70                  75                  80

Arg Val Pro Phe Ser Thr Tyr Gly Asp Val Leu Ala Pro Gly Gly Asp
                 85                  90                  95

Lys Gly Pro Trp Glu Arg Ala Thr Ala Ala Gln Gly Leu Asp Gly Arg
            100                 105                 110

Met Leu Val Glu Ala Pro Glu Val Gly Ala Pro Ala Asp Val Ala
            115                 120                 125

Ala Arg Leu Gly Ile Glu Pro Gly Ala Leu Val Val His Arg Arg
130                 135                 140

Arg Ala Thr Ile Gly Glu Asp Val Val Gln Leu Gln Asp Ala Trp Tyr
145                 150                 155                 160

Pro Leu Glu Ile Ala Arg Ala Ala Gly Leu Asp Arg Pro Gly Lys Val
                165                 170                 175

Val Gly Gly Val Leu Gly Ala Met Thr Gly Ala Gly Leu Ser Pro Thr
            180                 185                 190

Ser Thr Asp His Asp Val Glu Val Trp Val Pro Ser Ala Gln Gln Ala
            195                 200                 205

Ala Glu Leu Ser Leu Gly Ser Arg Val Ser Val Leu Val Glu Arg
210                 215                 220

Val Thr Tyr Asp Ala Thr Val Arg Val Leu Glu Leu Thr Arg His Thr
225                 230                 235                 240

Gly Ala Ala Asp Arg Leu Thr Leu Thr Tyr Lys Gly Leu Pro Leu Arg
                245                 250                 255

Ala Thr Gly Ala Glu Gly Ser Thr Ser
            260                 265

<210> SEQ ID NO 71
<211> LENGTH: 378
<212> TYPE: DNA
<213> ORGANISM: Bacteria
<220> FEATURE:
<221> NAME/KEY: CDS
<222> LOCATION: (1)...(378)

<400> SEQUENCE: 71 atg tcc acg acc acc aac gcg gtc acc tgg ttc gag gtc ggc acc gac      48
Met Ser Thr Thr Thr Asn Ala Val Thr Trp Phe Glu Val Gly Thr Asp
 1               5                  10                  15 cgg ccg gag gag acc ggg cgc ttc tac gcc gac ctg ttc ggt tgg gcg      96
Arg Pro Glu Glu Thr Gly Arg Phe Tyr Ala Asp Leu Phe Gly Trp Ala
                 20                  25                  30 ttc ggc gag cag ggg acg ccg gag gcg tcg tac cgg gtg acg gag ccg     144
Phe Gly Glu Gln Gly Thr Pro Glu Ala Ser Tyr Arg Val Thr Glu Pro
             35                  40                  45 ggg ccg gag ggc tcg atc cag ggc gcg atc cgg ggc acc ggg ggg gcg     192
Gly Pro Glu Gly Ser Ile Gln Gly Ala Ile Arg Gly Thr Gly Gly Ala
         50                  55                  60 agc ccg aac tac gcc atc ttc tac gtg cag gtg gcc gac gtg gcg gac     240
Ser Pro Asn Tyr Ala Ile Phe Tyr Val Gln Val Ala Asp Val Ala Asp
 65                  70                  75                  80 gcc tgc cgg cgc gcg gag gcg gcc ggt ggc aag gtg ctg gtg ccg gcg     288
Ala Cys Arg Arg Ala Glu Ala Ala Gly Gly Lys Val Leu Val Pro Ala
                 85                  90                  95
```

```
aag tcc acc gac aac ggg ctc acc ttc gcc cac ctg ctc gac ccg gtc     336
Lys Ser Thr Asp Asn Gly Leu Thr Phe Ala His Leu Leu Asp Pro Val
            100                 105                 110 ggc aac cac ttc ggc gtc ttc gcc ccg ccg ccg gcc gcc tga             378
Gly Asn His Phe Gly Val Phe Ala Pro Pro Pro Ala Ala *
        115                 120                 125

<210> SEQ ID NO 72
<211> LENGTH: 125
<212> TYPE: PRT
<213> ORGANISM: Bacteria

<400> SEQUENCE: 72

Met Ser Thr Thr Thr Asn Ala Val Thr Trp Phe Glu Val Gly Thr Asp
1               5                   10                  15

Arg Pro Glu Glu Thr Gly Arg Phe Tyr Ala Asp Leu Phe Gly Trp Ala
            20                  25                  30

Phe Gly Glu Gln Gly Thr Pro Glu Ala Ser Tyr Arg Val Thr Glu Pro
        35                  40                  45

Gly Pro Glu Gly Ser Ile Gln Gly Ala Ile Arg Gly Thr Gly Gly Ala
    50                  55                  60

Ser Pro Asn Tyr Ala Ile Phe Tyr Val Gln Val Ala Asp Val Ala Asp
65                  70                  75                  80

Ala Cys Arg Arg Ala Glu Ala Ala Gly Gly Lys Val Leu Val Pro Ala
                85                  90                  95

Lys Ser Thr Asp Asn Gly Leu Thr Phe Ala His Leu Leu Asp Pro Val
            100                 105                 110

Gly Asn His Phe Gly Val Phe Ala Pro Pro Pro Ala Ala
        115                 120                 125

<210> SEQ ID NO 73
<211> LENGTH: 741
<212> TYPE: DNA
<213> ORGANISM: Bacteria
<220> FEATURE:
<221> NAME/KEY: CDS
<222> LOCATION: (1)...(741)

<400> SEQUENCE: 73 gtg cgg cga cgg cct gaa tcg tgg ggc cgg aag ccg gag ccg ccg tcc     48
Val Arg Arg Arg Pro Glu Ser Trp Gly Arg Lys Pro Glu Pro Pro Ser
1               5                   10                  15 gcc ccg gcg agg ttg ccg ggg cgg acg gcg tac ggt cac ttg ccg gcc     96
Ala Pro Ala Arg Leu Pro Gly Arg Thr Ala Tyr Gly His Leu Pro Ala
            20                  25                  30 gag cct ccg cga ccg ccc ggg ccg gcc agg acg ccg gcc tcg gcg gcc     144
Glu Pro Pro Arg Pro Pro Gly Pro Ala Arg Thr Pro Ala Ser Ala Ala
        35                  40                  45 gcg gtg atc gcg tcc gcc tgc tcc tgg gtg agc ttg ccg tcc tcg acc     192
Ala Val Ile Ala Ser Ala Cys Ser Trp Val Ser Leu Pro Ser Ser Thr
    50                  55                  60 gcc tgc gcc agg cgc tcc ttc agc gcg gcc tgc cgg tcg gcg gag tca     240
Ala Cys Ala Arg Arg Ser Phe Ser Ala Ala Cys Arg Ser Ala Glu Ser
65                  70                  75                  80 ccc cgc tcg ggc cgg tcg gcc ggc ttc tgc gcc tcg cgc acc ttc tcc     288
Pro Arg Ser Gly Arg Ser Ala Gly Phe Cys Ala Ser Arg Thr Phe Ser
                85                  90                  95 agc gcg gcc gtc acc ttg tcg gtg tcg acg ccc agc tcc ttg gcc agg     336
Ser Ala Ala Val Thr Leu Ser Val Ser Thr Pro Ser Ser Leu Ala Arg
            100                 105                 110
```

-continued

```
gcc tcg gcg aac tcc gcc tgc cgc tcg gcc cgc tgc tgc cgc tcg        384
Ala Ser Ala Asn Ser Ala Cys Arg Ser Ala Arg Cys Cys Cys Arg Ser
        115                 120                 125 tca ctg ctg ctg ccg ctc tcg ctc gcg ctg gcg ctc ggc gtc gcg gtg    432
Ser Leu Leu Leu Pro Leu Ser Leu Ala Leu Ala Leu Gly Val Ala Val
130                 135                 140 ccg ccg tcc gcg gcg aac gcg acc gtc ggc gcc gcg atc ccc acg ccg    480
Pro Pro Ser Ala Ala Asn Ala Thr Val Gly Ala Ala Ile Pro Thr Pro
145                 150                 155                 160 aga acc ccg gcc gcg gcc agg ccg gcc agc agg tgc ttc ttc ttc atg    528
Arg Thr Pro Ala Ala Ala Arg Pro Ala Ser Arg Cys Phe Phe Phe Met
                165                 170                 175 gtg ccg gac atg ctg tcc tcc gtc gga tcg gtg gtt ggt gcg atg acc    576
Val Pro Asp Met Leu Ser Ser Val Gly Ser Val Val Gly Ala Met Thr
            180                 185                 190 tca ccc gac ggt gac cag ccc ggc tgg ggg aaa gcc gtg gtg aac ctg    624
Ser Pro Asp Gly Asp Gln Pro Gly Trp Gly Lys Ala Val Val Asn Leu
        195                 200                 205 tca gcg agc tgg caa tcc gcc cgc cgc gcc gga caa acg ggt tgc cgg    672
Ser Ala Ser Trp Gln Ser Ala Arg Arg Ala Gly Gln Thr Gly Cys Arg
    210                 215                 220 ggc gcc cgc cgc cgg tca ggg ttg gtg gtc ggc agg ccc cac cgg ggc    720
Gly Ala Arg Arg Arg Ser Gly Leu Val Val Gly Arg Pro His Arg Gly
225                 230                 235                 240 gga gca gac gac gga agg tga                                        741
Gly Ala Asp Asp Gly Arg  *
                245
```

<210> SEQ ID NO 74
<211> LENGTH: 246
<212> TYPE: PRT
<213> ORGANISM: Bacteria

<400> SEQUENCE: 74

```
Val Arg Arg Arg Pro Glu Ser Trp Gly Arg Lys Pro Glu Pro Pro Ser
1               5                   10                  15

Ala Pro Ala Arg Leu Pro Gly Arg Thr Ala Tyr Gly His Leu Pro Ala
            20                  25                  30

Glu Pro Pro Arg Pro Pro Gly Pro Ala Arg Thr Pro Ala Ser Ala Ala
        35                  40                  45

Ala Val Ile Ala Ser Ala Cys Ser Trp Val Ser Leu Pro Ser Ser Thr
    50                  55                  60

Ala Cys Ala Arg Arg Ser Phe Ser Ala Ala Cys Arg Ser Ala Glu Ser
65                  70                  75                  80

Pro Arg Ser Gly Arg Ser Ala Gly Phe Cys Ala Ser Arg Thr Phe Ser
                85                  90                  95

Ser Ala Ala Val Thr Leu Ser Val Ser Thr Pro Ser Ser Leu Ala Arg
            100                 105                 110

Ala Ser Ala Asn Ser Ala Cys Arg Ser Ala Arg Cys Cys Cys Arg Ser
        115                 120                 125

Ser Leu Leu Leu Pro Leu Ser Leu Ala Leu Ala Leu Gly Val Ala Val
    130                 135                 140

Pro Pro Ser Ala Ala Asn Ala Thr Val Gly Ala Ala Ile Pro Thr Pro
145                 150                 155                 160

Arg Thr Pro Ala Ala Ala Arg Pro Ala Ser Arg Cys Phe Phe Phe Met
                165                 170                 175

Val Pro Asp Met Leu Ser Ser Val Gly Ser Val Val Gly Ala Met Thr
            180                 185                 190
```

| | | | | | | | | | | | | |
|---|---|---|---|---|---|---|---|---|---|---|---|---|
| Ser | Pro | Asp | Gly | Asp | Gln | Pro | Gly | Trp | Gly | Lys | Ala | Val | Val | Asn | Leu |
| | | | 195 | | | | 200 | | | | 205 | | | | |

Ser Ala Ser Trp Gln Ser Ala Arg Arg Ala Gly Gln Thr Gly Cys Arg
    210                 215                 220

Gly Ala Arg Arg Arg Ser Gly Leu Val Val Gly Arg Pro His Arg Gly
225                 230                 235                 240

Gly Ala Asp Asp Gly Arg
            245

<210> SEQ ID NO 75
<211> LENGTH: 891
<212> TYPE: DNA
<213> ORGANISM: Bacteria
<220> FEATURE:
<221> NAME/KEY: CDS
<222> LOCATION: (1)...(891)

<400> SEQUENCE: 75

| gtg atc ctc gtg gcg ttg gcg aag atc cgg gaa gtc ccg ctc acc ggg | 48 |
|---|---|
| Val Ile Leu Val Ala Leu Ala Lys Ile Arg Glu Val Pro Leu Thr Gly | |
| 1               5                   10                  15     | |

| gcg gac gcc ggc ccg tac ggc gtc acc gtc ggc ccc gac ggc gcg ctc | 96 |
|---|---|
| Ala Asp Ala Gly Pro Tyr Gly Val Thr Val Gly Pro Asp Gly Ala Leu | |
|             20                  25                  30         | |

| tgg ctg acg ctg gtc cac gcc ggc gcg gtc gcc cgg gtg ggc gcg gac | 144 |
|---|---|
| Trp Leu Thr Leu Val His Ala Gly Ala Val Ala Arg Val Gly Ala Asp | |
|         35                  40                  45             | |

| ggc gac ctg cgc acc tgg cag gtg gcg gcc gac agc cgg ccg ctg atc | 192 |
|---|---|
| Gly Asp Leu Arg Thr Trp Gln Val Ala Ala Asp Ser Arg Pro Leu Ile | |
|     50                  55                  60                 | |

| gtc acg ccg ggc ccc gac ggc gcc ctc tgg ttc acc cgc tcc ggc gac | 240 |
|---|---|
| Val Thr Pro Gly Pro Asp Gly Ala Leu Trp Phe Thr Arg Ser Gly Asp | |
| 65                  70                  75                  80 | |

| gac cgg atc ggc cgg atc acc acc gac ggg gag cag agc gcc gtc gcg | 288 |
|---|---|
| Asp Arg Ile Gly Arg Ile Thr Thr Asp Gly Glu Gln Ser Ala Val Ala | |
|                 85                  90                  95     | |

| ctc ccg ccc ggg agc ggc ccc tgc ggc atc gcc gcc ggt ccc gac ggc | 336 |
|---|---|
| Leu Pro Pro Gly Ser Gly Pro Cys Gly Ile Ala Ala Gly Pro Asp Gly | |
|             100                 105                 110        | |

| gcc ctc tgg tac gcg gcg atg acc gcc gac gcg gtc ggc cgc gtc acc | 384 |
|---|---|
| Ala Leu Trp Tyr Ala Ala Met Thr Ala Asp Ala Val Gly Arg Val Thr | |
|         115                 120                 125            | |

| acc gac ggg aag gtg acg cag ttt ccg ctg ccg gtg agc ggc ggc ttc | 432 |
|---|---|
| Thr Asp Gly Lys Val Thr Gln Phe Pro Leu Pro Val Ser Gly Gly Phe | |
|     130                 135                 140                | |

| gcc tcg atg gtc gcc gcc ggc ccg gac gag gcc gtc tgg ttc acg ctc | 480 |
|---|---|
| Ala Ser Met Val Ala Ala Gly Pro Asp Glu Ala Val Trp Phe Thr Leu | |
| 145                 150                 155                 160 | |

| aac cag gcg aac gcg gtc ggc cgg atc ggc acg gac ggc gcg gtg gcg | 528 |
|---|---|
| Asn Gln Ala Asn Ala Val Gly Arg Ile Gly Thr Asp Gly Ala Val Ala | |
|                 165                 170                 175    | |

| ctg cac cca ctg ccg acc gag ggc gcc gcc ccg gtg ggc atc acg gcc | 576 |
|---|---|
| Leu His Pro Leu Pro Thr Glu Gly Ala Ala Pro Val Gly Ile Thr Ala | |
|             180                 185                 190        | |

| gga gcg gac ggc gcg ctc tgg ttc gtc gag atc ggc gcc ggc cag ctc | 624 |
|---|---|
| Gly Ala Asp Gly Ala Leu Trp Phe Val Glu Ile Gly Ala Gly Gln Leu | |
|         195                 200                 205            | |

| ggc cgg atc acc ccg gac ggg cgg atc gac gag tac ccg ctg ccg gac | 672 |
|---|---|
| Gly Arg Ile Thr Pro Asp Gly Arg Ile Asp Glu Tyr Pro Leu Pro Asp | |
|     210                 215                 220                | |

```
cgg gcg gcc cgg ccg cac gcg atc gtc gcc gac ccg gcg ggc ggc tgc      720
Arg Ala Ala Arg Pro His Ala Ile Val Ala Asp Pro Ala Gly Gly Cys
225                 230                 235                 240 tgg ttc acc gag tgg ggc ggc aac cgg atc ggc cac gtc gcc ccg gac      768
Trp Phe Thr Glu Trp Gly Gly Asn Arg Ile Gly His Val Ala Pro Asp
                245                 250                 255 ggc acg atc gtc acc cac gac ctt ccg acc ccg gcc gcc gag ccg cac      816
Gly Thr Ile Val Thr His Asp Leu Pro Thr Pro Ala Ala Glu Pro His
                260                 265                 270 ggc atc acc gtc gcc ccc gac ggc acg gtc tgg gcc gcc ctg gaa acg      864
Gly Ile Thr Val Ala Pro Asp Gly Thr Val Trp Ala Ala Leu Glu Thr
            275                 280                 285 ggc gct ctg gcc cac ctg acg ccc tga                                   891
Gly Ala Leu Ala His Leu Thr Pro *
        290                 295

<210> SEQ ID NO 76
<211> LENGTH: 125
<212> TYPE: PRT
<213> ORGANISM: Bacteria

<400> SEQUENCE: 76

Met Ser Thr Thr Thr Asn Ala Val Thr Trp Phe Glu Val Gly Thr Asp
1               5                   10                  15

Arg Pro Glu Glu Thr Gly Arg Phe Tyr Ala Asp Leu Phe Gly Trp Ala
                20                  25                  30

Phe Gly Glu Gln Gly Thr Pro Glu Ala Ser Tyr Arg Val Thr Glu Pro
            35                  40                  45

Gly Pro Glu Gly Ser Ile Gln Gly Ala Ile Arg Gly Thr Gly Gly Ala
        50                  55                  60

Ser Pro Asn Tyr Ala Ile Phe Tyr Val Gln Val Ala Asp Val Ala Asp
65                  70                  75                  80

Ala Cys Arg Arg Ala Glu Ala Ala Gly Gly Lys Val Leu Val Pro Ala
                85                  90                  95

Lys Ser Thr Asp Asn Gly Leu Thr Phe Ala His Leu Leu Asp Pro Val
            100                 105                 110

Gly Asn His Phe Gly Val Phe Ala Pro Pro Ala Ala
        115                 120         125

<210> SEQ ID NO 77
<211> LENGTH: 1086
<212> TYPE: DNA
<213> ORGANISM: Bacteria
<220> FEATURE:
<221> NAME/KEY: CDS
<222> LOCATION: (1)...(1086)

<400> SEQUENCE: 77 gtg acc gcg gcg ggc ccc gag cgc ctc cac cgg cgc ggc ggc ggc ctc       48
Val Thr Ala Ala Gly Pro Glu Arg Leu His Arg Arg Gly Gly Gly Leu
1               5                   10                  15 ccc cgg ccg acc gga gca ggc gtc cca cgc tcg gcg gag tgg gcc gac       96
Pro Arg Pro Thr Gly Ala Gly Val Pro Arg Ser Ala Glu Trp Ala Asp
                20                  25                  30 cgg tac gtg ggc ggc gcc ccg ccg cga cta ggc tct gcc gct gtg tcc      144
Arg Tyr Val Gly Gly Ala Pro Pro Arg Leu Gly Ser Ala Ala Val Ser
            35                  40                  45 gac cat gcc agc acg act ccc gcc acc gcc gta cga ccg ccg gtg ctg      192
Asp His Ala Ser Thr Thr Pro Ala Thr Ala Val Arg Pro Pro Val Leu
        50                  55                  60
```

```
tgc ccc ggc gac acg gtg atg ctg gtg tcg ccg tcg ggg ccg acc cgg      240
Cys Pro Gly Asp Thr Val Met Leu Val Ser Pro Ser Gly Pro Thr Arg
 65              70                  75                  80 ccc gag cgg gtg gcc cgg ggc atc gag ctg ctc acc ggc tgg ggg ctg      288
Pro Glu Arg Val Ala Arg Gly Ile Glu Leu Leu Thr Gly Trp Gly Leu
                 85                  90                  95 cgg ccg gtg ctg gcg ccg aac gcg tac gcc cgg cag ggt tac ctg gcc      336
Arg Pro Val Leu Ala Pro Asn Ala Tyr Ala Arg Gln Gly Tyr Leu Ala
            100                 105                 110 ggc gcg gac gag ctg cgc gcc gcc gac ctg aac gcg gcg ttc gcc gac      384
Gly Ala Asp Glu Leu Arg Ala Ala Asp Leu Asn Ala Ala Phe Ala Asp
        115                 120                 125 ccc gag gtg cgc ggg gtg atc tgc acg cgc ggc ggg tac ggc gcg cag      432
Pro Glu Val Arg Gly Val Ile Cys Thr Arg Gly Gly Tyr Gly Ala Gln
    130                 135                 140 cgg atc gtc gac gcg atc gac atg gcc gcc gta cgc cgg gac ccg aag      480
Arg Ile Val Asp Ala Ile Asp Met Ala Ala Val Arg Arg Asp Pro Lys
145                 150                 155                 160 gtg gtc gcc ggg ttc tcc gac atc acc gcg ctg cag ctc gcg ctg tgg      528
Val Val Ala Gly Phe Ser Asp Ile Thr Ala Leu Gln Leu Ala Leu Trp
                165                 170                 175 cgg ggc gcc cgg ctg gcc ggc gtg cac ggc ccc ggg gcg gcg tgg ctg      576
Arg Gly Ala Arg Leu Ala Gly Val His Gly Pro Gly Ala Ala Trp Leu
            180                 185                 190 gac gag cgc act ccg ctg cgg tcg gcc gag tcg ctg cac gcc gcc ctg      624
Asp Glu Arg Thr Pro Leu Arg Ser Ala Glu Ser Leu His Ala Ala Leu
        195                 200                 205 atg acc acc gaa ccg gtg acg gtg acc gcc gtc gcc gag gag gag acg      672
Met Thr Thr Glu Pro Val Thr Val Thr Ala Val Ala Glu Glu Glu Thr
    210                 215                 220 ttc ccg gtg cgg gtg ccc ggg cgg gcc acc ggc ccg ctg ctg ggc ggc      720
Phe Pro Val Arg Val Pro Gly Arg Ala Thr Gly Pro Leu Leu Gly Gly
225                 230                 235                 240 aac ctc tgc ctg gtc gtg gcg tcg ctg ggc acc ccg gac atg ccg gac      768
Asn Leu Cys Leu Val Val Ala Ser Leu Gly Thr Pro Asp Met Pro Asp
                245                 250                 255 ctg acc ggc gcg atc ctg ttg atc gag gac gtg cag gag ccg ccg tac      816
Leu Thr Gly Ala Ile Leu Leu Ile Glu Asp Val Gln Glu Pro Pro Tyr
            260                 265                 270 aag gtg gac cgg atg ctc acc cag ttg cgc cgg gcc ggc gcg ctg gac      864
Lys Val Asp Arg Met Leu Thr Gln Leu Arg Arg Ala Gly Ala Leu Asp
        275                 280                 285 ggg ctg gcc ggg gtg gcg gtc ggc cag ttc acc ggc tgc gcc gac ggc      912
Gly Leu Ala Gly Val Ala Val Gly Gln Phe Thr Gly Cys Ala Asp Gly
    290                 295                 300 tgg tcg acc agc gtc gcc gac gtg ctc tcc gag cgc ctc ggc gac ctc      960
Trp Ser Thr Ser Val Ala Asp Val Leu Ser Glu Arg Leu Gly Asp Leu
305                 310                 315                 320 ggc gtc ccg gtc ctc ggc ggc ctg ccc gtc ggc cac ggc gtc ggc cag     1008
Gly Val Pro Val Leu Gly Gly Leu Pro Val Gly His Gly Val Gly Gln
                325                 330                 335 ctc acc gtc ccg gtc ggc acc gac gcg acc ctc gac acg acg acg gcc     1056
Leu Thr Val Pro Val Gly Thr Asp Ala Thr Leu Asp Thr Thr Thr Ala
            340                 345                 350 acc ctc acg gtc acc ccc gcc gtc cgc tga                             1086
Thr Leu Thr Val Thr Pro Ala Val Arg  *
        355                 360

<210> SEQ ID NO 78
```

<211> LENGTH: 361
<212> TYPE: PRT
<213> ORGANISM: Bacteria

<400> SEQUENCE: 78

```
Val Thr Ala Ala Gly Pro Glu Arg Leu His Arg Arg Gly Gly Gly Leu
 1               5                  10                  15
Pro Arg Pro Thr Gly Ala Gly Val Pro Arg Ser Ala Glu Trp Ala Asp
             20                  25                  30
Arg Tyr Val Gly Gly Ala Pro Pro Arg Leu Gly Ser Ala Ala Val Ser
         35                  40                  45
Asp His Ala Ser Thr Thr Pro Ala Thr Ala Val Arg Pro Pro Val Leu
     50                  55                  60
Cys Pro Gly Asp Thr Val Met Leu Val Ser Pro Ser Gly Pro Thr Arg
 65                  70                  75                  80
Pro Glu Arg Val Ala Arg Gly Ile Glu Leu Leu Thr Gly Trp Gly Leu
                 85                  90                  95
Arg Pro Val Leu Ala Pro Asn Ala Tyr Ala Arg Gln Gly Tyr Leu Ala
            100                 105                 110
Gly Ala Asp Glu Leu Arg Ala Ala Asp Leu Asn Ala Ala Phe Ala Asp
        115                 120                 125
Pro Glu Val Arg Gly Val Ile Cys Thr Arg Gly Gly Tyr Gly Ala Gln
    130                 135                 140
Arg Ile Val Asp Ala Ile Asp Met Ala Ala Val Arg Arg Asp Pro Lys
145                 150                 155                 160
Val Val Ala Gly Phe Ser Asp Ile Thr Ala Leu Gln Leu Ala Leu Trp
                165                 170                 175
Arg Gly Ala Arg Leu Ala Gly Val His Gly Pro Gly Ala Ala Trp Leu
            180                 185                 190
Asp Glu Arg Thr Pro Leu Arg Ser Ala Glu Ser Leu His Ala Ala Leu
        195                 200                 205
Met Thr Thr Glu Pro Val Thr Val Thr Ala Val Ala Glu Glu Glu Thr
    210                 215                 220
Phe Pro Val Arg Val Pro Gly Arg Ala Thr Gly Pro Leu Leu Gly Gly
225                 230                 235                 240
Asn Leu Cys Leu Val Val Ala Ser Leu Gly Thr Pro Asp Met Pro Asp
                245                 250                 255
Leu Thr Gly Ala Ile Leu Leu Ile Glu Asp Val Gln Glu Pro Pro Tyr
            260                 265                 270
Lys Val Asp Arg Met Leu Thr Gln Leu Arg Arg Ala Gly Ala Leu Asp
        275                 280                 285
Gly Leu Ala Gly Val Ala Val Gly Gln Phe Thr Gly Cys Ala Asp Gly
    290                 295                 300
Trp Ser Thr Ser Val Ala Asp Val Leu Ser Glu Arg Leu Gly Asp Leu
305                 310                 315                 320
Gly Val Pro Val Leu Gly Gly Leu Pro Val Gly His Gly Val Gly Gln
                325                 330                 335
Leu Thr Val Pro Val Gly Thr Asp Ala Thr Leu Asp Thr Thr Thr Ala
            340                 345                 350
Thr Leu Thr Val Thr Pro Ala Val Arg
        355                 360
```

<210> SEQ ID NO 79
<211> LENGTH: 861
<212> TYPE: DNA

<213> ORGANISM: Bacteria
<220> FEATURE:
<221> NAME/KEY: CDS
<222> LOCATION: (1)...(861)

<400> SEQUENCE: 79

| | | | | | | | | | | | | | | | | |
|---|---|---|---|---|---|---|---|---|---|---|---|---|---|---|---|---|
| gtg | gga | cgc | ctg | ctc | cgg | tcg | gcc | ggg | gga | ggc | cgc | cgc | cgc | gcc | ggt | 48 |
| Val | Gly | Arg | Leu | Leu | Arg | Ser | Ala | Gly | Gly | Gly | Arg | Arg | Arg | Ala | Gly | |
| 1 | | | | 5 | | | | | 10 | | | | | 15 | | |
| gga | ggc | gct | cgg | ggc | ccg | ccg | cgg | tca | ccg | gct | agc | ctc | gac | gtc | gtg | 96 |
| Gly | Gly | Ala | Arg | Gly | Pro | Pro | Arg | Ser | Pro | Ala | Ser | Leu | Asp | Val | Val | |
| | | | 20 | | | | | 25 | | | | | 30 | | | |
| gct | acc | gcg | ttg | gtg | atc | gag | aac | gac | ccg | acc | gac | gac | gtc | cgc | cgg | 144 |
| Ala | Thr | Ala | Leu | Val | Ile | Glu | Asn | Asp | Pro | Thr | Asp | Asp | Val | Arg | Arg | |
| | | 35 | | | | | 40 | | | | | 45 | | | | |
| ctc | ggc | gag | tgg | ctg | acc | gag | gcg | ggt | ctc | gac | ctg | tgg | gtc | gtc | cgc | 192 |
| Leu | Gly | Glu | Trp | Leu | Thr | Glu | Ala | Gly | Leu | Asp | Leu | Trp | Val | Val | Arg | |
| | 50 | | | | | 55 | | | | | 60 | | | | | |
| gcg | cac | gcc | ggc | gat | cag | ctc | ccc | gcc | gac | ctg | gag | ggc | tac | tcc | gcg | 240 |
| Ala | His | Ala | Gly | Asp | Gln | Leu | Pro | Ala | Asp | Leu | Glu | Gly | Tyr | Ser | Ala | |
| 65 | | | | | 70 | | | | | 75 | | | | | 80 | |
| ctg | gtg | gtg | ctg | ggc | ggc | gag | cag | cag | gcg | tac | ccg | ctg | ccc | gac | ggc | 288 |
| Leu | Val | Val | Leu | Gly | Gly | Glu | Gln | Gln | Ala | Tyr | Pro | Leu | Pro | Asp | Gly | |
| | | | | 85 | | | | | 90 | | | | | 95 | | |
| tcg | ccc | ggc | gcg | ccc | tgg | ttc | ccc | gcc | gtc | gag | ggg | ctg | ctc | cgc | aag | 336 |
| Ser | Pro | Gly | Ala | Pro | Trp | Phe | Pro | Ala | Val | Glu | Gly | Leu | Leu | Arg | Lys | |
| | | | 100 | | | | | 105 | | | | | 110 | | | |
| gcc | gtc | cgg | gac | cgg | gtg | ccc | acc | ctg | ggc | atc | tgc | ctg | ggc | gcg | cag | 384 |
| Ala | Val | Arg | Asp | Arg | Val | Pro | Thr | Leu | Gly | Ile | Cys | Leu | Gly | Ala | Gln | |
| | | 115 | | | | | 120 | | | | | 125 | | | | |
| ttg | ctg | gcg | acc | gcc | cac | gcc | ggc | gag | gtc | gag | cgc | agc | gcg | tcc | ggg | 432 |
| Leu | Leu | Ala | Thr | Ala | His | Ala | Gly | Glu | Val | Glu | Arg | Ser | Ala | Ser | Gly | |
| | 130 | | | | | 135 | | | | | 140 | | | | | |
| ccg | gag | gtc | ggg | ccc | ggt | gtg | gtc | ggc | aag | cgg | gac | gcc | gcc | gac | gcc | 480 |
| Pro | Glu | Val | Gly | Pro | Gly | Val | Val | Gly | Lys | Arg | Asp | Ala | Ala | Asp | Ala | |
| 145 | | | | | 150 | | | | | 155 | | | | | 160 | |
| gac | ccg | ctg | ttc | cgc | tac | gtc | ccg | ctg | atc | ccc | gac | gtg | ctc | cag | tgg | 528 |
| Asp | Pro | Leu | Phe | Arg | Tyr | Val | Pro | Leu | Ile | Pro | Asp | Val | Leu | Gln | Trp | |
| | | | | 165 | | | | | 170 | | | | | 175 | | |
| cac | gcc | gac | gag | atc | acc | gag | ctg | ccc | cgg | ggc | gcc | acc | ctg | ctg | gcc | 576 |
| His | Ala | Asp | Glu | Ile | Thr | Glu | Leu | Pro | Arg | Gly | Ala | Thr | Leu | Leu | Ala | |
| | | | 180 | | | | | 185 | | | | | 190 | | | |
| gcc | tcc | acc | cgc | tac | ccg | cac | cag | gcg | ttc | cgc | ctc | ggc | gac | cgg | gcc | 624 |
| Ala | Ser | Thr | Arg | Tyr | Pro | His | Gln | Ala | Phe | Arg | Leu | Gly | Asp | Arg | Ala | |
| | | 195 | | | | | 200 | | | | | 205 | | | | |
| tgg | ggg | ctg | cag | ttc | cac | atc | gag | tgc | gac | acc | gcg | atg | atc | gcc | gac | 672 |
| Trp | Gly | Leu | Gln | Phe | His | Ile | Glu | Cys | Asp | Thr | Ala | Met | Ile | Ala | Asp | |
| 210 | | | | | 215 | | | | | 220 | | | | | | |
| tgg | gcc | acc | gac | tcg | acg | ctg | ctg | gcc | gag | ctg | ggc | tac | gac | ccg | gac | 720 |
| Trp | Ala | Thr | Asp | Ser | Thr | Leu | Leu | Ala | Glu | Leu | Gly | Tyr | Asp | Pro | Asp | |
| 225 | | | | | 230 | | | | | 235 | | | | | 240 | |
| ctg | gtg | gtg | gcg | gcc | tgc | cac | gcg | gtg | atg | gtc | gac | gtc | gag | gag | gtc | 768 |
| Leu | Val | Val | Ala | Ala | Cys | His | Ala | Val | Met | Val | Asp | Val | Glu | Glu | Val | |
| | | | | 245 | | | | | 250 | | | | | 255 | | |
| tgg | cag | ccg | ttc | gcc | gcc | cgg | ttc | gcc | gcg | ctg | gct | ctc | ggc | gag | ctg | 816 |
| Trp | Gln | Pro | Phe | Ala | Ala | Arg | Phe | Ala | Ala | Leu | Ala | Leu | Gly | Glu | Leu | |
| | | 260 | | | | | 265 | | | | | 270 | | | | |
| gac | gac | gac | acg | tcc | cgc | cgc | agc | ctg | ccg | ctg | ctc | ggg | cag | tga | | 861 |
| Asp | Asp | Asp | Thr | Ser | Arg | Arg | Ser | Leu | Pro | Leu | Leu | Gly | Gln | * | | |
| | 275 | | | | | 280 | | | | | 285 | | | | | |

<210> SEQ ID NO 80
<211> LENGTH: 286
<212> TYPE: PRT
<213> ORGANISM: Bacteria

<400> SEQUENCE: 80

```
Val Gly Arg Leu Leu Arg Ser Ala Gly Gly Arg Arg Ala Gly
 1               5                  10                  15

Gly Gly Ala Arg Gly Pro Pro Arg Ser Pro Ala Ser Leu Asp Val Val
                20                  25                  30

Ala Thr Ala Leu Val Ile Glu Asn Asp Pro Thr Asp Val Arg Arg
            35                  40                  45

Leu Gly Glu Trp Leu Thr Glu Ala Gly Leu Asp Leu Trp Val Val Arg
    50                  55                  60

Ala His Ala Gly Asp Gln Leu Pro Ala Asp Leu Glu Gly Tyr Ser Ala
65                  70                  75                  80

Leu Val Val Leu Gly Glu Gln Gln Ala Tyr Pro Leu Pro Asp Gly
                85                  90                  95

Ser Pro Gly Ala Pro Trp Phe Pro Ala Val Glu Gly Leu Leu Arg Lys
                100                 105                 110

Ala Val Arg Asp Arg Val Pro Thr Leu Gly Ile Cys Leu Gly Ala Gln
            115                 120                 125

Leu Leu Ala Thr Ala His Ala Gly Glu Val Glu Arg Ser Ala Ser Gly
    130                 135                 140

Pro Glu Val Gly Pro Gly Val Val Gly Lys Arg Asp Ala Ala Asp Ala
145                 150                 155                 160

Asp Pro Leu Phe Arg Tyr Val Pro Leu Ile Pro Asp Val Leu Gln Trp
                165                 170                 175

His Ala Asp Glu Ile Thr Glu Leu Pro Arg Gly Ala Thr Leu Leu Ala
                180                 185                 190

Ala Ser Thr Arg Tyr Pro His Gln Ala Phe Arg Leu Gly Asp Arg Ala
            195                 200                 205

Trp Gly Leu Gln Phe His Ile Glu Cys Asp Thr Ala Met Ile Ala Asp
    210                 215                 220

Trp Ala Thr Asp Ser Thr Leu Leu Ala Glu Leu Gly Tyr Asp Pro Asp
225                 230                 235                 240

Leu Val Val Ala Ala Cys His Ala Val Met Val Asp Val Glu Glu Val
                245                 250                 255

Trp Gln Pro Phe Ala Ala Arg Phe Ala Ala Leu Ala Leu Gly Glu Leu
                260                 265                 270

Asp Asp Asp Thr Ser Arg Arg Ser Leu Pro Leu Leu Gly Gln
            275                 280                 285
```

<210> SEQ ID NO 81
<211> LENGTH: 3033
<212> TYPE: DNA
<213> ORGANISM: Bacteria
<220> FEATURE:
<221> NAME/KEY: CDS
<222> LOCATION: (1)...(3033)

<400> SEQUENCE: 81

```
gtg atg agc cgg ccg acc agc gcc gcc gga cgg ctc gcc cgc tac ggt    48
Val Met Ser Arg Pro Thr Ser Ala Ala Gly Arg Leu Ala Arg Tyr Gly
 1               5                  10                  15 ttc ggc atc gtc ggc ggc gac ggc gcc acc cgc gcc gcc gac ctg ctc    96
Phe Gly Ile Val Gly Gly Asp Gly Ala Thr Arg Ala Ala Asp Leu Leu
```

-continued

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |

```
ggc ccc gac ggg ctg ggc ctg tgg cgg ccg gac gtg cag gag ccg acc       144
Gly Pro Asp Gly Leu Gly Leu Trp Arg Pro Asp Val Gln Glu Pro Thr
         35                  40                  45 gac gac cgc gcg gcg gag ctc ctc gcc gcg ctc tcc cgg gcc gcc gac       192
Asp Asp Arg Ala Ala Glu Leu Leu Ala Ala Leu Ser Arg Ala Ala Asp
 50                  55                  60 ccg gac ctg gcg ctg cgc cag ctc cac cgc atc gtc gag gcg gag cgc       240
Pro Asp Leu Ala Leu Arg Gln Leu His Arg Ile Val Glu Ala Glu Arg
 65                  70                  75                  80 cgg gcc gcc ggt ccg gcg gcc acc ggt tcg gcg ctg gtg gag gcg ctc       288
Arg Ala Ala Gly Pro Ala Ala Thr Gly Ser Ala Leu Val Glu Ala Leu
                 85                  90                  95 gcg gac gac ccg ggg ctg cgc cgc cgg ctg atc gcc gtc ctc ggc gcc       336
Ala Asp Asp Pro Gly Leu Arg Arg Arg Leu Ile Ala Val Leu Gly Ala
            100                 105                 110 tcc tcg gcg ctg ggc gac cac ctg gtc gcc aac ccc gac cag tgg ccg       384
Ser Ser Ala Leu Gly Asp His Leu Val Ala Asn Pro Asp Gln Trp Pro
        115                 120                 125 gcc ctg cgg acc gcc ccg gac ggg ctc gcg ccg acc gcg gag ggc cgg       432
Ala Leu Arg Thr Ala Pro Asp Gly Leu Ala Pro Thr Ala Glu Gly Arg
    130                 135                 140 ctc gac ctg tcc ggc gac ggg cag ccg gtc gcg gtg ctg cgc aag gcg       480
Leu Asp Leu Ser Gly Asp Gly Gln Pro Val Ala Val Leu Arg Lys Ala
145                 150                 155                 160 tac cgg ctg gcg ctg ctg cgg atc gcg gcg gcc gac ctg acc ggc gac       528
Tyr Arg Leu Ala Leu Leu Arg Ile Ala Ala Ala Asp Leu Thr Gly Asp
                165                 170                 175 cgg ggc ctg gag cag acg atg gcc gcg ctc tcc gcg ttg gcc gac gcg       576
Arg Gly Leu Glu Gln Thr Met Ala Ala Leu Ser Ala Leu Ala Asp Ala
            180                 185                 190 acc ctg gcg gcg gcg tac gag atc gcc gtc ggc gag ctg ccg gag ggc       624
Thr Leu Ala Ala Ala Tyr Glu Ile Ala Val Gly Glu Leu Pro Glu Gly
        195                 200                 205 acg ccc cgg ccc cgg ctc gcc gtc gtg gcg atg ggc aag tgc ggc ggt       672
Thr Pro Arg Pro Arg Leu Ala Val Val Ala Met Gly Lys Cys Gly Gly
    210                 215                 220 gac gag ctg aac tac gtc tcc gac gtc gac gtg atc ttc gtg gcc gcc       720
Asp Glu Leu Asn Tyr Val Ser Asp Val Asp Val Ile Phe Val Ala Ala
225                 230                 235                 240 gag gac gac gac ctc gcc gcg gcc acg acg gtc gcc acc cgg ctg atc       768
Glu Asp Asp Asp Leu Ala Ala Ala Thr Thr Val Ala Thr Arg Leu Ile
                245                 250                 255 cac gtc tgc ggg ctg gtc gcc tgg ccg gtc gac gcc gcc ctg cgg ccc       816
His Val Cys Gly Leu Val Ala Trp Pro Val Asp Ala Ala Leu Arg Pro
            260                 265                 270 gag ggc aat cgt ggc ccg ctg gtg cgc acc ctg gcc agc cac ctc gcc       864
Glu Gly Asn Arg Gly Pro Leu Val Arg Thr Leu Ala Ser His Leu Ala
        275                 280                 285 tac tac cgg cgc tgg gcg cgg acg tgg gag ttc cag gcg ctg ctc aag       912
Tyr Tyr Arg Arg Trp Ala Arg Thr Trp Glu Phe Gln Ala Leu Leu Lys
    290                 295                 300 gcc cgg ccg gcg gcc ggc gac ctg acc ctg ggc cgg gag tgg atc gac       960
Ala Arg Pro Ala Ala Gly Asp Leu Thr Leu Gly Arg Glu Trp Ile Asp
305                 310                 315                 320 cag ctc gcc ccg ctc gtg tgg cgg gcc gcc gag cgc ccc gag gcg gtc      1008
Gln Leu Ala Pro Leu Val Trp Arg Ala Ala Glu Arg Pro Glu Ala Val
                325                 330                 335 gag gac gtc cgc gcc atg cgg cgg aag atc atc gac aac gtc ccg ccg      1056
```

-continued

```
              Glu Asp Val Arg Ala Met Arg Arg Lys Ile Ile Asp Asn Val Pro Pro
                              340                 345                 350 aag gag ttg gag cgc gag atc aag cgc ggc ccg ggg ctg cgc gac       1104
Lys Glu Leu Glu Arg Glu Ile Lys Arg Gly Pro Gly Gly Leu Arg Asp
            355                 360                 365 atc gag ttc gcc gtc cag ctg ctg caa ctg gtg cac ggc cgg ggc gac   1152
Ile Glu Phe Ala Val Gln Leu Leu Gln Leu Val His Gly Arg Gly Asp
    370                 375                 380 gag tcg ctg cgg acg ccc ggc acc gtc ccg gcg ctg cgc gcg ctc gtc   1200
Glu Ser Leu Arg Thr Pro Gly Thr Val Pro Ala Leu Arg Ala Leu Val
385                 390                 395                 400 gcc ggc ggc tac gtc ggc cgg gcc gac ggg gag gcg ctg ctc cgc ggc   1248
Ala Gly Gly Tyr Val Gly Arg Ala Asp Gly Glu Ala Leu Leu Arg Gly
                405                 410                 415 tac cgc ttc ctg cgc ggc gtc gag cac cgc ctc cag ctc cag ggg ctg   1296
Tyr Arg Phe Leu Arg Gly Val Glu His Arg Leu Gln Leu Gln Gly Leu
            420                 425                 430 cgc cgc acc cac acc gtg ccg acc gag ccg gcc gcg ctg cgc tgg ttg   1344
Arg Arg Thr His Thr Val Pro Thr Glu Pro Ala Ala Leu Arg Trp Leu
    435                 440                 445 gcc gcc gcg ctg ggc tac gcg gcc acg ccg ggc cgc agc gcc gtc gag   1392
Ala Ala Ala Leu Gly Tyr Ala Ala Thr Pro Gly Arg Ser Ala Val Glu
450                 455                 460 gag ttc cgc gcc gag tgg gtc acc cac gcc acc gag gta cgc cgg ctg   1440
Glu Phe Arg Ala Glu Trp Val Thr His Ala Thr Glu Val Arg Arg Leu
465                 470                 475                 480 cac gcc aag ctg ctc tac cgg ccg ctg ctg gag tcg gtg gcc cgg gtg   1488
His Ala Lys Leu Leu Tyr Arg Pro Leu Leu Glu Ser Val Ala Arg Val
                485                 490                 495 ccg gcc gac ggg ctg cgg ctg acc ccg gag gcg gcc cgg cac cgg ctg   1536
Pro Ala Asp Gly Leu Arg Leu Thr Pro Glu Ala Ala Arg His Arg Leu
            500                 505                 510 gag atc ctc ggc ttc gcc gac ccc gcc ggg gcg ctg cgg cac ctc cag   1584
Glu Ile Leu Gly Phe Ala Asp Pro Ala Gly Ala Leu Arg His Leu Gln
    515                 520                 525 gcc ctc acc ggc ggg gtg agc cgc acg gcg gcc atc cag cgc acc ctg   1632
Ala Leu Thr Gly Gly Val Ser Arg Thr Ala Ala Ile Gln Arg Thr Leu
530                 535                 540 ctg ccg gtg ctg ctc agc gag ttc gcc gac gcc ccc gag ccg gac cgc   1680
Leu Pro Val Leu Leu Ser Glu Phe Ala Asp Ala Pro Glu Pro Asp Arg
545                 550                 555                 560 ggc ctg ctc aac tac cgg cag gtc tcc gac aag ctc ggc agc acg ccc   1728
Gly Leu Leu Asn Tyr Arg Gln Val Ser Asp Lys Leu Gly Ser Thr Pro
                565                 570                 575 tgg tac ctg cgc ctg ctg cgc gac tcc ggg ccg gtg gcc cgc cgg ctg   1776
Trp Tyr Leu Arg Leu Leu Arg Asp Ser Gly Pro Val Ala Arg Arg Leu
            580                 585                 590 gcc cgg gtg ctc tcc tcc tcc cgc tac gcc gcc gac ctg ctg gcc cgc   1824
Ala Arg Val Leu Ser Ser Ser Arg Tyr Ala Ala Asp Leu Leu Ala Arg
    595                 600                 605 gag ccg gag gcg ctg cgg atg ctg gcc gag gag agc gag ttg acc ccc   1872
Glu Pro Glu Ala Leu Arg Met Leu Ala Glu Glu Ser Glu Leu Thr Pro
610                 615                 620 cgg ccg agc ggg gtg ctc tgc gag ggc ttc gcc gcc gcc gca gcc cgg   1920
Arg Pro Ser Gly Val Leu Cys Glu Gly Phe Ala Ala Ala Ala Ala Arg
625                 630                 635                 640 cac gcc gac ccc gtc gaa gcc acc cgg gcg atc cgc gcg ctg cgc cgc   1968
His Ala Asp Pro Val Glu Ala Thr Arg Ala Ile Arg Ala Leu Arg Arg
                645                 650                 655
```

-continued

| | |
|---|---|
| cgg gag ctg gtc cgc atc gcc tgc gcg gac ctg ttg agc cgg gcc ggc<br>Arg Glu Leu Val Arg Ile Ala Cys Ala Asp Leu Leu Ser Arg Ala Gly<br>660                    665                    670 | 2016 |
| tcg ctg gcc ccg tcg ccg ccc cgg ccc gac ggc ggg cgg gcc gcg ctc<br>Ser Leu Ala Pro Ser Pro Pro Arg Pro Asp Gly Gly Arg Ala Ala Leu<br>675                    680                    685 | 2064 |
| ggt ctc gcc gac gtc gcc gcc gtg ggc acg gcg ctg gcc gac gtc acc<br>Gly Leu Ala Asp Val Ala Ala Val Gly Thr Ala Leu Ala Asp Val Thr<br>690                    695                    700 | 2112 |
| gac gcc acc ctg gcc gcg gcg ctg cgg gcc gcc cgg gcc gcc cag ccg<br>Asp Ala Thr Leu Ala Ala Ala Leu Arg Ala Ala Arg Ala Ala Gln Pro<br>705               710                    715                    720 | 2160 |
| ccc atg ccg ggg ctg cgc ttc gcc gtg atc ggc atg ggc cgc ctg ggc<br>Pro Met Pro Gly Leu Arg Phe Ala Val Ile Gly Met Gly Arg Leu Gly<br>725                    730                    735 | 2208 |
| ggg tac gag tcg aac tac ctc tcc gac gcc gac gtg ctc ttc gtc tac<br>Gly Tyr Glu Ser Asn Tyr Leu Ser Asp Ala Asp Val Leu Phe Val Tyr<br>740                    745                    750 | 2256 |
| gac ccc ccg ccc ggc gcc ggc gag agc gcg gcc ggc gcg gcg agc gcc<br>Asp Pro Pro Pro Gly Ala Gly Glu Ser Ala Ala Gly Ala Ala Ser Ala<br>755                    760                    765 | 2304 |
| gcc gcc cac ggg atc gcc gag gag ttg cgt cgg ctg ctc ggc atg ccc<br>Ala Ala His Gly Ile Ala Glu Glu Leu Arg Arg Leu Leu Gly Met Pro<br>770                    775                    780 | 2352 |
| gcg ccc gac ccg ccg ctg ggc gtg gac gcc gac ctg cgt ccc gag ggc<br>Ala Pro Asp Pro Pro Leu Gly Val Asp Ala Asp Leu Arg Pro Glu Gly<br>785               790                    795                    800 | 2400 |
| cgg cag ggt ccg ctc gtg cgc agc ctc gcc gcg tac gcg cag tac tac<br>Arg Gln Gly Pro Leu Val Arg Ser Leu Ala Ala Tyr Ala Gln Tyr Tyr<br>805                    810                    815 | 2448 |
| gcc cgc tgg tcg aag gtg tgg gag gcg cag gcg ctg ctg cgt gcc cgg<br>Ala Arg Trp Ser Lys Val Trp Glu Ala Gln Ala Leu Leu Arg Ala Arg<br>820                    825                    830 | 2496 |
| ttc gtc tgc ggc gac gcc gac ctc ggc gcg gag ttc gag gcg atg gtc<br>Phe Val Cys Gly Asp Ala Asp Leu Gly Ala Glu Phe Glu Ala Met Val<br>835                    840                    845 | 2544 |
| gac ccg gtc cgc tac ccg gcc gac ggg ttg acc cgc gag cag gtg gtg<br>Asp Pro Val Arg Tyr Pro Ala Asp Gly Leu Thr Arg Glu Gln Val Val<br>850               855                    860 | 2592 |
| gag atc cgg cgg atc aag gcg cgg gtg gag cac gag cgg ctg ccc cgg<br>Glu Ile Arg Arg Ile Lys Ala Arg Val Glu His Glu Arg Leu Pro Arg<br>865             870                    875                    880 | 2640 |
| ggc gcc gac ccg gcc acc cac acc aag ctc ggg cgg ggc ggc ctc gcc<br>Gly Ala Asp Pro Ala Thr His Thr Lys Leu Gly Arg Gly Gly Leu Ala<br>885                    890                    895 | 2688 |
| gac gtc gag tgg gcg gtg caa ctg ctc cag ctc cgg cac gcc ggg acg<br>Asp Val Glu Trp Ala Val Gln Leu Leu Gln Leu Arg His Ala Gly Thr<br>900                    905                    910 | 2736 |
| gtc ccg cgg ctg cgc ggc acg cgt acg ctc gac gcc ctc gcg gcg gcc<br>Val Pro Arg Leu Arg Gly Thr Arg Thr Leu Asp Ala Leu Ala Ala Ala<br>915                    920                    925 | 2784 |
| cgg gac gcg ggg ctg gtc gac ccg acg gac gcc acc gag atg gcg gcc<br>Arg Asp Ala Gly Leu Val Asp Pro Thr Asp Ala Thr Glu Met Ala Ala<br>930                    935                    940 | 2832 |
| ggc tgg acc ctg gcc gcg cag gtc cgc aac gcg ctg atg ctg gtc cgc<br>Gly Trp Thr Leu Ala Ala Gln Val Arg Asn Ala Leu Met Leu Val Arg<br>945             950                    955                    960 | 2880 |
| ggc cgg gcc ggc gac cag ttg ccc cgg cac ggc gtc gag ttg gcc ggg<br>Gly Arg Ala Gly Asp Gln Leu Pro Arg His Gly Val Glu Leu Ala Gly<br>965                    970                    975 | 2928 |

```
gtg gtc cgg ctg ctc ggc cgg gac gat ccc ggc gag ttc ctc gac gag      2976
Val Val Arg Leu Leu Gly Arg Asp Asp Pro Gly Glu Phe Leu Asp Glu
        980                 985                 990 tac ctg cgc acc ggc cgc cgc tcc cgc gcg gcg atg gag cgg gtc ctc      3024
Tyr Leu Arg Thr Gly Arg Arg Ser Arg Ala Ala Met Glu Arg Val Leu
        995                 1000                1005 gac gcc tga                                                          3033
Asp Ala *
    1010
```

<210> SEQ ID NO 82
<211> LENGTH: 296
<212> TYPE: PRT
<213> ORGANISM: Bacteria

<400> SEQUENCE: 82

```
Val Ile Leu Val Ala Leu Ala Lys Ile Arg Glu Val Pro Leu Thr Gly
  1               5                  10                  15

Ala Asp Ala Gly Pro Tyr Gly Val Thr Val Gly Pro Asp Gly Ala Leu
             20                  25                  30

Trp Leu Thr Leu Val His Ala Gly Ala Val Ala Arg Val Gly Ala Asp
         35                  40                  45

Gly Asp Leu Arg Thr Trp Gln Val Ala Ala Asp Ser Arg Pro Leu Ile
 50                  55                  60

Val Thr Pro Gly Pro Asp Gly Ala Leu Trp Phe Thr Arg Ser Gly Asp
 65                  70                  75                  80

Asp Arg Ile Gly Arg Ile Thr Thr Asp Gly Glu Gln Ser Ala Val Ala
             85                  90                  95

Leu Pro Pro Gly Ser Gly Pro Cys Gly Ile Ala Ala Gly Pro Asp Gly
            100                 105                 110

Ala Leu Trp Tyr Ala Ala Met Thr Ala Asp Ala Val Gly Arg Val Thr
        115                 120                 125

Thr Asp Gly Lys Val Thr Gln Phe Pro Leu Pro Val Ser Gly Gly Phe
    130                 135                 140

Ala Ser Met Val Ala Ala Gly Pro Asp Glu Ala Val Trp Phe Thr Leu
145                 150                 155                 160

Asn Gln Ala Asn Ala Val Gly Arg Ile Gly Thr Asp Gly Ala Val Ala
                165                 170                 175

Leu His Pro Leu Pro Thr Glu Gly Ala Ala Pro Val Gly Ile Thr Ala
            180                 185                 190

Gly Ala Asp Gly Ala Leu Trp Phe Val Glu Ile Gly Ala Gly Gln Leu
        195                 200                 205

Gly Arg Ile Thr Pro Asp Gly Arg Ile Asp Glu Tyr Pro Leu Pro Asp
    210                 215                 220

Arg Ala Ala Arg Pro His Ala Ile Val Ala Asp Pro Ala Gly Gly Cys
225                 230                 235                 240

Trp Phe Thr Glu Trp Gly Gly Asn Arg Ile Gly His Val Ala Pro Asp
                245                 250                 255

Gly Thr Ile Val Thr His Asp Leu Pro Thr Pro Ala Ala Glu Pro His
            260                 265                 270

Gly Ile Thr Val Ala Pro Asp Gly Thr Val Trp Ala Ala Leu Glu Thr
        275                 280                 285

Gly Ala Leu Ala His Leu Thr Pro
    290                 295
```

```
<210> SEQ ID NO 83
<211> LENGTH: 705
<212> TYPE: DNA
<213> ORGANISM: Bacteria
<220> FEATURE:
<221> NAME/KEY: CDS
<222> LOCATION: (1)...(705)

<400> SEQUENCE: 83 gtg cga cac gac gga acg gcc ggg gag cac cgg cac gac agg acg gcg      48
Val Arg His Asp Gly Thr Ala Gly Glu His Arg His Asp Arg Thr Ala
  1               5                  10                  15 gcg ccg gtg gac gac cat tgg cgg cac ccg gac gtg gac gag gag acc      96
Ala Pro Val Asp Asp His Trp Arg His Pro Asp Val Asp Glu Glu Thr
             20                  25                  30 gct cgg tac tgg gag gag ctc tac ggg cgg cgc gac cgg tac tgg agc     144
Ala Arg Tyr Trp Glu Glu Leu Tyr Gly Arg Arg Asp Arg Tyr Trp Ser
         35                  40                  45 ggg cgg gcg aac ccg atc ctg gtc gac gtc gcc ggg ccg ctg ccg gcc     192
Gly Arg Ala Asn Pro Ile Leu Val Asp Val Ala Gly Pro Leu Pro Ala
     50                  55                  60 ggc acc gcg ctg gac ctc ggc tgc ggc gag ggc ggc gac gcg atc tgg     240
Gly Thr Ala Leu Asp Leu Gly Cys Gly Glu Gly Gly Asp Ala Ile Trp
 65                  70                  75                  80 ctg gcc ggg cgg ggc tgg cgg gtg acg gcg gtg gac gtc gcc gag acc     288
Leu Ala Gly Arg Gly Trp Arg Val Thr Ala Val Asp Val Ala Glu Thr
                 85                  90                  95 gcc ctc gac cgg gcg tcc gca gcg gcc gag gcc ggg gtg gcg tcc         336
Ala Leu Asp Arg Ala Ser Ala Ala Ala Glu Ala Gly Val Ala Ser
            100                 105                 110 cgc atc gag ttc cgc cgg cac gac ctc acc cgg acc ttc ccg ccg ggc     384
Arg Ile Glu Phe Arg Arg His Asp Leu Thr Arg Thr Phe Pro Pro Gly
        115                 120                 125 gag ttc gac ctg gtc tcc gcg cag ttc ctc cag tcg ccg ctg gag ttc     432
Glu Phe Asp Leu Val Ser Ala Gln Phe Leu Gln Ser Pro Leu Glu Phe
    130                 135                 140 ccc cgg gga gag gtg ctg cgc tcg gcg gcc cgg gcc gtg gcc ccc ggc     480
Pro Arg Gly Glu Val Leu Arg Ser Ala Ala Arg Ala Val Ala Pro Gly
145                 150                 155                 160 ggc cgg ctg ctc gtc gtc gag cac ggc gag gtc ccg ccg tgg gga cgg     528
Gly Arg Leu Leu Val Val Glu His Gly Glu Val Pro Pro Trp Gly Arg
                165                 170                 175 cac gcg cac ccg gac gtg cgc ttc ccc acc ccg cag gag acc ctc gcc     576
His Ala His Pro Asp Val Arg Phe Pro Thr Pro Gln Glu Thr Leu Ala
            180                 185                 190 gag ctg gac ctc gac ccg gac cgg tgg ctc acc gag cgg ctc gac gcc     624
Glu Leu Asp Leu Asp Pro Asp Arg Trp Leu Thr Glu Arg Leu Asp Ala
        195                 200                 205 ccg cgc cgg cag gcc acc ggc ccg gac ggc cat acc ggg acc ctc gtc     672
Pro Arg Arg Gln Ala Thr Gly Pro Asp Gly His Thr Gly Thr Leu Val
    210                 215                 220 gac cac gtg gtg ctg gtc cgc cgc cgc ccg tag                         705
Asp His Val Val Leu Val Arg Arg Arg Pro *
225                 230

<210> SEQ ID NO 84
<211> LENGTH: 234
<212> TYPE: PRT
<213> ORGANISM: Bacteria

<400> SEQUENCE: 84

Val Arg His Asp Gly Thr Ala Gly Glu His Arg His Asp Arg Thr Ala
```

```
          1               5                  10                 15
        Ala Pro Val Asp Asp His Trp Arg His Pro Asp Val Asp Glu Glu Thr
                         20                 25                 30

Ala Arg Tyr Trp Glu Glu Leu Tyr Gly Arg Arg Asp Arg Tyr Trp Ser
                         35                 40                 45

Gly Arg Ala Asn Pro Ile Leu Val Asp Val Ala Gly Pro Leu Pro Ala
                50                 55                 60

Gly Thr Ala Leu Asp Leu Gly Cys Gly Glu Gly Gly Asp Ala Ile Trp
        65                 70                 75                 80

Leu Ala Gly Arg Gly Trp Arg Val Thr Ala Val Asp Val Ala Glu Thr
                         85                 90                 95

Ala Leu Asp Arg Ala Ser Ala Ala Ala Glu Ala Gly Val Ala Ser
                        100                105                110

Arg Ile Glu Phe Arg Arg His Asp Leu Thr Arg Thr Phe Pro Pro Gly
                        115                120                125

Glu Phe Asp Leu Val Ser Ala Gln Phe Leu Gln Ser Pro Leu Glu Phe
                130                135                140

Pro Arg Gly Glu Val Leu Arg Ser Ala Ala Arg Ala Val Ala Pro Gly
        145                150                155                160

Gly Arg Leu Leu Val Val Glu His Gly Glu Val Pro Pro Trp Gly Arg
                        165                170                175

His Ala His Pro Asp Val Arg Phe Pro Thr Pro Gln Glu Thr Leu Ala
                        180                185                190

Glu Leu Asp Leu Asp Pro Asp Arg Trp Leu Thr Glu Arg Leu Asp Ala
                        195                200                205

Pro Arg Arg Gln Ala Thr Gly Pro Asp Gly His Thr Gly Thr Leu Val
                210                215                220

Asp His Val Val Leu Val Arg Arg Pro
        225                230

<210> SEQ ID NO 85
<211> LENGTH: 1320
<212> TYPE: DNA
<213> ORGANISM: .
<220> FEATURE:
<221> NAME/KEY: CDS
<222> LOCATION: (1)...(1320)

<400> SEQUENCE: 85 gtg ggc atg cgg cgc agt cgg gtg gtg gcg gtg gcc gcc gcg tcc gcc        48
Val Gly Met Arg Arg Ser Arg Val Val Ala Val Ala Ala Ala Ser Ala
 1               5                  10                 15 gtg ctc ctc ggc gtg acg tat ctc gct ctt ccg ccg acc ggt tcc gac        96
Val Leu Leu Gly Val Thr Tyr Leu Ala Leu Pro Pro Thr Gly Ser Asp
                 20                 25                 30 ctc gcc gcg cag gtc gcc cgg gcc gac ttc ttc gcc gcc cac ggc ctc       144
Leu Ala Ala Gln Val Ala Arg Ala Asp Phe Phe Ala Ala His Gly Leu
            35                 40                 45 gcc ccg gtc gac ctg cgc tgg tac ggc ggg gtc cag cag ttc ggc tac       192
Ala Pro Val Asp Leu Arg Trp Tyr Gly Gly Val Gln Gln Phe Gly Tyr
        50                 55                 60 agc ctg gtc tcc cag ccg gtg atg gcg ctg ctc ggg gtg cgg gtc acc       240
Ser Leu Val Ser Gln Pro Val Met Ala Leu Leu Gly Val Arg Val Thr
65                 70                 75                 80 ggc gtg ctg gcg ctg gtg gcg gcg gcg acc gcg ttc gcg gcg ctg ctg       288
Gly Val Leu Ala Leu Val Ala Ala Ala Thr Ala Phe Ala Ala Leu Leu
                85                 90                 95
```

-continued

| | | |
|---|---|---|
| gtg cgc acc ggg gtg ccg cgc ccg ctg ctc ggc agc ctg gtc ggg gtg<br>Val Arg Thr Gly Val Pro Arg Pro Leu Leu Gly Ser Leu Val Gly Val<br>100                      105                    110 | 336 | |
| gtc acg atc gcc ggc aac ctg gtc tcg ggc cgg gtg acg tac ggc ctc<br>Val Thr Ile Ala Gly Asn Leu Val Ser Gly Arg Val Thr Tyr Gly Leu<br>115                      120                    125 | 384 | |
| ggg gtg gcc ttc ggc ctc ggc gcg ctc ctc gcc ctc acc ctc ccc cgc<br>Gly Val Ala Phe Gly Leu Gly Ala Leu Leu Ala Leu Thr Leu Pro Arg<br>130                      135                    140 | 432 | |
| ggc ccg gcc gca cgg gcc gcc gac tcc gac ccg gcc gca ccg gcc gac<br>Gly Pro Ala Ala Arg Ala Ala Asp Ser Asp Pro Ala Ala Pro Ala Asp<br>145                      150                    155                    160 | 480 | |
| tcc gac gcc gac ggg cgg gcg cgg cga cgg cag gtc gcg cgg ctc ggg<br>Ser Asp Ala Asp Gly Arg Ala Arg Arg Arg Gln Val Ala Arg Leu Gly<br>                    165                    170                    175 | 528 | |
| ctg gcg gtc gcc ggg gcg ctg ctg gcc tcg gcg gcg agc ccg gtg gcg<br>Leu Ala Val Ala Gly Ala Leu Leu Ala Ser Ala Ala Ser Pro Val Ala<br>                180                    185                    190 | 576 | |
| ggc ctc ttc gtc ggc ctg gcc ggc gcg gcg ctg ctc acc cgc cgg<br>Gly Leu Phe Val Gly Leu Ala Gly Ala Ala Leu Leu Thr Arg Arg<br>                195                    200                    205 | 624 | |
| tac gcc gac ggc ctg gcg ctc ggc gtc gcc gcc gcg ctg ccg ctc ggg<br>Tyr Ala Asp Gly Leu Ala Leu Gly Val Ala Ala Ala Leu Pro Leu Gly<br>210                      215                    220 | 672 | |
| gcg acc gcg ctg ctc ttc ggc gac ggc ggc tgg atg aac atc agc cgc<br>Ala Thr Ala Leu Leu Phe Gly Asp Gly Gly Trp Met Asn Ile Ser Arg<br>225                      230                    235                    240 | 720 | |
| acc gac acg ctg cgc gcc gtg ctg acc agc ctg ctg gtc gcc gcg ctg<br>Thr Asp Thr Leu Arg Ala Val Leu Thr Ser Leu Leu Val Ala Ala Leu<br>                    245                    250                    255 | 768 | |
| gtg gcg tac cgg ccg gtg cgg gtg ggc gcg ctc ctc tcg gcg gcc ggg<br>Val Ala Tyr Arg Pro Val Arg Val Gly Ala Leu Leu Ser Ala Ala Gly<br>                260                    265                    270 | 816 | |
| gtg ctg gcg gcg gcg ctg gtg cac acc ccg gtc ggg ctg aac gcc acc<br>Val Leu Ala Ala Ala Leu Val His Thr Pro Val Gly Leu Asn Ala Thr<br>275                      280                    285 | 864 | |
| cgg ctg gcg gtc atg ttc ggc ctg ccg ctg ctg gcc gcc gcc gcc cgc<br>Arg Leu Ala Val Met Phe Gly Leu Pro Leu Leu Ala Ala Ala Ala Arg<br>                290                    295                    300 | 912 | |
| ccc ccg gtc ggg ctg gcg cgg tgg tgg gcc cga cgc ggg cgg ggc gcg<br>Pro Pro Val Gly Leu Ala Arg Trp Trp Ala Arg Arg Gly Arg Gly Ala<br>305                      310                    315                    320 | 960 | |
| gcg cgg ggc ggg gtg ggc ggc cgg gac gcg gcg cag ggg cgg agc aag<br>Ala Arg Gly Gly Val Gly Gly Arg Asp Ala Ala Gln Gly Arg Ser Lys<br>                    325                    330                    335 | 1008 | |
| gtc cgg ggc cgc gtg gcg ctg gcc acg ctg ctg gcg gcc ggc tgc tgg<br>Val Arg Gly Arg Val Ala Leu Ala Thr Leu Leu Ala Ala Gly Cys Trp<br>                340                    345                    350 | 1056 | |
| tgg cag ccg ccg gtg ccc ccc gcc gac ctg cgc agc gtc gac gac ccg<br>Trp Gln Pro Pro Val Pro Pro Ala Asp Leu Arg Ser Val Asp Asp Pro<br>355                      360                    365 | 1104 | |
| acc ggc cgg gcc gcg tac ttg cgc cgc tgc ggg agt tcc tcg acg ggc<br>Thr Gly Arg Ala Ala Tyr Leu Arg Arg Cys Gly Ser Ser Ser Thr Gly<br>                370                    375                    380 | 1152 | |
| agc ggc tca ccg gcc ggg tcg agg tgc gcc cga ccc gca act act ggg<br>Ser Gly Ser Pro Ala Gly Ser Arg Cys Arg Arg Pro Ala Thr Thr Gly<br>385                      390                    395                    400 | 1200 | |
| agg cgg cgc ggc tgg gcg agg tgc cgc tgg ccc ggg gct ggc tgc ggc<br>Arg Arg Arg Gly Trp Ala Arg Cys Arg Trp Pro Gly Ala Gly Cys Gly<br>                405                    410                    415 | 1248 | |

-continued

```
agg ccg aca tcg acc gga acc ccc tct tct tca cca ccg tcc cgg gcg    1296
Arg Pro Thr Ser Thr Gly Thr Pro Ser Ser Ser Pro Pro Ser Arg Ala
            420                     425                 430 cgg ccg gca ccg ggg tgc cgc tga                                    1320
Arg Pro Ala Pro Gly Cys Arg *
        435
```

<210> SEQ ID NO 86
<211> LENGTH: 439
<212> TYPE: PRT
<213> ORGANISM: Bacteria

<400> SEQUENCE: 86

```
Val Gly Met Arg Arg Ser Arg Val Val Ala Val Ala Ala Ala Ser Ala
1               5                   10                  15

Val Leu Leu Gly Val Thr Tyr Leu Ala Leu Pro Pro Thr Gly Ser Asp
            20                  25                  30

Leu Ala Ala Gln Val Ala Arg Ala Asp Phe Phe Ala Ala His Gly Leu
        35                  40                  45

Ala Pro Val Asp Leu Arg Trp Tyr Gly Val Gln Gln Phe Gly Tyr
    50                  55                  60

Ser Leu Val Ser Gln Pro Val Met Ala Leu Leu Gly Val Arg Val Thr
65                  70                  75                  80

Gly Val Leu Ala Leu Val Ala Ala Thr Ala Phe Ala Ala Leu Leu
                85                  90                  95

Val Arg Thr Gly Val Pro Arg Pro Leu Gly Ser Leu Val Gly Val
                100                 105                 110

Val Thr Ile Ala Gly Asn Leu Val Ser Gly Arg Val Thr Tyr Gly Leu
                115                 120                 125

Gly Val Ala Phe Gly Leu Gly Ala Leu Leu Ala Leu Thr Leu Pro Arg
    130                 135                 140

Gly Pro Ala Ala Arg Ala Ala Asp Ser Asp Pro Ala Ala Pro Ala Asp
145                 150                 155                 160

Ser Asp Ala Asp Gly Arg Ala Arg Arg Gln Val Ala Arg Leu Gly
                165                 170                 175

Leu Ala Val Ala Gly Ala Leu Leu Ala Ser Ala Ser Pro Val Ala
                180                 185                 190

Gly Leu Phe Val Gly Leu Ala Ala Ala Leu Leu Leu Thr Arg Arg
            195                 200                 205

Tyr Ala Asp Gly Leu Ala Leu Gly Val Ala Ala Leu Pro Leu Gly
    210                 215                 220

Ala Thr Ala Leu Leu Phe Gly Asp Gly Gly Trp Met Asn Ile Ser Arg
225                 230                 235                 240

Thr Asp Thr Leu Arg Ala Val Leu Thr Ser Leu Leu Val Ala Ala Leu
                245                 250                 255

Val Ala Tyr Arg Pro Val Arg Val Gly Ala Leu Leu Ser Ala Ala Gly
                260                 265                 270

Val Leu Ala Ala Ala Leu Val His Thr Pro Val Gly Leu Asn Ala Thr
            275                 280                 285

Arg Leu Ala Val Met Phe Gly Leu Pro Leu Leu Ala Ala Ala Arg
    290                 295                 300

Pro Pro Val Gly Leu Ala Arg Trp Trp Ala Arg Arg Gly Arg Gly Ala
305                 310                 315                 320

Ala Arg Gly Gly Val Gly Gly Arg Asp Ala Ala Gln Gly Arg Ser Lys
                325                 330                 335
```

```
Val Arg Gly Arg Val Ala Leu Ala Thr Leu Leu Ala Ala Gly Cys Trp
            340                 345                 350

Trp Gln Pro Pro Val Pro Pro Ala Asp Leu Arg Ser Val Asp Asp Pro
        355                 360                 365

Thr Gly Arg Ala Ala Tyr Leu Arg Arg Cys Gly Ser Ser Thr Gly
    370                 375                 380

Ser Gly Ser Pro Ala Gly Ser Arg Cys Arg Arg Pro Ala Thr Thr Gly
385                 390                 395                 400

Arg Arg Arg Gly Trp Ala Arg Cys Arg Trp Pro Gly Ala Gly Cys Gly
                405                 410                 415

Arg Pro Thr Ser Thr Gly Thr Pro Ser Ser Ser Pro Pro Ser Arg Ala
            420                 425                 430

Arg Pro Ala Pro Gly Cys Arg
            435

<210> SEQ ID NO 87
<211> LENGTH: 1431
<212> TYPE: DNA
<213> ORGANISM: Bacteria
<220> FEATURE:
<221> NAME/KEY: CDS
<222> LOCATION: (1)...(1431)

<400> SEQUENCE: 87
```

| | | | | | | | | | | | | | | | | |
|---|---|---|---|---|---|---|---|---|---|---|---|---|---|---|---|---|
| atg tcc ggc gtg cct cac cac ctc gcg cgc tgg atc ggc ctg gcc ggc | | | | | | | | | | | | | | | | 48 |
| Met Ser Gly Val Pro His His Leu Ala Arg Trp Ile Gly Leu Ala Gly | | | | | | | | | | | | | | | | |
| 1 | | | | 5 | | | | | 10 | | | | | 15 | | |
| tcg acg ctg ctc gcc gtg gcc gcg ttc ctc ggc gga gcg ctg ccc gac | | | | | | | | | | | | | | | | 96 |
| Ser Thr Leu Leu Ala Val Ala Ala Phe Leu Gly Gly Ala Leu Pro Asp | | | | | | | | | | | | | | | | |
| | | | 20 | | | | | 25 | | | | | 30 | | | |
| ggc gat ttg cgc ccc acc ccg ctc agc atc tgg cag ggc ccg cac ggc | | | | | | | | | | | | | | | | 144 |
| Gly Asp Leu Arg Pro Thr Pro Leu Ser Ile Trp Gln Gly Pro His Gly | | | | | | | | | | | | | | | | |
| | | 35 | | | | | 40 | | | | | 45 | | | | |
| ccg ttg atc atc gcc acc tgg gcg gtc ggc acg ggc ctg atg gcg tac | | | | | | | | | | | | | | | | 192 |
| Pro Leu Ile Ile Ala Thr Trp Ala Val Gly Thr Gly Leu Met Ala Tyr | | | | | | | | | | | | | | | | |
| 50 | | | | | 55 | | | | | 60 | | | | | | |
| gcc tgg tgg gcg ctg cgc gac cgg gtg ccg tcg acc cgc tgg gcc gtg | | | | | | | | | | | | | | | | 240 |
| Ala Trp Trp Ala Leu Arg Asp Arg Val Pro Ser Thr Arg Trp Ala Val | | | | | | | | | | | | | | | | |
| 65 | | | | 70 | | | | | 75 | | | | | 80 | | |
| gtc acc gcc ggg ctc tgg ctg ctg ccg ctg ctg gtc gcg ccg ccg ctg | | | | | | | | | | | | | | | | 288 |
| Val Thr Ala Gly Leu Trp Leu Leu Pro Leu Leu Val Ala Pro Pro Leu | | | | | | | | | | | | | | | | |
| | | | 85 | | | | | 90 | | | | | 95 | | | |
| ggc agc cga gac gtc tac gcg tac gcc tgc cag ggc gcc agc tac tcc | | | | | | | | | | | | | | | | 336 |
| Gly Ser Arg Asp Val Tyr Ala Tyr Ala Cys Gln Gly Ala Ser Tyr Ser | | | | | | | | | | | | | | | | |
| | | 100 | | | | | 105 | | | | | 110 | | | | |
| gcc ggc atc aac ccg tac gag cag ggt gtc tcg gca ctg ccc tgc ccg | | | | | | | | | | | | | | | | 384 |
| Ala Gly Ile Asn Pro Tyr Glu Gln Gly Val Ser Ala Leu Pro Cys Pro | | | | | | | | | | | | | | | | |
| | 115 | | | | | 120 | | | | | 125 | | | | | |
| tgg ctg gac acc atc tcc tac atc tgg cgg gac acc tcg gcc ccg tac | | | | | | | | | | | | | | | | 432 |
| Trp Leu Asp Thr Ile Ser Tyr Ile Trp Arg Asp Thr Ser Ala Pro Tyr | | | | | | | | | | | | | | | | |
| 130 | | | | | 135 | | | | | 140 | | | | | | |
| ggg ccg ctg ttc ctg ctg atc gcc ggg gcg gtg gtc gag gcg acc ggg | | | | | | | | | | | | | | | | 480 |
| Gly Pro Leu Phe Leu Leu Ile Ala Gly Ala Val Val Glu Ala Thr Gly | | | | | | | | | | | | | | | | |
| 145 | | | | 150 | | | | | 155 | | | | | 160 | | |
| tcg ctg acc ggc agc atc gtg ctg ttc cgg ctg ctg gcg gtg gcc ggg | | | | | | | | | | | | | | | | 528 |
| Ser Leu Thr Gly Ser Ile Val Leu Phe Arg Leu Leu Ala Val Ala Gly | | | | | | | | | | | | | | | | |
| | | | 165 | | | | | 170 | | | | | 175 | | | |
| gtg ggg ctg acc gcg gcc tgc ctg ccg ccg ctg gcc cgg cgc tgc ggc | | | | | | | | | | | | | | | | 576 |
| Val Gly Leu Thr Ala Ala Cys Leu Pro Pro Leu Ala Arg Arg Cys Gly | | | | | | | | | | | | | | | | |

```
                        180                185                190
gtg ccg gcc ggc cgg gcg gtc tgg ctg gcg ctg ggc tcg ccg ctg atc        624
Val Pro Ala Gly Arg Ala Val Trp Leu Ala Leu Gly Ser Pro Leu Ile
        195                200                205 ggg gtg cac ctg atc tcg ggc gcg cac aac gac gcg ctg atg gtg ggg        672
Gly Val His Leu Ile Ser Gly Ala His Asn Asp Ala Leu Met Val Gly
    210                215                220 ctg ctc gtg gcc ggg ctg gcg atg gtg gtg gcc cgg ccg ggc cgc ccc        720
Leu Leu Val Ala Gly Leu Ala Met Val Val Ala Arg Pro Gly Arg Pro
225                230                235                240 ggc ccg ctg ctc gcc ggg gga gcg ctg ctc ggc ctc gcc ggc gcc gtc        768
Gly Pro Leu Leu Ala Gly Gly Ala Leu Leu Gly Leu Ala Gly Ala Val
            245                250                255 aag gtc acc gcg ctg gtg gtg gtg ccg ttc gcg gcg ctc gcc gcg atc        816
Lys Val Thr Ala Leu Val Val Val Pro Phe Ala Ala Leu Ala Ala Ile
        260                265                270 gtc ggg gcg tac tcg atc agg gcg ttg atc cgc gac ggt ggg tgg gtg        864
Val Gly Ala Tyr Ser Ile Arg Ala Leu Ile Arg Asp Gly Gly Trp Val
    275                280                285 gtc ggc ggg gcg ctc gcg gcg gtc gtc ggc gcg acc ctc gcc agc ggc        912
Val Gly Gly Ala Leu Ala Ala Val Val Gly Ala Thr Leu Ala Ser Gly
290                295                300 ctg ggc ttc ggc tgg gtc acc ggg ctg gag cag ggc ggc ctg gtg atc        960
Leu Gly Phe Gly Trp Val Thr Gly Leu Glu Gln Gly Gly Leu Val Ile
305                310                315                320 gcc tgg acc tcg ccc ccg acg gcg gtg ggg cag acc gtc gcc tac ctc       1008
Ala Trp Thr Ser Pro Pro Thr Ala Val Gly Gln Thr Val Ala Tyr Leu
            325                330                335 gcc gcg ccg ttc ggc tgg cac ggc gat ccg ctg ccg gtc acc cgg ggc       1056
Ala Ala Pro Phe Gly Trp His Gly Asp Pro Leu Pro Val Thr Arg Gly
        340                345                350 atc ggg atg gcc gtg ctc gcg ctg gtg ctg atc tgg ctg tgg tgg cgg       1104
Ile Gly Met Ala Val Leu Ala Leu Val Leu Ile Trp Leu Trp Trp Arg
    355                360                365 gcc cgc acc cgg gag ccg ctg tgg cac gcc ggc ctg gcg ctg gcc gcc       1152
Ala Arg Thr Arg Glu Pro Leu Trp His Ala Gly Leu Ala Leu Ala Ala
370                375                380 acg gtc gcg ctc gcc ccg ctg ttc cac ccc tgg tac tgg acc tgg ccg       1200
Thr Val Ala Leu Ala Pro Leu Phe His Pro Trp Tyr Trp Thr Trp Pro
385                390                395                400 ctg gcc gtg ctc gcg gcc acg tcg cgg cgc acc ggc tgg ttc gcg ctc       1248
Leu Ala Val Leu Ala Ala Thr Ser Arg Arg Thr Gly Trp Phe Ala Leu
            405                410                415 gtc gcg gtg ctc tcg gcg ttc ctg gtc ctc gcg gac ggc acc ggg ctg       1296
Val Ala Val Leu Ser Ala Phe Leu Val Leu Ala Asp Gly Thr Gly Leu
        420                425                430 gcc cgg tac agc aag acg gtc ggc gcc ccg ctg atg acg ctg ttg gtg       1344
Ala Arg Tyr Ser Lys Thr Val Gly Ala Pro Leu Met Thr Leu Leu Val
    435                440                445 atg gtg gtg gcc gtc cgc ttg gta cgg tcg gct tgg gcg gcc cgc cgg       1392
Met Val Val Ala Val Arg Leu Val Arg Ser Ala Trp Ala Ala Arg Arg
450                455                460 tcg gct cgg gcg gcc cgc cgg ccg gcc gcc gtg aac tga                   1431
Ser Ala Arg Ala Ala Arg Arg Pro Ala Ala Val Asn *
465                470                475

<210> SEQ ID NO 88
<211> LENGTH: 476
<212> TYPE: PRT
<213> ORGANISM: Bacteria
```

```
<400> SEQUENCE: 88

Met Ser Gly Val Pro His His Leu Ala Arg Trp Ile Gly Leu Ala Gly
  1               5                  10                  15

Ser Thr Leu Leu Ala Val Ala Ala Phe Leu Gly Gly Ala Leu Pro Asp
             20                  25                  30

Gly Asp Leu Arg Pro Thr Pro Leu Ser Ile Trp Gln Gly Pro His Gly
         35                  40                  45

Pro Leu Ile Ile Ala Thr Trp Ala Val Gly Thr Gly Leu Met Ala Tyr
     50                  55                  60

Ala Trp Trp Ala Leu Arg Asp Arg Val Pro Ser Thr Arg Trp Ala Val
 65                  70                  75                  80

Val Thr Ala Gly Leu Trp Leu Leu Pro Leu Val Ala Pro Pro Leu
                 85                  90                  95

Gly Ser Arg Asp Val Tyr Ala Tyr Ala Cys Gln Gly Ala Ser Tyr Ser
                100                 105                 110

Ala Gly Ile Asn Pro Tyr Glu Gln Gly Val Ser Ala Leu Pro Cys Pro
                115                 120                 125

Trp Leu Asp Thr Ile Ser Tyr Ile Trp Arg Asp Thr Ser Ala Pro Tyr
        130                 135                 140

Gly Pro Leu Phe Leu Ile Gly Ala Val Val Glu Ala Thr Gly
145                 150                 155                 160

Ser Leu Thr Gly Ser Ile Val Leu Phe Arg Leu Leu Ala Val Ala Gly
                165                 170                 175

Val Gly Leu Thr Ala Ala Cys Leu Pro Pro Leu Ala Arg Arg Cys Gly
                180                 185                 190

Val Pro Ala Gly Arg Ala Val Trp Leu Ala Leu Gly Ser Pro Leu Ile
            195                 200                 205

Gly Val His Leu Ile Ser Gly Ala His Asn Asp Ala Leu Met Val Gly
        210                 215                 220

Leu Leu Val Ala Gly Leu Ala Met Val Val Ala Arg Pro Gly Arg Pro
225                 230                 235                 240

Gly Pro Leu Leu Ala Gly Gly Ala Leu Leu Gly Leu Ala Gly Ala Val
                245                 250                 255

Lys Val Thr Ala Leu Val Val Pro Phe Ala Ala Leu Ala Ala Ile
                260                 265                 270

Val Gly Ala Tyr Ser Ile Arg Ala Leu Ile Arg Asp Gly Gly Trp Val
            275                 280                 285

Val Gly Gly Ala Leu Ala Ala Val Val Gly Ala Thr Leu Ala Ser Gly
        290                 295                 300

Leu Gly Phe Gly Trp Val Thr Gly Leu Glu Gln Gly Gly Leu Val Ile
305                 310                 315                 320

Ala Trp Thr Ser Pro Pro Thr Ala Val Gly Gln Thr Val Ala Tyr Leu
                325                 330                 335

Ala Ala Pro Phe Gly Trp His Gly Asp Pro Leu Pro Val Thr Arg Gly
                340                 345                 350

Ile Gly Met Ala Val Leu Ala Leu Val Leu Ile Trp Leu Trp Trp Arg
            355                 360                 365

Ala Arg Thr Arg Glu Pro Leu Trp His Ala Gly Leu Ala Leu Ala Ala
        370                 375                 380

Thr Val Ala Leu Ala Pro Leu Phe His Pro Trp Tyr Trp Thr Trp Pro
385                 390                 395                 400

Leu Ala Val Leu Ala Ala Thr Ser Arg Arg Thr Gly Trp Phe Ala Leu
```

```
              405                 410                 415
Val Ala Val Leu Ser Ala Phe Leu Val Leu Ala Asp Gly Thr Gly Leu
            420                 425                 430

Ala Arg Tyr Ser Lys Thr Val Gly Ala Pro Leu Met Thr Leu Leu Val
            435                 440                 445

Met Val Ala Val Arg Leu Val Arg Ser Ala Trp Ala Ala Arg Arg
450                 455                 460

Ser Ala Arg Ala Ala Arg Arg Pro Ala Ala Val Asn
465                 470                 475

<210> SEQ ID NO 89
<211> LENGTH: 1509
<212> TYPE: DNA
<213> ORGANISM: Bacteria
<220> FEATURE:
<221> NAME/KEY: CDS
<222> LOCATION: (1)...(1509)

<400> SEQUENCE: 89 gtg acc aca ccc ggc tcc ccg tcg acc tcg ccc gac gtc tcg ccg tcg        48
Val Thr Thr Pro Gly Ser Pro Ser Thr Ser Pro Asp Val Ser Pro Ser
 1               5                  10                  15 ccg gat gcc gcc cgg ctc gcc cgg tac gcg ggc ctg ggc ggg gcg gtg        96
Pro Asp Ala Ala Arg Leu Ala Arg Tyr Ala Gly Leu Gly Gly Ala Val
                20                  25                  30 ctg ttg gcc gtc gcc ggc tgg cgg ggg gcg ctg ccg tcg acc ccg           144
Leu Leu Ala Val Ala Gly Trp Arg Gly Gly Ala Leu Pro Ser Thr Pro
            35                  40                  45 ctg gac gtc ccc ccg ggg gac cgt tgg ctg tcg gac ggt ggg ccg ctg       192
Leu Asp Val Pro Pro Gly Asp Arg Trp Leu Ser Asp Gly Gly Pro Leu
        50                  55                  60 acg ctg ggg gtc tgg ctg gtc ggc acg gcc ctg ctg gtc ggc gcc tgg       240
Thr Leu Gly Val Trp Leu Val Gly Thr Ala Leu Leu Val Gly Ala Trp
 65                  70                  75                  80 tgg gcg ctg cgc cgg ggc gcg ccg tcc acg cgg tgg gcg tac ctg acc       288
Trp Ala Leu Arg Arg Gly Ala Pro Ser Thr Arg Trp Ala Tyr Leu Thr
                85                  90                  95 gcc ggg ctg tgg gcg ctg ccg ctg ctg gtc acc ccg ccg ctg ggc agc       336
Ala Gly Leu Trp Ala Leu Pro Leu Leu Val Thr Pro Pro Leu Gly Ser
            100                 105                 110 cgg gac gtc tac tcc tac gcc tgc cag ggc tgg gcg tac gcg cac ggc       384
Arg Asp Val Tyr Ser Tyr Ala Cys Gln Gly Trp Ala Tyr Ala His Gly
        115                 120                 125 gtc gac ccg tac gcg acc ggg gtg gcc gag gcc ggc tgc ccc tgg gtg       432
Val Asp Pro Tyr Ala Thr Gly Val Ala Glu Ala Gly Cys Pro Trp Val
    130                 135                 140 gag tcg gtc gcg ccg atc tgg cgg gac acg ccc gcc ccg tac ggg ccg       480
Glu Ser Val Ala Pro Ile Trp Arg Asp Thr Pro Ala Pro Tyr Gly Pro
145                 150                 155                 160 ttc ttc gtg ctg ctc gcc gcg ctc gcg gtg acc ctc ggc ggc ggc ctg       528
Phe Phe Val Leu Leu Ala Ala Leu Ala Val Thr Leu Gly Gly Gly Leu
                165                 170                 175 gtg ggc gct gtc gtg gcg ttc cgc ctg ctc gcg gtc gcc ggg gtg ttg       576
Val Gly Ala Val Val Ala Phe Arg Leu Leu Ala Val Ala Gly Val Leu
            180                 185                 190 ctg gcc gcc ctc tgc ctg gtg ggc ctg gcc cgc gcc gcg ggc gtg ccc       624
Leu Ala Ala Leu Cys Leu Val Gly Leu Ala Arg Ala Ala Gly Val Pro
        195                 200                 205 acc cgc agg gcg gcc tgg ctg gcg ctg gcc tgc ccg ctg gtc ggg gtc       672
Thr Arg Arg Ala Ala Trp Leu Ala Leu Ala Cys Pro Leu Val Gly Val
```

```
          210                 215                 220
cac ctg gtg gcc ggc gcg cac aac gac gcg gtg atg ctc ggc ctg ctg      720
His Leu Val Ala Gly Ala His Asn Asp Ala Val Met Leu Gly Leu Leu
225                 230                 235                 240 ctg ctg ggc ctg ctg gtg ctg gtg cgc ggg ccc ggc aag ccg aag ccg      768
Leu Leu Gly Leu Leu Val Leu Val Arg Gly Pro Gly Lys Pro Lys Pro
                245                 250                 255 ctg ttg gtg gcc ggg gcc ctc ggg ctg gcg gtg acg gtg aag gcc          816
Leu Leu Val Ala Gly Ala Leu Leu Gly Leu Ala Val Thr Val Lys Ala
            260                 265                 270 acc gcc gtg gtg gtg ctt ccc ttc gcg gcg ctg gcc gcg gtg ctg ggc      864
Thr Ala Val Val Val Leu Pro Phe Ala Ala Leu Ala Ala Val Leu Gly
                275                 280                 285 cgc tac acc gtg cgg gcg ctg ctg cgc gac gcc ggc tgg ctg gcc ggc      912
Arg Tyr Thr Val Arg Ala Leu Leu Arg Asp Ala Gly Trp Leu Ala Gly
290                 295                 300 ggg acg ctc ggc gcg gtg ggg gtc acc tcg ctg ctg tcc ggc ctc gga      960
Gly Thr Leu Gly Ala Val Gly Val Thr Ser Leu Leu Ser Gly Leu Gly
305                 310                 315                 320 ctc ggc tgg ata cgc ggg ctg acc cgc agc ggg gac tcc gag cag tgg     1008
Leu Gly Trp Ile Arg Gly Leu Thr Arg Ser Gly Asp Ser Glu Gln Trp
                325                 330                 335 acg tcg ccc ccg acg gcg gtg ggc ttc gtc gtc gac tac gcg ggc gag     1056
Thr Ser Pro Pro Thr Ala Val Gly Phe Val Val Asp Tyr Ala Gly Glu
                340                 345                 350 ctc gcc ggg cgg gac ccg ggc gcg gtg ccg gcg acc cgc gcg gcg gcg     1104
Leu Ala Gly Arg Asp Pro Gly Ala Val Pro Ala Thr Arg Ala Ala Ala
                355                 360                 365 ctg ctg ctg ctc gcc gtg ctc gtg gcg gcg ctg tgg tgg cgg gcc tgg     1152
Leu Leu Leu Leu Ala Val Leu Val Ala Ala Leu Trp Trp Arg Ala Trp
370                 375                 380 tcg ggg ctg cgc cgg ctg aac gac gtc cgg cag cgg gtg gcc cgc ctg     1200
Ser Gly Leu Arg Arg Leu Asn Asp Val Arg Gln Arg Val Ala Arg Leu
385                 390                 395                 400 gac gcc gcc cgc ccc cgg gtg acc ctg ctc ggc gcg ggg ctg gcg ctg     1248
Asp Ala Ala Arg Pro Arg Val Thr Leu Leu Gly Ala Gly Leu Ala Leu
                405                 410                 415 gcc gcc acg gtc ctc ctc gcc ccg gtc ttc cac ccc tgg tac gcc acc     1296
Ala Ala Thr Val Leu Leu Ala Pro Val Phe His Pro Trp Tyr Ala Thr
                420                 425                 430 tgg ccg ctg gcc ctg ctc gcg gtc gcc gcg acg cgg acc acc tgg ttc     1344
Trp Pro Leu Ala Leu Leu Ala Val Ala Ala Thr Arg Thr Thr Trp Phe
            435                 440                 445 gtg gcg ccc tgc gcg gcg gcg gcc ttc ctc acc ctg ccc gac ggc acc     1392
Val Ala Pro Cys Ala Ala Ala Ala Phe Leu Thr Leu Pro Asp Gly Thr
450                 455                 460 aac ctg gcc cgg ttc acc aag gcc ccg ggc gcg atc gcg atg acc gcg     1440
Asn Leu Ala Arg Phe Thr Lys Ala Pro Gly Ala Ile Ala Met Thr Ala
465                 470                 475                 480 ctg gtg gcc ggg ctg gcg gtg tgg ggc ctg ctc cgg ctg cgc cgg acc     1488
Leu Val Ala Gly Leu Ala Val Trp Gly Leu Leu Arg Leu Arg Arg Thr
                485                 490                 495 cgt gcc gcg cgc ccc ggc tga                                         1509
Arg Ala Ala Arg Pro Gly *
                500

<210> SEQ ID NO 90
<211> LENGTH: 502
<212> TYPE: PRT
<213> ORGANISM: Bacteria
```

```
<400> SEQUENCE: 90

Val Thr Thr Pro Gly Ser Pro Ser Thr Ser Pro Asp Val Ser Pro Ser
 1               5                  10                  15

Pro Asp Ala Ala Arg Leu Ala Arg Tyr Ala Gly Leu Gly Gly Ala Val
            20                  25                  30

Leu Leu Ala Val Ala Gly Trp Arg Gly Ala Leu Pro Ser Thr Pro
        35                  40                  45

Leu Asp Val Pro Pro Gly Asp Arg Trp Leu Ser Asp Gly Gly Pro Leu
    50                  55                  60

Thr Leu Gly Val Trp Leu Val Gly Thr Ala Leu Leu Val Gly Ala Trp
65                  70                  75                  80

Trp Ala Leu Arg Arg Gly Ala Pro Ser Thr Arg Trp Ala Tyr Leu Thr
                85                  90                  95

Ala Gly Leu Trp Ala Leu Pro Leu Leu Val Thr Pro Pro Leu Gly Ser
            100                 105                 110

Arg Asp Val Tyr Ser Tyr Ala Cys Gln Gly Trp Ala Tyr Ala His Gly
            115                 120                 125

Val Asp Pro Tyr Ala Thr Gly Val Ala Glu Ala Gly Cys Pro Trp Val
    130                 135                 140

Glu Ser Val Ala Pro Ile Trp Arg Asp Thr Pro Ala Pro Tyr Gly Pro
145                 150                 155                 160

Phe Phe Val Leu Leu Ala Ala Leu Ala Val Thr Leu Gly Gly Gly Leu
                165                 170                 175

Val Gly Ala Val Val Ala Phe Arg Leu Leu Ala Val Ala Gly Val Leu
            180                 185                 190

Leu Ala Ala Leu Cys Leu Val Gly Leu Ala Arg Ala Ala Gly Val Pro
            195                 200                 205

Thr Arg Arg Ala Ala Trp Leu Ala Leu Ala Cys Pro Leu Val Gly Val
    210                 215                 220

His Leu Val Ala Gly Ala His Asn Asp Ala Val Met Leu Gly Leu Leu
225                 230                 235                 240

Leu Leu Gly Leu Leu Val Leu Val Arg Gly Pro Gly Lys Pro Lys Pro
                245                 250                 255

Leu Leu Val Ala Gly Ala Leu Leu Gly Leu Ala Val Thr Val Lys Ala
            260                 265                 270

Thr Ala Val Val Leu Pro Phe Ala Ala Leu Ala Ala Val Leu Gly
    275                 280                 285

Arg Tyr Thr Val Arg Ala Leu Leu Arg Asp Ala Gly Trp Leu Ala Gly
    290                 295                 300

Gly Thr Leu Gly Ala Val Gly Val Thr Ser Leu Leu Ser Gly Leu Gly
305                 310                 315                 320

Leu Gly Trp Ile Arg Gly Leu Thr Arg Ser Gly Asp Ser Glu Gln Trp
                325                 330                 335

Thr Ser Pro Pro Thr Ala Val Gly Phe Val Val Asp Tyr Ala Gly Glu
            340                 345                 350

Leu Ala Gly Arg Asp Pro Gly Ala Val Pro Ala Thr Arg Ala Ala Ala
            355                 360                 365

Leu Leu Leu Ala Val Leu Val Ala Ala Leu Trp Trp Arg Ala Trp
        370                 375                 380

Ser Gly Leu Arg Arg Leu Asn Asp Val Arg Gln Arg Val Ala Arg Leu
385                 390                 395                 400

Asp Ala Ala Arg Pro Arg Val Thr Leu Leu Gly Ala Gly Leu Ala Leu
```

-continued

```
                      405                 410                 415
  Ala Ala Thr Val Leu Ala Pro Val Phe His Pro Trp Tyr Ala Thr
                  420                 425                 430

Trp Pro Leu Ala Leu Ala Val Ala Ala Thr Arg Thr Thr Trp Phe
                  435                 440                 445

Val Ala Pro Cys Ala Ala Ala Phe Leu Thr Leu Pro Asp Gly Thr
                  450                 455                 460

Asn Leu Ala Arg Phe Thr Lys Ala Pro Gly Ala Ile Ala Met Thr Ala
  465                 470                 475                 480

Leu Val Ala Gly Leu Ala Val Trp Gly Leu Leu Arg Leu Arg Arg Thr
                  485                 490                 495

Arg Ala Ala Arg Pro Gly
              500

<210> SEQ ID NO 91
<211> LENGTH: 750
<212> TYPE: DNA
<213> ORGANISM: Bacteria
<220> FEATURE:
<221> NAME/KEY: CDS
<222> LOCATION: (1)...(750)

<400> SEQUENCE: 91 atg agc aca gcc gag gaa tcg ttg ccg ggc aac gcc acc acc ggc gtg      48
Met Ser Thr Ala Glu Glu Ser Leu Pro Gly Asn Ala Thr Thr Gly Val
  1               5                  10                  15 gtg cgc gtc ggc gac acc gtg cgc cgt ccg gtc ggc ccc tgg agc gac      96
Val Arg Val Gly Asp Thr Val Arg Arg Pro Val Gly Pro Trp Ser Asp
                 20                  25                  30 gtg gtg gac gcc ctg ctg gaa cac ctg cac gcg gtg gga ttc gcc ggt     144
Val Val Asp Ala Leu Leu Glu His Leu His Ala Val Gly Phe Ala Gly
             35                  40                  45 gcc ccc cgg cct ctg ggt cgc gac gcg cag ggc cgg cag gtg ctg gag     192
Ala Pro Arg Pro Leu Gly Arg Asp Ala Gln Gly Arg Gln Val Leu Glu
         50                  55                  60 tac gtc cca ggc gag gtc ggc gag gcg tcg ggc acg tac ccg gtg gcg     240
Tyr Val Pro Gly Glu Val Gly Glu Ala Ser Gly Thr Tyr Pro Val Ala
 65                  70                  75                  80 gac ctg ttc gcg atc ggc cgg atg ctg gcc gag ctg cac gag gcg ctg     288
Asp Leu Phe Ala Ile Gly Arg Met Leu Ala Glu Leu His Glu Ala Leu
                 85                  90                  95 gcc ggg ttc acc ccg ccg gcc ggc gcg gcg tgg cag cgg ctc atc ccg     336
Ala Gly Phe Thr Pro Pro Ala Gly Ala Ala Trp Gln Arg Leu Ile Pro
            100                 105                 110 ccg gac cgg gag gaa ctc gtc tgc cac aac gac gtg gcc ccg tgg aac     384
Pro Asp Arg Glu Glu Leu Val Cys His Asn Asp Val Ala Pro Trp Asn
        115                 120                 125 ctg atc agg gcg gac cgg ggc tgg gtg ctg atc gac tgg gac tgc gcg     432
Leu Ile Arg Ala Asp Arg Gly Trp Val Leu Ile Asp Trp Asp Cys Ala
    130                 135                 140 gcg ccg ggc tcc cgg ctc tgg gac ctc gcg tac gcc gcg cag agc atg     480
Ala Pro Gly Ser Arg Leu Trp Asp Leu Ala Tyr Ala Ala Gln Ser Met
145                 150                 155                 160 gcc ggc ctg cgc ccg gac cgg ccg gtg gcc gag tcg gcg gcc cgg ctg     528
Ala Gly Leu Arg Pro Asp Arg Pro Val Ala Glu Ser Ala Ala Arg Leu
                165                 170                 175 cgc gcc ttc gcc gac ggc tac cgg ctg gac gag gcg tcc cgc ccg gcc     576
Arg Ala Phe Ala Asp Gly Tyr Arg Leu Asp Glu Ala Ser Arg Pro Ala
            180                 185                 190
```

```
ctg gcc gcc atg ctg ggt cgc cgc gcc cgg gcc atg tac gac ctg ttg      624
Leu Ala Ala Met Leu Gly Arg Arg Ala Arg Ala Met Tyr Asp Leu Leu
        195                 200                 205 cgc gag ggc gcg gaa cag cgg cgc gag ccg tgg gcc cgg atc tgg acc      672
Arg Glu Gly Ala Glu Gln Arg Arg Glu Pro Trp Ala Arg Ile Trp Thr
    210                 215                 220 gag gac ggc ccg tac tgg ctg gcc acc gcc gaa cac ctc gac gcc cac      720
Glu Asp Gly Pro Tyr Trp Leu Ala Thr Ala Glu His Leu Asp Ala His
225                 230                 235                 240 acc gag gca tgg gag atc gcc ctg cgc tga                              750
Thr Glu Ala Trp Glu Ile Ala Leu Arg *
                245

<210> SEQ ID NO 92
<211> LENGTH: 249
<212> TYPE: PRT
<213> ORGANISM: Bacteria

<400> SEQUENCE: 92

Met Ser Thr Ala Glu Glu Ser Leu Pro Gly Asn Ala Thr Thr Gly Val
  1               5                  10                  15

Val Arg Val Gly Asp Thr Val Arg Arg Pro Val Gly Pro Trp Ser Asp
                 20                  25                  30

Val Val Asp Ala Leu Leu Glu His Leu His Ala Val Gly Phe Ala Gly
             35                  40                  45

Ala Pro Arg Pro Leu Gly Arg Asp Ala Gln Gly Arg Gln Val Leu Glu
         50                  55                  60

Tyr Val Pro Gly Glu Val Gly Glu Ala Ser Gly Thr Tyr Pro Val Ala
 65                  70                  75                  80

Asp Leu Phe Ala Ile Gly Arg Met Leu Ala Glu Leu His Glu Ala Leu
                 85                  90                  95

Ala Gly Phe Thr Pro Pro Ala Gly Ala Ala Trp Gln Arg Leu Ile Pro
            100                 105                 110

Pro Asp Arg Glu Glu Leu Val Cys His Asn Asp Val Ala Pro Trp Asn
        115                 120                 125

Leu Ile Arg Ala Asp Arg Gly Trp Val Leu Ile Asp Trp Asp Cys Ala
130                 135                 140

Ala Pro Gly Ser Arg Leu Trp Asp Leu Tyr Ala Ala Gln Ser Met
145                 150                 155                 160

Ala Gly Leu Arg Pro Asp Arg Pro Val Ala Glu Ser Ala Ala Arg Leu
                165                 170                 175

Arg Ala Phe Ala Asp Gly Tyr Arg Leu Asp Glu Ala Ser Arg Pro Ala
            180                 185                 190

Leu Ala Ala Met Leu Gly Arg Arg Ala Arg Ala Met Tyr Asp Leu Leu
        195                 200                 205

Arg Glu Gly Ala Glu Gln Arg Arg Glu Pro Trp Ala Arg Ile Trp Thr
    210                 215                 220

Glu Asp Gly Pro Tyr Trp Leu Ala Thr Ala Glu His Leu Asp Ala His
225                 230                 235                 240

Thr Glu Ala Trp Glu Ile Ala Leu Arg
                245

<210> SEQ ID NO 93
<211> LENGTH: 1315
<212> TYPE: DNA
<213> ORGANISM: Bacteria

<400> SEQUENCE: 93
```

```
catcctccct cgcctaaagg cgggggagtc cgaccctcgc gggttggggt tcctggttca      60
ccgcagaccg cacggaagga ggtccttcgt gtctgacgtc cgctccgcag gcgttttcg      120 tctcggccag cccggccgcg acggtgatgt tcttggctgc gttgacgtcc cggtcatgcc     180
gggtgccgca actcggacac gtccagtggc gtgtgccgag ggagagtgtg gcgagcaggt     240
gcccgcacgc cgagcaggtc ttcgacgacg gtaccagcg gtccaccacc gcgagggtgc      300
ggccgtcgcg gtgcgccttg taggtgagca gggtgcggaa ctcggcccag ccggtacgcg     360
agatcgcttt ggccagggag tggttgcgga ccatgttcgc cacggccagg tcctccacgg     420
cgatggcggc gaaccggcgc accagggcgg tggactgctg gtggaggaag tcccggcggg     480
cgtcgcgcac ctgcgaatgc gctcgggcga ccattcgttt ggctttggcg cggttggcgg     540
agcccttctg tcggcgggcc attatccgct gataccgctt gagtcggcgt cccgccgtt     600 ccatgtgctt cgggtggggg atgcgttcgc cggtggacag caccgcgaag tcggtcaggc     660
cgaggtccac gcccaccgcc tcgccggtgg gttcgggtgc ggcgggtgtg tcgacgtcga     720
cggcgaaggt cacgaaccag cggccgtccg ggtcacgcga caccgtcacc atcgtcggat     780
ccaaccccgc cggatccacg ttcggcaacg accacacgaa ccgcagcacc ccgggtgtct     840
ttcccaacga caggttcccg ctgcggaggc ggaacgccga ccgggtgtaa ctggcggact     900
ggcggccgtg tcgggacttg tagcgcgggt accgggcccg cttggcgaag aaggcggtca     960
tggcggtgtg ctggtgccgc aggtctgctg caacgcgcac cgacgacacc tcacccagat    1020
acgccaggtc gggctgcttc ttcatctccg tcaacgcccg atcggtctcc gcgtaggagg    1080
tggatctccg ttcggtgtgc cagcgggcgt gacgggcggc gagcgtgcgg ttccagacga    1140
cacgtacaca cccgaacgtg cggttcagca ccgccgcctg ctccgggtc gggtacgccc     1200 gacacctgta cgccgtccgc acaggaccag ccctaccaga aggacagtc gtggctgaca     1260 acgcatccgc cgttcgtccc cgccctgaag gacgtggcat cctggcggtg atccg         1315
```

<210> SEQ ID NO 94
<211> LENGTH: 1263
<212> TYPE: DNA
<213> ORGANISM: Bacteria
<220> FEATURE:
<221> NAME/KEY: CDS
<222> LOCATION: (1)...(1263)

<400> SEQUENCE: 94

```
gtg cta gat atg act caa gta gac ggg tcg ccc ctg cca act ctg gaa      48
Val Leu Asp Met Thr Gln Val Asp Gly Ser Pro Leu Pro Thr Leu Glu
 1               5                  10                  15 agg caa gtg atc acc gtg cgt gtg ctg ttc gcc agt ctc gga acc cat      96
Arg Gln Val Ile Thr Val Arg Val Leu Phe Ala Ser Leu Gly Thr His
                20                  25                  30 ggc cac acc tac ccc ctg ctg cca ctg gcc acg gcc gcc cgt gcg gcg     144
Gly His Thr Tyr Pro Leu Leu Pro Leu Ala Thr Ala Ala Arg Ala Ala
            35                  40                  45 ggc cac gag gtc acc ttc gcc acc ggc gag ggc ttc gcg ggc acc ctg     192
Gly His Glu Val Thr Phe Ala Thr Gly Glu Gly Phe Ala Gly Thr Leu
        50                  55                  60 cgg aag ctg ggc ttc gag ccg gtc gcg acc ggg atg ccg gtc ttc gac     240
Arg Lys Leu Gly Phe Glu Pro Val Ala Thr Gly Met Pro Val Phe Asp
 65                  70                  75                  80 ggg ttc ctg gcg gcg ctg cgg atc cgc ttc gac acc gac agc ccc gag     288
Gly Phe Leu Ala Ala Leu Arg Ile Arg Phe Asp Thr Asp Ser Pro Glu
                85                  90                  95
```

```
ggg ctg acc ccc gag cag ctc agt gag ctg ccg cag atc gtg ttc ggg      336
Gly Leu Thr Pro Glu Gln Leu Ser Glu Leu Pro Gln Ile Val Phe Gly
            100                 105                 110 cgg gtc atc ccg cag cgc gtc ttc gac gag ctc cag ccg gtg atc gaa      384
Arg Val Ile Pro Gln Arg Val Phe Asp Glu Leu Gln Pro Val Ile Glu
        115                 120                 125 cgg ttg cga ccc gac ctc gtg gtg cag gag atc agc aac tac ggc gcc      432
Arg Leu Arg Pro Asp Leu Val Val Gln Glu Ile Ser Asn Tyr Gly Ala
    130                 135                 140 ggc ctg gcc gcc ctg aag gcg ggc atc ccg acc atc tgc cac ggg gtc      480
Gly Leu Ala Ala Leu Lys Ala Gly Ile Pro Thr Ile Cys His Gly Val
145                 150                 155                 160 ggc cgg gac acg ccg gac gac ctg acc cgg tcc atc gag gag gag gtg      528
Gly Arg Asp Thr Pro Asp Asp Leu Thr Arg Ser Ile Glu Glu Glu Val
                165                 170                 175 cgg ggg ctg gcc cag cgg ctc ggc ctc gac ctg ccg ccc ggg cgc atc      576
Arg Gly Leu Ala Gln Arg Leu Gly Leu Asp Leu Pro Pro Gly Arg Ile
            180                 185                 190 gac ggc ttc ggc aac ccc ttc atc gac atc ttc ccg ccg tcg ctg cag      624
Asp Gly Phe Gly Asn Pro Phe Ile Asp Ile Phe Pro Pro Ser Leu Gln
        195                 200                 205 gag ccg gag ttc cgg gcc cgc ccg cgg cgc cac gag ctg cgc ccg gtg      672
Glu Pro Glu Phe Arg Ala Arg Pro Arg Arg His Glu Leu Arg Pro Val
    210                 215                 220 ccc ttc gcc gag cag ggt gac ctc ccg gcc tgg ctg tcc tcg cgc gac      720
Pro Phe Ala Glu Gln Gly Asp Leu Pro Ala Trp Leu Ser Ser Arg Asp
225                 230                 235                 240 acg gcc cgc ccg ctg gtc tac ctg acg ctc ggc acg tcc agc ggc ggc      768
Thr Ala Arg Pro Leu Val Tyr Leu Thr Leu Gly Thr Ser Ser Gly Gly
                245                 250                 255 acc gtc gag gtg ctg cgg gcg gcg atc gac ggg ctc gcc ggc ctc gac      816
Thr Val Glu Val Leu Arg Ala Ala Ile Asp Gly Leu Ala Gly Leu Asp
            260                 265                 270 gcc gac gtc ctg gtc gcc agc ggc ccg tcc ctc gac gtc agc gga ctg      864
Ala Asp Val Leu Val Ala Ser Gly Pro Ser Leu Asp Val Ser Gly Leu
        275                 280                 285 ggc gag gtg ccg gca aac gta cgg ctc gag tcg tgg gtg ccg cag gcg      912
Gly Glu Val Pro Ala Asn Val Arg Leu Glu Ser Trp Val Pro Gln Ala
    290                 295                 300 gcc ctg ctg ccc cac gtc gac ctg gtg gtg cac cac ggg ggc agc ggc      960
Ala Leu Leu Pro His Val Asp Leu Val Val His His Gly Gly Ser Gly
305                 310                 315                 320 act acg ctc ggc gca ctg ggc gcc ggc gtg ccg cag ctg tcc ttc ccg     1008
Thr Thr Leu Gly Ala Leu Gly Ala Gly Val Pro Gln Leu Ser Phe Pro
                325                 330                 335 tgg gcg ggg gac tcg ttc gcc aac gcg cag gcg gtg gcg cag gcc ggc     1056
Trp Ala Gly Asp Ser Phe Ala Asn Ala Gln Ala Val Ala Gln Ala Gly
            340                 345                 350 gcc ggt gac cac ctg ctg ccc gac aac atc agc ccc gac tcg gtg tcg     1104
Ala Gly Asp His Leu Leu Pro Asp Asn Ile Ser Pro Asp Ser Val Ser
        355                 360                 365 ggc gcc gcg aag cgc ctg ttg gcc gag gag agc tac cgg gcc ggg gcg     1152
Gly Ala Ala Lys Arg Leu Leu Ala Glu Glu Ser Tyr Arg Ala Gly Ala
    370                 375                 380 cgg gcc gtg gcg gcc gag atc gcg gcc atg ccg ggc ccc gac gag gtc     1200
Arg Ala Val Ala Ala Glu Ile Ala Ala Met Pro Gly Pro Asp Glu Val
385                 390                 395                 400 gtc cgc ctg ctg ccg ggc ttc gcc tcc agg agc gcg ggc tga ccg gcg     1248
Val Arg Leu Leu Pro Gly Phe Ala Ser Arg Ser Ala Gly  *  Pro Ala
```

-continued

```
              405                 410                 415
cta cgt ctg ccg tag                                              1263
Leu Arg Leu Pro *
```

<210> SEQ ID NO 95
<211> LENGTH: 419
<212> TYPE: PRT
<213> ORGANISM: Bacteria

<400> SEQUENCE: 95

```
Val Leu Asp Met Thr Gln Val Asp Gly Ser Pro Leu Pro Thr Leu Glu
 1               5                  10                  15

Arg Gln Val Ile Thr Val Arg Val Leu Phe Ala Ser Leu Gly Thr His
             20                  25                  30

Gly His Thr Tyr Pro Leu Leu Pro Leu Ala Thr Ala Ala Arg Ala Ala
         35                  40                  45

Gly His Glu Val Thr Phe Ala Thr Gly Glu Gly Phe Ala Gly Thr Leu
     50                  55                  60

Arg Lys Leu Gly Phe Glu Pro Val Ala Thr Gly Met Pro Val Phe Asp
 65                  70                  75                  80

Gly Phe Leu Ala Ala Leu Arg Ile Arg Phe Asp Thr Asp Ser Pro Glu
                 85                  90                  95

Gly Leu Thr Pro Glu Gln Leu Ser Glu Leu Pro Gln Ile Val Phe Gly
            100                 105                 110

Arg Val Ile Pro Gln Arg Val Phe Asp Glu Leu Gln Pro Val Ile Glu
        115                 120                 125

Arg Leu Arg Pro Asp Leu Val Val Gln Glu Ile Ser Asn Tyr Gly Ala
    130                 135                 140

Gly Leu Ala Ala Leu Lys Ala Gly Ile Pro Thr Ile Cys His Gly Val
145                 150                 155                 160

Gly Arg Asp Thr Pro Asp Asp Leu Thr Arg Ser Ile Glu Glu Glu Val
                165                 170                 175

Arg Gly Leu Ala Gln Arg Leu Gly Leu Asp Leu Pro Pro Gly Arg Ile
            180                 185                 190

Asp Gly Phe Gly Asn Pro Phe Ile Asp Ile Phe Pro Pro Ser Leu Gln
        195                 200                 205

Glu Pro Glu Phe Arg Ala Arg Pro Arg Arg His Glu Leu Arg Pro Val
    210                 215                 220

Pro Phe Ala Glu Gln Gly Asp Leu Pro Ala Trp Leu Ser Ser Arg Asp
225                 230                 235                 240

Thr Ala Arg Pro Leu Val Tyr Leu Thr Leu Gly Thr Ser Ser Gly Gly
                245                 250                 255

Thr Val Glu Val Leu Arg Ala Ala Ile Asp Gly Leu Ala Gly Leu Asp
            260                 265                 270

Ala Asp Val Leu Val Ala Ser Gly Pro Ser Leu Asp Val Ser Gly Leu
        275                 280                 285

Gly Glu Val Pro Ala Asn Val Arg Leu Glu Ser Trp Val Pro Gln Ala
    290                 295                 300

Ala Leu Leu Pro His Val Asp Leu Val Val His His Gly Ser Gly
305                 310                 315                 320

Thr Thr Leu Gly Ala Leu Gly Ala Gly Val Pro Gln Leu Ser Phe Pro
                325                 330                 335

Trp Ala Gly Asp Ser Phe Ala Asn Ala Gln Ala Val Ala Gln Ala Gly
            340                 345                 350
```

-continued

```
Ala Gly Asp His Leu Leu Pro Asp Asn Ile Ser Pro Asp Ser Val Ser
        355                 360                 365

Gly Ala Ala Lys Arg Leu Leu Ala Glu Glu Ser Tyr Arg Ala Gly Ala
        370                 375                 380

Arg Ala Val Ala Ala Glu Ile Ala Ala Met Pro Gly Pro Asp Glu Val
385                 390                 395                 400

Val Arg Leu Leu Pro Gly Phe Ala Ser Arg Ser Ala Gly Pro Ala Leu
                405                 410                 415

Arg Leu Pro
```